US007678792B2

(12) United States Patent
Chianelli et al.

(10) Patent No.: US 7,678,792 B2
(45) Date of Patent: Mar. 16, 2010

(54) COMPOSITIONS AND METHODS FOR MODULATING C-KIT AND PDGFR RECEPTORS

(75) Inventors: Donatella Chianelli, San Diego, CA (US); Christopher Cow, San Diego, CA (US); Yun He, Shanghai (CN); Songchun Jiang, San Diego, CA (US); Xiaolin Li, San Diego, CA (US); Xiaodong Liu, San Diego, CA (US); Zuosheng Liu, San Diego, CA (US); Jon Loren, San Diego, CA (US); Valentina Molteni, San Diego, CA (US); Juliet Nabakka, Santee, CA (US); Pingda Ren, San Diego, CA (US); Taebo Sim, Seoul (KR); Xiaodong Wang, Chapel Hill, NC (US); Shuli You, Shanghai (CN)

(73) Assignee: IRM LLC, Hamilton (BM)

( * ) Notice: Subject to any disclaimer, the term of this patent is extended or adjusted under 35 U.S.C. 154(b) by 17 days.

(21) Appl. No.: 11/873,196

(22) Filed: Oct. 16, 2007

(65) Prior Publication Data

US 2008/0176846 A1 Jul. 24, 2008

Related U.S. Application Data

(60) Provisional application No. 60/862,430, filed on Oct. 20, 2006.

(51) Int. Cl.
| | |
|---|---|
| C07D 471/04 | (2006.01) |
| A61K 31/4375 | (2006.01) |
| A61K 31/497 | (2006.01) |
| A61K 31/501 | (2006.01) |
| A61K 31/5355 | (2006.01) |
| A61K 31/506 | (2006.01) |
| C07D 413/14 | (2006.01) |
| C07D 213/69 | (2006.01) |
| C07D 213/61 | (2006.01) |
| C07D 213/74 | (2006.01) |
| C07D 213/80 | (2006.01) |
| C07C 205/06 | (2006.01) |
| C07C 301/00 | (2006.01) |
| C07C 255/07 | (2006.01) |
| C07C 69/73 | (2006.01) |
| A61P 17/10 | (2006.01) |
| A61P 29/00 | (2006.01) |
| A61P 3/10 | (2006.01) |
| A61P 31/00 | (2006.01) |
| A61P 27/14 | (2006.01) |

(52) U.S. Cl. .......... 514/232.5; 514/300; 514/253.04; 514/252.04; 514/234.5; 514/275; 544/362; 544/238; 544/127; 544/331; 544/80; 544/119; 546/296; 546/318; 546/310; 546/297; 546/122; 568/705; 558/44; 558/410; 560/60

(58) Field of Classification Search .............. 514/300, 514/253.04, 252.04, 234.5, 275, 232.5; 546/123; 544/362, 238, 127, 331, 80, 119
See application file for complete search history.

(56) References Cited

FOREIGN PATENT DOCUMENTS

| WO | WO 02/28853 A1 | 4/2002 |
|---|---|---|
| WO | WO 2005034869 | * 10/2003 |
| WO | WO 2005/034869 A2 | 4/2005 |
| WO | WO 2007136465 | * 5/2006 |
| WO | WO 2006/071940 | 7/2006 |
| WO | WO 2006/081034 | 8/2006 |
| WO | WO 2008034008 | * 9/2006 |
| WO | WO 2007/136465 | 11/2007 |

OTHER PUBLICATIONS

Palmer, et al., "Structure-activity relationships for 2-anilino-6-phenylpyrido[2,3-d]pyrimdin-7(8H)-ones as inhibitors of the cellular checkpoint kinase Wee1" *Bioorganic & Medicinal Chemistry Letters*, vol. 15, No. 7, pp. 1931-1935, 2005.
Okram, et al., "A General Strategy for Creating 'Inactive-Conformation' Abl Inhibitors", *Chemistry & Biology*, vol. 13, No. 7, pp. 779-786, Jul. 2006.

* cited by examiner

*Primary Examiner*—James O Wilson
*Assistant Examiner*—Cecilia M Jaisle
(74) *Attorney, Agent, or Firm*—Emily Tongco Wu; Genomics Institute of the Novartis Research Foundation

(57) ABSTRACT

The invention provides compounds and pharmaceutical compositions thereof, which are useful as protein kinase inhibitors, as well as methods for using such compounds to treat, ameliorate or prevent a condition associated with abnormal or deregulated kinase activity. In some embodiments, the invention provides methods for using such compounds to treat, ameliorate or prevent diseases or disorders that involve abnormal activation of c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf or b-raf kinase, or mutant forms thereof.

17 Claims, No Drawings

COMPOSITIONS AND METHODS FOR MODULATING C-KIT AND PDGFR RECEPTORS

CROSS-REFERENCE TO RELATED APPLICATIONS

This application claims the benefit of U.S. provisional application Ser. No. 60/862,430, filed Oct. 20, 2006, which is incorporated herein by reference in its entirety.

TECHNICAL FIELD

The invention relates to protein kinase inhibitors, and methods of using such compounds.

BACKGROUND ART

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGFR), the receptor kinase for stem cell factor (c-kit), the nerve growth factor receptor (trkB), the fibroblast growth factor receptor (FGFR3) and the colony stimulating factor 1 receptor (CSF1R); non-receptor tyrosine kinases such as Abl, the fusion kinase BCR-Abl, Fes, Lck and Syk; and serine/threonine kinases such as b-RAF, MAP kinases (e.g., MKK6) and SAPK2β. Aberrant kinase activity has been observed in many disease states including benign and malignant proliferative disorders as well as diseases resulting from inappropriate activation of the immune and nervous systems.

DISCLOSURE OF THE INVENTION

The invention provides compounds and pharmaceutical compositions thereof, which may be useful as protein kinase inhibitors.

In one aspect, the invention provides compounds having Formula (1):

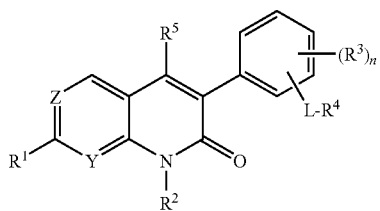

or pharmaceutically acceptable salts thereof, wherein:

Y and Z are independently CR or N;

L is NR—C(O), C(O)NR, C(O)NRC(O)NR, NRC(O)NR, NRC(O)NRC(O), NRC(S)NRCO, NRS(O)$_{0-2}$ or NRCONRS(O)$_{0-2}$;

$R^1$ and $R^3$ are independently halo, $(CR_2)_k R^6$, $(CR_2)_k NR^7R^8$, $(CR_2)_k OR^9$, $(CR_2)_k SR^9$, or an optionally substituted $C_{1-6}$ alkyl, $C_{2-6}$ alkenyl or $C_{2-6}$ alkynyl;

$R^2$ is $(CR_2)_k R^6$, $(CR_2)_{1-4} OR^9$, $(CR_2)_{1-4} NR^7R^8$, or an optionally substituted $C_{1-6}$ alkyl, $C_{2-6}$ alkenyl or $C_{2-6}$ alkynyl;

$R^4$ is $(CR_2)_k R^6$, $(CR_2)_k OR^9$, or an optionally substituted $C_{1-6}$ alkyl, $C_{2-6}$ alkenyl or $C_{2-6}$ alkynyl;

$R^5$ is H, halo or $C_{1-6}$ alkyl;

$R^6$ is an optionally substituted $C_{3-7}$ cycloalkyl, or an optionally substituted 5-12 membered aryl, heterocycle or heteroaryl;

$R^7$ and $R^8$ are independently H, $(CR_2)_k NR^7R^8$, $(CR_2)_k OR^9$, $(CR_2)_k$—$R^6$, or an optionally substituted $C_{1-6}$ alkyl, $C_{2-6}$ alkenyl or $C_{2-6}$ alkynyl; or $R^7$ and $R^8$ together with N in each $NR^7R^8$ may form an optionally substituted ring;

$R^9$ is H, $(CR_2)_k$—$R^6$, or an optionally substituted $C_{1-6}$ alkyl, $C_{2-6}$ alkenyl or $C_{2-6}$ alkynyl;

each R is H or $C_{1-6}$alkyl having a carbon that is optionally substituted or replaced with N, O, =O, S; or two alkylene groups in $(CR_2)_k$ may form an alkenyl or alkynyl;

each optionally substituted $C_{1-6}$ alkyl, $C_{2-6}$ alkenyl or $C_{2-6}$ alkynyl is optionally halogenated or optionally substituted with N, O or S;

k is 0-6; and n is 0-2;

provided L is C(O)NRC(O)NR, NRC(O)NR, NRC(O)NRC(O), NRC(S)NRCO or NRCONRS(O)$_{0-2}$ when $R^1$ is halo, $(CR_2)_k NR^7R^8$ or $C_{5-8}$ heterocycloalkyl and $R^2$ is $C_{1-6}$ alkyl.

In the above Formula (1), Y may be CH. In other examples, Z is N. In yet other examples, n is 1; and $R^3$ is halo or $C_{1-6}$ alkyl.

In the above Formula (1), $R^4$ may be $C_{1-6}$ alkyl, $(CR_2)_k O(C_{1-6}$ alkyl) or $(CR^2)_k R^6$;

$R^6$ is an optionally substituted phenyl, $C_{3-7}$ cycloalkyl, or a 5-12 membered heterocycle or heteroaryl containing N, O or S; and k is 0-4.

In one embodiment, the invention provides compounds of Formula (2):

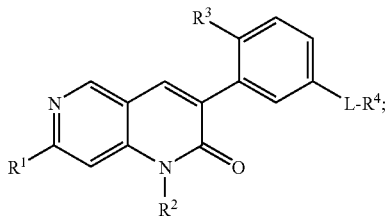

wherein $R^1$ is halo, $(CR_2)_k R^6$, $(CR_2)_k NR^7R^8$, $(CR_2)_k OR^9$, $(CR_2)_k SR^9$, or an optionally substituted $C_{1-6}$ alkyl or $C_{2-6}$ alkenyl;

$R^2$ is $C_{1-6}$ alkyl, $(CR^2)R^{6'}$, $(CR_2)_{1-4} OR^9$ or $(CR^2)_{1-4} NR^7R^8$;

$R^3$ is halo or $C_{1-6}$ alkyl;

$R^4$ is $C_{1-6}$ alkyl, $(CR_2)_k O(C_{1-6}$ alkyl) or $(CR^2)_k R^6$;

$R^{6'}$ is an optionally substituted phenyl, $C_{3-7}$ cycloalkyl or a 5-7 membered heterocycle or heteroaryl containing N, O or S;

$R^6$ is an optionally substituted phenyl, $C_{3-7}$ cycloalkyl or a 5-12 membered heterocycle or heteroaryl containing N, O or S;

$R^7$, $R^8$ and $R^9$ are independently H or $C_{1-6}$ alkyl; or $R^7$ and $R^8$ together may form an optionally substituted 5-7 membered heterocyclic ring; and each k is 0-4.

In the above Formula (2), $R^{6'}$ may optionally be substituted with halo or an optionally halogenated $C_{1-6}$ alkyl; and $R^6$ may optionally be substituted with one or more substituents as defined below.

In other embodiments, the invention provides a compound of Formula (3):

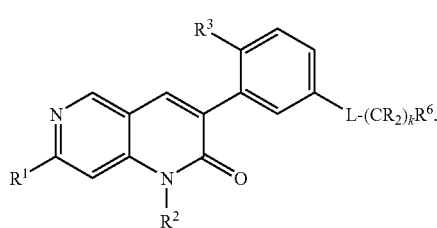

In the above Formula (1), (2) or (3), $R^1$ is halo, $(CR_2)_kR^6$, $(CR_2)_kNR^7R^8$, $(CR_2)_kOR^9$, $(CR_2)_kSR^9$, or an optionally substituted $C_{1-6}$ alkyl or $C_{2-6}$ alkenyl;

$R^2$ is $C_{1-6}$ alkyl, $C_{2-6}$ alkenyl, $(CR_2)_kR^6$, $(CR_2)_{1-4}OR^9$ or $(CR_2)_{1-4}NR^7R^8$;

$R^6$ is phenyl, $C_{3-7}$ cycloalkyl or a 5-7 membered heterocycle or heteroaryl containing N, O or S, each of which is optionally substituted with halo or an optionally halogenated $C_{1-6}$ alkyl;

$R^7$, $R^8$ and $R^9$ are independently H or $C_{1-6}$ alkyl; or $R^7$ and $R^8$ together may form an optionally substituted 5-7 membered heterocyclic ring; and each k is 0-4.

Examples of suitable 5-12 membered heterocycle or heteroaryl $R^6$ groups in the above Formula (1), (2) and (3) include but are not limited to thiazolyl, thienyl, piperidinyl, piperazinyl, pyridinyl, pyridazinyl, pyrimidinyl, pyrazinyl, imidazolyl, pyrazolyl, furanyl, pyrrolyl, dihydropyrrolyl, oxazolyl, isoxazolyl, triazolyl, azetidinyl, thiadiazolyl, benzimidazolyl, quinolinyl, tetrahydroquinolinyl, benzothiazolyl, benzothiophenyl, benzodioxolyl, indazolyl, indolyl, indenyl, dihydroindenyl or dihydrobenzofuran.

Examples of suitable $R^{10}$ groups include but are not limited to an optionally substituted phenyl, piperazin-2-onyl, morpholinyl, thiazolyl, thienyl, piperidinyl, piperazinyl, pyridinyl, pyridazinyl, pyrimidinyl, pyrazinyl, imidazolyl, imidazolidin-2-onyl, pyrazolyl, furanyl, pyrrolyl, dihydropyrrolyl, oxazolyl, isoxazolyl, triazolyl, azetidinyl, thiadiazolyl, or tetrahydropyranyl.

In the above Formula (1), (2), or (3), each optionally substituted $C_{1-6}$ alkyl, $C_{2-6}$ alkenyl or $C_{2-6}$ alkynyl may optionally be halogenated or optionally substituted with N, O or S (e.g., hydroxyl, ureayl or guanidinyl).

In the above Formula (1), (2) or (3), each said optionally substituted phenyl, $C_{3-7}$ cycloalkyl, or 5-12 membered heterocycle or heteroaryl containing N, O or S, may optionally be substituted with one or more substituents selected from the group consisting of halo, cyano, nitro, $NR^7R^8$, $NRCOR^7$, $NRCO(CR_2)_pNR^7R^8$, $NRCONR(CR_2)_pNR^7R^8$, $(CR_2)_pOR^9$, $(CR_2)_pR^{10}$, and a $C_{1-6}$ alkyl optionally substituted with halo, hydroxyl, $C_{1-6}$ alkoxy or cyano;

each R is H or $C_{1-6}$ alkyl having a carbon that is optionally substituted or replaced with N, O, =O, S; or two alkylene groups in $(CR_2)_p$ may form an alkenyl or alkynyl;

$R^7$ and $R^8$ are independently H, $C_{1-6}$ alkyl or $(CR_2)_p$—$R^{10}$; or $R^7$ and $R^8$ together with N in each $NR^7R^8$ may form an optionally substituted ring;

$R^9$ is H, an optionally halogenated $C_{1-6}$ alkyl or $(CR_2)_pR^{10}$;

$R^{10}$ is $C_{3-7}$ cycloalkyl, aryl, or 5-7 membered heterocycle or heteroaryl containing N, O or S, each of which is optionally substituted with one or more said substituents; and p is 0-4.

In another aspect, the present invention provides pharmaceutical compositions comprising a therapeutically effective amount of a compound having Formula (1), (2) or (3), and a pharmaceutically acceptable excipient.

In yet another aspect, the present invention provides methods for modulating kinase activity, comprising administering to a system or a subject in need thereof, a therapeutically effective amount of a compound having Formula (1), (2) or (3), or pharmaceutically acceptable salts or pharmaceutical compositions thereof, thereby modulating said kinase activity. In one embodiment, the invention provides methods for modulating c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf or b-raf kinase, or mutant forms thereof. In other embodiments, the invention provides methods for modulating c-kit, PDGFRα, PDGFRβ, or mutant forms thereof, and may directly contact c-kit, PDGFRα or PDGFRβ in vitro or in vivo.

The present invention also provides methods for treating a disease or condition wherein modulation of kinase activity can prevent, inhibit or ameliorate the pathology and/or symptomology of the disease or condition, comprising administering to a system or subject, a therapeutically effective amount of a compound having Formula (1), (2) or (3), or pharmaceutically acceptable salts or pharmaceutical compositions thereof, and optionally in combination with a therapeutically effective amount of a second agent. When administered with a second agent, the compound of Formula (1), (2) or (3), or pharmaceutically acceptable salts or pharmaceutical compositions thereof may be administered prior to, simultaneously with, or after the second agent. In one example, the second agent is a bronchodilator, an anti-inflammatory agent, a leukotriene antagonist, or an IgE blocker.

In one embodiment, the invention provides methods for treating a disease or condition mediated by c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAP 2, BRK, KDR, c-raf or b-raf kinase, or mutant forms thereof, comprising administering to a system or subject, a therapeutically effective amount of a compound of Formula (1), (2) or (3), or pharmaceutically acceptable salts or pharmaceutical compositions thereof. In particular examples, the invention provides methods for treating a disease of condition mediated by c-kit, PDGFRα or PDGFRβ, or mutant forms thereof.

Examples of kinase mediated disease or conditions which may be mediated using the compounds and compositions of the invention include but are not limited to a neoplastic disorder, an allergy disorder, an inflammatory disorder, irritable bowel syndrome (IBS), an autoimmune disorder, a graft-versus-host disease, a mast cell associated disease, a metabolic syndrome, a CNS related disorder, a neurodegenerative disorder, a pain condition, a substance abuse disorder, a prion disease, a cancer, a heart disease, a fibrotic disease, idiopathic arterial hypertension (IPAH), primary pulmonary hypertension (PPH), glioma and a cardiovascular disease.

Examples of a mast cell associated disease which may be treated using compounds and compositions of the invention include but are not limited to acne and *Propionibacterium acnes*, *Fibrodysplasia ossificans progressiva* (FOP), inflammation and tissue destruction induced by exposure to chemical or biological weapons (such as anthrax and sulfur-mustard), cystic fibrosis; renal disease, inflammatory muscle disorders, HIV, type II diabetes, cerebral ischemia, mastocytosis, macular degeneration, nasal polyposys, drug dependence and withdrawal symptoms, CNS disorders, preventing and minimizing hair loss, bacterial infections, interstitial cystitis, inflammatory bowel diseases (e.g., Crohn's disease, ulcerative colitis, indeterminate colitis, and infectious colitis), tumor angiogenesis, autoimmune diseases, inflammatory diseases, multiple sclerosis (MS), allergic disorders (including asthma), and bone loss.

Examples of neoplastic disorders which may be treated using the compounds and compositions of the invention include but are not limited to mastocytosis, gastrointestinal stromal tumor, small cell lung cancer, non-small cell lung cancer, acute myelocytic leukemia, acute lymphocytic leukemia, myelodyplastic syndrome, chronic myelogenous leukemia, colorectal carcinoma, gastric carcinoma, testicular cancer, glioblastoma and astrocytoma.

Examples of allergy disorders which may be treated using the compounds and compositions of the invention include but are not limited to asthma, allergic rhinitis, allergic sinusitis, anaphylactic syndrome, urticaria, angioedema, atopic dermatitis, allergic contact dermatitis, erythema nodosum, erythema multifonne, cutaneous necrotizing venulitis, insect bite skin inflammation, and blood sucking parasite infestation.

Examples of inflammatory disorders which may be treated using the compounds and compositions of the invention include but are not limited to rheumatoid arthritis, conjunctivitis, rheumatoid spondylitis, osteoarthritis and gouty arthritis.

Examples of autoimmune disorders which may be treated using the compounds and compositions of the invention include but are not limited to multiple sclerosis, psoriasis, intestine inflammatory disease, inflammatory bowel disease (IBD), ulcerative, indeterminate or infectious colitis, Crohn's disease, rheumatoid arthritis, polyarthritis, local or systemic scleroderma, systemic lupus erythematosus, discoid lupus erythematosis, cutaneous lupus, dermatomyositis, polymyositis, Sjogren's syndrome, nodular panarteritis, autoimmune enteropathy and proliferative glomerulonephritis.

Examples of graft-versus-host diseases which may be treated using the compounds and compositions of the invention include but are not limited to organ transplantation graft rejection, such as kidney transplantation, pancreas transplantation, liver transplantation, heart transplantation, lung transplantation, and bone marrow transplantation.

Examples of metabolic syndrome which may be treated using the compounds and compositions of the invention include but are not limited to type I diabetes, type II diabetes, and obesity.

Examples of CNS related disorders which may be treated using the compounds and compositions of the invention include but are not limited to depression, dysthymic disorder, cyclothymic disorder, anorexia, bulimia, premenstrual syndrome, post-menopause syndrome, mental slowing, loss of concentration, pessimistic worry, agitation, self-deprecation and decreased libido, an anxiety disorder, a psychiatric disorder and schizophrenia.

Examples of depression conditions which may be treated using the compounds and compositions of the invention include but are not limited to bipolar depression, severe or melancholic depression, atypical depression, refractory depression, and seasonal depression. Examples of anxiety disorders which may be treated using the compounds and compositions of the invention include but are not limited to anxiety associated with hyperventilation and cardiac arrhythmias, phobic disorders, obsessive-compulsive disorder, post-traumatic stress disorder, acute stress disorder, and generalized anxiety disorder. Examples of psychiatric disorders which may be treated using the compounds and compositions of the invention include but are not limited to panic attacks, including psychosis, delusional disorders, conversion disorders, phobias, mania, delirium, dissociative episodes including dissociative amnesia, dissociative fugue and dissociative suicidal behavior, self-neglect, violent or aggressive behavior, trauma, borderline personality, and acute psychosis such as schizophrenia, including paranoid schizophrenia, disorganized schizophrenia, catatonic schizophrenia, and undifferentiated schizophrenia.

Examples of neurodegenerative disorder which may be treated using the compounds and compositions of the invention include but are not limited to Alzheimer's disease, Parkinson's disease, Huntington's disease, the prion diseases, Motor Neuron Disease (MND), and Amyotrophic Lateral Sclerosis (ALS).

Examples of pain conditions which may be treated using the compounds and compositions of the invention include but are not limited to acute pain, postoperative pain, chronic pain, nociceptive pain, cancer pain, neuropathic pain and psychogenic pain syndrome.

Examples of substance use disorders which may be treated using the compounds and compositions of the invention include but are not limited to drug addiction, drug abuse, drug habituation, drug dependence, withdrawal syndrome and overdose.

Examples of cancers which may be treated using the compounds and compositions of the invention include but are not limited to melanoma, gastrointestinal stromal tumor (GIST), small cell lung cancer, and other solid tumors.

Examples of fibrotic diseases which may be treated using the compounds and compositions of the invention include but are not limited to cardiac fibrosis, hepatitis C (HCV), liver fibrosis, nonalcoholic steatohepatitis (NASH), cirrhosis in liver, pulmonary fibrosis, and bone marrow fibrosis.

Examples of cardiovascular diseases which may be treated using the compounds and compositions of the invention include but are not limited to angina pectoris, myocardial infarction, congestive heart failure, cardiomyopathy, hypertension, arterial stenosis, and venous stenosis.

In one embodiment, compounds having Formula (1), (2) or (3) may be used for treating hypereosinophilia, fibrosis, pulmonary hypertension, glioma, and a cardiovascular disease.

Furthermore, the present invention provides for the use of a compound having Formula (1), (2) or (3), or pharmaceutically acceptable salts or pharmaceutical compositions thereof, and optionally in combination with a therapeutically effective amount of a second agent, in the manufacture of a medicament for treating a disease or condition modulated by kinase activity, particularly c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf or b-raf kinase, or mutant forms thereof. In particular embodiments, the compounds of the invention are used in the manufacture of a medicament for treating a disease or condition modulated by PDGFRα, PDGFRβ, the c-kit kinase receptor, or mutant forms thereof.

In the above methods for using the compounds of the invention, a compound having Formula (1), (2) or (3) may be administered to a system comprising cells or tissues. In other embodiments, a compound having Formula (1), (2) or (3) may be administered to a human or animal subject.

DEFINITIONS

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., CF$_3$), or may have one or more carbons that is substituted or replaced with a heteroatom, such as NR, O or S (e.g., —OCH$_2$CH$_2$O—, alkylthiols, thioalkoxy, alkylamines, etc).

"Aryl" refers to a monocyclic or fused bicyclic aromatic ring containing carbon atoms. For example, aryl may be phenyl or naphthyl. "Arylene" means a divalent radical derived from an aryl group.

"Heteroaryl" as used herein is as defined for aryl above, where one or more of the ring members is a heteroatom. Examples of heteroaryls include but are not limited to pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —S(O)$_2$, or —NR— wherein R may be hydrogen, C$_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, etc.

Unless otherwise indicated, when a substituent is deemed to be "optionally substituted," it is meant that the substituent is a group that may be substituted with one or more group(s) individually and independently selected from, for example, an optionally halogenated alkyl, alkenyl, alkynyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof. The protecting groups that may form the protected compounds of the above substituents are known to those of skill in the art and may be found in references such as Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference in their entirety.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" or "administering" of the subject compound means providing a compound of the invention and prodrugs thereof to a subject in need of treatment.

"Mutant forms of BCR-Abl" means single or multiple amino acid changes from the wild-type sequence. One group of mutations (G250E, Q252R, Y253F/H, E255K/V) includes amino acids that form the phosphate-binding loop for ATP (also known as the P-loop). A second group of mutations (M351T, E355G) clusters in close proximity to the catalytic domain. A third group of mutations (H396R/P) is located in the activation loop, whose conformation is the molecular switch controlling kinase activation/inactivation. A fourth group of mutations (V289A, F311L, T315I, F317L) have also been reported. Unless otherwise stated for this invention, Bcr-Abl refers to wild-type and mutant forms of the enzyme.

MODES OF CARRYING OUT THE INVENTION

The present invention provides compounds and pharmaceutical compositions thereof, which may be useful as protein kinase inhibitors.

In one aspect, the invention provides compounds having Formula (1):

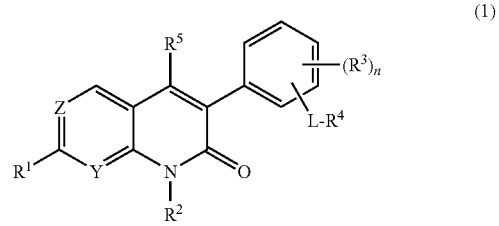

or pharmaceutically acceptable salts thereof, wherein:

Y and Z are independently CR or N;

L is NR—C(O), C(O)NR, C(O)NRC(O)NR, NRC(O)NR, NRC(O)NRC(O), NRC(S)NRCO, NRS(O)$_{0-2}$ or NRCONRS(O)$_{0-2}$;

R$^1$ and R$^3$ are independently halo, (CR$_2$)$_k$R$^6$, (CR$_2$)$_k$NR$^7$R$^8$, (CR$_2$)$_k$OR$^9$, (CR$_2$)$_k$SR$^9$, or an optionally substituted C$_{1-6}$ alkyl, C$_{2-6}$ alkenyl or C$_{2-6}$ alkynyl;

R$^2$ is (CR$_2$)$_k$R$^6$, (CR$_2$)$_{1-4}$OR$^9$, (CR$_2$)$_{1-4}$NR$^7$R$^8$, or an optionally substituted C$_{1-6}$ alkyl, C$_{2-6}$ alkenyl or C$_{2-6}$ alkynyl;

R$^4$ is (CR$_2$)$_k$R$^6$, (CR$_2$)$_k$OR$^9$, or an optionally substituted C$_{1-6}$ alkyl, C$_{2-6}$ alkenyl or C$_{2-6}$ alkynyl;

R$^5$ is H, halo or C$_{1-6}$ alkyl;

R$^6$ is an optionally substituted C$_{3-7}$ cycloalkyl, or an optionally substituted 5-12 membered aryl, heterocycle or heteroaryl;

$R^7$ and $R^8$ are independently H, $(CR_2)_k NR^7R^8$, $(CR_2)_k OR^9$, $(CR_2)_k$—$R^6$, or an optionally substituted $C_{1-6}$ alkyl, $C_{2-6}$ alkenyl or $C_{2-6}$ alkynyl; or $R^7$ and $R^8$ together with N in each $NR^7R^8$ may form an optionally substituted ring;

$R^9$ is H, $(CR_2)_k$—$R^6$, or an optionally substituted $C_{1-6}$ alkyl, $C_{2-6}$ alkenyl or $C_{2-6}$ alkynyl;

each R is H or $C_{1-6}$ alkyl having a carbon that is optionally substituted or replaced with N, O, =O, S; or two alkylene groups in $(CR_2)_k$ may form an alkenyl or alknynyl;

each optionally substituted $C_{1-6}$ alkyl, $C_{2-6}$ alkenyl or $C_{2-6}$ alkynyl is optionally halogenated or optionally substituted with N, O or S;

k is 0-6; and n is 0-2;

provided L is C(O)NRC(O)NR, NRC(O)NR, NRC(O)NRC(O), NRC(S)NRCO or NRCONRS(O)$_{0-2}$ when $R^1$ is halo, $(CR_2)_k NR^7R^8$ or $C_{5-8}$ heterocycloalkyl and $R^2$ is $C_{1-6}$ alkyl.

In one embodiment, the invention provides compounds of Formula (2):

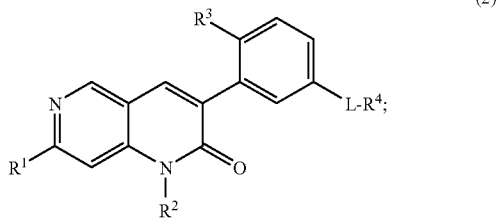

(2)

wherein $R^1$ is halo, $(CR_2)_k R^6$, $(CR_2)_k NR^7R^8$, $(CR_2)_k OR^9$, $(CR_2)_k SR^9$, or an optionally substituted $C_{1-6}$ alkyl or $C_{2-6}$ alkenyl;

$R^2$ is $C_{1-6}$ alkyl, $(CR_2)R^{6'}$, $(CR_2)_{1-4}OR^9$ or $(CR^2)_{1-4}NR^7R^8$;

$R^3$ is halo or $C_{1-6}$ alkyl;

$R^4$ is $C_{1-6}$ alkyl, $(CR_2)_k O(C_{1-6}$ alkyl) or $(CR^2)_k R^6$;

$R^{6'}$ is an optionally substituted phenyl, $C_{3-7}$ cycloalkyl or a 5-7 membered heterocycle or heteroaryl containing N, O or S;

$R^6$ is an optionally substituted phenyl, $C_{3-7}$ cycloalkyl or a 5-12 membered heterocycle or heteroaryl containing N, O or S;

$R^7$, $R^8$ and $R^9$ are independently H or $C_{1-6}$ alkyl; or $R^7$ and $R^8$ together may form an optionally substituted 5-7 membered heterocyclic ring; and each k is 0-4.

In other embodiments, the invention provides a compound of Formula (3),

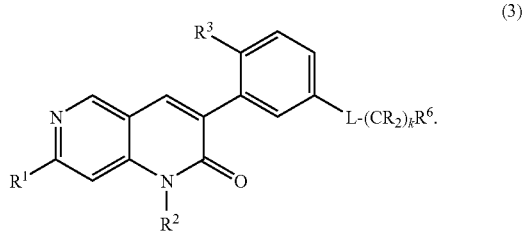

(3)

In the above Formula (1), (2) or (3), other substituents for $R^1$, $R^2$ and $R^3$ that would be apparent to those known in the art may be used. For example, $R^1$ and $R^3$ may be cyano, nitro, or other electron-withdrawing or electron-donating substituents.

Compounds having Formula (1), (2) or (3) may be useful as protein kinase inhibitors. For example, compounds having Formula (1), (2) or (3), and pharmaceutically acceptable salts, solvates, N-oxides, prodrugs and isomers thereof, may be used for the treatment of a kinase-mediated condition or disease, such as diseases mediated by c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf or b-raf kinase, or mutant forms thereof.

The compounds of the invention may also be used in combination with a second therapeutic agent, for ameliorating a condition mediated by a protein kinase, such as a c-kit, PDGFRα or PDGFRβ-mediated condition. In some embodiments, the compounds of the invention may be used in combination with a second therapeutic agent for treating asthma. For example, the second therapeutic agent may be a bronchodilator, an anti-inflammatory agent, a leukotriene antagonist, or an IgE blocker.

The compounds of the invention may also be used in combination with a chemotherapeutic agent to treat a cell proliferative disorder, including but not limited to, lymphoma, osteosarcoma, melanoma, or a tumor of breast, renal, prostate, colorectal, thyroid, ovarian, pancreatic, neuronal, lung, uterine or gastrointestinal tumor. Examples of chemotherapeutic agents which may be used in the compositions and methods of the invention include but are not limited to anthracyclines, alkylating agents (e.g., mitomycin C), alkyl sulfonates, aziridines, ethylenimines, methylmelamines, nitrogen mustards, nitrosoureas, antibiotics, antimetabolites, folic acid analogs (e.g., dihydrofolate reductase inhibitors such as methotrexate), purine analogs, pyrimidine analogs, enzymes, podophyllotoxins, platinum-containing agents, interferons, and interleukins. Particular examples of known chemotherapeutic agents which may be used in the compositions and methods of the invention include, but are not limited to, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluorouracil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elformithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethane, vinblastine, vincristine, and vindesine.

Pharmacology and Utility

Compounds of the invention modulate the activity of protein tyrosine kinases and are useful for treating diseases or disorders in which protein tyrosine kinases contribute to the pathology and/or symptomology of the disease, particularly c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf or b-raf kinase, or mutant forms thereof.

c-Kit

Mast cells are tissue elements derived from a particular subset of hematopoietic stem cells that express CD34, c-kit and CD13 antigens. Mast cells are characterized by their heterogeneity, not only regarding tissue location and structure but also at the functional and histochemical levels. Immature mast cell progenitors circulate in the bloodstream and differentiate into various tissues. These differentiation and proliferation processes are under the influence of cytokines, one of importance being Stem Cell Factor (SCF), also termed Kit ligand, Steel factor or Mast Cell Growth Factor. The Stem Cell Factor receptor is encoded by the protooncogene, c-kit, which is expressed in hematopoietic progenitor cells, mast cells, germ cells, interstitial cells of Cajal (ICC), and some human tumors, and is also expressed by non hematopoietic cells.

Tyrosine kinases are receptor type or non-receptor type proteins, which transfer the terminal phosphate of ATP to tyrosine residues of proteins thereby activating or inactivating signal transduction pathways. The Stem Cell Factor receptor, c-kit, is a Type III transmembrane receptor protein tyrosine kinase which initiates cell growth and proliferation signal transduction cascades in response to SCF binding. Ligation of c-kit receptor by SCF induces its dimerization followed by its transphorylation, leading to the recruitment and activation of various intracytoplasmic substrates. These activated substrates induce multiple intracellular signaling pathways responsible for cell proliferation and activation. These proteins are known to be involved in many cellular mechanisms, which in case of disruption, lead to disorders such as abnormal cell proliferation and migration, as well as inflammation. The compounds of the present invention may inhibit cellular processes involving SCF, such as inhibiting SCF receptor autophosphorylation and SCF-stimulated activation of MAPK kinase (mitogen-activated protein kinase).

The activity of the c-kit receptor protein tyrosine kinase is regulated in normal cells, and the normal functional activity of the c-kit gene product is important for the maintenance of normal hematopoeisis, melanogenesis, genetogensis, and growth and differentiation of mast cells. In addition to its importance in normal cellular physiologic activities, c-kit plays a role in the biological aspects of certain human cancers, and unregulated c-kit kinase activity is implicated in the pathogenesis of human cancers, and in certain tumors types. Proliferation of tumor cell growth mediated by c-kit can occur by a specific mutation of the c-kit polypeptide that results in ligand independent activation or by autocrine stimulation of the receptor. In the former case, mutations that cause constitutive activation of c-kit kinase activity in the absence of SCF binding are implicated in malignant human cancers, including germ cell tumors, mast cell tumors, gastrointestinal stromal tumors, small-cell lung cancer, melanoma, breast cancer, acute myelogenous leukemia, neuroblastoma and mastocytosis.

Mast cells present in tissues of patients are implicated in or contribute to the genesis of diseases such as autoimmune diseases (multiple sclerosis, rheumatoid arthritis, inflammatory bowel diseases (IBD)), allergic diseases (allergic sinusitis, allergic rhinitis and asthma), tumor angiogenesis, inflammatory diseases, and interstitial cystitis. In these diseases, mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-LA, MIP-1b, MIP-2 and IFN-y).

Humans are more and more afflicted in modern societies with allergic disorders such as allergic sinusitis, allergic rhinitis and asthma. For example, in the USA alone, it is estimated that more than 87 million people are coping with some form of allergic diseases. These allergic diseases include allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation, but bronchial asthma is the most prevalent and recurrent disease severely afflicting the human population.

Asthma is characterized by airflow obstruction, bronchial hyper responsiveness and airway inflammation. Airway inflammation is the major factor in the development and perpetuation of asthma. In allergic asthma, allergens are thought to initiate the inflammatory process by inducing a T-lymphocyte mediated response (TH2) that results in the production of allergen-specific IgE. IgE binds to its high-affinity receptor FcεRI on pulmonary mast cells, triggering a type I (IgE-mediated) immediate allergic response.

Mast cell activation induces diverse effector responses, such as secretion of allergic mediators, proteases, chemokines such as MCP-1 and RANTES, leukotrienes, prostaglandins and neurotrophins; and induction of cytokine gene transcription (IL-4, IL-5, IL-6, IL-13, TNFA and GM-CSF). These mediators contribute to creating the asthmatic phenotype by their effects on endothelial cells, smooth muscle cells and fibroblasts and on extracellular matrix, and by recruiting other inflammatory cells.

Mast cells may play a role in asthma as suggested by the humanized anti-IgE monoclonal antibody treatment. The rationale of anti-IgE therapy is to specifically target IgE with the result of inactivating free anti-IgE and halting further IgE production. In addition, since IgE levels are a major regulator of the level of expression of IgE receptor FcεRI, one aim of this therapy is to decrease FcεRI expression on mast cells and basophils, and, as a consequence, to decrease the capacity of these cells to be activated. The capacity of the anti-IgE therapy to decrease FcεRI expression has been demonstrated on basophils. The decrease in FcεRI expression on basophils is associated with a decrease in the capacity of basophils to secrete mediators upon activation.

C-kit inhibitors may also be used in the treatment of non-insulin-dependent diabetes mellitus (NLDDM), also known as type II diabetes, a chronic disease appearing when insulin is inefficient in promoting glucose uptake by cells, resulting in increased levels of glucose in the blood. This disease affects about 100 million people world-wide, 75% of which are obese at the time of diagnosis. Over many years, the failure of the glucose uptake regulation leads to the development of Type II diabetes, and the blood glucose level needs to be regulated with medicinal products. Ultimately, unregulated blood glucose level is responsible for blood vessels, kidney and eye damages, as well as cardiovascular diseases. This tissue damages contribute to mortality in diabetics.

In addition, the activation of mast cells by different stimuli such as stress, trauma, infection as well as neurotransmitters, may participate in the exacerbation of the chemical imbalance causing CNS disorders. More specifically, mast cell degranulation is stimulated by common neurotransmitters such as neurotensin, somatostatin, substance P and acetylcholine, by growth or survival factors, notably such as NGF. Mast cells involved in the response to such stimulus can be brain mast cells but also other mast cells releasing the content of their granules in the blood stream that ultimately reach sensory, motor or brain neurons. Brain mast cells staining is CTMC staining-like but they show the secretory pattern of MMC, implying that they constitute a particular subset of mast cells presenting specificities.

Following mast cells activation, released granules liberate various factors capable of modulating and altering neurotransmission and neurons survival. Among such factors, serotonin is important since an increase of the level of free serotonin has been observed in depressed patients. Alternatively, the sudden burst of serotonin may be followed by a period of serotonin shortage, leading to pain and migraine. As a consequence, it is believed that mast cells exacerbate in autocrine or paracrine manner the deregulation of neurotransmission. For example, anxiety or stress-induced release of neurotransmitters such as serotonin activates mast cells, which in turn release the content of their granules, further contributing to the chemical imbalance in the brain leading to CNS disorders.

Other mediators released by mast cells can be categorized into vasoactive, nociceptive, proinflammatory and other neurotransmitters. Taken together, these factors are able to induce great disturbance in the activity of neurons, whether they are sensory, motor, or CNS neurons. In addition, patients afflicted with mastocytosis are more inclined to develop CNS disorders than the normal population. This can be explained by the presence of activating mutations in the c-kit receptor, which induce degranulation of mast cells and a burst of factors contributing to chemical imbalance and neurotransmission alteration.

In some cases, activated mast cells can also participate in the destruction of neuronal tissues by releasing a cocktail of different proteases and mediators categorized into three groups: preformed granule-associated mediators (histamine, proteoglycans, and neutral proteases), lipid-derived mediators (prostaglandins, thromboxanes and leucotrienes), and various cytokines (IL-1, IL-2, IL-3, IL-4, IL-5, IL-6, IL-8, TNF-A, GM-CSF, MIP-LA, MIP-1b, MIP-2 and IFN-y). The liberation by activated mast cells of mediators (TNF-A, histamine, leukotrienes, prostaglandins etc.) as well as proteases may i) induce inflammation and vasodilatation and ii) participate in the neuronal tissue destruction process. Inhibition of c-kit activity reduces cellular proliferation, depleting the mast cells responsible for diseases and/or conditions, thereby suggesting a role for use of inhibitors of c-kit in the treatment of c-kit dependent diseases and/or conditions, such as CNS disorders.

Mast cells have also been identified to be involved in or to contribute to drug dependence and withdrawal symptoms. Drug dependence is the result of a phenomenon called tolerance, which is the need to increase the dose of the drug to maintain its full effect, and of physical dependence, which is the habituation of the body to a drug. When the intake of a drug is discontinued, individual may experience unpleasant withdrawal syndrome.

The activation of mast cells by different drugs, including, but not limited to, salicylic derivatives, morphine derivatives, opioids, heroin, amphetamines, alcohol, nicotine, analgesics, anesthetics, and anxyolitics results in the degranulation of mast cells, which participate in the exacerbation of the chemical imbalance responsible for drug habituation and withdrawal syndrome. Following mast cells activation, released granules liberate various factors capable of modulating and altering neurotransmission. Among such factors is morphine which is bound or stored in mast cells granules. Tobacco smoke also induces the release of mediators from canine mast cells and modulates prostaglandin production leading to asthma. In addition, patients afflicted with mastocytosis are more incline to develop substance use disorders than the normal population. This can be explained by the presence of activating mutations in the c-kit receptor, which induce degranulation of mast cells and a burst of factors contributing to chemical imbalance and neurotransmission alteration.

Presently, there is no treatment providing relief and help for individuals to withdraw from their substance addiction. C-kit inhibitors may be used for treating substance abuse disorders, particularly drug addiction, drug abuse, drug habituation, drug dependence, withdrawal syndrome and overdose, comprising administering a compound capable of depleting mast cells to a human in need of such treatment.

c-Kit has a substantial homology to the PDGF receptor and to the CSF-1 receptor (c-Fms). Investigations on various erythroid and myeloid cell lines indicate an expression of the c-Kit gene in early stages of differentiation (Andre et al., Oncogene 1989 4:1047-1049). Certain tumors such as glioblastoma cells likewise exhibit a pronounced expression of the c-Kit gene.

PDGF (Platelet-Derived Growth Factor)

PDGF (Platelet-derived Growth Factor) is a commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention may inhibit PDGF receptor (PDGFR) activity, and may therefore be suitable for the treatment of tumor diseases, such as gliomas, sarcomas, prostate tumors, and tumors of the colon, breast, and ovary.

Compounds of the present invention may be used not only as a tumor-inhibiting substance, for example in small cell lung cancer, but also as an agent to treat non-malignant proliferative disorders, such as atherosclerosis, thrombosis, psoriasis, scleroderma and fibrosis. Compounds of the present invention may also be useful for the protection of stem cells, for example to combat the hemotoxic effect of chemotherapeutic agents, such as 5-fluorouracil; and may also be useful for the treatment of asthma and hypereosinophilia. Compounds of the invention may especially be used for the treatment of diseases, which respond to an inhibition of the PDGF receptor kinase.

Compounds of the present invention may exhibit useful effects in the treatment of disorders arising as a result of transplantation, for example, allogenic transplantation, especially tissue rejection, such as obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention may also be effective against fibrosis and against diseases associated with vascular smooth-muscle cell migration and proliferation (where PDGF and PDGFR often also play a role), such as restenosis and atherosclerosis. These effects and the consequences thereof for the proliferation or migration of vascular smooth-muscle cells in vitro and in vivo may be demonstrated by administration of the compounds of the present invention, and also by investigating its effect on the thickening of the vascular intima following mechanical injury in vivo.

CSF1R (FMS)

The protein encoded by this gene is the receptor for colony stimulating factor 1, a cytokine which controls the production, differentiation, and function of macrophages. CSFR1 mediates most if not all of the biological effects of this cytokine. The encoded protein is a tyrosine kinase transmembrane receptor and member of the CSF1/PDGF receptor family of tyrosine-protein kinases. Mutations in this gene have been associated with a predisposition to myeloid malignancy. (See e.g., Casas et al., Leuk. Lymphoma 2003, 44:1935-41).

Abl, Trk, Syk, Ras, Raf, MAPK, TGFβ, FGFR3, c-Src, SAPK, Lck, Fes, Csk

Abelson tyrosine kinase (i.e. Abl, c-Abl) is involved in the regulation of the cell cycle, in the cellular response to genotoxic stress, and in the transmission of information about the cellular environment through integrin signaling. The Abl protein appears to serve a complex role as a cellular module that integrates signals from various extracellular and intracellular sources and that influences decisions in regard to cell cycle and apoptosis. Abelson tyrosine kinase includes sub-type derivatives such as the chimeric fusion (oncoprotein) BCR-Abl with deregulated tyrosine kinase activity or the v-Abl.

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells.

BCR-Abl is important in the pathogenesis of 95% of chronic myelogenous leukemia (CML) and 10% of acute lymphocytic leukemia. STI-571 (GLEEVEC®) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date, such as G250E, E255V, T315I, F317L and M351T.

Compounds of the present invention may inhibit abl kinase, for example, v-abl kinase. The compounds of the present invention may also inhibit wild-type BCR-Abl kinase and mutations of BCR-Abl kinase, and thus may be suitable for the treatment of Bcr-abl-positive cancer and tumor diseases, such as leukemias (especially chronic myeloid leukemia and acute lymphoblastic leukemia, where especially apoptotic mechanisms of action are found). Compounds of the present invention may also be effective against leukemic stem cells, and may be potentially useful for the purification of these cells in vitro after removal of said cells (for example, bone marrow removal), and reimplantation of the cells once they have been cleared of cancer cells (for example, reimplantation of purified bone marrow cells).

The Trk family of neurotrophin receptors (trkA, trkB, trkC) is able to control tumor cell growth and survival as well as differentiation, migration and metastasis. The signaling pathway downstream of the Trk receptors involves the cascade of MAPK activation through the Shc, activated Ras, ERK-1 and ERK-2 genes, and the PLC-gamma transduction pathway (Sugimoto et al., Jpn J Cancer Res. 2001, 92: 152-60). There is evidence that Trk tyrosine kinases play a role in the development of a variety of cancers including, for example, breast and prostate cancer. (Guate et al., Expression of p75LNGFR and Trk Neurotrophin Receptors in Normal and Neoplastic Human Prostate, BJU Int. 1999, 84:495 502; Tagliabue et al., J. Biol. Chem. 2000, 275:5388 5394.) Further, there is evidence that mediation of the Trk kinase signaling will provide beneficial biological effects. (LeSauteur et al., Adv. Behav. Biol. 1998, 49:615 625; Zhu et al., (1999) J. Clin. Oncology, 1999, 17:2419 28; Friess et al., Annals of Surgery 1999, 230:615-24.)

Syk is a tyrosine kinase that plays an important role in mast cell degranulation and eosinophil activation. Accordingly, Syk kinase is implicated in various allergic disorders, particularly asthma. It has been shown that Syk binds to the phosphorylated gamma chain of the FcεR1 receptor via N-terminal SH2 domains and is important for downstream signaling.

The Ras-Raf-MEK-ERK signaling pathway mediates cellular response to growth signals. Ras is mutated to an oncogenic form in ~15% of human cancer. The Raf family belongs to the serine/threonine protein kinase and includes three members, A-Raf, B-Raf and c-Raf (or Raf-1). B-Raf may have a prominent role in the formation of certain tumors with no requirement for an activated Ras allele (Nature 2002, 417:949-954). B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

Multiple forms of p38 MAPK ($\alpha$, $\beta$, $\gamma$, $\delta$), each encoded by a separate gene, form part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNFα. P38 functions by phosphorylating downstream substrates that include other kinases and transcription factors. Agents that inhibit p38 kinase have been shown to block the production of cytokines including but not limited to TNFα, IL-6, IL-8 and IL-1β.

Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS. P38 inhibitors are efficacious in animal models of inflammatory disease. The destructive effects of many disease states are caused by overproduction of pro-inflammatory cytokines. The ability of p38 inhibitors to regulate this overproduction makes them useful as disease modifying agents.

Molecules that block p38 function have been shown to be effective in inhibiting bone resorption, inflammation, and other immune and inflammation-based pathologies. Thus, a safe and effective p38 inhibitor would provide a means to treat debilitating diseases that can be regulated by modulation of p38 signaling. Therefore, compounds of the invention that inhibit p38 activity are useful for the treatment of inflammation, osteoarthritis, rheumatoid arthritis, cancer, autoimmune diseases, and for the treatment of other cytokine mediated diseases.

Transforming growth factor-beta (TGFβ) denotes a superfamily of proteins that includes, for example, TGFβ1, TGFβ2, and TGFβ3, which are pleotropic modulators of cell growth and differentiation, embryonic and bone development, extracellular matrix formation, hematopoiesis, immune and inflammatory responses. The members of the TGFβ family initiate intracellular signaling pathways leading ultimately to the expression of genes that regulate the cell cycle, control proliferative responses, or relate to extracellular matrix proteins that mediate outside-in cell signaling, cell adhesion, migration and intercellular communication.

Consequently, compounds of the invention that are inhibitors of the TGFβ intracellular signaling pathway are useful therapeutics for fibroproliferative diseases, including kidney disorders associated with unregulated TGFβ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGFβ activity include adult respiratory distress syndrome, COPD, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Fibroproliferative conditions can be associated with surgical eye procedures. Such procedures include retinal reattachment surgery accompanying proliferative vitreoretinopathy, cataract extraction with intraocular lens implantation, and post glaucoma drainage surgery.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3. One mutation, TDII FGFR3, has a constitutive tyrosine kinase activity which activates the transcription factor Stat1, leading to expression of a cell-cycle inhibitor, growth arrest and abnormal bone development (Su et al., Nature 1997, 386:288-292). FGFR3 is also often expressed in multiple myeloma-type cancers.

The kinase, c-Src, transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions, among them is a key role in the regulation of mRNA translation during protein biosynthesis (Eur. J. Biochem 2000, 267(21): 6321-30; Exp Cell Res. 1999, 253 (1):100-9; Mol Cell Endocrinol. 1999, 151(1-2):65-77). The phosphorylation of the S6 ribosomal protein by p70S6 has also been implicated in the regulation of cell motility (Immunol. Cell Biol. 2000, 78(4):447-51) and cell growth (Prog. Nucleic Acid Res. Mol. Biol. 2000, 65:101-27), and hence, may be important in tumor metastasis, the immune response and tissue repair as well as other disease conditions.

The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Agents that inhibit SAPK activity in a cell prevent DNA repair and sensitize the cell to those cancer therapeutic modalities that act by inducing DNA damage.

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

Fes is strongly expressed in myeloid hematopoietic cells and is implicated in both differentiation and survival signaling pathways in myeloid leukocytes. CSK is implicated in cancers, particularly colorectal and breast cancers.

In accordance with the foregoing, the present invention further provides a method for preventing or treating any of the diseases or disorders described above in a subject in need of such treatment, which method comprises administering to said subject a therapeutically effective amount of a compound of Formula (1), (2) or (3), or a pharmaceutically acceptable salt thereof. For any of the above uses, the required dosage will vary depending on the mode of administration, the particular condition to be treated and the effect desired. (See, "Administration and Pharmaceutical Compositions," infra).

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention may be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating or coating methods. For example, oral compositions may be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragacanth, methylcellulose, sodium carboxymethylcellulose and/or polyvinylpyrrolidone; and if desired, d) disintegrants, e.g., starches, agar, alginic acid or its sodium salt, or effervescent mixtures; and/or e) absorbents, colorants, flavors and sweeteners. Injectable compositions may be aqueous isotonic solutions or suspensions, and suppositories may be prepared from fatty emulsions or suspensions.

The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier may include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, may be aqueous solutions, ointments, creams or gels well-known in the art. Such may contain solubilizers, stabilizers, tonicity enhancing agents, buffers and preservatives.

Compounds of the invention may be administered in therapeutically effective amounts in combination with one or more therapeutic agents (pharmaceutical combinations). For example, synergistic effects may occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit may comprise instructions for its administration.

Processes for Making Compounds of the Invention

General procedures (A-N) for preparing compounds of the invention are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice, for example, see T. W. Greene and P. G. M. Wuts in "Protective Groups in Organic Chemistry", John Wiley and Sons, 1991.

A compound of the invention may be prepared as a pharmaceutically acceptable acid addition salt by reacting the free base form of the compound with a pharmaceutically acceptable inorganic or organic acid. Alternatively, a pharmaceutically acceptable base addition salt of a compound of the invention may be prepared by reacting the free acid form of the compound with a pharmaceutically acceptable inorganic or organic base. Alternatively, the salt forms of the compounds of the invention may be prepared using salts of the starting materials or intermediates.

The free acid or free base forms of the compounds of the invention may be prepared from the corresponding base addition salt or acid addition salt from, respectively. For example, a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention may be conveniently prepared or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, compounds having Formula (1), (2) or (3) may be made by a process which involves:

(a) that of general procedures as described in the Examples; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

The following examples are offered to illustrate but not to limit the invention. Insofar as the production of the starting materials is not particularly described, the compounds are known or may be prepared analogously to methods known in the art or as disclosed in the Examples hereinafter. One of skill in the art will appreciate that the examples below are only representative of methods for preparation of the compounds of the present invention, and that other well known methods may similarly be used.

EXAMPLE 1

Synthesis of Intermediates 3-(5-amino-2-methylphenyl)-7-chloro-1-methyl-1,6-naphthyridin-2(1H)-one (8)

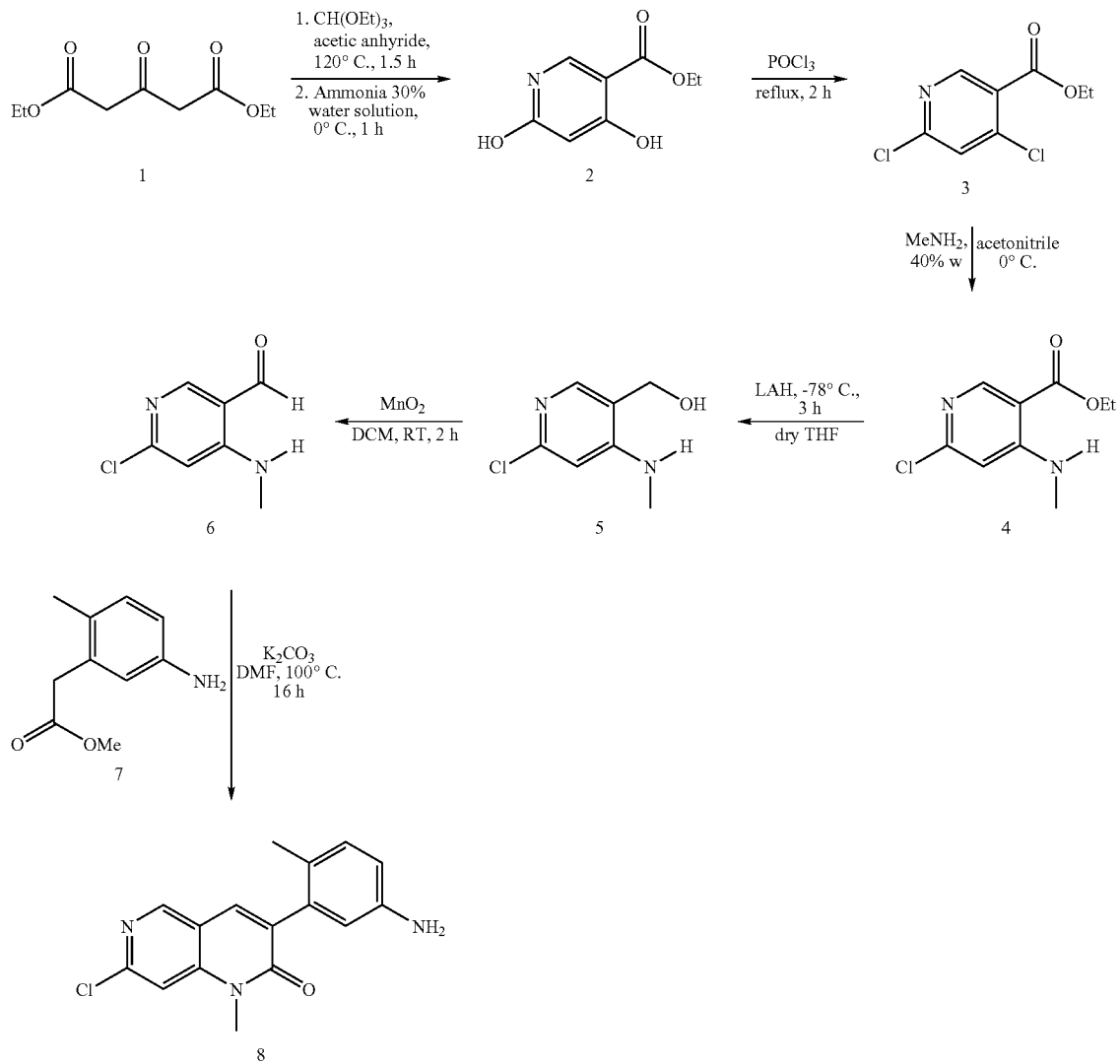

Into a 2 L flask are placed diethyl 1,3-acetonedicarboxylate 1 (160 g, 0.79 mol), triethyl orthoformate (129 g, 0.87 mol), and acetic anhydride (161 g, 1.58 mol). The resulting mixture is heated to 120° C. for 1.5 h. The mixture is cooled to rt and volatiles are removed by vacuum distillation (150-200 mm Hg) at 90-100° C. Light-yellow oil is collected in the condenser. The residue left in the flask is then cooled in an ice bath and mixed with 30% ammonia (65 mL). The reaction is allowed to stand in the ice bath for 1 h and is then acidified with 2N HCl to pH<5. The mixture is concentrated in vacuo and the crude product is purified using flash chromatography (ethyl acetate:petroleum ether=1:1). The product 2 is isolated as colorless oil.

4,6-Dihydroxynicotinic acid ethyl ester 2 (5 g, 0.3 mol) is mixed with $POCl_3$ (500 mL) in a 2 L flask and heated to 110° C. for 3 h. After cooling to rt, most of the $POCl_3$ is removed in vacuo. The crude dark-colored product is poured into a small amount of ice-water mixture, and neutralized with aqueous saturated sodium carbonate. The product is extracted twice with ethyl acetate. The combined organic layer is washed using aqueous saturated sodium chloride and dried over $Na_2SO_4$. Purification using flash chromatography (ethyl acetate:petroleum ether=1:3) affords the product, 4,6-dichloronicotinic acid ethyl ester 3, as a white solid. $^1$H NMR (300 MHz, $CDCl_3$) δ 8.85 (s, 1H), 7.47 (s, 1H), 4.43 (q, J=7.2 Hz, 2H), 1.41 (t, J=7.2 Hz, 3H).

4,6-Dichloronicotinic acid ethyl ester 3 (43 g, 195 mmol) is dissolved in acetonitrile (600 mL), cooled to 0° C. and methylamine (125 mL of a 40% water solution, 977 mmol) is slowly added. The reaction is stirred at 0° C. for 30 minutes and warmed to rt for another 3 h. Solvent is removed in vacuo and the crude product is purified using flash chromatography (ethyl acetate:petroleum ether=1:1). The product 4 is isolated as a white solid. $^1$H NMR (300 MHz, $CDCl_3$) δ 8.66 (s, 1H), 8.12 (bs, 1H), 6.53 (s, 1H), 4.34 (q, J=7.2 Hz, 2H), 2.92 (s, 3H), 1.37 (t, J=7.2 Hz, 3H).

6-Chloro-4-methylaminonicotinic acid ethyl ester 4 (33 g, 156 mmol) is dissolved in anhydrous THF (500 mL) and cooled to −78° C. To the solution is slowly added a solution of LAH (12.5 g, 329 mmol) in THF (500 mL). After the addition is complete, the reaction is kept at −78° C. for 1 h. The mixture is warmed to rt and a small amount of MeOH:ethyl acetate=1:1 is slowly added to destroy the excess LAH. The crude product is filtered through a celite plug and is washed twice using ethyl acetate. After solvent removal in vacuo, the crude product is purified by flash chromatography (ethyl acetate:petroleum ether=1:1). The product 5 is obtained as a white solid. $^1$H NMR (300 MHz, $CDCl_3$) δ 7.36 (s, 1H), 6.48 (s, 1H), 5.55 (bs, 1H), 4.63 (s, 2H), 2.89 (d, J=5.1 Hz, 3H).

Compound 5 (20 g, 116 mmol) is dissolved in DCM (250 mL) and $MnO_2$ (100 g, 1.16 mol) is added. The reaction is stirred at rt overnight, then filtered through a celite plug and washed using ethyl acetate. After removing the solvent in vacuo, 6 is obtained and is used in the next step without further purification. $^1$H NMR (300 MHz, $CDCl_3$) δ 9.85 (s, 1H), 8.59 (bs, 1H), 8.31 (s, 1H), 6.59 (s, 1H), 2.96 (d, J=5.1 Hz, 3H).

6-Chloro-4-methylamino-pyridine-3-carbaldehyde 6 (19.8 g, 116 mmol) is mixed with 2-(5-amino-2-methyl-phenyl)acetic acid methyl ester 7 (27 g, 151 mmol) and potassium carbonate (48.1 g, 348 mmol) in DMF (1 L). The mixture is heated to 100° C. for 16 h. After cooling to rt and removing solvent in vacuo, the crude product is purified using flash chromatography (ethyl acetate:petroleum ether=1:1). The title compound 8 is obtained as a pale solid. $^1$H NMR (300 MHz, $CDCl_3$) δ 8.56 (s, 1H), 7.63 (s, 1H), 7.27 (s, 1H), 7.06 (d, J=8.1 Hz, 1H), 6.74 (dd, J=2.4, 8.1 Hz, 1H), 6.58 (d, J=2.4 Hz, 1H), 3.71 (s, 2H), 2.10 (s, 3H).

Methyl 2-(5-amino-2-methylphenyl)acetate (7)

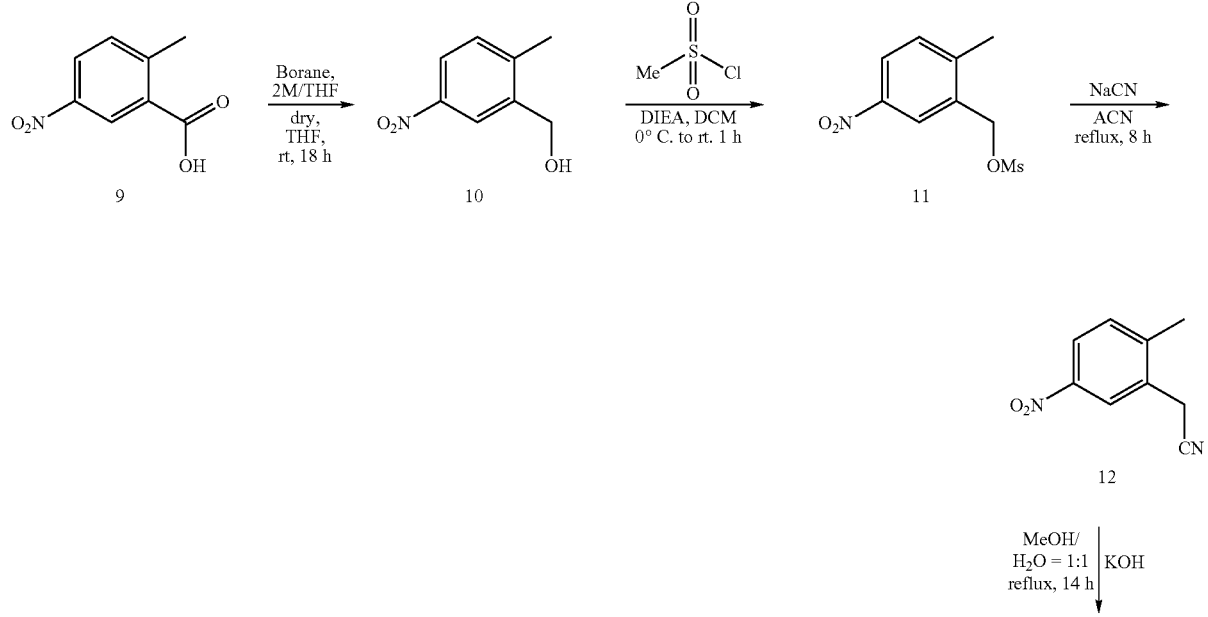

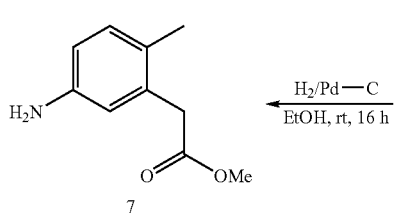 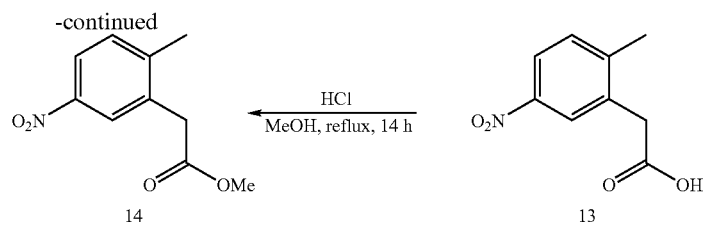

2-Methyl-5-nitrobenzoic acid 9 (125 g, 690 mmol) is dissolved in anhydrous THF (1.25 L). After adding borane (517 mL of a 2 M solution in THF, 1.04 mol), the reaction is stirred at rt for 18 h. The reaction is quenched using an aqueous solution of potassium carbonate (112.5 g in 2.5 L). After removing THF in vacuo, the aqueous solution is extracted with DCM and the combined organic layer is washed with brine and dried over sodium sulfate. After filtering and removing the solvent in vacuo, the product 10 is obtained as a pale yellow solid. $^1$H NMR (300 MHz, CDCl$_3$) δ 8.29 (d, J=3 Hz, 1H), 8.50 (m, 1H), 7.29 (m, 1H), 4.78 (s, 2H), 2.41 (s, 3H).

(2-Methyl-5-nitrophenyl)methanol 10 (96 g, 574 mmol) is dissolved in anhydrous DCM (2.5 L), cooled to 0° C., treated with methanesulfonyl chloride (72 g, 632 mmol) and di-isopropylethylamine (89 g, 689 mmol) for 30 minutes. The reaction is warmed to rt and stirred for another 30 minutes. It is quenched by adding water (600 mL). The organic layer is washed with brine, dried over sodium sulfate and filtered. After removing the solvent in vacuo, the product 11 is isolated as yellow oil and used in the next step without further purification.

To a solution of crude 11 (141 g, 0.575 mol) in acetonitrile (4 L) is added sodium cyanide (84.4 g, 1.7 mol), and the resulting mixture is heated at reflux for 8 h. The reaction is cooled to rt and solvent is removed in vacuo. The crude product is dissolved in DCM and filtered. The filtrate is washed with brine and dried over sodium sulfate. After removing solvent in vacuo, the crude product is purified using flash chromatography (ethyl acetate:petroleum ether=1:1). The product 12 is obtained as a yellow solid. $^1$H NMR (300 MHz, CDCl$_3$) δ 8.25 (d, J=2.4 Hz, 1H), 8.13 (dd, J=2.4, 8.1 Hz, 1H), 7.41 (d, J=8.1 Hz, 1H), 3.78 (s, 2H), 2.48 (s, 3H).

2-(2-Methyl-5-nitrophenyl)ethanenitrile 12 (87 g, 494 mmol) is dissolved in methanol:water=1:1 (1.2 L). Potassium hydroxide (277 g, 4.94 mol) in water (1 L) is added and the reaction is heated at reflux for 14 h. After cooling to rt and removing the methanol in vacuo, the aqueous layer is washed with DCM and ether. The combined organic layer is washed with brine, dried over sodium sulfate, and filtered. After removing the solvent in vacuo, the product 13 is obtained as an orange solid. $^1$H NMR (300 MHz, CDCl$_3$) δ 8.07 (m, 2H), 7.35 (d, J=8.1 Hz, 1H), 3.78 (s, 2H), 2.43 (s, 3H).

2-(2-Methyl-5-nitrophenyl)acetic acid 13 (30 g, 154 mmol) is dissolved in methanol (700 mL) and HCl (79 mL of a 4 M solution in 1,4-dioxane, 316 mmol) is added. The reaction is heated to reflux for 14 h. After cooling to rt and removing solvent in vacuo, the crude product is dissolved in water (500 mL) and basified to pH>12 using 2N sodium hydroxide. The solution is extracted using ethyl acetate and the combined organic layer is washed with brine, dried over sodium sulfate and filtered. After removing the solvent in vacuo, the product 14 is obtained as a dark yellow solid. $^1$H NMR (300 MHz, CDCl$_3$) δ 8.06 (m, 2H), 7.33 (d, J=8.4 Hz, 1H), 3.73 (s, 3H), 3.72 (s, 2H), 2.41 (s, 3H).

2-(2-Methyl-5-nitrophenyl)acetic acid methyl ester 14 (32 g, 153 mmol) is dissolved in ethanol (750 mL). To this solution is added 10% palladium on carbon (3.2 g). After purging the reaction flask of oxygen, a balloon filled with hydrogen is fitted. The reaction is stirred at rt for 16 h. After removing the catalyst by filtering through a celite plug and removing the solvent in vacuo, the crude product is purified using flash chromatography (ethyl acetate:petroleum ether=5:1). The product 7 is isolated as a yellow oil. $^1$H NMR (300 MHz, CDCl$_3$) δ 6.9 (d, J=7.8 Hz), 6.59 (m, 1H), 6.56 (m, 1H), 3.69 (s, 3H).

3-(5-amino-2-methylphenyl)-1,7-dimethyl-1,6-naphthyridin-2(1H)-one (15)

Scheme 3

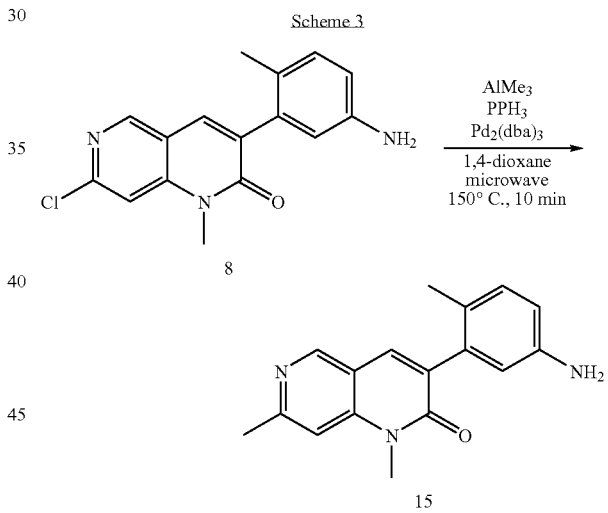

To a solution of 3-(5-amino-2-methylphenyl)-7-chloro-1-methyl-1,6-naphthyridin-2-one 8 (0.53 mmol) in dioxane (3 mL) is added triphenylphosphine (0.08 mmol), Pd$_2$(dba)$_3$ (16 umol) and trimethylaluminum (0.8 mL of a 2.0 molar solution in toluene). The mixture is degassed for 10 minutes then the reaction vial sealed and heated via microwave for 10 minutes at 150° C. The reaction is cooled to rt and poured into 1M HCl (30 mL) and washed with EtOAc. The aqueous layer is made basic with 3M NaOH and extracted with EtOAc (3×20 mL). The combined organic layers are dried over magnesium sulfate, filtered and reduced to dryness. The crude yellow oil is purified by flash chromatography on silica with dichloromethane 3-5% MeOH as eluant to yield a yellow glassy solid 15. $^1$H NMR (400 MHz, CDCl$_3$) δ 8.67 (s, 1H), 7.63 (s, 1H), 7.08 (s, 1H), 7.05 (d, J=8.4 Hz, 1H), 6.65 (dd, J=8.4, 2.4 Hz, 1H), 6.57 (d, J=2.4 Hz, 1H), 3.72 (s, 3H), 2.70 (s, 3H), 2.11 (s, 3H). MS (m/z) (M+1)$^+$: 280.1.

3-(5-Amino-2-methyl-phenyl)-7-methyl-1-phenyl-1H-[1,6]naphthyridin-2-one (20)

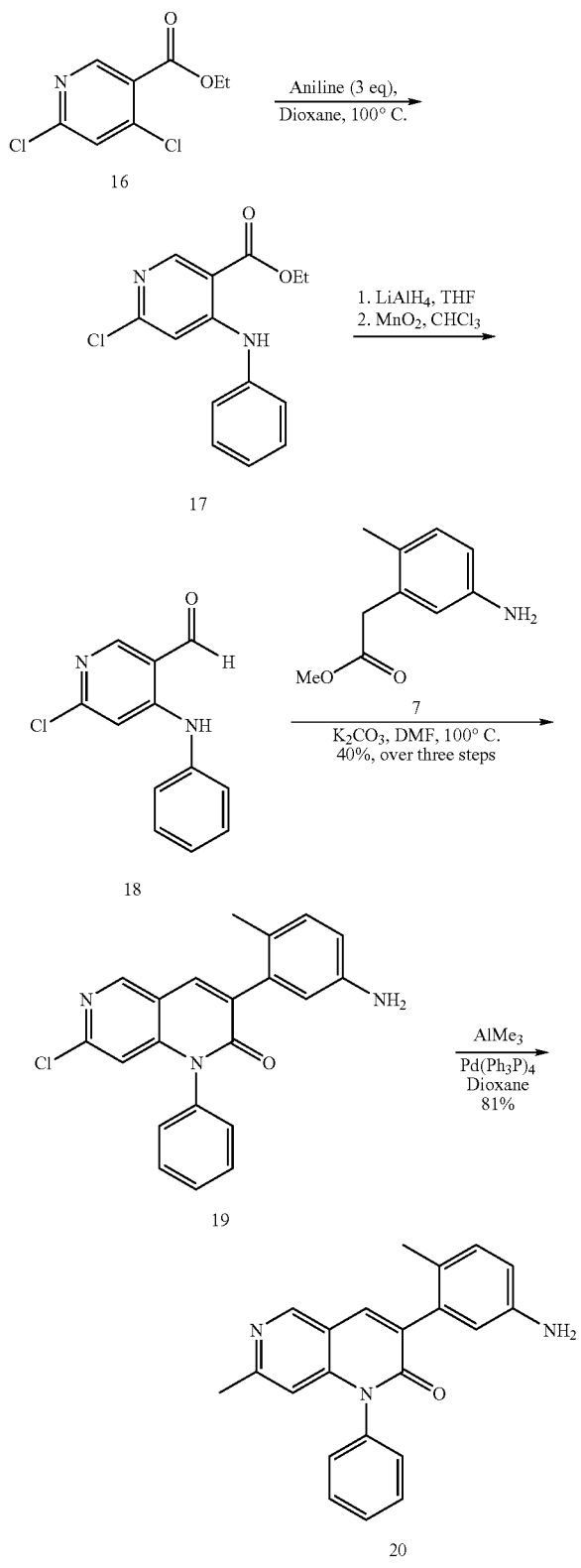

Scheme 4

4,6-Dichloronicotinic acid ethyl ester 16 (500 mg, 2.27 mmol) is dissolved in anhydrous dioxane (10 mL) and aniline (0.66 mL, 7.72 mmol) is added. The reaction is stirred at 100° C. overnight. The solvent is removed in vacuo and the crude product is purified using flash chromatography (hexane:ethyl acetate=10:1) to give 6-chloro-4-phenylamino-nicotinic acid ethyl ester 17. $^1$H NMR (400 MHz, CDCl$_3$) δ 9.77 (s, 1H), 8.70 (s, 1H), 7.33-7.37 (m, 2H), 7.15-7.21 (m, 3H), 6.80 (s, 1H), 4.31 (q, 2H), 1.34 (t, 3H).

6-Chloro-4-phenylaminonicotinic acid ethyl ester 17 (35 mg, 0.126 mmol) is dissolved in 1.2 mL of anhydrous THF and cooled to −78° C. To the solution is slowly added a solution of LAH (1M in THF, 0.14 mL, 0.14 mmol). After the addition is complete, the reaction is kept at −78° C. for an additional hour. The mixture is warmed to rt over 2 h and a small amount of MeOH:ethyl acetate=1:1 is slowly added to destroy the excess LAH. The crude product is filtered through a celite plug and washed with ethyl acetate. After solvent removal in vacuo, the crude product is purified using flash chromatography (hexane:ethyl acetate=4:1). The corresponding alcohol is obtained as a yellow solid. The alcohol (26 mg, 0.11 mmol) is dissolved in DCM (2 mL) and MnO$_2$ (56 mg, 0.55 mmol) is added. The reaction is stirred at rt overnight, then filtered through a celite plug and washed with ethyl acetate. After removing the solvent in vacuo, 6-chloro-4-phenylamino-pyridine-3-carbaldehyde 18 is obtained and used in the next step without further purification.

6-Chloro-4-phenylamino-pyridine-3-carbaldehyde 18 (21 mg, 0.09 mmol) is mixed with 2-(5-amino-2-methyl-phenyl) acetic acid methyl ester 7 (18 mg, 0.1 mmol) and potassium carbonate (37 mg, 0.27 mmol) in DMF (2 mL). The mixture is heated to 100° C. for 16 h. After cooling to rt and removing solvent in vacuo, the crude product is purified using flash chromatography (hexane:ethyl acetate=1:1). The title compound 3-(5-amino-2-methyl-phenyl)-7-chloro-1-phenyl-1H-[1,6]naphthyridin-2-one 19 is obtained as a pale solid. $^1$H NMR (400 MHz, CDCl$_3$) δ 8.53 (s, 1H), 7.68 (s, 1H), 7.53-7.57 (m, 2H), 7.47-7.51 (dt 1H), 7.20-7.23 (m, 2H), 6.96 (d, 1H), 6.59 (dd, 1H), 6.58 (s, 1H), 6.52 (s, 1H), 2.05 (s, 3H).

A vial is charged with 19 (208 mg, 0.575 mmol), Pd$_2$(dba)$_3$ (26 mg, 0.028 mmol) and Ph$_3$P (37 mg, 0.14 mmol). The vial is evacuated and refilled with N$_2$. Dioxane (12 mL) is added to the vial and the solution is treated with AlMe$_3$ (0.86 mL of a 2M solution in hexane, 1.72 mmol). The mixture is heated in a microwave oven at 140° C. for 20 min. The vial is cooled down to rt and the mixture is extracted with ethyl acetate. The organic phase is washed with 1N NaOH solution, saturated NaHCO$_3$ solution and brine. The solvent is removed in vacuo and the crude product is purified using flash chromatography (hexane:ethyl acetate=2:1) to give 3-(5-amino-2-methyl-phenyl)-7-methyl-1-phenyl-1H-[1,6]naphthyridin-2-one 20. $^1$H NMR (400 MHz, CDCl$_3$) δ 8.71 (s, 1H), 7.75 (s, 1H), 7.58-7.63 (m, 2H), 7.52-7.56 (m, 1H), 7.28-7.30 (m, 2H), 7.03 (d, 1H), 6.67 (d, 1H), 6.64 (d, 1H), 6.38 (s, 1H), 5.32 (s, 1H), 3.60 (brs, 2H), 2.46 (s, 3H), 2.18 (s, 3H).

3-bromo-5-(trifluoromethyl)-N-(3-(1,2-dihydro-1,7-dimethyl-2-oxo-1,6-naphthyridin-3-yl)-4-methylphenyl)benzamide (22)

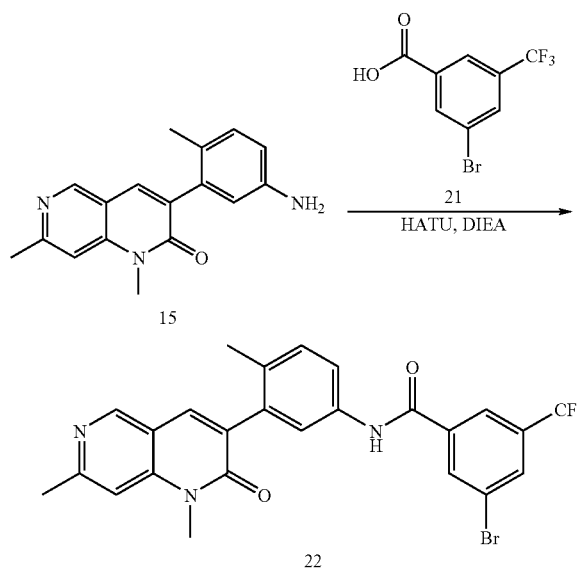

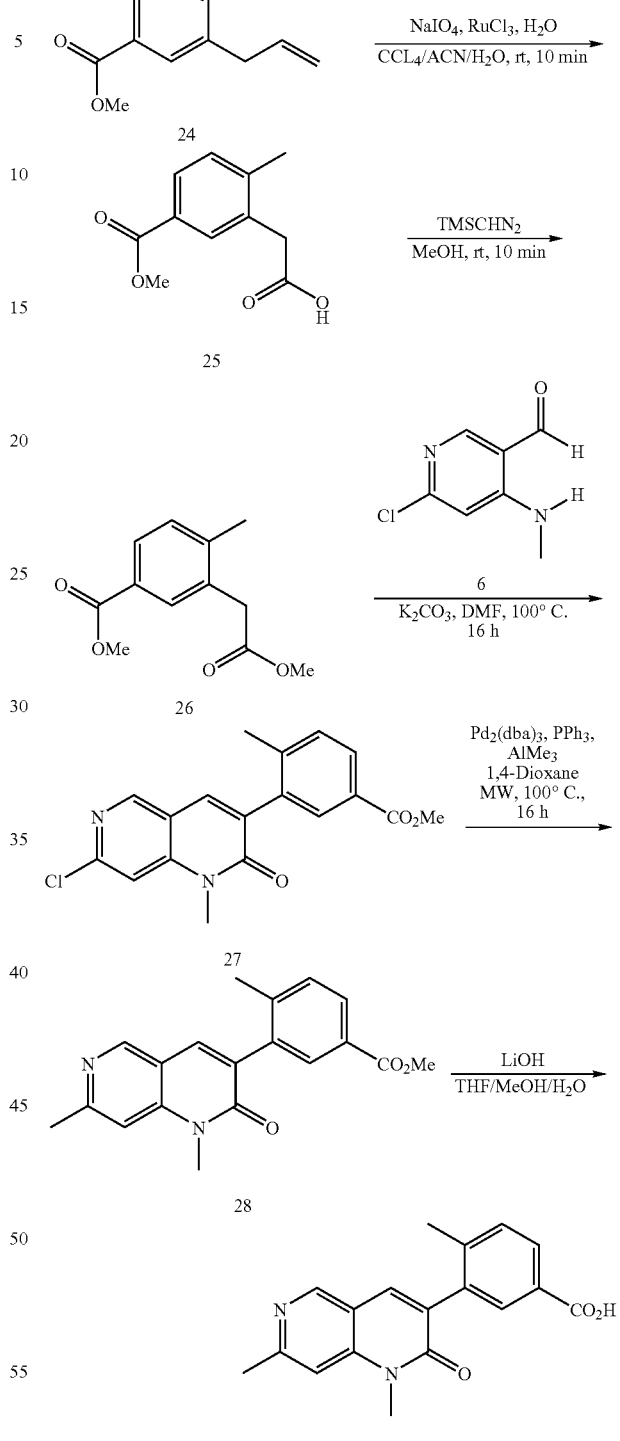

To a solution of 3-bromo-5-trifluoromethyl-benzoic acid 21 (193 mg, 0.716 mmol) in DMF (5 mL) is added HATU (272 mg, 0.716 mmol) and di-isopropylethylamine (278 mg, 2.15 mmol) at rt. The resulting mixture is stirred for 2 min. A solution of 3-(5-amino-2-methyl-phenyl)-1,7-dimethyl-1H-[1,6]naphthyridin-2-one 15 (200 mg, 0.716 mmol) in DMF (5 mL) is added. The reaction mixture is stirred at rt overnight, diluted with EtOAc, and washed with brine three times. The organic layer is dried (MgSO$_4$) and concentrated. The residue is purified by automated chromatography to give the desired product 22 as an off-white solid. $^1$H NMR (400 MHz, DMSO-d$_6$) δ 10.50 (s, 1H), 8.99 (s, 1H), 8.38 (s, 1H), 8.22 (s, 1H), 8.17 (s, 1H), 8.00 (s, 1H), 7.72 (s, 1H), 7.66 (d, J=2.1 Hz, 1H), 7.62 (dd, J=8.3, 2.2 Hz, 1H), 7.25 (d, J=8.4 Hz, 1H), 3.63 (s, 3H), 2.65 (s, 3H), 2.08 (s, 3H).

3-(1,7-dimethyl-2-oxo-1,2-dihydro-1,6-naphthyridin-3-yl)-4-methylbenzoic acid (29)

Scheme 6

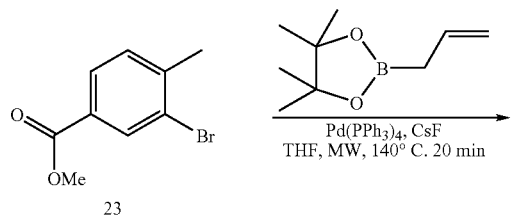

Methyl 3-bromo-4-methylbenzoate 23 (2.28 g, 10.0 mmol), boronic ester (10 mmol), CsF (3.04 g, 20.0 mmol) and Pd(PPh$_3$)$_4$ (1.16 g, 1 mmol) are added to a 10-mL Schlenk flask equipped with a stir bar. The flask is evacuated and refilled with nitrogen five times. THF (8 mL) is added by syringe. The Schlenk flask is sealed and heated at 140° C. for 20 min under microwave conditions. After the reaction is complete, the solvent is removed in vacuo. The residue is dissolved in DCM (200 mL) and washed with water. The organic phase is dried with $Na_2SO_4$, filtered and concentrated to yield a crude product. Purification by silica gel column chromatography (ethyl acetate:hexane=1:7) gives a mixture of two isomers which can be used in the next step without further purification.

The mixture containing methyl 3-allyl-4-methylbenzoate 24 (1.18 g, 6.18 mmol) is dissolved in $CCl_4$:ACN:$H_2O$ (60 mL: 60 mL: 80 mL). Then $NaIO_4$ (6.6 g) and $RuCl_3H_2O$ (0.21 g) are added. The reaction mixture is stirred at rt for 10 min. The mixture is poured into water (100 mL) and extracted with DCM (100 mL). The organic layer is dried with $Na_2SO_4$, filtered and concentrated to yield crude product. Crude product 25 is dissolved in MeOH (100 mL) and $TMSCHN_2$ (18.0 mL, 2M in hexane) is added slowly to the solution. The reaction mixture is stirred at rt for another 10 min. After the reaction is completed, the solvent is removed to give a crude product 26 which is purified by silica gel column chromatography. $^1$H NMR (400 MHz, DMSO-$d_6$) δ 7.86 (s, 1H), 7.84 (d, J=10 Hz, 1H), 7.23 (d, J=10 Hz, 1H), 3.88 (s, 3H), 3.68 (m, 5H), 2.34 (s, 3H). LC/MS (M+Na, m/z): 245.

6-Chloro-4-methylamino-pyridine-3-carbaldehyde 6 (233 mg, 1.36 mmol) is mixed with methyl 3-((methoxycarbonyl) methyl)-4-methylbenzoate 26 (303 mg, 1.36 mmol) and potassium carbonate (564 mg, 4.08 mmol) in DMF (8 mL). The mixture is heated to 100° C. for 16 h. After cooling to rt and removing solvent in vacuo, the crude product is purified using flash chromatography (ethyl acetate:hexane=1:1). Compound 27 is obtained as a solid. $^1$H NMR (400 MHz, DMSO-$d_6$) δ 8.73 (s, 1H), 8.05 (s, 1H), 7.88 (dd, J=9.4, 2.5 Hz, 1H), 7.78 (d, J=2.5 Hz, 1H), 7.66 (s, 1H), 7.43 (d, J=9.4 Hz, 1H), 3.82 (s, 3H), 3.62 (s, 3H), 2.21 (s, 3H). LC/MS (M+Na, m/z): 365, 367.

Methyl 3-(1,7-dimethyl-2-oxo-1,2-dihydro-1,6-naphthyridin-3-yl)-4-methylbenzoate 27 (3 g, 8.6 mmol), $AlMe_3$ (13.2 mL, 26.4 mmol), $PPh_3$ (318 mg, 1.29 mmol) and $Pd_2(dba)_3$ (240 mg, 0.018 mmol) are added to a 50-mL Schlenk flask equipped with a stir bar. The flask is evacuated and refilled with nitrogen five times. 1,4-Dioxane (50 mL) is added by syringe. The Schlenk flask is sealed and heated at 100° C. for 16 h. After the reaction is completed, 1N HCl is added slowly (100 mL) to quench the reaction. The mixture is extracted with DCM (200 mL). The organic phase is further washed with 1 N HCl (2×50 mL). The combined aqueous phase is treated with 6N LiOH until pH=10. The yellow solid is filtered and dried under vacuum to give product 28, which is purified by silica gel chromatography (5-10% MeOH in DCM). LC/MS (M+1, m/z): 323.1.

Methyl 3-(1,7-dimethyl-2-oxo-1,2-dihydro-1,6-naphthyridin-3-yl)-4-methylbenzoate 28 (3 g, 9 mmol) is suspended in a mixture of MeOH/water (1:1, mL) and treated with NaOH (2.2 g, 55 mmol) at 80° C. for 2 h. MeOH is removed in vacuo. The resultant mixture is acidified to pH=7, and the solid product is filtered and washed with water and dried overnight to yield 29. $^1$H NMR (400 MHz, DMSO-$d_6$) δ 8.8 (s, 1H), 8.02 (s, 1H), 7.88 (dd, J=7.9, 1.8 Hz, 1H), 7.78 (d, J=1.7 Hz, 1H), 7.44 (s, 1H), 7.42 (d, J=8 Hz, 1H), 3.65 (s, 3H), 2.62 (s, 3H), 2.23 (s, 3H). LC/MS (M+1, m/z): 309.1.

3-(1,7-dimethyl-2-oxo-1,2-dihydro-1,6-naphthyridin-3-yl)-4-methylbenzoyl isocyanate (31)

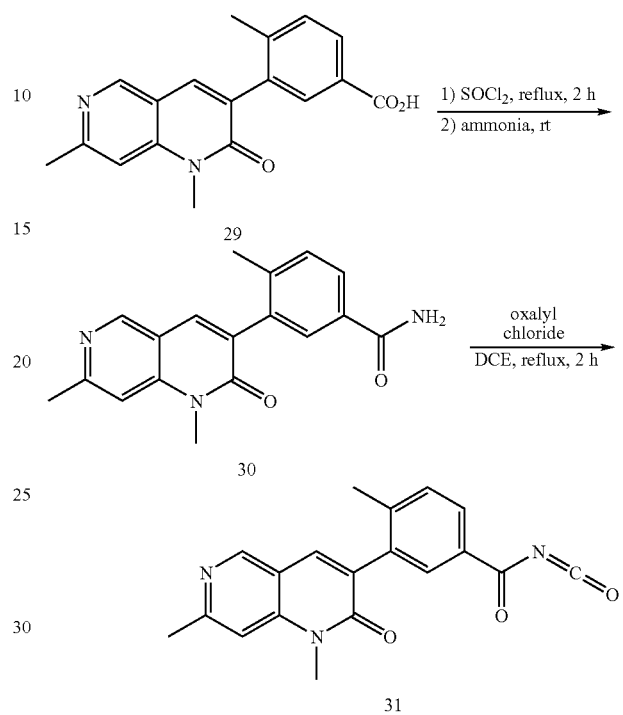

A solution of 3-(1,7-dimethyl-2-oxo-1,2-dihydro-1,6-naphthyridin-3-yl)-4-methylbenzoic acid 29 (620 mg, 2 mmol) in $SOCl_2$ (2 mL) is heated at reflux for 2 h. Excess $SOCl_2$ is removed in vacuo, and the resultant solid is suspended in THF and added to aqueous ammonia at rt. The resulting solid is filtered and dried under vacuum to yield 30 as a white solid. LC/MS (M+1, m/z): 308.1.

3-(1,7-Dimethyl-2-oxo-1,2-dihydro-1,6-naphthyridin-3-yl)-4-methylbenzamide 30 (310 mg, 1 mmol) is heated with oxalyl chloride (1 mL) in 1,2-dichloroethane (2 mL) at reflux for 2 h. Solvent is evaporated to give 31 as a white solid which is used without purification.

Preparation of Exemplary Compounds

EXAMPLE 2

3-(5-amino-2-methylphenyl)-7-chloro-1-methyl-1,6-naphthyridin-2(1H)-one (A1)

General Procedure A

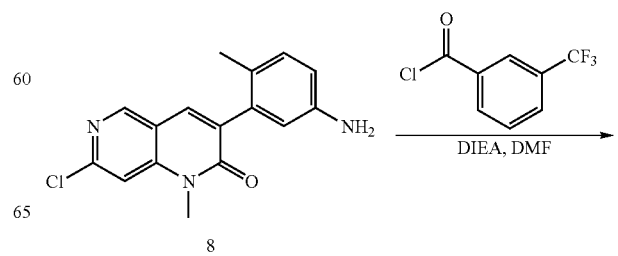

-continued

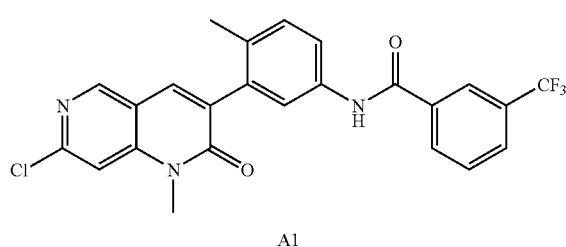

A1

To a solution of 3-(5-amino-2-methyl-phenyl)-7-chloro-1-methyl-1H-[1,6]naphthyridin-2-one 8 (749 mg, 2.50 mmol) and 3-trifluoromethylbenzoyl chloride (521 mg, 2.50 mmol) in DCM (25 mL) is added di-isopropylethylamine (452 mg, 3.5 mmol) at 0° C. The reaction mixture is warmed to rt and stirred for 16 h. The solvent is removed in vacuo. The residue is purified by automated chromatography with a gradient of ethyl acetate:hexane (0:100 to 100:0) to give the desired product A1 as a light yellow solid. $^1$H NMR (400 MHz, CDCl$_3$) δ 8.59 (s, 1H), 8.25 (s, 1H), 8.13 (s, 1H), 8.08 (d, J=8.0 Hz, 1H), 7.78 (d, J=7.9 Hz, 1H), 7.71 (s, 1H), 7.65-7.60 (m, 2H), 7.45 (dd, J=8.2, 2.0 Hz, 1H), 7.32 (s, 1H), 7.20 (d, J=8.4 Hz, 1H), 3.76 (s, 3H), 2.04 (s, 3H).

Compounds of structure of type A can also be made with the same procedure using other N-substituted naphthyridinones which can be synthesized according to Scheme 4. Table 1 describes compounds prepared following procedures described in Example 2, using appropriate reagents.

EXAMPLE 3

N-[3-(1,7-Dimethyl-2-oxo-1,2-dihydro-[1,6]naph-thyridin-3-yl)-4-methyl-phenyl]-3-(4-ethyl-piper-azin-1-yl)-5-trifluoromethyl-benzamide (B1)

General Procedure B

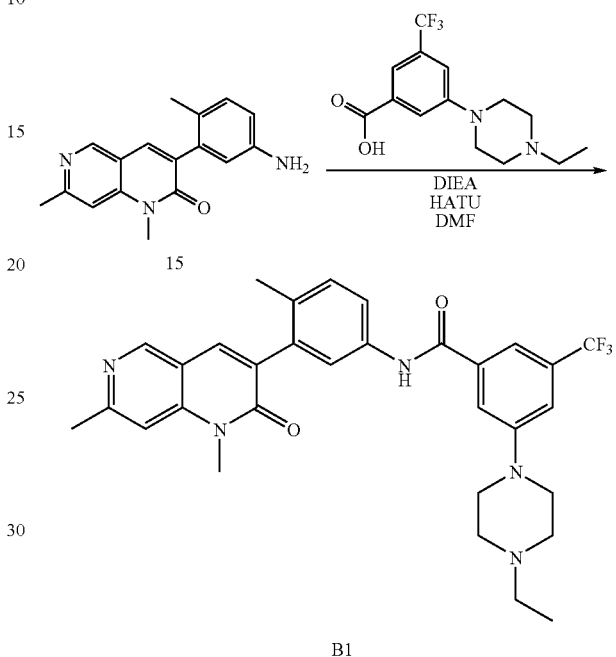

B1

TABLE 1

| A# | Structure | Physical Data $^1$H NMR 400 MHz and/or MS (m/z) |
|---|---|---|
| 1 | 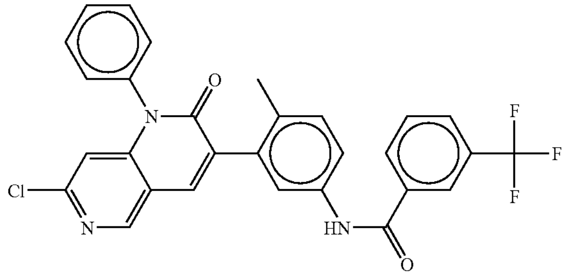 | $^1$H NMR (400 MHz, CDCl$_3$) δ 8.61 (s, 1H), 8.27 (s, 1H), 8.10 (s, 1H), 8.01 (d, 1H), 7.81 (s, 1H), 7.74 (d, 1H), 7.71 (d, 1H), 7.60-7.65 (m, 2H), 7.56-7.59 (m, 2H), 7.37 (dd, 1H), 7.28-7.31 (m, 2H), 7.17 (d, 1H), 6.60 (s, 1H), 2.12 (s, 3H); MS m/z 534.1 (M + 1) |
| 2 | 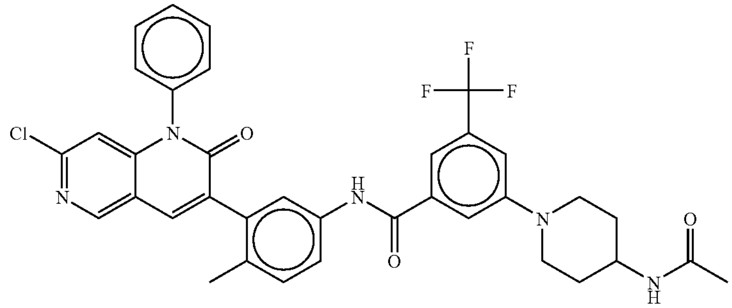 | $^1$H NMR (400 MHz, CDCl$_3$) δ 8.78 (s, 1H), 8.64 (dd, 1H), 8.60 (s, 1H), 8.29 (dd, 1H), 7.81 (s, 1H), 7.70 (brs, 1H), 7.52-7.61 (m, 2H), 7.42 (s, 1H), 7.33 (dd, 1H), 7.24 (s, 1H), 7.17 (d, 1H), 7.14 (s, 1H), 6.55 (s, 1H), 6.03 (d, 1H), 3.86-3.93 (m, 2H), 3.68-3.71 (m, 2H), 3.56-3.60 (m, 1H), 2.20 (s, 3H), 1.90 (s, 3H), 1.40-1.50 (m, 4H); MS m/z 674.2 (M + 1) |

To a solution of 3-(4-ethyl-piperazin-1-yl)-5-trifluoromethyl-benzoic acid HCl salt (15.0 mg, 0.044 mmol) and diisopropylethylamine (21 uL, 0.121 mmol) in DMF (0.8 mL), is added HATU (16.5 mg, 0.043 mmol). After stirring for 10 min at rt a solution of 3-(5-amino-2-methyl-phenyl)-1,7-dimethyl-1H-[1,6]naphthyridin-2-one 15 (11.4 mg, 0.041 mmol) in DMF (0.25 mL) is added to the reaction. The reaction mixture is stirred at rt for 1 h. The reaction mixture is diluted with DMSO (1 mL) and purified by LCMS to afford the title compound B1 as a TFA salt. MS m/z 564.5 (M+1).

Table 2 describes compounds prepared following procedures described in Example 3, using appropriate reagents.

TABLE 2

| B# | Structure | Physical Data<br>$^1$H NMR 400 MHz and/or MS (m/z) |
|---|---|---|
| 1 | 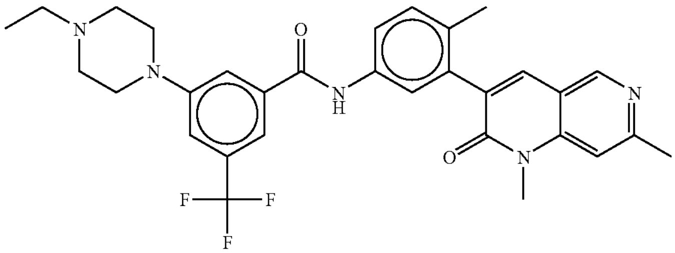 | MS m/z 564.5 (M + 1) |
| 2 | 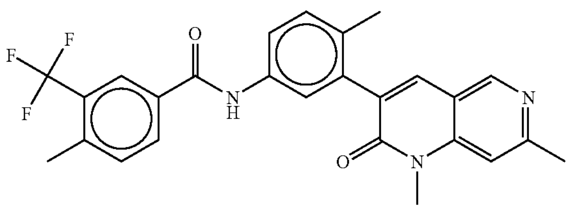 | $^1$H NMR (400 MHz, d$_6$-DMSO) δ 10.44 (s, 1H), 9.04 (s, 1H), 8.24 (s, 1H), 8.14 (d, J = 8.0 Hz, 1H), 8.06 (s, 1H), 7.74 (m, 2H), 7.68 (m, 1H), 7.62 (d, J = 8.4 Hz, 1H), 7.29 (d, J = 8.4 Hz, 1H), 3.69 (s, 3H), 2.71 (s, 3H), 2.55 (s, 3H), 2.14 (s, 3H). MS m/z 466.2 (M + 1) |
| 3 | 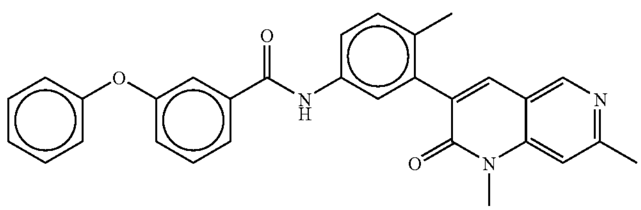 | $^1$H NMR (400 MHz, d$_6$-DMSO) δ 10.31 (s, 1H), 9.05 (s, 1H), 8.06 (s, 1H), 7.78 (m, 3H), 7.67 (m, 1H), 7.58 (m, 2H), 7.43 (m, 2H), 7.29 (m, 3H), 7.07 (d, J = 7.6 Hz, 2H), 3.70 (s, 3H), 2.72 (s, 3H), 2.13 (s, 3H). MS m/z 476.2 (M + 1) |
| 4 | 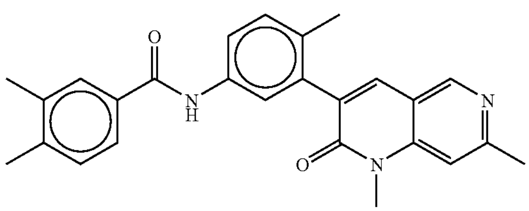 | $^1$H NMR (400 MHz, d$_6$-DMSO) δ 10.16 (s, 1H), 9.07 (s, 1H), 8.07 (s, 1H), 7.80 (m, 4H), 7.27 (d, J = 8.4 Hz, 2H), 3.70 (s, 3H), 2.72 (s, 3H), 2.47 (s, 3H), 2.30 (s, 3H), 2.13 (s, 3H). MS m/z 412.2 (M + 1) |
| 5 | 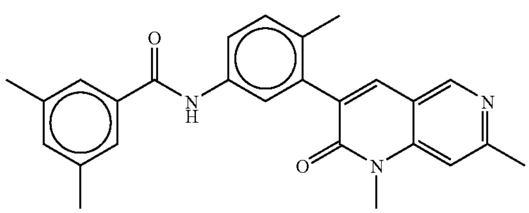 | $^1$H NMR (400 MHz, d$_6$-DMSO) δ 10.19 (s, 1H), 9.09 (s, 1H), 8.08 (s, 1 H), 7.82 (s, 1H), 7.76 (s, 1H), 7.67 (m, 3H), 7.55 (s, 2H), 7.26 (m, 2H), 3.74 (s, 3H), 2.73 (s, 3H), 2.36 (s, 6H), 2.13 (s, 3H). MS m/z 412.2 (M + 1) |
| 6 | 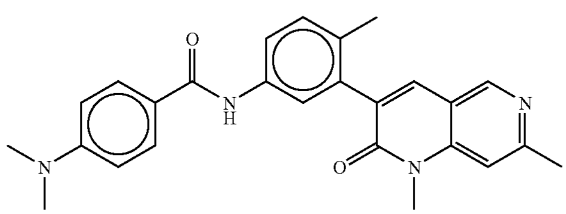 | $^1$H NMR (400 MHz, d$_6$-DMSO) δ 9.90 (s, 1H), 9.10 (s, 1H), 8.07 (s, 1H), 7.87 (m, 2H), 7.77 (m, 2H), 7.68 (m, 1H), 7.24 (d, J = 8.0 Hz, 1H), 6.77 (m, 2H), 3.71 (s, 3H), 2.99 (s, 6H), 2.74 (s, 3H), 2.13 (s, 3H). MS m/z 427.2 (M + 1) |

TABLE 2-continued

| B# | Structure | Physical Data<br>¹H NMR 400 MHz and/or MS (m/z) |
|---|---|---|
| 7 | 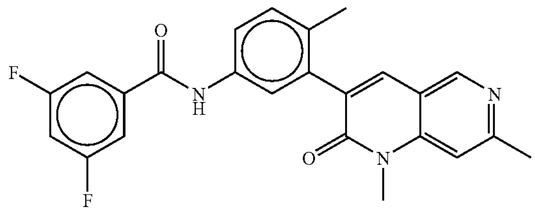 | ¹H NMR (400 MHz, d₆-DMSO) δ 10.4 (s, 1H), 9.06 (s, 1H), 8.07 (s, 1H), 7.78 (m, 2H), 7.67 (m, 3H), 7.55 (m, 1H), 7.32 (m, 1H), 3.74 (s, 3H), 2.72 (s, 3H), , 2.15 (s, 3H). MS m/z 420.2 (M + 1) |
| 8 | 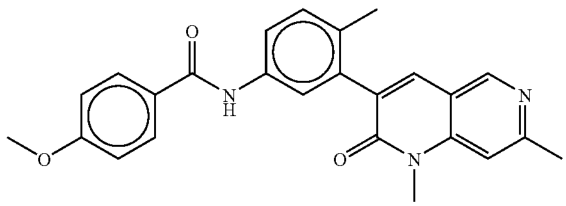 | MS m/z 414.2 (M + 1) |
| 9 | 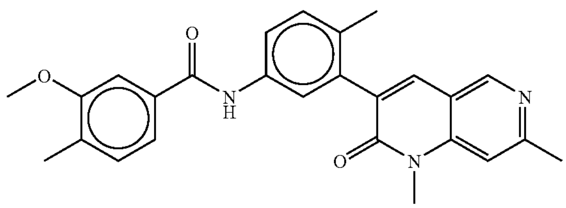 | ¹H NMR (400 MHz, d₆-DMSO) δ 10.2 (s, 1H), 9.07 (s, 1H), 8.07 (s, 1H), 7.80 (s, 1H), 7.71 (m, 2H), 7.48 (m, 2H), 7.29 (m, 2H), 3.88 (s, 3H), 3.71 (s, 3H), 2.73 (s, 3H), 2.22 (s, 3H), 2.14 (s, 3H). MS m/z 428.2 (M + 1) |
| 10 | 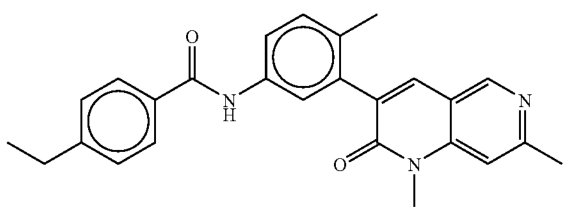 | ¹H NMR (400 MHz, d₆-DMSO) δ 10.2 (s, 1H), 9.06 (s, 1H), 8.07 (s, 1H), 7.88 (m, 2H), 7.78 (m, 2H), 7.68 (m, 1H), 7.38 (m, 2H), 7.29 (m, 1H), 3.71 (s, 3H), 2.72 (s, 3H), 2.70 (m, 2H), 2.13 (s, 3H), 1.21 (t, J = 6.4 Hz, 3H). MS m/z 412.2 (M + 1) |
| 11 | 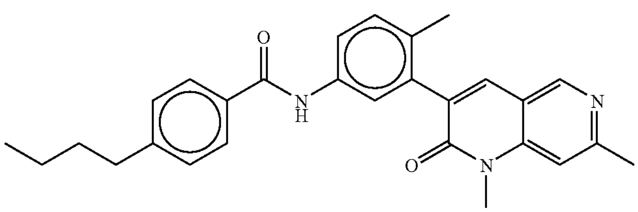 | ¹H NMR (400 MHz, d₆-DMSO) δ 10.2 (s, 1H), 9.08 (s, 1H), 8.07 (s, 1H), 7.86 (d, J = 8.4 Hz, 2H), 7.80 (m, 2H), 7.68 (m, 1H), 7.34 (d, J = 8.0 Hz, 2H), 7.27 (d, J = 8.0 Hz, 1H), 3.71 (s, 3H), 2.73 (s, 3H), 2.66 (m, 2H), 2.13 (s, 3H), 1.59 (m, 2H), 1.32 (m, 2H), 0.91 (t, J = 7.2Hz, 3H). MS m/z 440.2 (M + 1) |
| 12 | 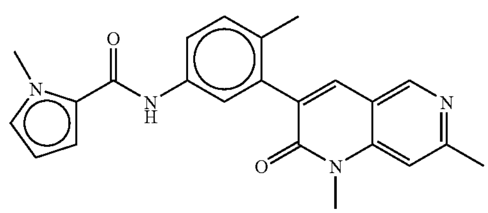 | ¹H NMR (400 MHz, d₆-DMSO) δ 9.78 (s, 1H), 9.09 (s, 1H), 8.06 (s, 1H), 7.82 (s, 1H), 7.72 (s, 1H), 7.60 (m, 1H), 7.24 (d, J = 8.4 Hz, 1H), 7.03 (m, 2H), 6.09 (m, 1H), 3.85 (s, 3H), 3.71 (s, 3H), 2.73 (s, 3H), 2.11 (s, 3H). MS m/z 387.1 (M + 1) |
| 13 | 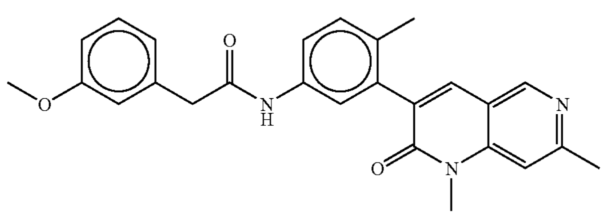 | ¹H NMR (400 MHz, d₆-DMSO) δ 10.18 (s, 1H), 9.02 (s, 1H), 8.01 (s, 1H), 7.76 (s, 1H), 7.60 (s, 1H), 7.46 (m, 1H), 7.23 (m, 2H), 6.91 (m, 3H), 3.74 (s, 3H), 3.68 (s, 3H), 2.71 (s, 3H), 2.10 (s, 3H). MS m/z 428.2 (M + 1) |

TABLE 2-continued

| B# | Structure | Physical Data $^1$H NMR 400 MHz and/or MS (m/z) |
|---|---|---|
| 14 | 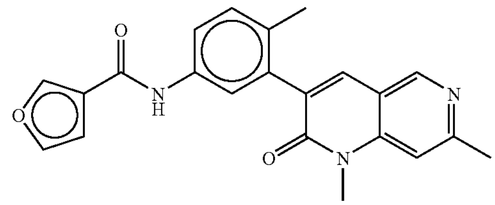 | $^1$H NMR (400 MHz, d$_6$-DMSO) δ 9.96 (s, 1H), 9.06 (s, 1H), 8.36 (s, 1H), 8.06 (s, 1H), 7.80 (s, 2H), 7.64 (m, 2H), 7.27 (d, J = 8.4 Hz, 1H), 6.99 (s, 1H), 3.70 (s, 3H), 2.73 (s, 3H), 2.13 (s, 3H). MS m/z 374.1 (M + 1) |
| 15 | 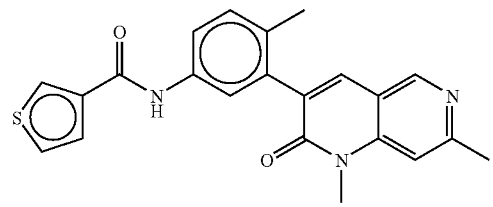 | $^1$H NMR (400 MHz, d$_6$-DMSO) δ 10.08 (s, 1H), 9.06 (s, 1H), 8.33 (s, 1H), 8.06 (s, 1H), 7.78 (s, 1H), 7.72 (s, 1H), 7.67 (m, 3H), 7.27 (d, J = 8.4 Hz, 1H), 3.71 (s, 3H), 2.72 (s, 3H), 2.13 (s, 3H). MS m/z 390.1 (M + 1) |
| 16 | 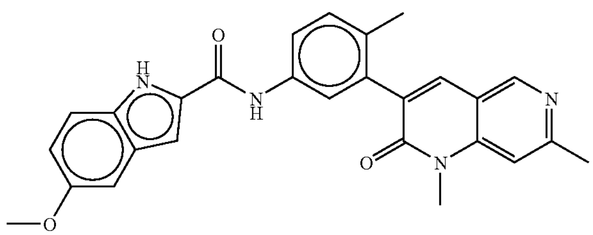 | $^1$H NMR (400 MHz, d$_6$-DMSO) δ 11.5 (s, 1H), 10.2 (s, 1H), 9.05 (s, 1H), 8.08 (s, 1H), 7.77 (m, 3H), 7.35 (m, 2H), 7.13 (s, 1H), 6.88 (m, 1H), 3.78 (s, 3H), 3.71 (s, 3H), 2.72 (s, 3H), 2.14 (s, 3H). MS m/z 453.2 (M + 1) |
| 17 | 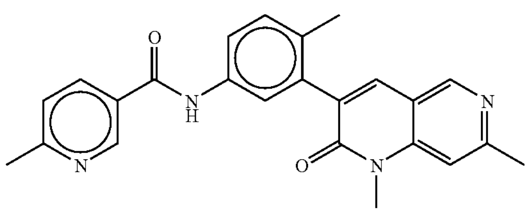 | $^1$H NMR (400 MHz, d$_6$-DMSO) δ 10.4 (s, 1H), 9.09 (s, 1H), 9.01 (s, 1H), 8.26 (m, 1H), 8.08 (s, 1H), 7.83 (s, 1H), 7.75 (s, 1H), 7.67 (m, 1H), 7.48 (m, 1H), 7.30 (m, 1H), 3.71 (s, 3H), 2.14 (s, 3H), 1.26 (s, 3H), 1.24 (s, 3H). MS m/z 399.1 (M + 1) |
| 18 | 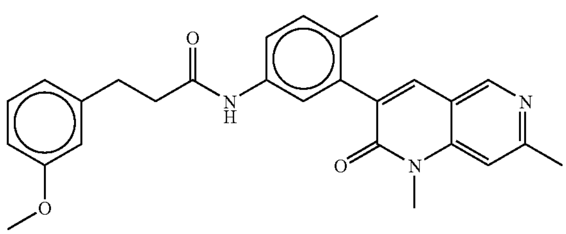 | $^1$H NMR (400 MHz, d$_6$-DMSO) δ 9.94 (s, 1H), 9.05 (s, 1H), 8.02 (s, 1H), 7.78 (s, 1H), 7.59 (s, 1H), 7.43 (m, 1H), 7.20 (m, 2H), 6.80 (m, 2H), 6.74 (m, 1H), 3.72 (s, 3H), 3.70 (s, 3H), 2.87 (m, 2H), 2.79 (m, 2H), 2.72 (s, 3H), 2.09 (s, 3H). MS m/z 442.2 (M + 1) |
| 19 | 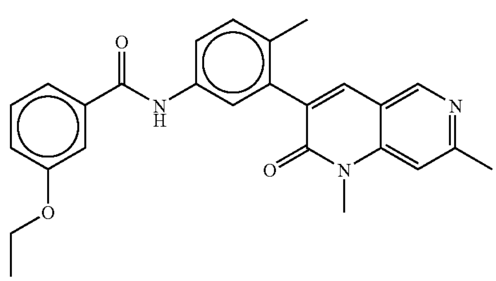 | $^1$H NMR (400 MHz, d$_6$-DMSO) δ 10.23 (s, 1H), 9.08 (s, 1H), 8.08 (s, 1H), 7.82 (s, 1H), 7.77 (s, 1H), 7.67 (m, 1H), 7.48 (m, 3H), 7.28 (d, J = 8.4 Hz, 1H), 7.16 (m, 1H), 4.09 (m, 2H), 3.71 (s, 3H), 2.73 (s, 3H), 2.14 (s, 3H), 1.36 (t, J = 6.8 Hz, 3H). MS m/z 428.2 (M + 1) |

TABLE 2-continued

| B# | Structure | Physical Data<br>¹H NMR 400 MHz and/or MS (m/z) |
|---|---|---|
| 20 | 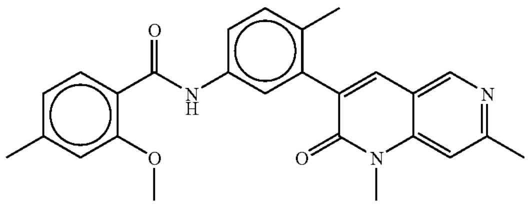 | ¹H NMR (400 MHz, d₆-DMSO) δ 10.04 (s, 1H), 9.08 (s, 1H), 8.07 (s, 1H), 7.81 (s, 1H), 7.74 (s, 1H), 7.60 (m, 2H), 7.26 (d, J = 8.4 Hz, 1H), 7.02 (s, 1H), 6.88 (d, J = 8.0 Hz, 1H), 3.91 (s, 3H), 3.71 (s, 3H), 2.73 (s, 3H), 2.37 (s, 3H), 2.12 (s, 3H). MS m/z 428.2 (M + 1) |
| 21 | 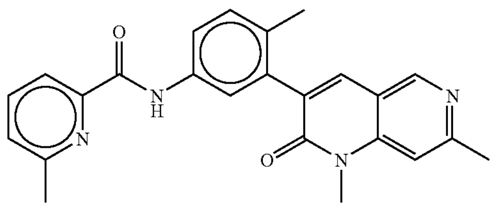 | ¹H NMR (400 MHz, d₆-DMSO) δ 10.46 (s, 1H), 9.09 (s, 1H), 8.09 (s, 1H), 7.87 (m, 5H), 7.53 (m, 1H), 7.31 (d, J = 8.4 Hz, 1H), 3.72 (s, 3H), 2.74 (s, 3H), 2.63 (s, 3H), 2.15 (s, 3H). MS m/z 399.2 (M + 1) |
| 22 | 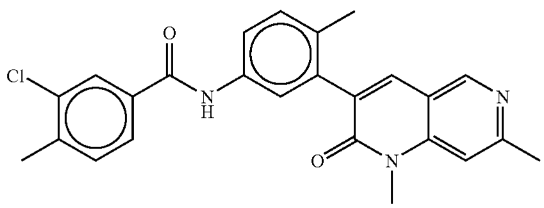 | ¹H NMR (400 MHz, d₆-DMSO) δ 10.31 (s, 1H), 9.07 (s, 1H), 8.07 (s, 1H), 8.02 (s, 1H), 7.84 (d, J = 8.0 Hz, 1H), 7.77 (m, 1H), 7.67 (m, 1H), 7.52 (d, J = 8.0 Hz, 1H), 7.29 (d, J = 8.4 Hz, 1H), 3.71 (s, 3H), 2.73 (s, 3H), 2.41 (s, 3H), 2.14 (s, 3H). MS m/z 432.1 (M + 1) |
| 23 | 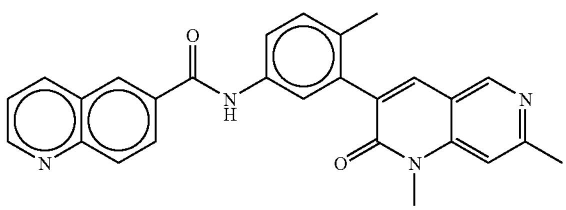 | ¹H NMR (400 MHz, d₆-DMSO) δ 9.12 (s, 1H), 9.04 (m, 1H), 8.65 (s, 1H), 8.57 (d, J = 8.0 Hz, 1H), 8.27 (m, 1H), 8.15 (m, 2H), 7.84 (d, J = 9.2 Hz, 2H), 7.73 (m, 2H), 7.32 (d, J = 8.4 Hz, 1H), 3.72 (s, 3H), 2.75 (s, 3H), 2.16 (s, 3H). MS m/z 435.2 (M + 1) |
| 24 | 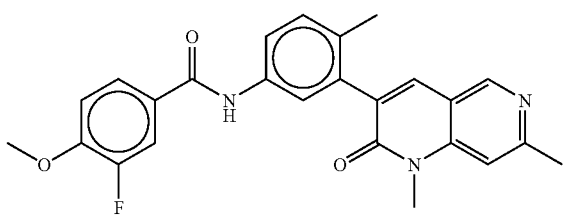 | ¹H NMR (400 MHz, d₆-DMSO) δ 10.2 (s, 1H), 9.07 (s, 1H), 8.07 (s, 1H), 7.84 (m, 2H), 7.77 (m, 2H), 7.66 (d, J = 8.8 Hz, 1H), 7.28 (m, 2H), 3.93 (s, 3H), 3.71 (s, 3H), 2.73 (s, 3H), 2.14 (s, 3H). MS m/z 432.2 (M + 1) |
| 25 | 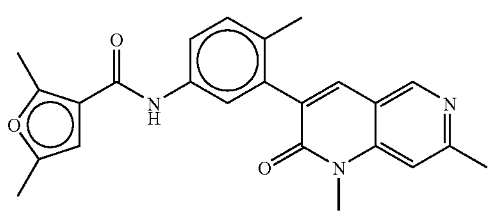 | ¹H NMR (400 MHz, d₆-DMSO) δ 9.62 (s, 1H), 9.09 (s, 1H), 8.06 (s, 1H), 7.82 (s, 1H), 7.73 (s, 1H), 7.59 (d, J = 7.6 Hz, 1H), 7.24 (d, J = 8.0 Hz, 1H), 6.66 (s, 1H), 3.72 (s, 3H), 2.73 (s, 3H), 2.47 (s, 3H), 2.26 (s, 3H), 2.12 (s, 3H). MS m/z 402.2 (M + 1) |
| 26 | 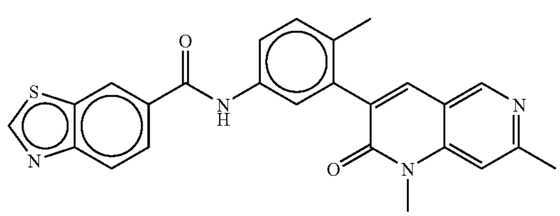 | ¹H NMR (400 MHz, d₆-DMSO) δ 10.5 (s, 1H), 9.57 (s, 1H), 9.09 (s, 1H), 8.78 (s, 1H), 8.22 (d, J = 8.8 Hz, 1H), 8.09 (m, 2H), 7.82 (m, 2H), 7.69 (d, J = 8.4 Hz, 1H), 7.30 (d, J = 8.4 Hz, 1H), 3.71 (s, 3H), 2.73 (s, 3H), 2.15 (s, 3H). MS m/z 441.1 (M + 1) |

TABLE 2-continued

| B# | Structure | Physical Data<br>¹H NMR 400 MHz and/or MS (m/z) |
|---|---|---|
| 27 | 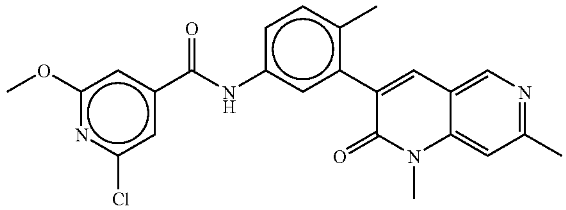 | MS m/z 449.1 (M + 1) |
| 28 | 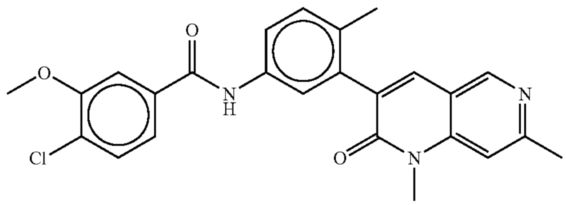 | ¹H NMR (400 MHz, d₆-DMSO) δ 10.32 (s, 1H), 9.06 (s, 1H), 8.06 (s, 1H), 7.78 (s, 1H), 7.66 (m, 2H), 7.56 (m, 3H), 7.30 (d, J = 8.0 Hz, 1H), 3.96 (s, 3H), 3.71 (s, 3H), 2.72 (s, 3H), 2.14 (s, 3H). MS m/z 448.1 (M + 1) |
| 29 | 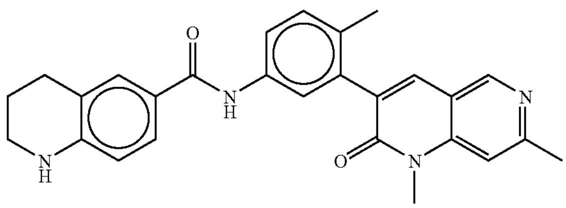 | ¹H NMR (400 MHz, d₆-DMSO) δ 9.75 (s, 1H), 9.12 (s, 1H), 8.07 (s, 1H), 7.87 (s, 1H), 7.63 (d, J = 8.8 Hz, 1H), 7.54 (s, 2H), 7.45 (s, 3H), 7.23 (d, J = 8.0 Hz, 1H), 6.46 (d, J = 9.2Hz, 1H), 3.74 (s, 3H), 2.74 (s, 3H), 2.66 (s, 2H), 2.12 (s, 3H). MS m/z 439.2 (M + 1) |
| 30 | 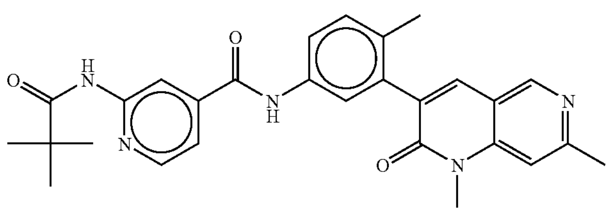 | ¹H NMR (400 MHz, d₆-DMSO) δ 10.6 (s, 1H), 10.04 (s, 1H), 9.10 (s, 1H), 8.49 (s, 2H), 8.10 (s, 1H), 7.85 (s, 1H), 7.76 (s, 1H), 7.67 (d, J = 8.0 Hz, 1H), 7.55 (m, 1H), 7.31 (d, J = 8.4 Hz, 1H), 3.72 (s, 3H), 2.74 (s, 3H), 2.15 (s, 2H), 1.22 (s, 9H). MS m/z 484.2 (M + 1) |
| 31 | 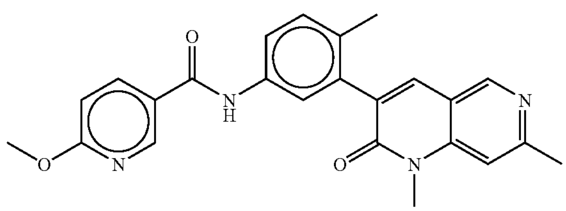 | ¹H NMR (400 MHz, d₆-DMSO) δ 10.3 (s, 1H), 9.08 (s, 1H), 8.78 (s, 1H), 8.22 (d, J = 8.4 Hz, 1H), 8.07 (s, 1H), 7.81 (s, 1H), 7.74 (s, 1H), 7.65 (d, J = 8.0 Hz, 1H), 7.29 (d, J = 8.4 Hz, 1H), 6.95 (d, J = 8.8 Hz, 1H), 3.94 (s, 3H), 3.71 (s, 3H), 2.73 (s, 3H), 2.14 (s, 3H). MS m/z 415.2 (M + 1) |
| 32 | 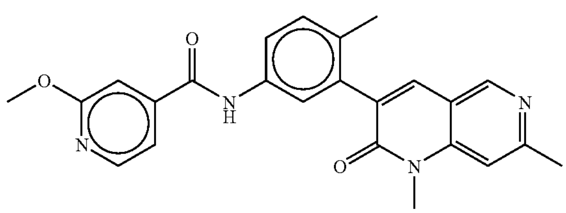 | ¹H NMR (400 MHz, d₆-DMSO) δ 10.5 (s, 1H), 9.08 (s, 1H), 8.36 (m, 1H), 8.07 (s, 1H), 7.81 (s, 1H), 7.76 (s, 1H), 7.66 (m, 1H), 7.43 (m, 1H), 7.30 (m, 2H), 3.92 (s, 3H), 3.71 (s, 3H), 2.73 (s, 3H), 2.14 (s, 3H). MS m/z 415.2 (M + 1) |
| 33 | 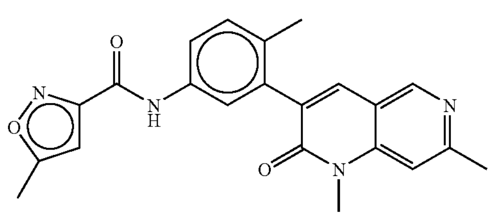 | ¹H NMR (400 MHz, d₆-DMSO) δ 10.7 (s, 1H), 9.06 (s, 1H), 8.06 (s, 1H), 7.77 (m, 2H), 7.67 (m, 1H), 7.29 (d, J = 9.6 Hz, 1H), 6.64 (s, 1H), 3.70 (s, 3H), 2.72 (s, 3H), 2.55 (s, 3H), 2.13 (s, 3H). MS m/z 389.1 (M + 1) |

TABLE 2-continued

| B# | Structure | Physical Data<br>¹H NMR 400 MHz and/or MS (m/z) |
|---|---|---|
| 34 | 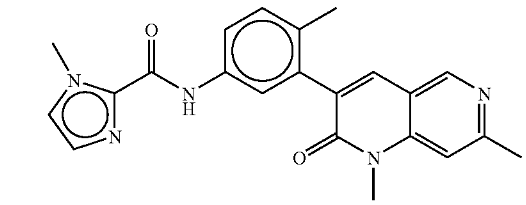 | ¹H NMR (400 MHz, d₆-DMSO) δ 10.36 (s, 1H), 9.11 (s, 1H), 8.08 (s, 1H), 7.85 (s, 2H), 7.68 (m, 1H), 7.45 (s, 1H), 7.26 (d, J = 8.0 Hz, 1H), 7.10 (s, 1H), 3.97 (s, 3H), 3.71 (s, 3H), 2.74 (s, 3H), 2.12 (s, 3H). MS m/z 388.2 (M + 1) |
| 35 | 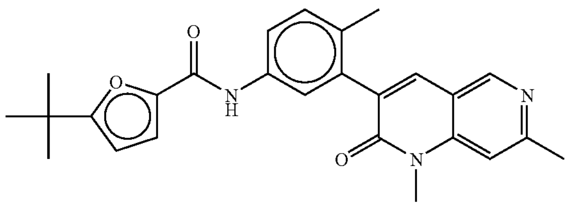 | ¹H NMR (400 MHz, d₆-DMSO) δ 9.94 (s, 1H), 9.08 (s, 1H), 8.07 (s, 1H), 7.81 (s, 1H), 7.67 (m, 2H), 7.28 (d, J = 8.4 Hz, 1H), 7.20 (d, J = 3.6 Hz, 1H), 6.30 (d, J = 3.2Hz, 1H), 3.71 (s, 3H), 2.73 (s, 3H), 2.13 (s, 3H), 1.31 (s, 9H). MS m/z 430.2 (M + 1) |
| 36 | 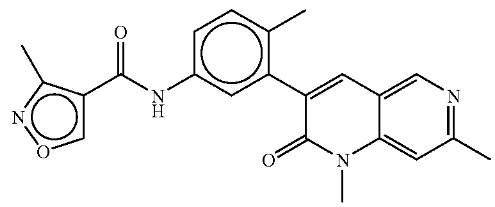 | ¹H NMR (400 MHz, d₆-DMSO) δ 10.25 (s, 1H), 9.43 (s, 1H), 9.05 (s, 1H), 8.06 (s, 1H), 7.78 (s, 1H), 7.68 (s, 1H), 7.54 (d, J = 8.4 Hz, 1H), 7.28 (d, J = 8.4 Hz, 1H), 3.70 (s, 3H), 2.72 (s, 3H), 2.41 (s, 3H), 2.13 (s, 3H). MS m/z 389.1 (M + 1) |
| 37 | 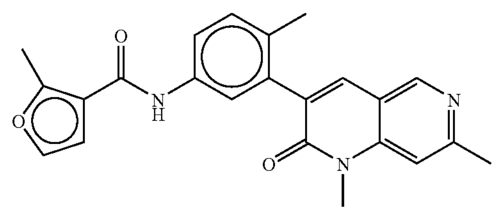 | ¹H NMR (400 MHz, d₆-DMSO) δ 9.73 (s, 1H), 9.06 (s, 1H), 8.05 (s, 1H), 7.79 (s, 1H), 7.71 (s, 1H), 7.61 (d, J = 8.4 Hz, 1H), 7.60 (s, 1H), 7.25 (d, J = 8.4 Hz, 1H), 7.07 (s, 1H), 3.70 (s, 3H), 2.72 (s, 3H), 2.51 (s, 3H), 2.13 (s, 3H). MS m/z 388.2 (M + 1) |
| 38 | 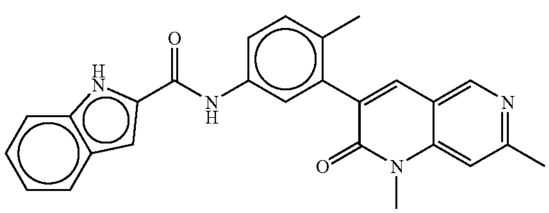 | MS m/z 423.2 (M + 1) |
| 39 | 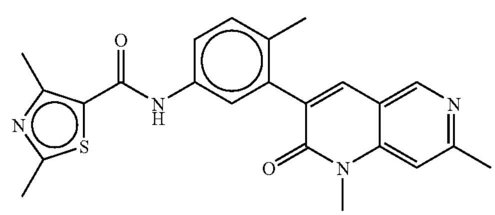 | ¹H NMR (400 MHz, CD₂Cl₂) δ 9.00 (s, 1H), 7.83 (s, 1H), 7.68 (s, 1H), 7.56 (s, 1H), 7.46 (d, J = 8.4 Hz, 1H), 7.38 (s, 1H), 7.31 (d, J = 8.4 Hz, 1H), 3.78 (s, 3H), 2.90 (s, 3H), 2.80 (s, 3H), 2.71 (s, 3H), 2.20 (s, 3H). MS m/z 419.1 (M + 1) |
| 40 | 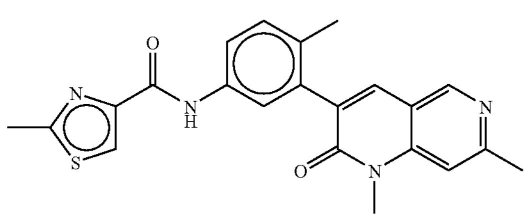 | ¹H NMR (400 MHz, CD₂Cl₂) δ 9.30 (s, 1H), 8.99 (s, 1H), 8.03 (s, 1H), 7.84 (s, 1H), 7.73 (d, J = 2.0 Hz, 1H), 7.58 (d, J = 8.4, 2.0 Hz, 1H), 7.38 (s, 1H), 7.30 (d, J = 8.4 Hz, 1H), 3.78 (s, 3H), 2.89 (s, 3H), 2.74 (s, 3H), 2.20 (s, 3H). MS m/z 405.1 (M + 1) |

TABLE 2-continued

| B# | Structure | Physical Data $^1$H NMR 400 MHz and/or MS (m/z) |
|---|---|---|
| 41 | 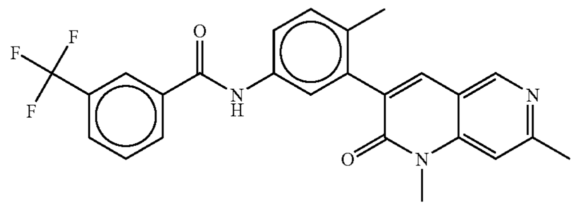 | $^1$H NMR (400 MHz, CD$_2$Cl$_2$) δ 10.51 (s, 1H), 9.05 (s, 1H), 8.26 (m, 2H), 8.07 (s, 1H), 7.97 (d, J = 7.6 Hz, 1H), 7.77 (m, 3H), 7.69 (d, J = 8.4 Hz, 1H), 7.30 (d, J = 8.0 Hz, 1H), 3.70 (s, 3H), 2.72 (s, 3H), 2.14 (s, 3H). MS m/z 452.1 (M + 1) |
| 42 | 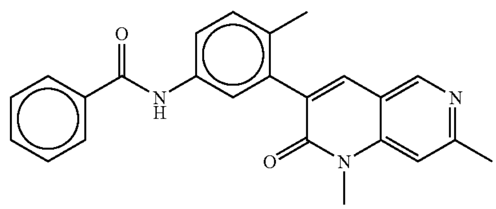 | $^1$H NMR (400 MHz, CD$_2$Cl$_2$) δ 10.3 (s, 1H), 9.07 (s, 1H), 8.07 (s, 1H), 7.94 (d, J = 8.0 Hz, 2H), 7.78 (s, 2H), 7.67 (m, 1H), 7.58 (m, 1H), 7.55 (m, 2H), 7.28 (d, J = 8.4 Hz, 1H), 3.71 (s, 3H), 2.72 (s, 3H), 2.14 (s, 3H). MS m/z 384.1 (M + 1) |
| 43 | 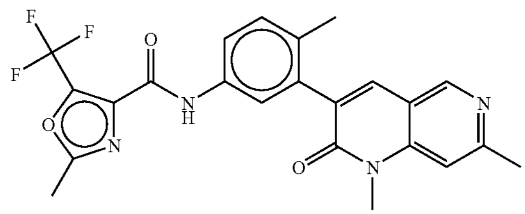 | $^1$H NMR (400 MHz, CD$_2$Cl$_2$) δ 10.58 (s, 1H), 9.06 (s, 1H), 8.06 (s, 1H), 7.85 (m, 1H), 7.78 (s, 1H), 7.64 (m, 1H), 7.28 (d, J = 8.4 Hz, 1H), 3.69 (s, 3H), 2.72 (s, 3H), 2.61 (s, 3H), 2.13 (s, 3H). MS m/z 457.2 (M + 1) |
| 44 | 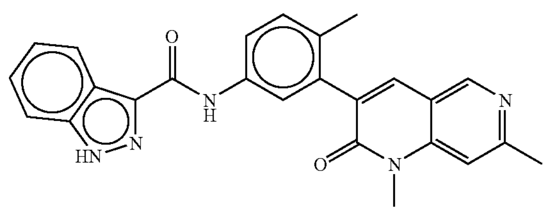 | MS m/z 424.2 (M + 1) |
| 45 | 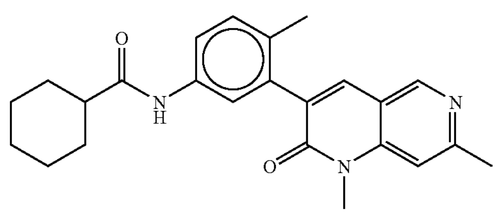 | $^1$H NMR (400 MHz, CD$_2$Cl$_2$) δ 9.82 (s, 1H), 9.02 (s, 1H), 8.01 (s, 1H), 7.74 (s, 1H), 7.62 (s, 1H), 7.44 (m, 1H), 7.20 (m, 1H), 3.68 (s, 3H), 2.71 (s, 3H), 2.29 (m, 2H), 1.76 (m, 2H), 1.65 (m, 2H), 1.39 (m, 2H), 1.24 (m, 2H). MS m/z 390.5 (M + 1) |
| 46 | 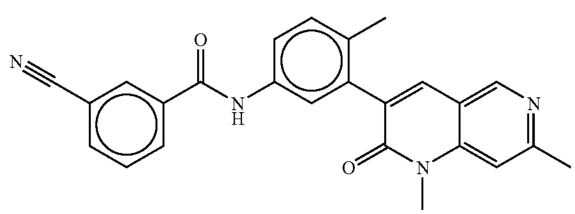 | $^1$H NMR (400 MHz, CD$_2$Cl$_2$) δ 10.5 (s, 1H), 9.01 (s, 1H), 8.39 (s, 1H), 8.25 (s, 1H), 8.05 (m, 2H), 7.73 (m, 3H), 7.67 (m, 1H), 7.31 (m, 1H), 3.70 (s, 3H), 2.70 (s, 3H), 2.14 (m, 3H). MS m/z 409.2 (M + 1) |
| 47 | 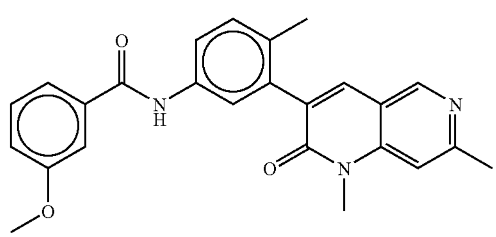 | $^1$H NMR (400 MHz, CD$_2$Cl$_2$) δ 10.24 (s, 1H), 9.02 (s, 1H), 8.05 (s, 1H), 7.73 (m, 2H), 7.66 (m, 1H), 7.53 (m, 1H), 7.47 (m, 2H), 7.31 (m, 1H), 7.16 (m, 1H), 3.83 (s, 3H), 3.70 (s, 3H), 2.71 (s, 3H), 2.13 (m, 3H). MS m/z 414.2 (M + 1) |

TABLE 2-continued

| B# | Structure | Physical Data<br>¹H NMR 400 MHz and/or MS (m/z) |
|---|---|---|
| 48 | 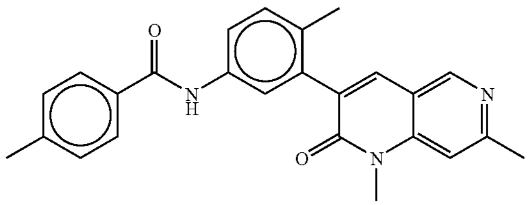 | ¹H NMR (400 MHz, CD₂Cl₂) δ 10.19 (s, 1H), 9.05 (s, 1H), 8.06 (s, 1H), 7.86 (m, 2H), 7.76 (m, 2H), 7.65 (m, 1H), 7.33 (m, 2H), 7.28 (m, 1H), 3.70 (s, 3H), 2.72 (s, 3H), 2.38 (m, 3H), 2.13 (s, 3H). MS m/z 398.2 (M + 1) |
| 49 | 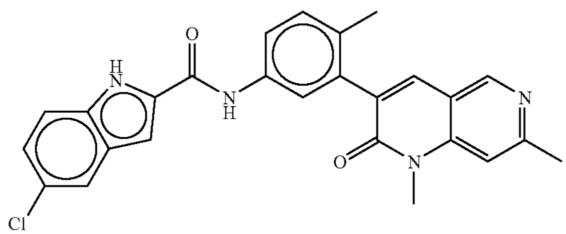 | ¹H NMR (400 MHz, CDCl₃) δ 11.9 (s, 1H), 10.32 (s, 1H), 9.02 (s, 1H), 8.06 (s, 1H), 7.73 (m, 4H), 7.48 (d, J = 8.4 Hz, 1H), 7.39 (m, 1H), 7.30 (d, J = 8.4 Hz, 1H), 7.22 (m, 1H), 3.70 (s, 3H), 2.71 (s, 3H), 2.14 (s, 3H). MS m/z 457.4 (M + 1) |
| 50 | 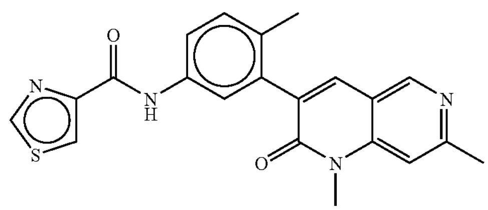 | ¹H NMR (400 MHz, CDCl₃) δ 9.26 (s, 1H), 8.80 (d, J = 2.0 Hz, 1H), 8.72 (s, 1H), 8.25 (d, J = 2.0 Hz, 1H), 7.73 (s, 1H), 7.70 (d, J = 2.0 Hz, 1H), 7.61 (d, J = 8.0, 2.4 Hz, 1H), 7.29 (d, J = 8.0 Hz, 1H), 7.16 (s, 1H), 3.76 (s, 3H), 2.80 (s, 3H), 2.22 (s, 3H). MS m/z 391.1 (M + 1) |
| 51 | 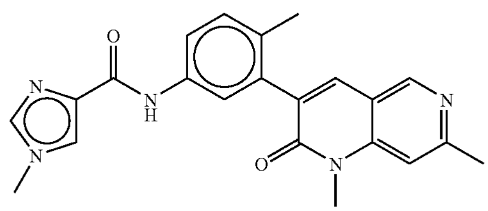 | MS m/z 388.5 (M + 1) |
| 52 | 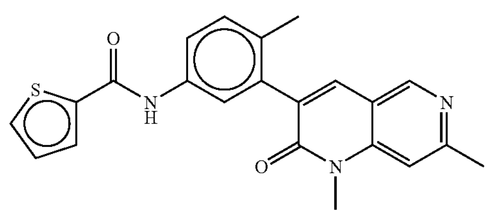 | MS m/z 390.1 (M + 1) |
| 53 | 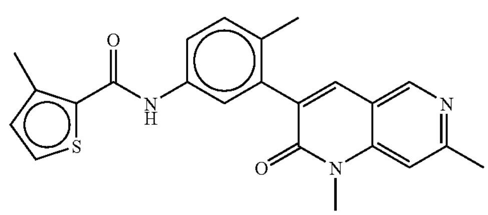 | MS m/z 404.1 (M + 1) |
| 54 | 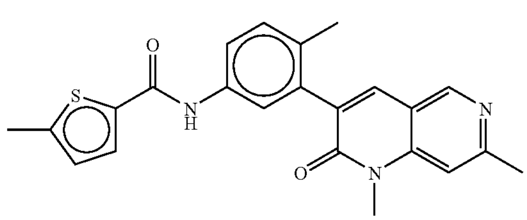 | MS m/z 404.1 (M + 1) |

TABLE 2-continued

| B# | Structure | Physical Data<br>¹H NMR 400 MHz and/or MS (m/z) |
|---|---|---|
| 55 | 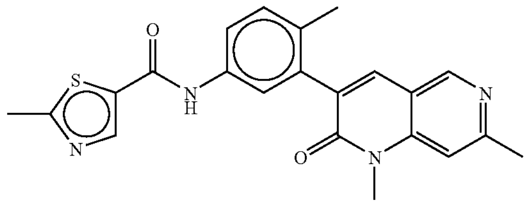 | MS m/z 405.1 (M + 1) |
| 56 | 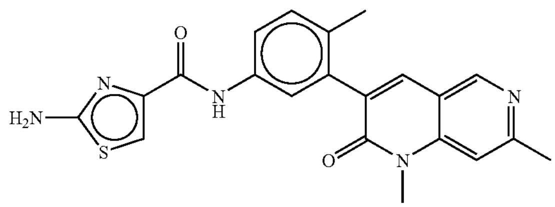 | MS m/z 406.1 (M + 1) |
| 57 | 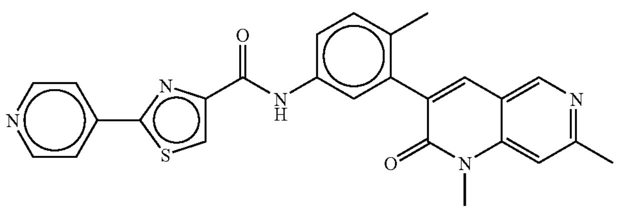 | MS m/z 468.1 (M + 1) |
| 58 | 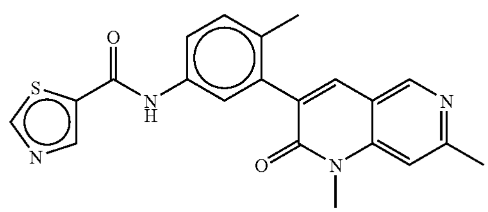 | MS m/z 391.1 (M + 1) |
| 59 | 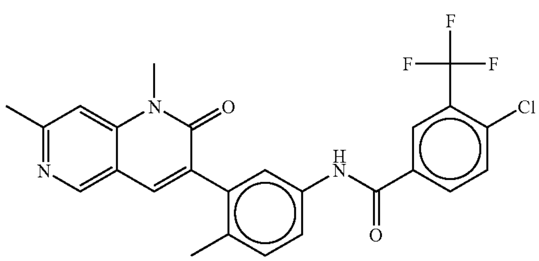 | MS m/z 486.1 (M + 1) |
| 60 | 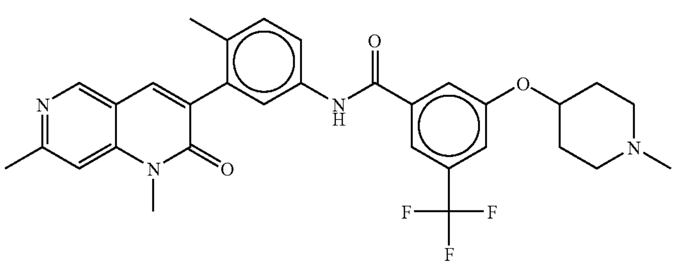 | ¹H NMR 400 MHz (Acetone-d6) δ 9.83 (s, 1H), 9.19 (s, 1H), 8.20 (s, 1H), 7.95 (m, 2H), 7.82 (s, 1H), 7.74 (d, 1H), 7.54 (d, 1H), 7.31 (d, 1H), 5.05 (m, 1H), 3.88 (s, 3H), 3.77 (m, 1H), 3.47 (m, 2H), 3.35 (m, 1H), 2.99 (s, 3H), 2.90 (s, 3H), 2.48 (m, 4H), 2.23 (s, 3H); MS m/z 565.2 (M + 1) |

TABLE 2-continued

| B# | Structure | Physical Data<br>¹H NMR 400 MHz and/or MS (m/z) |
|---|---|---|
| 61 | 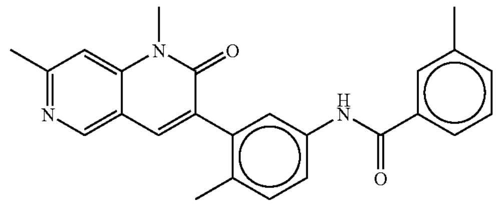 | ¹H NMR 400 MHz (CDCl₃) δ 8.97 (s, 1H), 8.09 (s, 1H), 7.75 (s, 1H), 7.69 (s, 1H), 7.66 (s, 1H), 7.62 (t, 1H), 7.50 (d, 1H), 7.34 (d, 2H), 7.30 (s, 1H), 3.78 (s, 3H), 2.90 (s, 3H), 2.40 (s, 3H), 2.17 (s, 3H); MS m/z 398.2 (M + 1) |
| 62 | 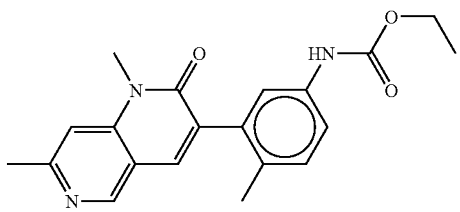 | ¹H NMR 400 MHz (CDCl₃) δ 9.03 (s, 1H), 7.78 (s, 1H), 7.35 (s, 2H), 7.23 (d, 1H), 7.18 (d, 2H), 4.18 (q, 2H), 3.80 (s, 3H), 2.90 (s, 3H), 2.15 (s, 3H), 1.29 (t, 3H); MS m/z 352.1 (M + 1) |
| 63 | 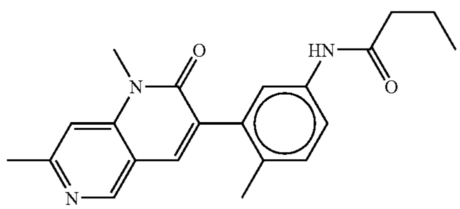 | ¹H NMR 400 MHz (CDCl₃) δ 9.02 (s, 1H), 7.80 (s, 1H), 7.55 (d, 2H), 7.34 (m, 2H), 7.22 (d, 1H), 3.80 (s, 3H), 2.93 (s, 3H), 2.77 (s, 1H), 2.36 (t, 2H), 2.17 (s, 3H), 1.73 (m, 2H), 0.99 (t, 3H); MS m/z 350.1 (M + 1) |
| 64 | 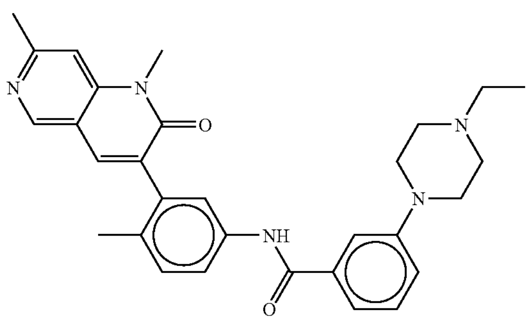 | ¹H NMR 400 MHz (Acetone-d6) δ 9.13 (s, 1H), 8.15 (s, 1H), 7.89 (s, 1H), 7.83 (d, 1H), 7.74 (dd, 1H), 7.62 (s, 1H), 7.50 (d, 1H), 7.39 (t, 1H), 7.27 (d, 1H), 7.23 (dd, 1H), 4.00 (m, 2H), 3.84 (s, 3H), 3.76 (m, 2H), 3.30 (m, 6H), 2.88 (s, 3H), 2.58 (s, 3H), 2.21 (s, 3H), 1.41 (t, 3H); MS m/z 496.3 (M + 1) |
| 65 | 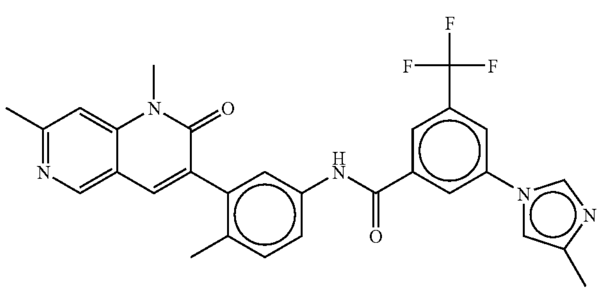 | MS m/z 532.2 (M + 1) |
| 66 | 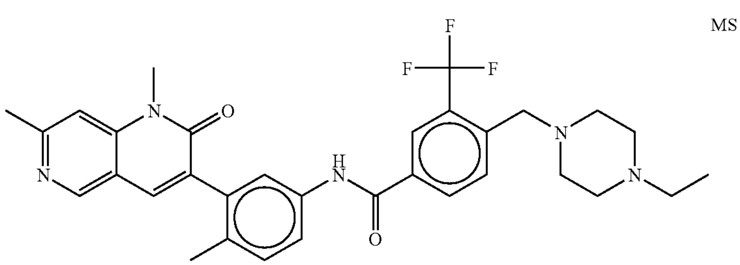 | MS m/z 578.3 (M + 1) |

TABLE 2-continued

| B# | Structure | Physical Data<br>¹H NMR 400 MHz and/or MS (m/z) |
|---|---|---|
| 67 | 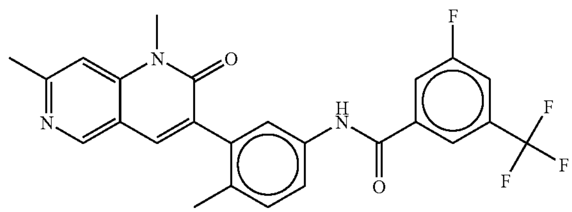 | ¹H NMR 400 MHz (DMSO-d₆) δ 10.55 (s, 1H), 9.00-8.99 (m, 1H), 8.18(s, 1H), 8.13-8.10 (m, 1H), 8.05 (s, 1H), 8.00-7.97 (m, 1H), 7.72-7.68 (m, 3H), 7.31 (d, 1H), 3.69 (s, 3H), 2.69 (s, 3H), 2.15 (s, 3H); MS m/z 470.1 (M + 1) |
| 68 | 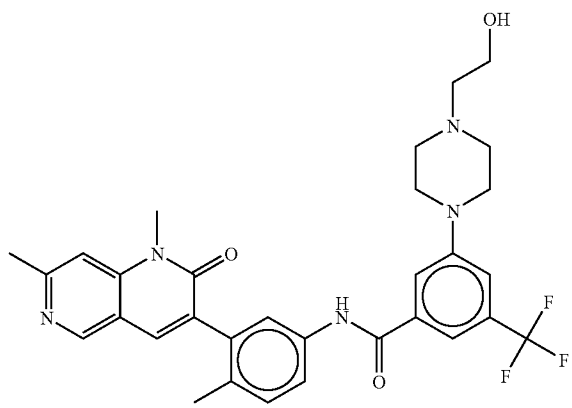 | ¹H NMR 400 MHz (Acetone-d6) δ 9.82 (s, 1H), 9.22 (s, 1H), 8.19 (s, 1H), 8.00 (s, 1H), 7.88 (s, 1H), 7.83 (d, 1H), 7.76 (s, 1H), 7.71 (dd, 1H), 7.53 (s, 1H), 7.30 (d, 1H), 4.04 (m, 2H), 3.87 (s, 3H), 3.70 (m, 8H), 3.50 (m, 2H), 2.90 (s, 3H), 2.62 (s, 1H), 2.23 (s, 3H); MS m/z 580.3 (M + 1) |
| 69 | 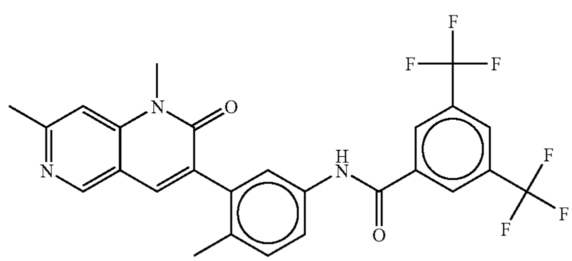 | ¹H NMR 400 MHz (DMSO-d₆) δ 10.69 (s, 1H), 8.97 (s, 1H), 8.62 (s, 2H), 8.39 (s, 1H), 8.04 (s, 1H), 7.74-7.71 (m, 3H), 7.33 (d, 1H), 3.69 (s, 3H), 2.68 (s, 3H), 2.16 (s, 3H); MS m/z 520.1 (M + 1) |
| 70 | 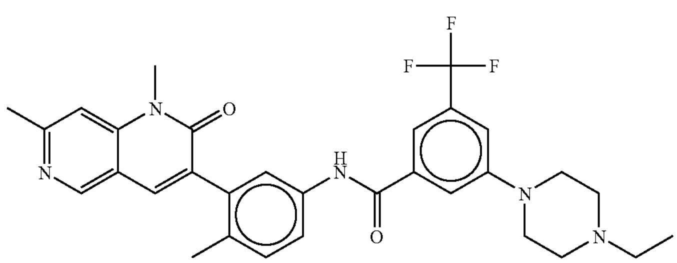 | ¹H NMR 400 MHz (DMSO-d₆) δ 9.04 (s, 1H), 8.06 (s, 1H), 7.75 (m, 3H), 7.70 (s, 1H), 7.53 (s, 1H), 7.37 (m, 1H), 7.31 (d, 1H), 5.76 (s, 3H), 5.00 (s, 1H), 4.12 (d, 2H), 3.70 (s, 3H), 3.61 (d, 2H), 3.23 (d, 2H), 3.12 (m, 2H), 2.71 (s, 3H), 2.15 (s, 3H), 1.27 (t, 3H); MS m/z 564.3 (M + 1) |
| 71 | 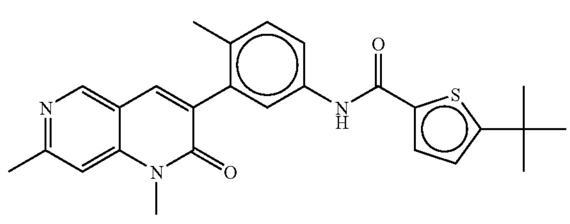 | ¹H NMR 400 MHz (CDCl₃) δ 8.87 (s, 1H), 8.26 (s, 1H), 7.67 (s, 1H), 7.57 (s, 1H), 7.52 (d, 1H), 7.46 (d, 1H), 7.30 (s, 1H), 7.15 (d, 1H), 6.82 (d, 1H), 3.74 (s, 3H), 2.85 (s, 3H), 2.11 (s, 3H), 1.38 (s, 9H); MS m/z 446.2 (M + 1) |

TABLE 2-continued

| B# | Structure | Physical Data ¹H NMR 400 MHz and/or MS (m/z) |
|---|---|---|
| 72 | 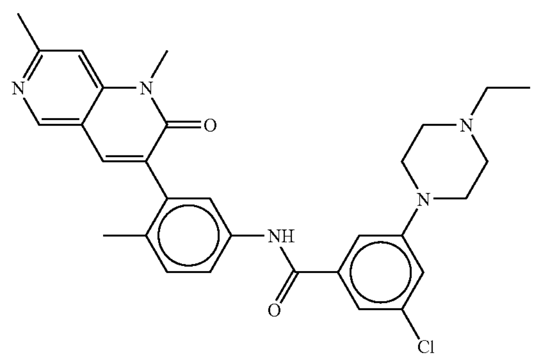 | ¹H NMR 400 MHz (Acetone-d6) δ 9.07 (s, 1H), 8.11 (s, 1H), 7.79 (m, 2H), 7.75 (dd, 1H), 7.57 (s, 1H), 7.45 (s, 1H), 7.28 (d, 1H), 7.24 (s, 1H), 4.04 (m, 2H), 3.83 (s, 3H), 3.72 (m, 2H), 3.45 (m, 2H), 3.29 (m, 4H), 2.84 (s, 3H), 2.22 (s, 3H), 1.42 (t, 3H); MS m/z 530.2 (M + 1) |
| 73 | 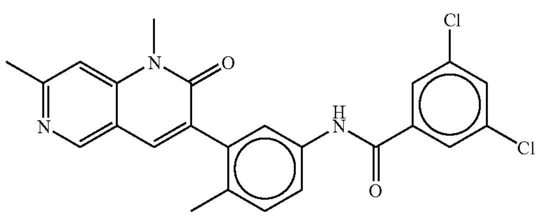 | ¹H NMR 400 MHz (CDCl₃) δ 8.94 (s, 1H), 8.71 (s, 1H), 7.70 (s, 2H), 7.67 (s, 1H), 7.63 (s, 1H), 7.44 (m, 2H), 7.29 (s, 1H), 7.11 (d, 1H), 3.78 (s, 3H), 2.86 (s, 3H), 2.01 (s, 3H); MS m/z 452.1 (M + 1) |
| 74 | 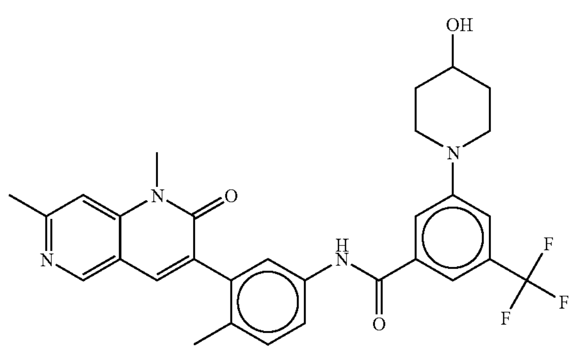 | ¹H NMR 400 MHz (Acetone-d6) δ 9.80 (s, 1H), 9.26 (s, 1H), 8.19 (s, 1H), 8.03 (s, 1H), 7.85 (s, 1H), 7.67 (s, 1H), 7.30 (d, 1H), 5.27 (m, 1H), 3.89 (s, 3H), 3.77 (m, 2H), 3.43 (m, 1H), 3.18 (m, 2H), 2.95 (s, 3H), 2.22 (s, 3H), 1.99 (m, 2H), 1.67 (m, 2H); MS m/z 551.2 (M + 1) |
| 75 | 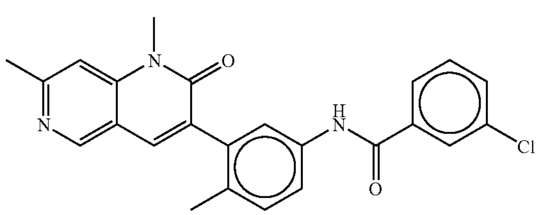 | ¹H NMR 400 MHz (CDCl₃) δ 8.93 (s, 1H), 8.41 (s, 1H), 7.79 (s, 1H), 7.71 (m, 2H), 7.64 (s, 1H), 7.48 (t, 2H), 7.37 (t, 1H), 7.29 (s, 1H), 7.17 (d, 1H), 3.76 (s, 3H), 2.86 (s, 3H), 2.08 (s, 3H); MS m/z 418.1 (M + 1) |
| 76 | 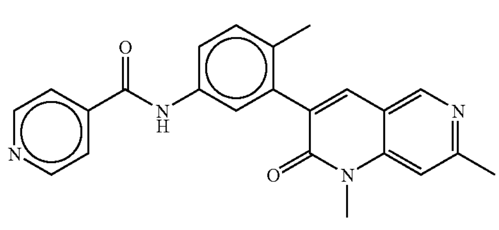 | ¹H NMR 400 MHz (DMSO-d₆) δ 10.57 (s, 1H), 9.09 (s, 1H), 8.80 (d, J = 2Hz, 2H), 8.08 (s, 1H), 7.88 (d, J = 2Hz, 2H), 7.82 (s, 1H), 7.76 (s, 1H), 7.66 (m, 1H), 7.31 (m, 1H), 3.71 (s, 3H), 2.73 (s, 3H), 2.15 (s, 3H); MS m/z 385.2 (M + 1) |

TABLE 2-continued

| B# | Structure | Physical Data<br>¹H NMR 400 MHz and/or MS (m/z) |
|---|---|---|
| 77 | 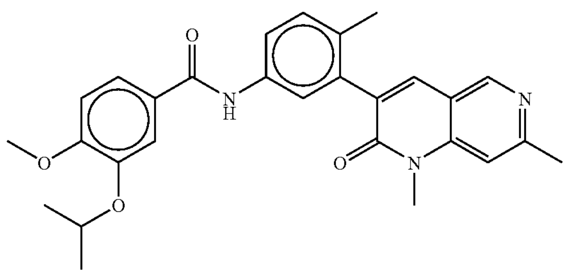 | ¹H NMR 400 MHz (DMSO-d₆) δ 10.1 (s, 1H), 9.07 (s, 1H), 8.06 (s, 1H), 7.66 (d, J = 8 Hz, 1H), 7.61 (d, J = 7.2 Hz, 1H), 7.53 (m, 1H), 7.43 (m, 1H), 7.27 (d, J = 8.4 Hz, 1H), 7.07 (m, 1H), 4.53 (m, 1H), 3.83 (s, 6H), 3.71 (s, 3H), 2.73 (s, 3H), 2.55 (s, 3H), 2.13 (s, 3H); MS m/z 473.2 (M + 1) |
| 78 | 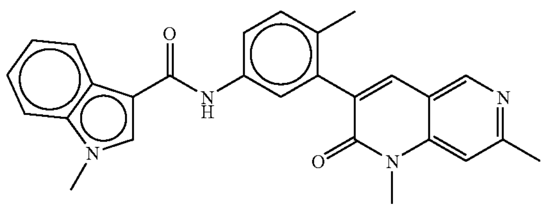 | MS m/z 438.2 (M + 1) |
| 79 | 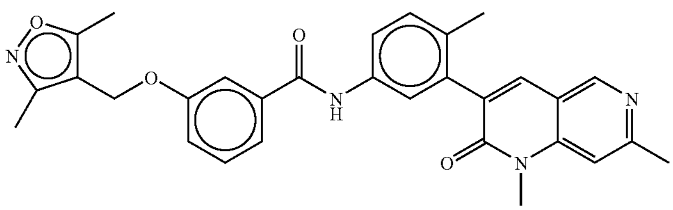 | ¹H NMR 400 MHz (DMSO-d₆) δ 10.2 (s, 1H), 9.07 (s, 1H), 8.07 (s, 1H), 7.77 (m, 2H), 7.68 (d, J = 8 Hz, 1H), 7.57 (m, 1H), 7.47 (m, 2H), 7.27 (m, 1H), 2.73 (s, 3H), 2.43 (s, 6H), 2.24 (s, 3H), 2.14 (s, 3H); MS m/z 509.2 (M + 1) |
| 80 | 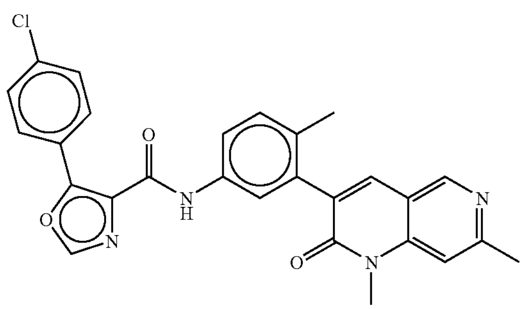 | ¹H NMR 400 MHz (DMSO-d₆) δ 10.3 (s, 1H), 9.02 (s, 1H), 8.20 (d, J = 8.4 Hz, 2H), 8.05 (s, 1H), 7.84 (s, 1H), 7.73 (s, 1H), 7.68 (d, J = 8 Hz, 1H), 7.59 (d, J = 8 Hz, 2H), 7.27 (d, J = 8.4 Hz, 1H), 2.71 (s, 3H), 2.55 (s, 3H), 2.13 (s, 3H); MS m/z 487.2 (M + 1) |
| 81 | 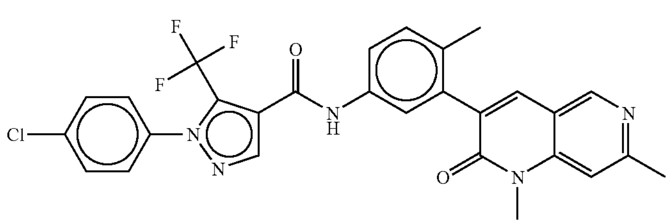 | ¹H NMR 400 MHz (DMSO-d₆) δ 10.6 (s, 1H), 9.08 (s, 1H), 8.34 (s, 1H), 8.08 (s, 1H), 7.79 (s, 1H), 7.70 (m, 2H), 7.58 (m, 3H), 7.30 (d, J = 8.4 Hz, 1H), 2.73 (s, 3H), 2.55 (s, 3H), 2.14 (s, 3H); MS m/z 552.1 (M + 1) |
| 82 | 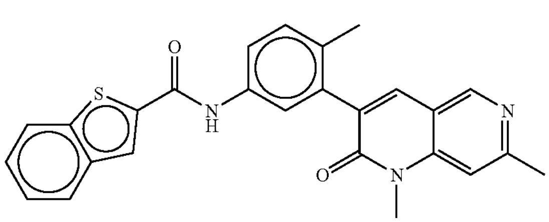 | ¹H NMR 400 MHz (DMSO-d₆) δ 10.4 (s, 1H), 8.88 (s, 1H), 8.18 (s, 1H), 7.87 (m, 3H), 7.58 (m, 2H), 7.50 (m, 1H), 7.32 (m, 2H), 7.14 (d, J = 8.4 Hz, 1H), 2.55 (s, 3H), 2.37 (s, 3H), 1.98 (s, 3H); MS m/z 440.1 (M + 1) |

TABLE 2-continued

| B# | Structure | Physical Data $^1$H NMR 400 MHz and/or MS (m/z) |
|---|---|---|
| 83 | 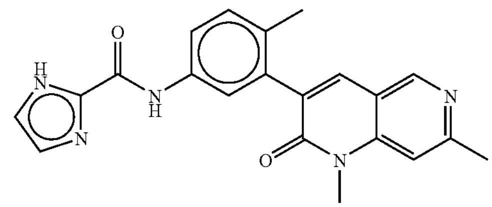 | MS m/z 374.1 (M + 1) |
| 84 | 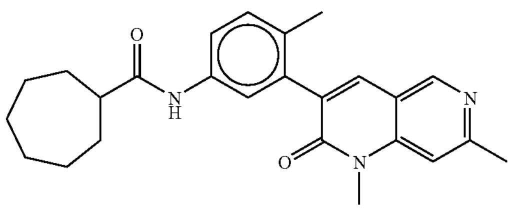 | MS m/z 404.2 (M + 1) |
| 85 | 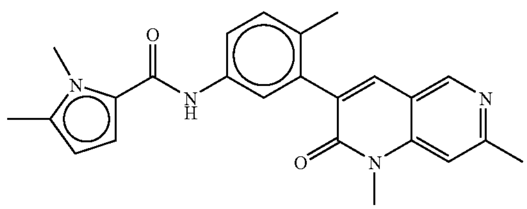 | MS m/z 401.1 (M + 1) |
| 86 | 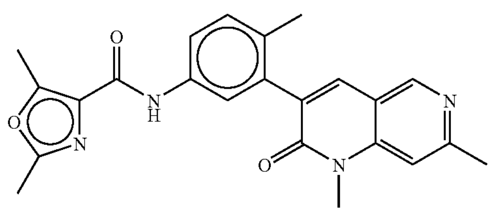 | $^1$H NMR 400 MHz (CDCl$_3$) δ 8.73 (s, 1H), 8.70 (s, 1H), 7.73 (s, 1H), 7.69 (d, J = 2 Hz, 1H), 7.54 (dd, J = 2,8 Hz, 1H), 7.27 (d, J = 8 Hz, 1H), 7.11 (s, 1H), 3.74 (s, 3H), 2.73 (s, 3H), 2.65 (s, 3H), 2.45 (s, 3H), 2.23 (s, 3H); MS m/z 403.1 (M + 1) |
| 87 | 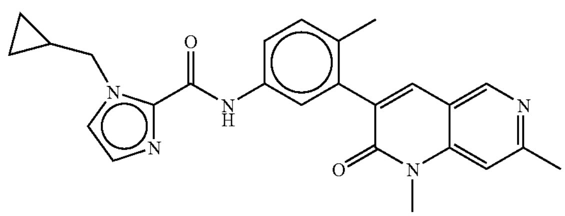 | MS m/z 428.2 (M + 1) |
| 88 | 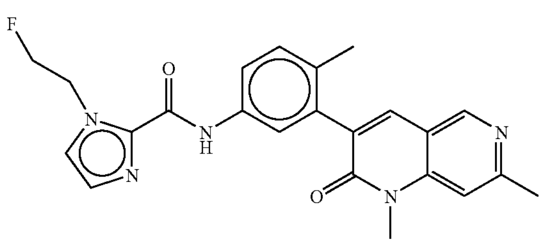 | MS m/z 420.2 (M + 1) |
| 89 | 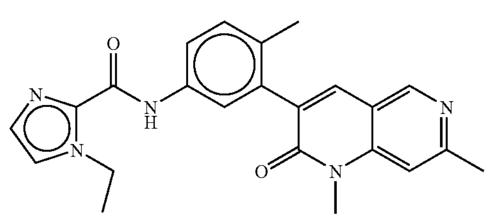 | MS m/z 402.2 (M + 1) |

TABLE 2-continued

| B# | Structure | Physical Data<br>¹H NMR 400 MHz and/or MS (m/z) |
|---|---|---|
| 90 | 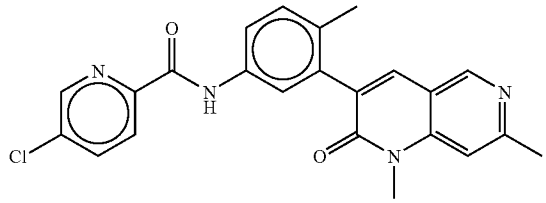 | MS m/z 419.2 (M + 1) |
| 91 | 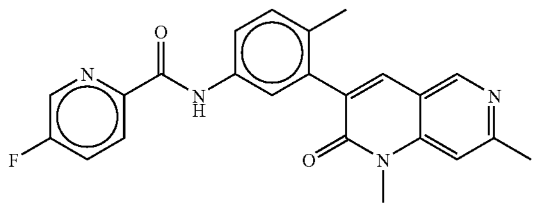 | MS m/z 403.2 (M + 1) |
| 92 | 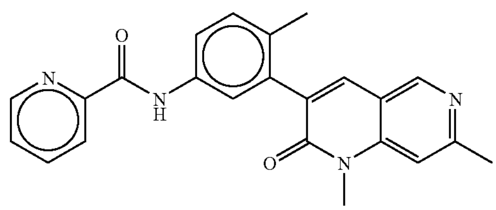 | MS m/z 385.1 (M + 1) |
| 93 | 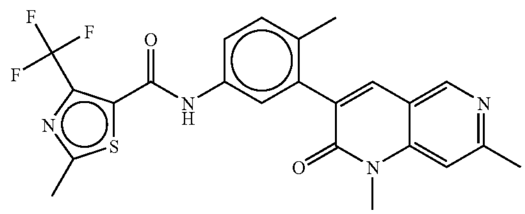 | MS m/z 473.1 (M + 1) |
| 94 | 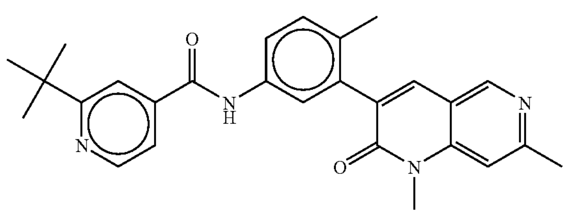 | ¹H NMR (400 MHz, CD$_3$OD) δ 9.07 (s, 1H), 8.71 (d, 1H), 8.07 (s, 1H), 8.04 (d, 1H), 7.89 (s, 1H), 7.81 (s, 1H), 7.78 (d, 1H), 7.61 (dd, 1H), 7.34 (d, 1H), 3.84 (s, 3H), 2.85 (s, 3H), 2.23 (s, 3H), 1.46 (s, 9H); MS m/z 441.2 (M + 1) |
| 95 | 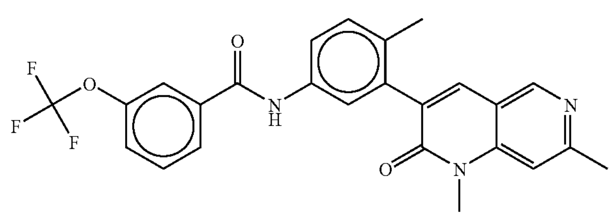 | ¹H NMR (400 MHz, CD$_3$OD) δ 9.02 (s, 1H), 8.05 (s, 1H), 7.95 (d, 1H), 7.85 (d, 1H), 7.82 (s, 1H), 7.74 (d, 1H), 7.63 (t, 1H), 7.59 (dd, 1H), 7.51 (d, 1H), 7.32 (d, 1H), 3.83 (s, 3H), 2.82 (s, 3H), 2.22 (s, 3H); MS m/z 468.1 (M + 1) |
| 96 | 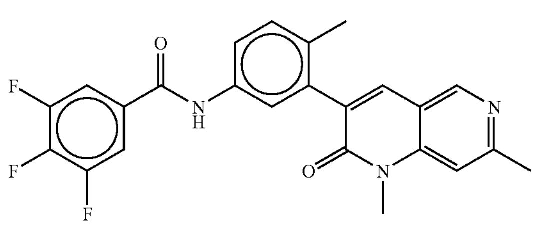 | ¹H NMR (400 MHz, CD$_3$OD) δ 9.02 (s, 1H), 8.04 (s, 1H), 7.82 (s, 1H), 7.78 (d, 1H), 7.76 (d, 1H), 7.71 (d, 1H), 7.57 (dd, 1H), 7.32 (d, 1H), 3.82 (s, 3H), 2.82 (s, 3H), 2.22 (s, 3H); MS m/z 438.1 (M + 1) |

TABLE 2-continued

| B# | Structure | Physical Data<br>¹H NMR 400 MHz and/or MS (m/z) |
|---|---|---|
| 97 | 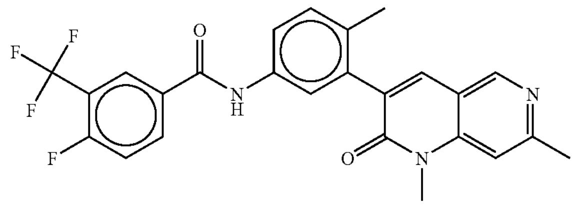 | ¹H NMR (400 MHz, CD₃OD), δ 9.03 (s, 1H), 8.31 (d, 1H), 8.27 (ddd, 1H), 8.05 (s, 1H), 7.83 (s, 1H), 7.74 (s, 1H), 7.58 (dd, 1H), 7.51 (t, 1H), 7.33 (d, 1H), 3.83 (s, 3H), 2.82 (s, 3H), 2.22 (s, 3H); MS m/z 470.1 (M + 1) |
| 98 | 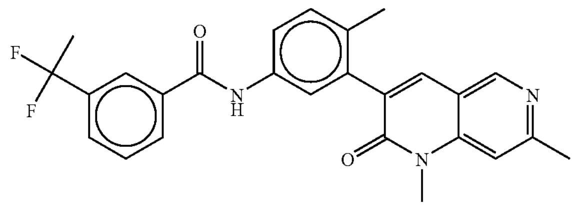 | ¹H NMR (400 MHz, CD₃OD) δ 9.01 (d, 1H), 8.11 (s, 1H), 8.05 (d, 1H), 7.76 (dd, 1H), 7.75 (s, 1H), 7.62 (t, 1H), 7.59 (dt, 1H), 7.32 (d, 1H), 3.84 (s, 3H), 2.81 (s, 3H), 2.23 (s, 3H), 1.98 (t, 3H); MS m/z 448.1 (M + 1) |
| 99 | 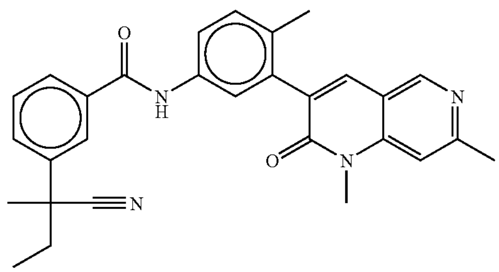 | ¹H NMR (400 MHz, CD₃OD) δ 9.07 (s, 1H), 8.06 (s, 1H), 8.03 (t, 1H), 7.89 (dd, 1H), 7.88 (s, 1H), 7.74 (d, 1H), 7.71 (ddd, 1H), 7.59 (d, 1H), 7.57 (dd, 1H), 7.32 (d, 1H), 3.83 (s, 3H), 2.84 (s, 3H), 2.22 (s, 3H), 2.05 (t, 2H), 1.78 (s, 3H), 0.97 (t, 3H); MS m/z 465.2 (M + 1) |
| 100 | 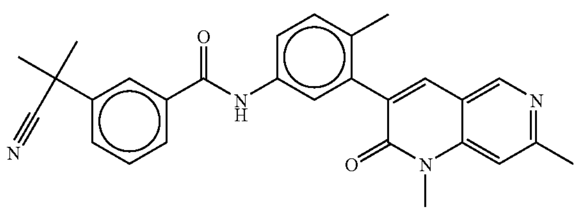 | ¹H NMR (400 MHz, CD₃OD) δ 9.04 (s, 1H), 8.08 (t, 1H), 8.06 (s, 1H), 7.89 (dd, 1H), 7.85 (s, 1H), 7.76 (ddd, 1H), 7.74 (d, 1H), 7.59 (d, 1H), 7.57 (dd, 1H), 7.32 (d, 1H), 3.83 (s, 3H), 2.83 (s, 3H), 2.22 (s, 3H), 1.79 (s, 6H); MS m/z 451.2 (M + 1) |
| 101 | 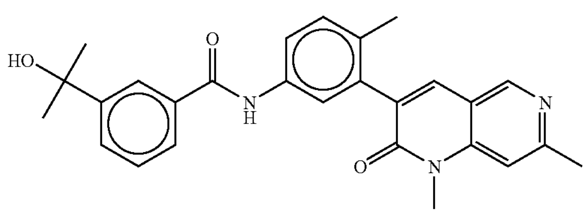 | ¹H NMR (400 MHz, CD₃OD, rotamer) δ 9.01 (s, 1H), 8.19 (t, 0.5H), 8.06 (t, 0.5H), 8.05 (s, 1H), 7.87 (d, 0.5H), 7.80 (s, 1H), 7.78 (d, 0.5H), 7.71-7.74 (m, 2H), 7.58 (dd, 1H), 7.47 (t, 1H), 7.32 (d, 1H), 3.82 (s, 3H), 2.81 (s, 3H), 2.22 (s, 3H), 1.58 (s, 3H), 1.55 (s, 3H); MS m/z 451.2 (M + 1) |
| 102 | 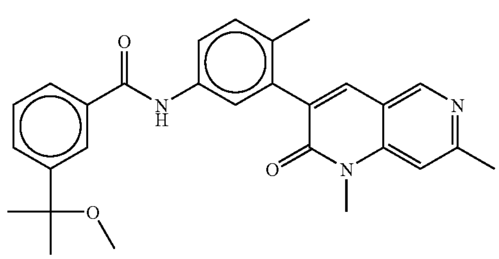 | ¹H NMR (400 MHz, CD₃OD) δ 9.03 (s, 1H), 8.05 (s, 1H), 7.98 (t, 1H), 7.89 (s, 1H), 7.82 (t, 1H), 7.73 (d, 1H), 7.65 (ddd, 1H), 7.59 (dd, 1H), 7.51 (t, 1H), 7.32 (d, 1H), 3.83 (s, 3H), 3.10 (s, 3H), 2.82 (s, 3H), 2.22 (s, 3H), 1.58 (s, 6H); MS m/z 456.2 (M + 1) |

TABLE 2-continued

| B# | Structure | Physical Data<br>¹H NMR 400 MHz and/or MS (m/z) |
|---|---|---|
| 103 | 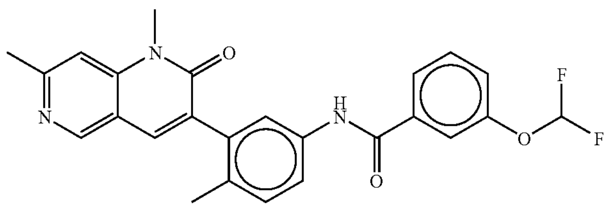 | ¹H NMR (400 MHz, CD₃OD) δ 9.02 (s, 1H), 8.05 (s, 1H), 7.83 (s, 1H), 7.79 (d, 1H), 7.72 (d, 1H), 7.70 (t, 1H), 7.58 (dd, 1H), 7.55 (t, 1H), 7.37 (dd, 1H), 7.32 (d, 1H), 6.92 (t, 1H), 3.82 (s, 3H), 2.82 (s, 3H), 2.21 (s, 3H); MS m/z 450.2 (M + 1) |
| 104 | 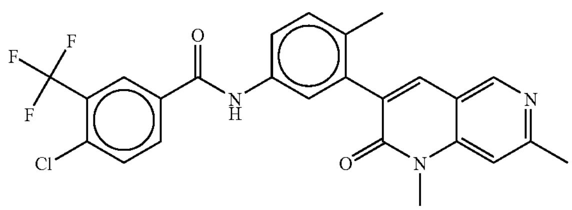 | ¹H NMR (400 MHz, CD₃OD) δ 9.01 (s, 1H), 8.34 (d, 1H), 8.17 (dd, 1H), 8.04 (s, 1H), 7.80 (s, 1H), 7.79 (d, 1H), 7.74 (d, 1H), 7.60 (dd, 1H), 7.32 (d, 1H), 3.82 (s, 3H), 2.81 (s, 3H), 2.21 (s, 3H); MS m/z 486.1 (M + 1) |
| 105 | 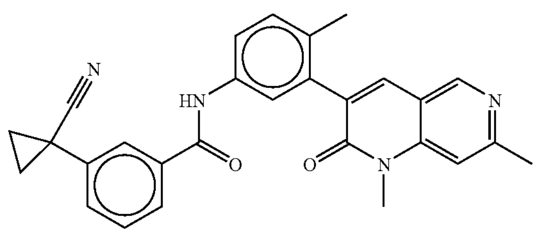 | ¹H NMR (400 MHz, CD₃OD) δ 9.00 (s, 1H), 8.04 (s, 1H), 8.00 (t, 1H), 7.87 (d, 1H), 7.86 (dd, 1H), 7.78 (d, 1H), 7.72 (s, 1H), 7.59 (dt, 1H), 7.56 (dd, 1H), 7.32 (d, 1H), 3.82 (s, 3H), 2.81 (s, 3H), 2.21 (s, 3H), 1.79 (dd, 1H), 1.66 (dd, 1H); MS m/z 449.2 (M + 1) |
| 106 | 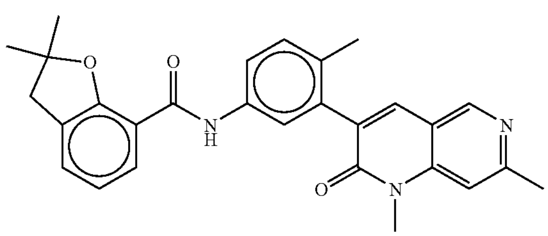 | ¹H NMR (400 MHz, CD₃OD) δ 9.01 (s, 1H), 8.05 (s, 1H), 7.82 (s, 1H), 7.79 (d, 1H), 7.71 (d, 1H), 7.51 (dd, 1H), 7.32 (d, 1H), 7.00 (t, 1H), 6.86 (t, 1H), 3.82 (s, 3H), 3.16 (s, 1H), 3.06 (s, 1H), 2.82 (s, 3H), 2.21 (s, 3H), 1.61 (s, 3H), 1.51 (s, 3H); MS m/z 454.2 (M + 1) |
| 107 | 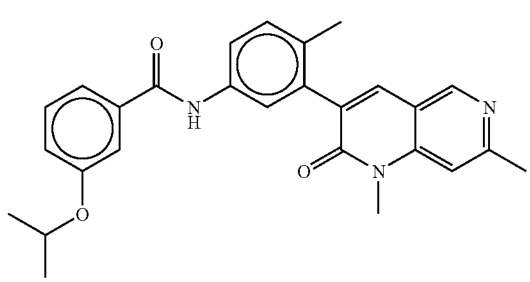 | ¹H NMR (400 MHz, CD₃OD) δ 9.02 (s, 1H), 8.04 (s, 1H), 7.79 (s, 1H), 7.71 (d, 1H), 7.59 (dd, 1H), 7.47 (dt, 1H), 7.44 (dt, 1H), 7.40 (t, 1H), 7.32 (d, 1H), 7.11 (dd, 1H), 4.69 (hept, 1H), 3.82 (s, 3H), 2.81 (s, 3H), 2.21 (s, 3H), 1.34 (d, 6H); MS m/z 442.2 (M + 1) |

TABLE 2-continued

| B# | Structure | Physical Data<br>¹H NMR 400 MHz and/or MS (m/z) |
|---|---|---|
| 108 | 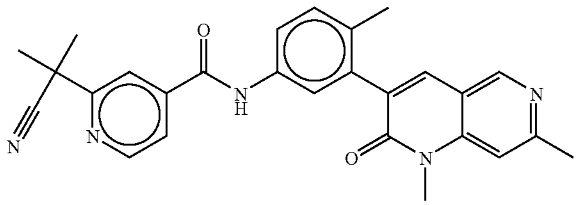 | ¹H NMR (400 MHz, CD₃OD) δ 9.03 (s, 1H), 8.77 (d, 1H), 8.05 (s, 2H), 7.83 (s, 1H), 7.80 (dd, 1H), 7.76 (d, 1H), 7.61 (dd, 1H), 7.32 (d, 1H), 3.83 (s, 3H), 2.82 (s, 3H), 2.22 (s, 3H), 1.81 (s, 6H); MS m/z 452.2 (M + 1) |
| 109 | 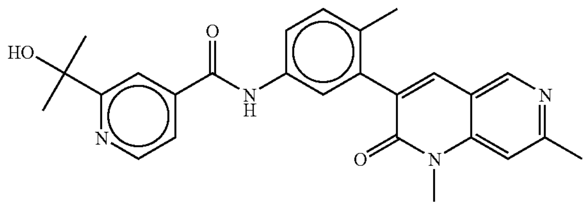 | ¹H NMR (400 MHz, CD₃OD) δ 9.07 (s, 1H), 8.71 (d, 1H), 8.28 (d, 1H), 8.07 (s, 1H), 7.89 (d, 2H), 7.79 (d, 1H), 7.62 (t, 1H), 7.32 (d, 1H), 3.84 (s, 3H), 2.84 (s, 3H), 2.23 (s, 3H), 1.63 (s, 6H); MS m/z 443.2 (M + 1) |
| 110 | 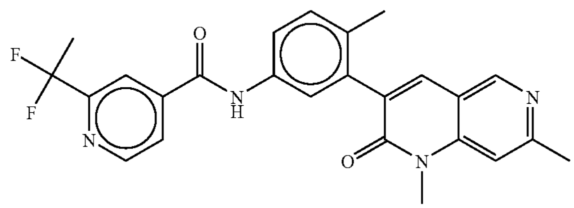 | ¹H NMR (400 MHz, CD₃OD) δ 9.01 (s, 1H), 8.81 (d, 1H), 8.17 (s, 1H), 8.05 (s, 1H), 7.95 (dd, 1H), 7.80 (s, 1H), 7.78 (d, 1H), 7.61 (dd, 1H), 7.34 (d, 1H), 3.84 (s, 3H), 2.81 (s, 3H), 2.22 (s, 3H), 2.04 (t, 3H); MS m/z 449.1 (M + 1) |

EXAMPLE 4

N-[4-Methyl-3-(7-methyl-2-oxo-1-phenyl-1,2-dihydro-[1,6]naphthyridin-3-yl)-phenyl]-3-(4-methyl-piperazin-1-yl)-5-trifluoromethyl-benzamide (C1)

General Procedure C

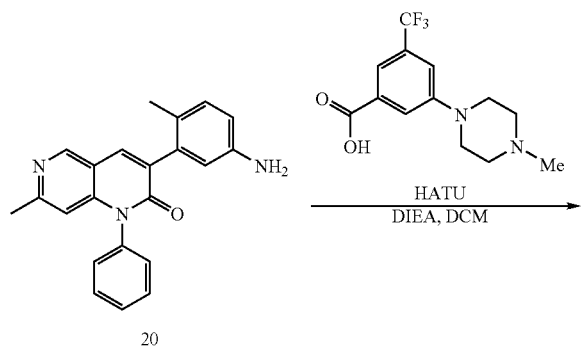

To a solution of amine 20 (18.7 mg, 0.0548 mmol) and 3-(trifluoromethyl)-5-(4-methylpiperazin-1-yl)benzoic acid (21.4 mg, 0.065 mmol) in DCM (1 mL) and DMF (0.3 mL) are added di-isopropylethylamine (28 μL, 0.16 mmol) and HATU (21 mg, 0.082 mmol). The mixture is stirred at rt overnight. Solvent is removed in vacuo and the crude product is purified using flash chromatography (hexane:ethyl acetate=2:1) to give C1. ¹H NMR (400 MHz, DMSO-d₆) δ 10.36 (s, 1H), 8.88 (s, 1H), 8.11 (s, 1H), 7.70-7.73 (m, 3H), 7.58-7.67 (m, 4H), 7.40-7.42 (m, 2H), 7.36 (s, 1H), 7.27 (d, 1H), 6.31 (s, 1H), 3.25-3.30 (m, 4H), 2.3-2.50 (m, 4H), 2.40 (s, 3H), 2.21 (s, 3H), 2.18 (s, 3H).

Compounds of structure of type C can also be made with the same procedure using other N-substituted naphthyridinones, which can be synthesized according to Scheme 4. Table 3 describes compounds prepared following procedures described in Example 4, using appropriate reagents.

TABLE 3

| C# | Structure | Physical Data<br>¹H NMR 400 MHz and/or MS (m/z) |
|---|---|---|
| 1 | 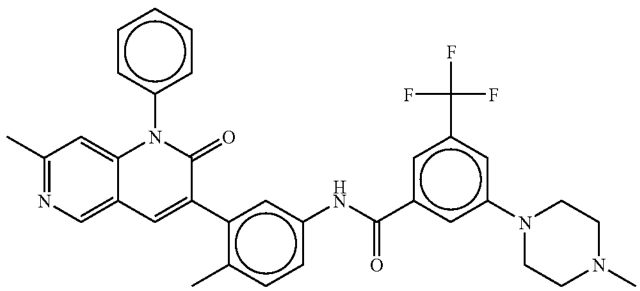 | ¹H NMR (400 MHz, DMSO-d₆) δ 10.36 (s, 1H), 8.88 (s, 1H), 8.11 (s, 1H), 7.70-7.73 (m, 3H), 7.58-7.67 (m, 4H), 7.40-7.42 (m, 2H), 7.36 (s, 1H), 7.27 (d, 1H), 6.31 (s, 1H), 3.25-3.30 (m, 4H), 2.3-2.50 (m, 4H), 2.40 (s, 3H), 2.21 (s, 3H), 2.18 (s, 3H); MS m/z 612.3 (M + 1) |
| 2 | 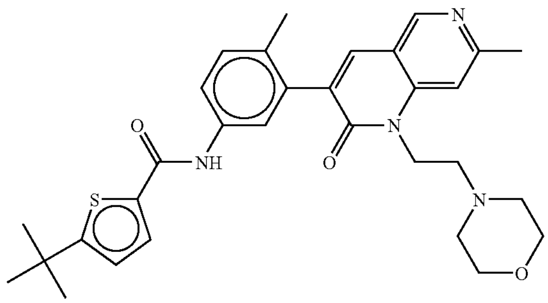 | ¹H NMR 400 MHz (Acetone-d6) δ 9.16 (s, 1H), 8.22 (s, 1H), 8.12 (s, 1H), 7.82 (d, 1H), 7.74 (d, 1H), 7.52 (dd, 1H), 7.21 (d, 1H), 6.96 (d, 1H), 4.95 (m, 2H), 4.01 (m, 4H), 3.65 (m, 2H), 2.83 (s, 3H), 2.19 (s, 1H), 2.07 (m, 4H), 1.40 (s, 9H); MS m/z 545.3 (M + 1) |
| 3 | 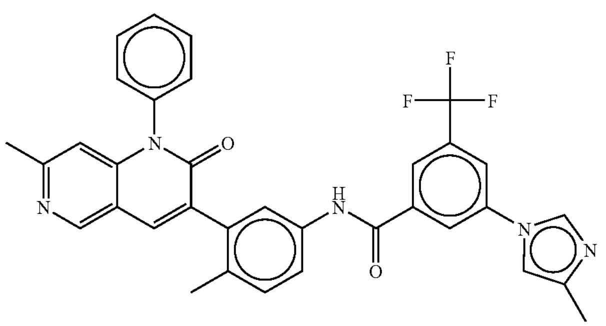 | ¹H NMR (400 MHz, CDCl₃) δ 8.97 (brs, 1H), 8.67 (s, 1H), 8.10 (s, 1H), 8.07 (s, 1H), 7.80 (brs, 1H), 7.78 (s, 1H), 7.68 (brs, 1H), 7.43-7.52 (m, 4H), 7.15-7.20 (m, 3H), 7.09 (s, 1H), 6.37 (s, 1H), 2.48 (s, 3H), 2.22 (s, 3H) 2.18 (s, 3H); MS m/z 594.2 (M + 1) |
| 4 | 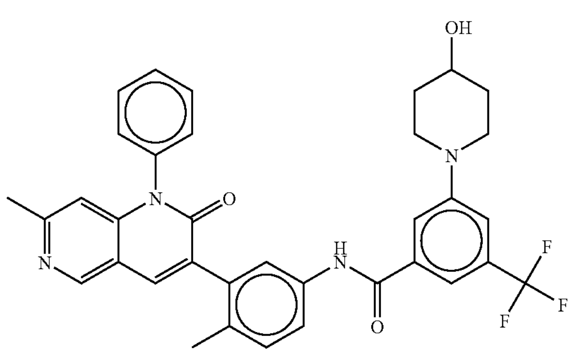 | ¹H NMR (400 MHz, DMSO-d₆) δ 10.34 (s, 1H), 8.88 (s, 1H), 8.11 (s, 1H), 7.70-7.71 (m, 3H), 7.63-7.67 (m, 2H), 7.59 (d, 1H), 7.56 (s, 1H), 7.42 (d, 2H), 7.34 (s, 1H), 7.27 (d, 1H), 6.30 (s, 1H), 4.75 (d, 1H), 3.64-3.73 (m, 2H), 2.99-3.03 (m, 2H), 2.41 (s, 3H), 2.18 (s, 3H), 1.82-1.85 (m, 2H), 1.42-1.51 (m, 2H); MS m/z 613.2 (M + 1) |

TABLE 3-continued

| C# | Structure | Physical Data<br>¹H NMR 400 MHz and/or MS (m/z) |
|---|---|---|
| 5 | 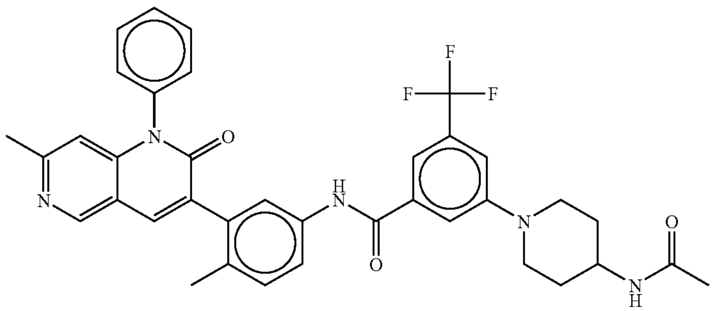 | ¹H NMR (400 MHz, CD₃OD) δ 8.83 (s, 1H), 8.10 (s, 1H), 7.59-7.71 (m, 6H), 7.35-7.38 (m, 3H), 7.28 (d, 1H), 6.50 (s, 1H), 3.80-3.89 (m, 3H), 2.92-3.02 (m, 2H), 2.47 (s, 3H), 2.26 (s, 3H), 1.95-2.02 (m, 2H), 1.94 (s, 3H), 1.55-1.65 (m, 2H); MS m/z 654.3 (M + 1) |
| 6 | 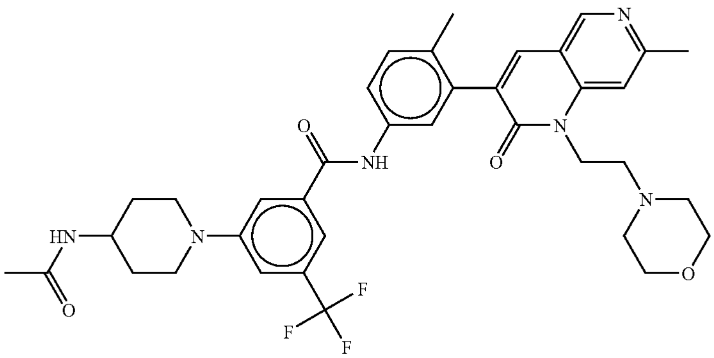 | ¹H NMR (400 MHz, DMSO-d₆) δ 10.35 (s, 1H), 8.81 (s, 1H), 7.97 (s, 1H), 7.84 (d, 1H), 7.76 (s, 1H), 7.63 (d, 1H), 7.59 (s, 1H), 7.46 (s, 1H), 7.37 (s, 1H), 7.27 (d, 1H), 4.39-4.40 (m, 2H), 3.52-3.53 (m, 5H), 2.93-2.99 (m, 4H), 2.61 (s, 3H), 2.60-2.61 (m, 2H), 2.41 (q, 2H), 2.14 (s, 3H), 1.81-1.86 (m, 2H), 1.44-1.47 (m, 2H); MS m/z 691.3 (M + 1) |
| 7 | 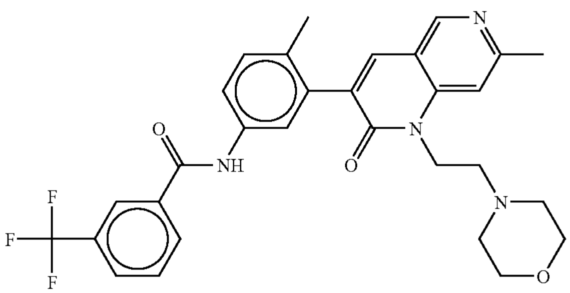 | ¹H NMR 400 MHz (Acetone-d6) δ 9.91 (s, 1H), 9.21 (s, 1H), 8.30 (d, 1H), 8.22 (s, 1H), 7.94 (m, 2H), 7.78 (t, 1H), 7.66 (dd, 1H), 7.29 (d, 1H), 5.00 (m, 2H), 4.02 (m, 4H), 3.71 (m, 2H), 2.86 (s, 3H), 2.24 (s, 3H), 2.07 (m, 4H); MS m/z 551.2 (M + 1) |
| 8 | 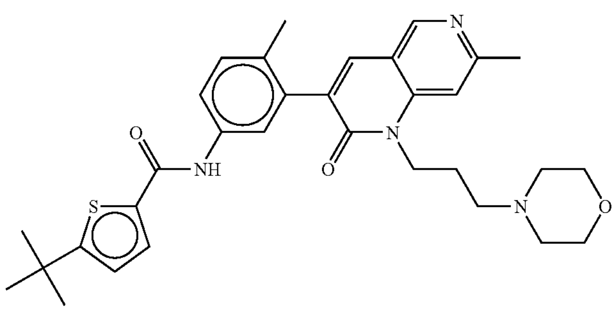 | ¹H NMR 400 MHz (Acetone-d6) δ 9.19 (s, 1H), 8.18 (s, 1H), 8.09 (s, 1H), 7.84 (d, 2H), 7.75 (d, 1H), 7.63 (dd, 1H), 7.25 (d, 1H), 6.97 (d, 1H), 4.60 (m, 2H), 4.03 (d, 2H), 3.87 (t, 2H), 3.57 (d, 2H), 3.47 (t, 2H), 3.18 (t, 2H), 2.87 (s, 3H), 2.45 (m, 2H), 2.21 (s, 3H), 1.40 (s, 9H); MS m/z 559.3 (M + 1) |

TABLE 3-continued

| C# | Structure | Physical Data<br>¹H NMR 400 MHz and/or MS (m/z) |
|---|---|---|
| 9 | 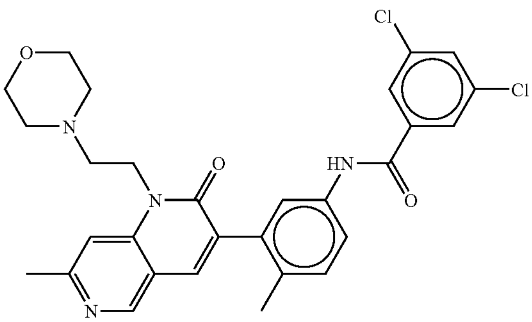 | ¹H NMR 400 MHz (Acetone-d6) δ 9.16 (s, 1H), 8.20 (s, 1H), 8.16 (s, 1H), 7.91 (m, 3H), 7.67 (t, 1H), 7.61 (dd, 1H), 7.25 (d, 1H), 4.97 (m, 2H), 4.00 (m, 4H), 3.67 (m, 2H), 2.84 (s, 3H), 2.18 (s, 3H), 2.07 (m, 4H); MS m/z 551.2 (M + 1) |
| 10 | 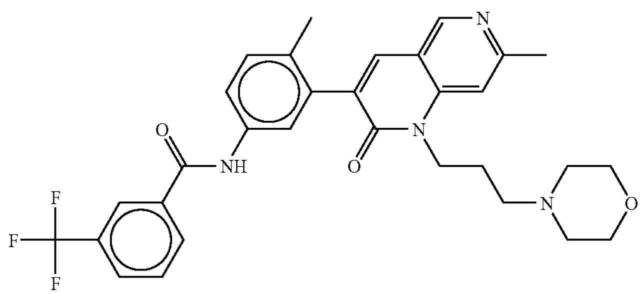 | ¹H NMR 400 MHz (Acetone-d6) δ 9.22 (s, 1H), 8.30 (m, 2H), 8.21 (s, 1H), 8.10 (s, 1H), 7.94 (m, 2H), 7.78 (t, 1H), 7.69 (dd, 1H), 7.29 (d, 1H), 4.61 (m, 2H), 4.03 (d, 2H), 3.88 (t, 2H), 3.57 (d, 2H), 3.47 (t, 2H), 3.20 (t, 2H), 2.88 (s, 3H), 2.47 (m, 2H), 2.23 (s, 3H); MS m/z 565.2 (M + 1) |
| 11 | 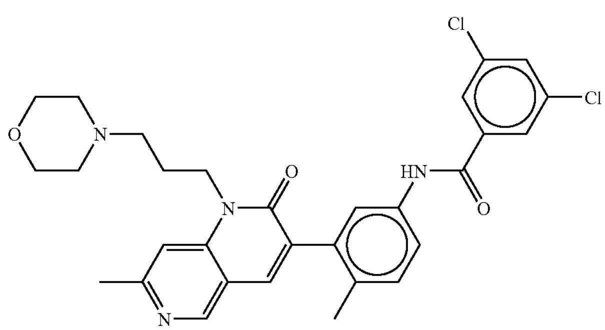 | ¹H NMR 400 MHz (Acetone-d6) δ 9.19 (s, 1H), 8.18 (s, 1H), 8.09 (s, 1H), 7.94 (d, 2H), 7.90 (d, 1H), 7.68 (d, 1H), 7.66 (dd, 1H), 7.27 (d, 1H), 4.60 (m, 2H), 4.03 (d, 2H), 3.88 (t, 2H), 3.55 (d, 2H), 3.48 (t, 2H), 3.18 (t, 2H), 2.88 (s, 3H), 2.45 (m, 2H), 2.21 (s, 3H); MS m/z 565.2 (M + 1) |
| 12 | 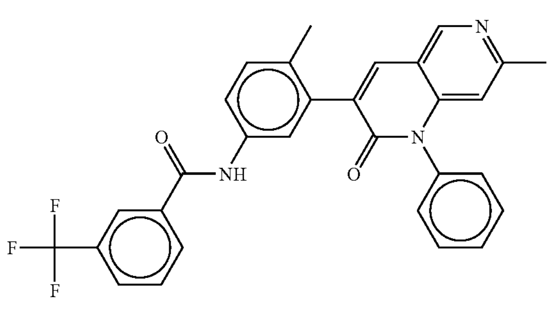 | ¹H NMR (400 MHz, CDCl₃) δ 8.71 (brs, 1H), 8.27 (s, 1H), 8.04 (s, 1H), 7.95 (d, 1H), 7.73 (s, 1H), 7.69 (d, 1H), 7.46-7.59 (m, 6H), 7.36-7.40 (m, 2H), 7.21 (d, 2H), 7.18 (d, 1H), 6.38 (brs, 1H), 2.42 (s, 3H), 2.14 (s, 3H); MS m/z 514.2 (M + 1) |

TABLE 3-continued

| C# | Structure | Physical Data<br>¹H NMR 400 MHz and/or MS (m/z) |
|---|---|---|
| 13 | 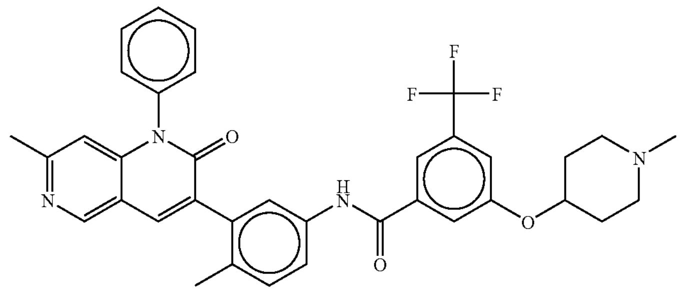 | ¹H NMR (400 MHz, DMSO-d₆) δ 10.42 (s, 1H), 8.88 (s, 1H), 8.11 (s, 1H), 7.84 (s, 1H), 7.79 (s, 1H), 7.74 (d, 1H), 7.70 (dd, 1H), 7.60-7.67 (, 2H), 7.57 (d, 1H), 7.40-7.42 (m, 2H), 7.27 (d, 1H), 6.30 (s, 1H), 4.61-4.65 (m, 1H), 2.58-2.66 (m,, 2H), 2.40 (s, 3H), 2.20-2.23 (m, 2H), 2.19 (s, 3H), 2.17 (s, 3H), 1.93-1.97 (m, 2H), 1.66-1.69 (m, 2H); MS m/z 627.3 (M + 1) |
| 14 | 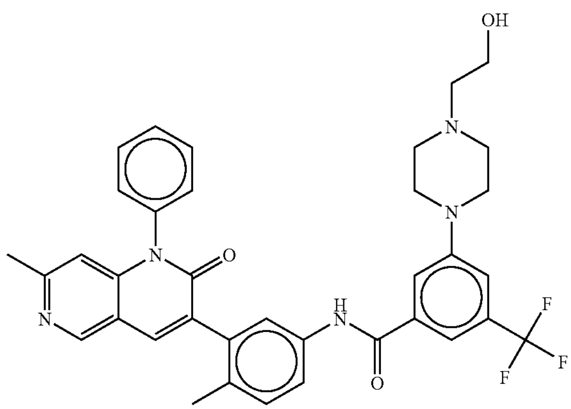 | ¹H NMR (400 MHz, DMSO-d₆) δ 10.44 (s, 1H), 8.88 (s, 1H), 8.11 (s, 1H), 7.71-7.72 (m, 3H), 7.56-7.67 (m, 4H), 7.42 (d, 1H), 7.40 (s, 1H), 7.35 (s, 1H), 7.26 (d, 1H), 6.31 (s, 1H), 3.54 (t, 2H), 3.26-3.29 (m, 2H), 2.56-2.58 (m, 4H), 2.44 (t, 4H), 2.41 (s, 3H), 2.18 (s, 3H); MS m/z 642.3 (M + 1) |

EXAMPLE 5

N-[3-(1,7-Dimethyl-2-oxo-1,2-dihydro-[1,6]naph-thyridin-3-yl)-4-methyl-phenyl]-3-piperazin-1-yl-5-trifluoromethyl-benzamide (D1)

General Procedure D

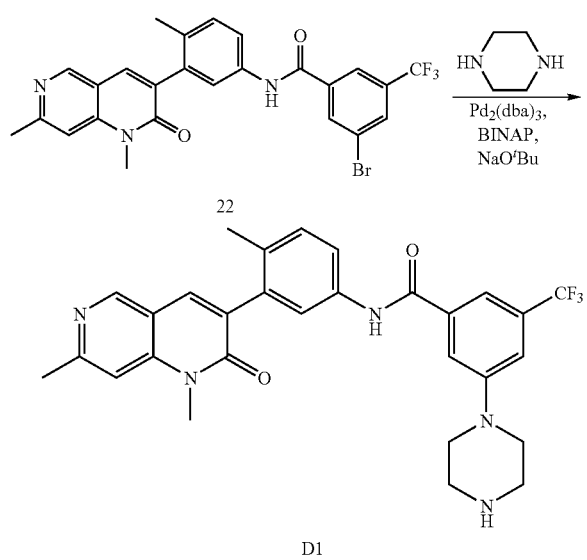

A sealed tube is charged with 3-bromo-N-[3-(1,7-dimethyl-2-oxo-1,2-dihydro-[1,6]naphthyridin-3-yl)-4-methyl-phenyl]-5-trifluoromethyl-benzamide 22 (25 mg, 0.047 mmol), piperazine (4.9 mg, 0.056 mmol), Pd₂(dba)₃ (4.3 mg, 0.0047 mmol), sodium tert-butoxide (6.3 mg, 0.066 mmol), BINAP (5.9 mg, 0.094 mmol), and toluene (0.30 mL) under nitrogen atmosphere. The sealed tube is heated in an oil bath at 80° C. for 16 h. The solvent is removed in vacuo. The residue is dissolved in DMSO (2 mL) and purified by preparative LCMS to give product D1 as a white solid. ¹H NMR (400 MHz, MeOD) δ 8.67 (s, 1H), 7.86 (s, 1H), 7.63 (s, 1H), 7.57-7.52 (m, 3H), 7.38 (s, 1H), 7.29 (s, 1H), 7.20 (d, J=7.7 Hz, 1H), 3.67 (s, 3H), 3.28-3.26 (m, 4H), 3.03-3.02 (m, 4H), 2.60 (s, 3H), 2.10 (s, 3H), 1.82 (s, 3H).

Table 4 describes compounds prepared following procedures described in Example 5, using appropriate reagents.

TABLE 4
| D# | Structure | Physical Data<br>$^1$H NMR 400 MHz and/or MS (m/z) |
|---|---|---|
| 1 | 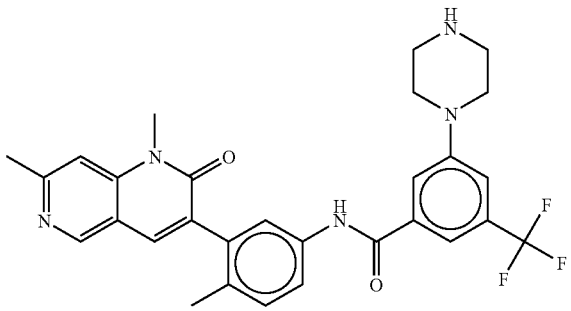 | $^1$H NMR 400 MHz (MeOD) δ 8.67 (s, 1H), 7.86 (s, 1H), 7.63 (s, 1H), 7.57-7.52 (m, 3H), 7.38 (s, 1H), 7.29 (s, 1H), 7.20 (d, 1H), 3.67 (s, 3H), 3.28-3.26 (m, 4H), 3.03-3.02 (m, 4H), 2.60 (s, 3H), 2.10 (s, 3H), 1.82 (s, 3H); MS m/z 536.2 (M + 1) |
| 2 | 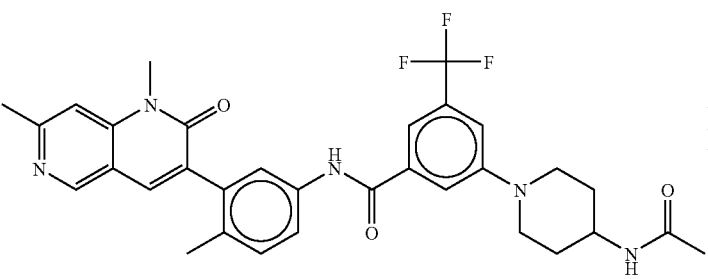 | $^1$H NMR 400 MHz (MeOD) δ 8.67 (s, 1H), 7.86 (s, 1H), 7.62 (s, 1H), 7.55 (dd, 1H), 7.51 (d, 2H), 7.38 (s, 1H), 7.25 (s, 1H), 7.19 (d, 1H), 3.78-3.75 (m, 3H), 3.67 (s, 3H), 2.90 (t, 2H), 2.59 (s, 3H), 2.10 (s, 3H), 1.91-1.86 (m, 2H), 1.84 (s, 3H), 1.55-1.46 (m, 2H); MS m/z 592.3 (M + 1) |
| 3 | 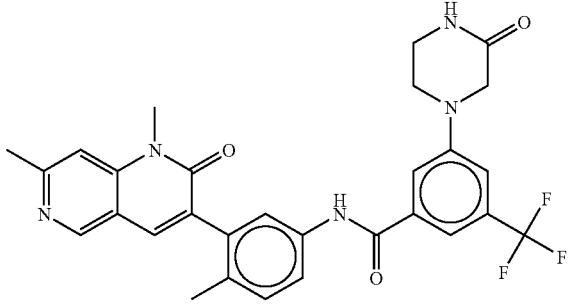 | $^1$H NMR 400 MHz (MeOD) δ 8.68 (s, 1H), 7.87 (s, 1H), 7.60-7.53 (m, 4H), 7.38 (s, 1H), 7.25 (s, 1H), 7.21 (d, 1H), 3.90 (s, 2H), 3.67 (s, 3H), 3.54 (t, 2H), 3.41 (t, 2H), 2.60 (s, 3H), 2.11 (s, 3H); MS m/z 550.2 (M + 1) |
| 4 | 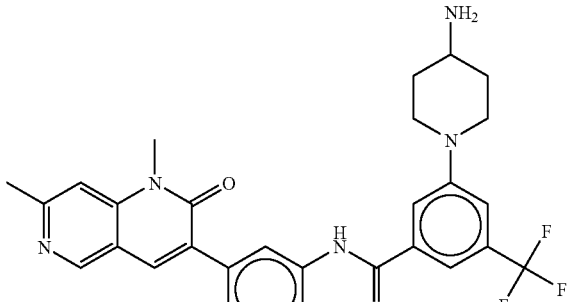 | $^1$H NMR 400 MHz (MeOD) δ 9.03 (s, 1H), 8.05 (s, 1H), 7.83 (s, 1H), 7.75-7.73 (m, 2H), 7.66 (s, 1H), 7.61 (d, 1H), 7.42 (s, 1H), 7.33 (d, 1H), 4.04-3.99 (m, 2H), 3.83 (s, 3H), 3.03-2.96 (m, 2H), 2.83 (s, 3H), 2.22 (s, 3H), 2.15-2.11 (m, 2H), 1.80-1.71 (m, 2H); MS m/z 550.2 (M + 1) |

EXAMPLE 6

N-[4-Methyl-3-(1-methyl-2-oxo-7-propyl-1,2-dihydro-[1,6]naphthyridin-3-yl)-phenyl]-3-trifluoromethyl-benzamide (E2)

General Procedure E

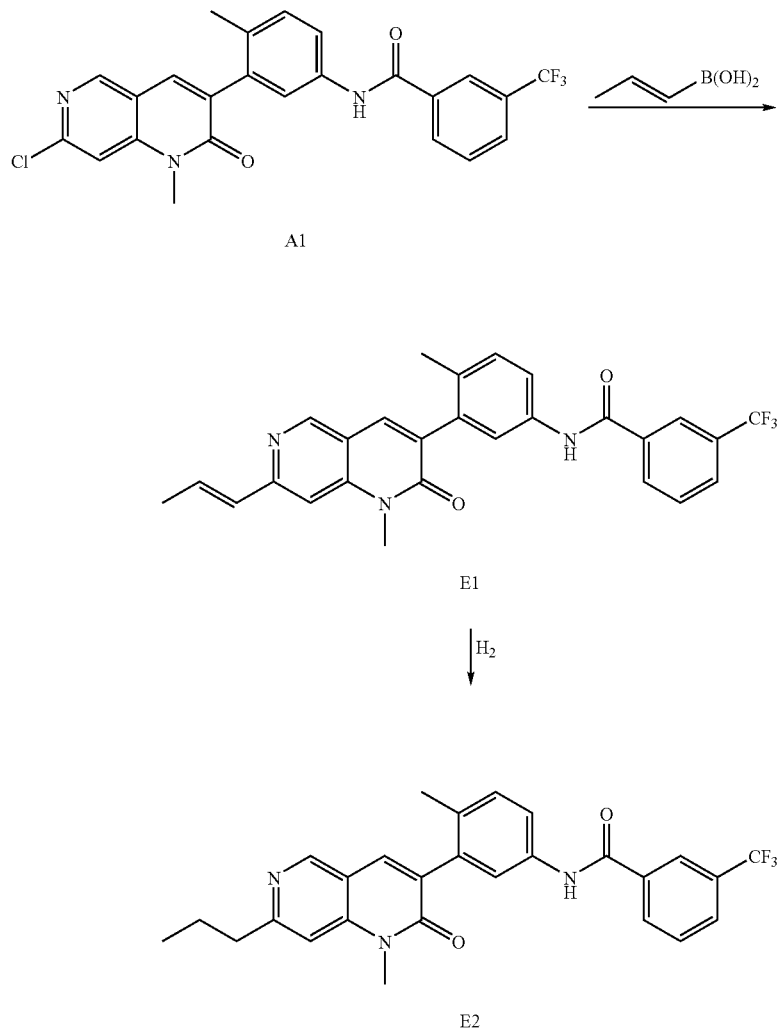

A suspension of N-[3-(7-chloro-1-methyl-2-oxo-1,2-dihydro-[1,6]naphthyridin-3-yl)-4-methyl-phenyl]-3-trifluoromethyl-benzamide A1 (35.4 mg, 0.075 mmol), trans-propenyl-boronic acid (9.7 mg, 0.113 mmol), PdCl$_2$(PPh$_3$)$_2$ (5.3 mg, 0.0075 mmol), and Na$_2$CO$_3$ (55.6 mg, 0.525 mmol) in a mixture of THF and water (4:1, 0.75 mL) is degassed with nitrogen and heated at 90° C. for 16 h. The solvent is removed in vacuo. The residue is purified by preparative LCMS to give the desired product E1 as a white solid. $^1$H NMR (400 MHz, MeOD) δ 8.97 (s, 1H), 8.26 (s, 1H), 8.21 (d, J=7.6 Hz, 1H), 8.04 (s, 1H), 7.90 (d, J=7.2 Hz, 1H), 7.84 (s, 1H), 7.76-7.73 (m, 2H), 7.61 (d, J=5.4 Hz, 1H), 7.33 (d, J=8.1 Hz, 1H), 7.18-7.12 (m, 1H), 6.73 (d, J=15.9 Hz, 1H), 3.84 (s, 3H), 2.23 (s, 3H), 2.10 (d, J=6.8 Hz, 3H).

To a solution of N-[4-methyl-3-(1-methyl-2-oxo-7-propenyl-1,2-dihydro-[1,6]naphthyridin-3-yl)-phenyl]-3-trifluoromethyl-benzamide E1 (12 mg, 0.025 mmol) in MeOH (2 mL) is added 10% palladium on active carbon (wet, 12 mg). The resulting mixture is stirred under hydrogen at rt for 1 h. The Pd/C is filtered off, and the filtrate is concentrated. The residue is purified by preparative LCMS to give the desired product E2 as a white solid. $^1$H NMR (400 MHz, DMSO-d$_6$) δ 10.48 (s, 1H), 8.84 (s, 1H), 8.31 (s, 1H), 8.27 (d, J=8.0 Hz, 1H), 7.98 (s, 1H), 7.96 (d, J=8.0 Hz, 1H), 7.79 (t, J=7.7 Hz, 1H), 7.73 (dd, J=8.5, 2.2 Hz, 1H), 7.67 (s, 1H), 7.41 (s, 1H), 7.29 (d, J=8.5 Hz, 1H), 3.67 (s, 3H), 2.84 (t, J=7.5 Hz, 2H), 2.14 (s, 3H), 1.78 (q, J=7.5 Hz, 3H), 0.96 (t, J=7.3 Hz, 3H).

Table 5 describes compounds prepared following procedures described in Example 6, using appropriate reagents.

TABLE 5

| E# | Structure | Physical Data<br>¹H NMR 400 MHz and/or MS (m/z) |
|----|-----------|---------------------------------------------------|
| 1 | 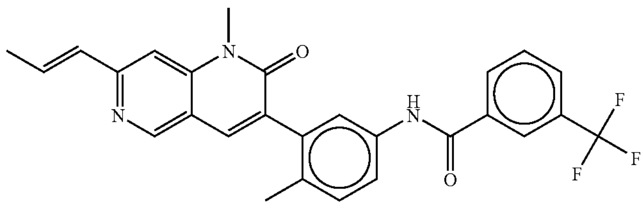 | ¹H NMR 400 MHz (MeOD) δ 8.97 (s, 1H), 8.26 (s, 1H), 8.21 (d, 1H), 8.04 (s, 1H), 7.90 (d, 1H), 7.84 (s, 1H), 7.76-7.73 (m, 2H), 7.61 (d, 1H), 7.33 (d, 1H), 7.18-7.12 (m, 1H), 6.73 (d, 1H), 3.84 (s, 3H), 2.23 (s, 3H), 2.10 (d, 3H); MS m/z 478.2 (M + 1) |
| 2 | 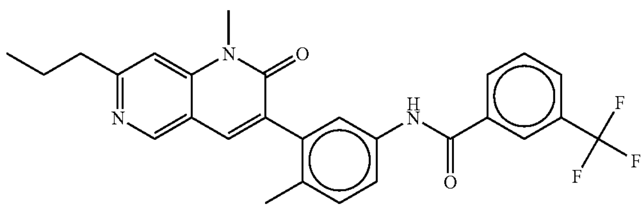 | ¹H NMR 400 MHz (DMSO-$d_6$) δ 10.48 (s, 1H), 8.84 (s, 1H), 8.31 (s, 1H), 8.27 (d, 1H), 7.98 (s, 1H), 7.96 (d, 1H), 7.79 (t, 1H), 7.73 (dd, 1H), 7.67 (s, 1H), 7.41 (s, 1H), 7.29 (d, 1H), 3.67 (s, 3H), 2.84 (t, 2H), 2.14 (s, 3H), 1.78 (q, 3H), 0.96 (t, 3H); MS m/z 480.2 (M + 1) |
| 3 | 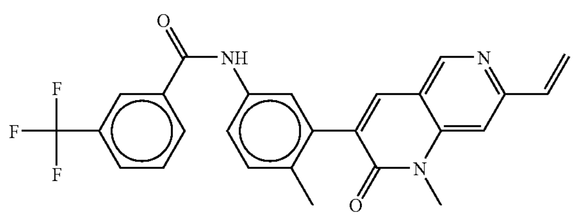 | MS m/z 464.2 (M + 1) |
| 4 | 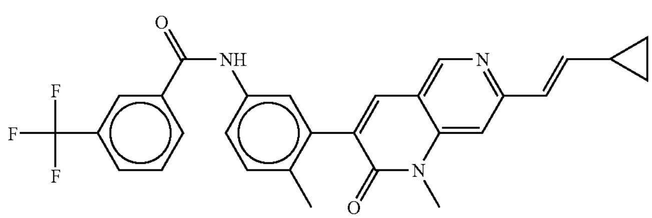 | ¹H NMR 400 MHz (DMSO-$d_6$) δ 10.40 (s, 1H), 8.73 (s, 1H), 8.23 (s, 1H), 8.19 (d, 1H), 7.90 (d, 1H), 7.88 (s, 1H), 7.72 (t, 1H), 7.65 (dd, 1H), 7.60 (d, 1H), 7.33 (s, 1H), 7.21 (d, 1H), 6.65 (d, 1H), 6.46 (dd, 1H), 3.59 (s, 3H), 2.07 (s, 3H), 1.64-1.58 (m, 1H), 0.85-0.82 (m, 2H), 0.58-0.56 (m, 2H); MS m/z 504.2 (M + 1) |
| 5 | 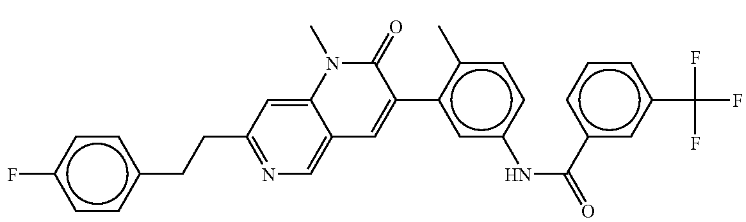 | ¹H NMR 400 MHz (DMSO-$d_6$) δ 10.50 (s, 1H), 8.96-8.92 (m, 1H), 8.30 (s, 1H), 8.27 (dd, 1H), 8.02 (s, 1H), 7.98 (d, 1H), 7.80 (t, 1H), 7.72-7.70 (m, 2H), 7.34-7.29 (m, 3H), 7.13 (t, 2H), 3.66 (s, 3H), 3.23-3.18 (m, 2H), 3.12-3.06 (m, 2H), 2.15 (s, 3H); MS m/z 560.2 (M + 1) |
| 6 | 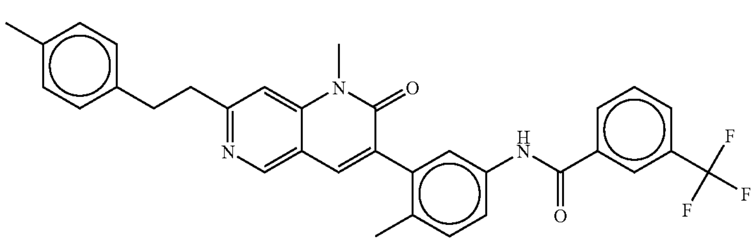 | ¹H NMR 400 MHz (DMSO-$d_6$) δ 10.42 (s, 1H), 8.79 (s, 1H), 8.23 (s, 1H), 8.19 (d, 1H), 7.92 (s, 1H), 7.90 (d, 1H), 7.72 (t, 1H), 7.64 (dd, 1H), 7.60 (d, 1H), 7.36 (s, 1H), 7.21 (d, 1H), 7.10 (d, 2H), 7.03 (d, 2H), 3.57 (s, 3H), 3.10-3.06 (m, 2H), 2.98-2.94 (m, 2H), 2.20 (s, 3H), 2.07 (s, 3H); MS m/z 556.2 (M + 1) |

TABLE 5-continued

| E# | Structure | Physical Data<br>¹H NMR 400 MHz and/or MS (m/z) |
|---|---|---|
| 7 | 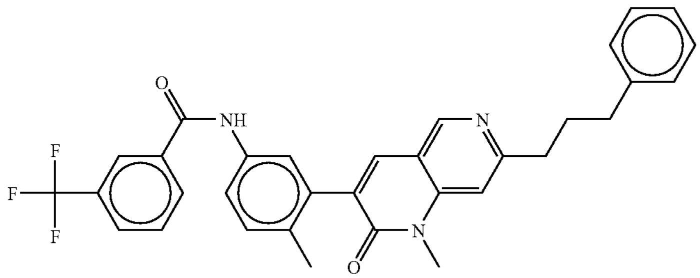 | MS m/z 556.2 (M + 1) |
| 8 | 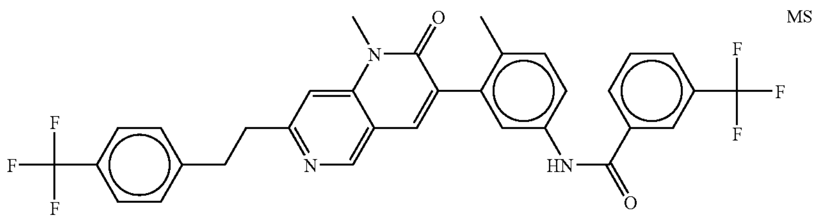 | MS m/z 610.2 (M + 1) |
| 9 | 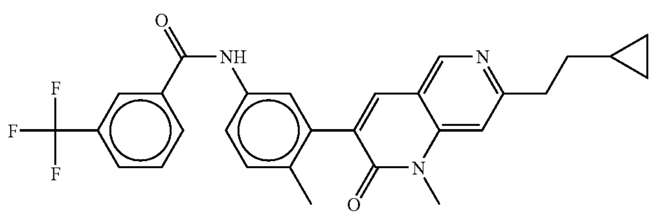 | ¹H NMR 400 MHz (DMSO-d₆) δ 10.41 (s, 1H), 8.76 (s, 1H), 8.23 (s, 1H), 8.19 (d, 1H), 7.90 (s, 1H), 7.89 (d, 1H), 7.72 (t, 1H), 7.65 (dd, 1H), 7.59 (d, 1H), 7.35 (s, 1H), 7.21 (d, 1H), 3.59 (s, 3H), 2.87 (t, 2H), 2.06 (s, 3H), 1.59 (q, 2H), 0.73-0.66 (m, 1H), 0.37-0.33 (m, 2H), 0.03- -0.01 (m, 2H); MS m/z 506.2 (M + 1) |
| 10 | 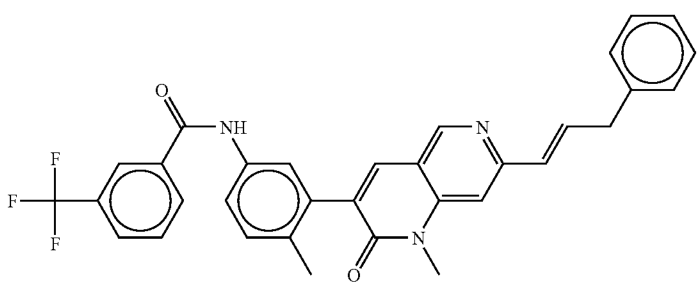 | ¹H NMR 400 MHz (DMSO-d₆) δ 10.40 (s, 1H), 8.76 (s, 1H), 8.23 (s, 1H), 8.19 (d, 1H), 7.90 (s, 1H), 7.89 (d, 1H), 7.71 (t, 1H), 7.65 (dd, 1H), 7.59 (d, 1H), 7.42 (s, 1H), 7.30-7.16 (m, 6H), 7.09-7.02 (m, 1H), 6.60 (d, 1H), 3.60 (s, 3H), 3.56 (d, 2H), 2.07 (s, 3H); MS m/z 554.2 (M + 1) |
| 11 | 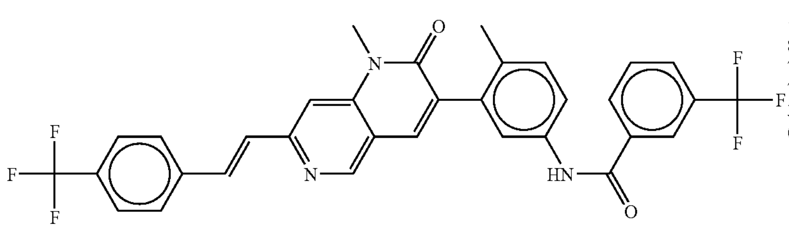 | ¹H NMR 400 MHz (MeOD) δ 9.01 (s, 1H), 8.26 (s, 1H), 8.21 (d, 1H), 8.06 (s, 1H), 7.96-7.90 (m, 5H), 7.78-7.72 (m, 4H), 7.65 (d, 1H), 7.56 (d, 1H), 7.34 (d, 1H), 3.88 (s, 3H), 2.24 (s, 3H); MS m/z 608.2 (M + 1) |
| 12 | 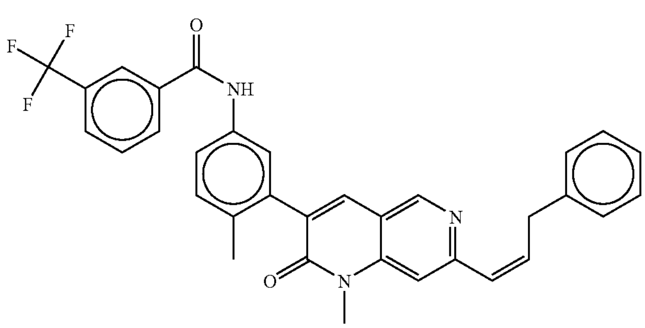 | ¹H NMR 400 MHz (MeOD) δ 10.41 (s, 1H), 8.80 (s, 1H), 8.23 (s, 1H), 8.19 (d, 1H), 7.93 (s, 1H), 7.89 (d, 1H), 7.72 (t, 1H), 7.66 (dd, 1H), 7.60 (d, 1H), 7.42-7.36 (m, 3H), 7.27-7.15 (m, 4H), 6.52 (s, 1H), 3.76-3.75 (m, 2H), 3.60 (s, 3H), 2.06 (s, 3H); MS m/z 554.2 (M + 1) |

TABLE 5-continued

| E# | Structure | Physical Data<br>¹H NMR 400 MHz and/or MS (m/z) |
|---|---|---|
| 13 | 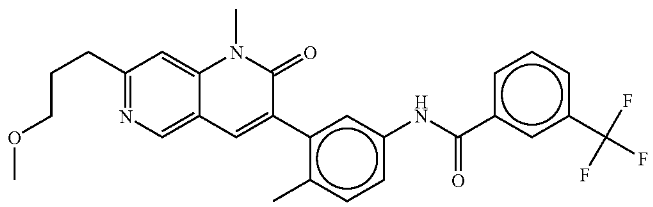 | ¹H NMR 400 MHz (DMSO-d₆) δ 10.50 (s, 1H), 8.97-8.91 (m, 1H), 8.30 (s, 1H), 8.27 (d, 1H), 8.02 (s, 1H), 7.97 (d, 1H), 7.79 (t, 1H), 7.71 (d, 1H), 7.70 (s, 1H), 7.60-7.52 (m, 1H), 7.30 (d, 1H), 3.69 (s, 3H), 3.26 (s, 3H), 2.97-2.92 (d, 2H), 2.14 (s, 3H), 2.04-1.96 (m, 2H); MS m/z 510.2 (M + 1) |
| 14 | 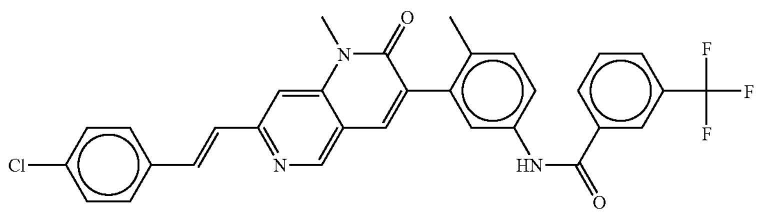 | MS m/z 574.2 (M + 1) |
| 15 | 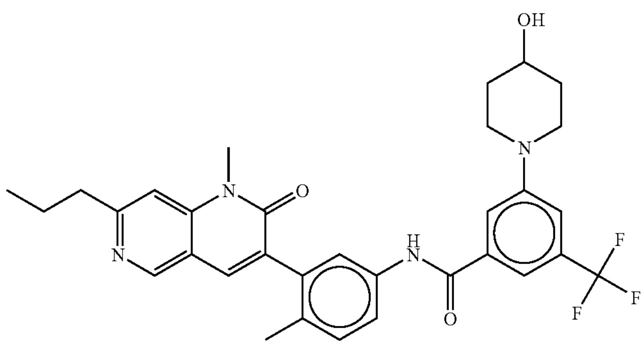 | ¹H NMR 400 MHz (DMSO-d₆) δ 10.36 (s, 1H), 9.02-8.97 (m, 1H), 8.04 (s, 1H), 7.72-7.68 (m, 3H), 7.56 (s, 1H), 7.35 (s, 1H), 7.29 (d, 1H), 3.70 (s, 3H), 3.08-2.99 (m, 2H), 2.95-2.88 (m, 2H), 2.14 (s, 3H), 1.88-1.77 (m, 4H), 1.53-1.43 (m, 2H), 0.97 (t, 3H); MS m/z 579.3 (M + 1) |
| 16 | 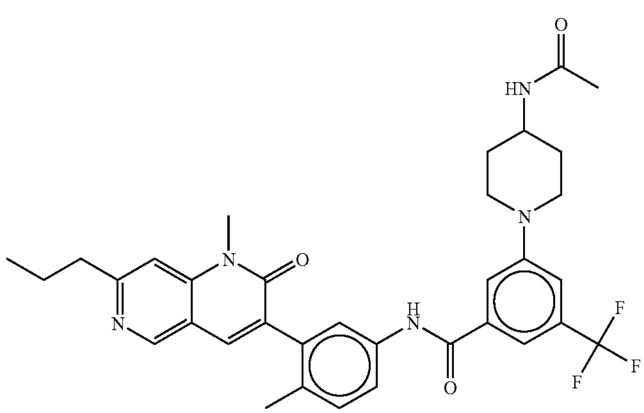 | ¹H NMR 400 MHz (DMSO-d₆) δ 10.36 (s, 1H), 8.02 (s, 1H), 7.84 (d, 1H), 7.72-7.70 (m, 2H), 7.67 (s, 1H), 7.59 (s, 1H), 7.37 (s, 1H), 7.29 (d, 1H), 3.88-3.83 (m, 2H), 3.69 (s, 3H), 3.00-2.87 (m, 4H), 2.14 (s, 3H), 1.86-1.78 (m, 4H), 1.80 (s, 3H), 1.50-1.40 (m, 2H), 0.97 (t, 3H); MS m/z 620.3 (M + 1) |
| 17 | 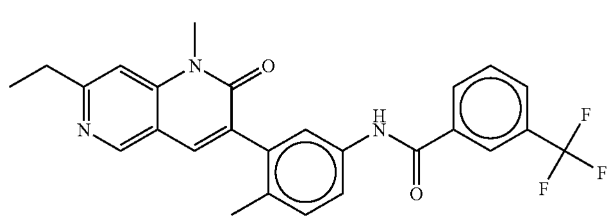 | MS m/z 466.2 (M + 1) |

TABLE 5-continued
| E# | Structure | Physical Data<br>¹H NMR 400 MHz and/or MS (m/z) |
|---|---|---|
| 18 | 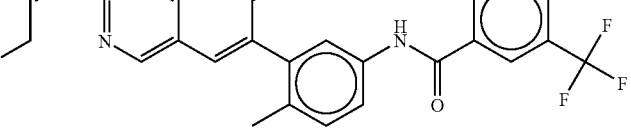 | MS m/z 508.2 (M + 1) |
| 19 | 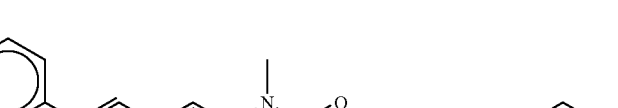 | MS m/z 554.2 (M + 1) |
| 20 | 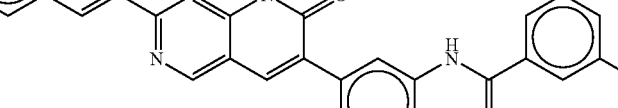 | MS m/z 508.2 (M + 1) |
| 21 | 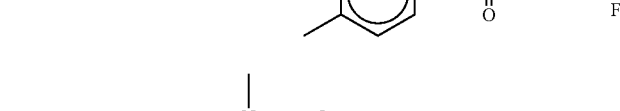 | ¹H NMR 400 MHz (DMSO-d₆) δ 10.42 (s, 1H), 8.85 (s, 1H), 8.24 (s, 1H), 8.20 (d, 1H), 7.95 (s, 1H), 7.90 (d, 1H), 7.81 (d, 1H), 7.73-7.62 (m, 5H), 7.58 (s, 1H), 7.38 (d, 1H), 7.24-7.19 (m, 3H), 3.64 (s, 3H), 2.09 (s, 3H); MS m/z 558.2 (M + 1) |
| 22 | 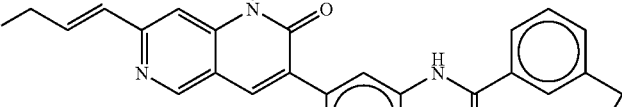 | ¹H NMR 400 MHz (MeOD) δ 8.67 (s, 1H), 7.86 (s, 1H), 7.63 (s, 1H), 7.57-7.52 (m, 3H), 7.38 (s, 1H), 7.29 (s, 1H), 7.20 (d, 1H), 3.67 (s, 3H), 3.28-3.26 (m, 4H), 3.03-3.02 (m, 4H), 2.60 (s, 3H), 2.10 (s, 3H), 1.82 (s, 3H); MS m/z 536.2 (M + 1) |
| 23 | 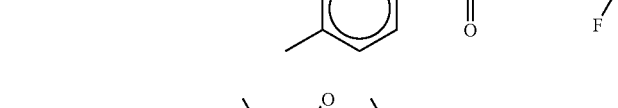 | ¹H NMR 400 MHz (MeOD) δ 8.67 (s, 1H), 7.86 (s, 1H), 7.62 (s, 1H), 7.55 (dd, 1H), 7.51 (d, 2H), 7.38 (s, 1H), 7.25 (s, 1H), 7.19 (d, 1H), 3.78-3.75 (m, 3H), 3.67 (s, 3H), 2.90 (t, 2H), 2.59 (s, 3H), 2.10 (s, 3H), 1.91-1.86 (m, 2H), 1.84 (s, 3H), 1.55-1.46 (m, 2H); MS m/z 592.3 (M + 1) |

TABLE 5-continued

| E# | Structure | Physical Data<br>¹H NMR 400 MHz and/or MS (m/z) |
|---|---|---|
| 24 | 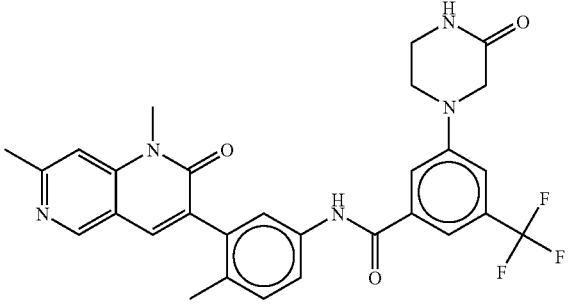 | ¹H NMR 400 MHz (MeOD) δ 8.68 (s, 1H), 7.87 (s, 1H), 7.60-7.53 (m, 4H), 7.38 (s, 1H), 7.25 (s, 1H), 7.21 (d, 1H), 3.90 (s, 2H), 3.67 (s, 3H), 3.54 (t, 2H), 3.41 (t, 2H), 2.60 (s, 3H), 2.11 (s, 3H); MS m/z 550.2 (M + 1) |
| 25 | 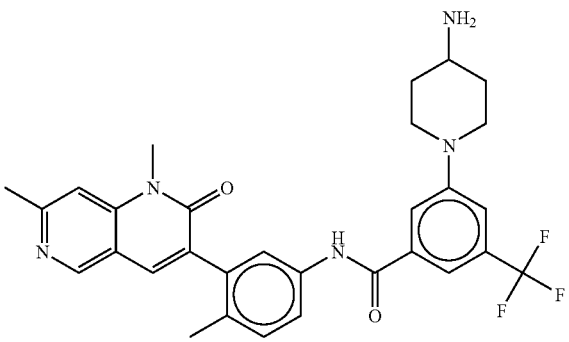 | ¹H NMR 400 MHz (MeOD) δ 9.03 (s, 1H), 8.05 (s, 1H), 7.83 (s, 1H), 7.75-7.73 (m, 2H), 7.66 (s, 1H), 7.61 (d, 1H), 7.42 (s, 1H), 7.33 (d, 1H), 4.04-3.99 (m, 2H), 3.83 (s, 3H), 3.03-2.96 (m, 2H), 2.83 (s, 3H), 2.22 (s, 3H), 2.15-2.11 (m, 2H), 1.80-1.71 (m, 2H); MS m/z 550.2 (M + 1) |
| 26 | 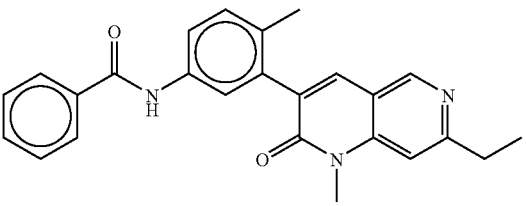 | ¹H NMR 400 MHz (MeOD) δ 9.08 (s, 1H), 8.06 (s, 1H), 7.94-7.92 (m, 2H), 7.85 (s, 1H), 7.75 (m, 1H), 7.60-7.50 (m, 4H), 7.32 (d, J = 8 Hz, 1H), 3.85 (s, 3H), 3.12 (q, J = 7.6 Hz, 2H), 2.22 (s, 3H), 1.48 (t, J = 7.6 Hz, 3H); MS m/z 398.2 (M + 1) |
| 27 | 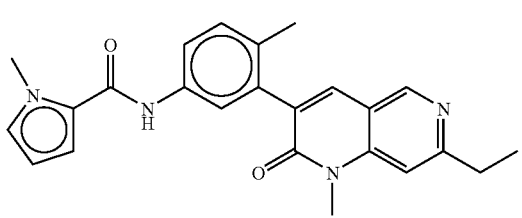 | ¹H NMR 400 MHz (MeOD) δ 9.03 (s, 1H), 8.03 (s, 1H), 7.83 (s, 1H), 7.64 (s, 1H), 7.49 (d, J = 8 Hz, 1H), 7.24 (d, J = 8 Hz, 1H), 6.92 (dd, J = 2, 8 Hz, 1H), 6.43 (d, J = 2 Hz, 1H), 6.10 (m, 1H), 3.90 (s, 3H), 3.81 (s, 3H), 3.12 (q, J = 7.6 Hz, 2H), 2.81 (s, 3H), 1.48 (t, J = 7.6 Hz, 3H); MS m/z 401.2 (M + 1) |
| 28 | 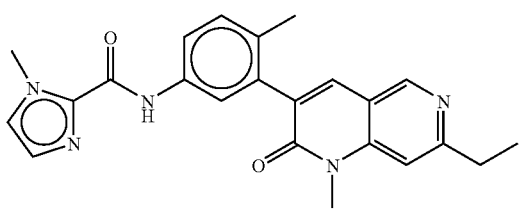 | ¹H NMR 400 MHz (MeOD) δ 9.09 (s, 1H), 8.06 (s, 1H), 7.88 (s, 1H), 7.71 (d, J = 2 Hz, 1H), 7.64 (dd, J = 2, 8 Hz, 1H), 7.46 (bs, 1H), 7.32 (d, J = 8 Hz, 1H), 7.29 (bs, 1H), 4.09 (s, 3H), 3.85 (s, 3H), 3.15 (q, J = 7.6 Hz, 2H), 2.21 (s, 3H), 1.50 (t, J = 7.6 Hz, 3H); MS m/z 402.2 (M + 1) |

EXAMPLE 7

1-(3-(1,7-dimethyl-2-oxo-1,2-dihydro-1,6-naphthyridin-3-yl)-4-methylphenyl)-3-(4-methylbenzyl)urea (F24)

General Procedure F

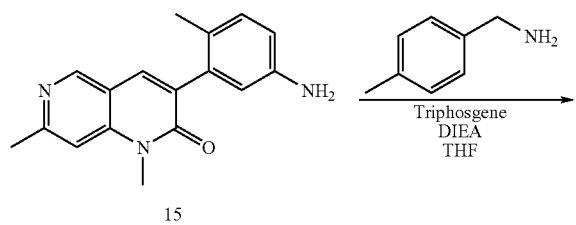

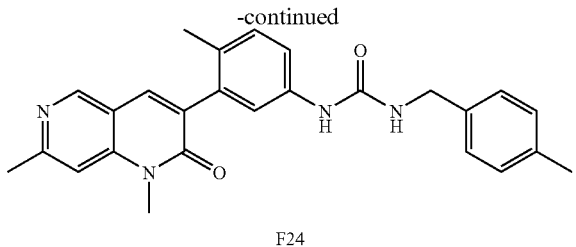

F24

To a solution of 3-(5-amino-2-methylphenyl)-1,7-dimethyl-1,6-naphthyridin-2(1H)-one 15 (20 mg, 0.072 mmol) in THF (1 mL) is added triphosgene (6.38 mg, 0.022 mmol) and DIEA (0.158 mmol). The reaction mixture is stirred at rt for 30 min then 4-methylbenzylamine (0.108 mmol) is added and stirring continued for 8 h at rt. The filtrate is concentrated. The residue is purified by preparative LCMS to give the desired product F24. $^1$H NMR (400 MHz, DMSO-$d_6$) δ 9.04 (s, 1H), 8.57 (s, 1H), 8.0 (s, 1H), 7.77 (s, 1H), 7.42 (s, 1H), 7.23 (d, J=8.8 Hz, 1H), 7.16 (m, 4H), 4.22 (d, J=5.6 Hz, 2H), 2.71 (s, 3H), 2.49 (s, 3H), 2.27 (s, 3H), 2.06 (s, 3H).

Table 6 describes compounds prepared following procedures described in Example 7, using appropriate reagents.

TABLE 6

| F# | Structure | Physical Data $^1$H NMR 400 MHz and/or MS (m/z) |
|---|---|---|
| 1 | 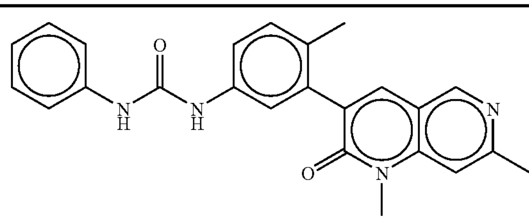 | $^1$H NMR 400 MHz (MeOD) δ 9.01 (s, 1H), 8.02 (s, 1H), 7.85 (s, 1H), 7.49 (d, J = 2 Hz, 1H), 7.40 (m, 2H), 7.29-7.21 (m, 4H), 7.02 (m, 2H), 3.81 (s, 3H), 2.83 (s, 3H), 2.17 (s, 3H); MS m/z 399.2 (M + 1) |
| 2 | 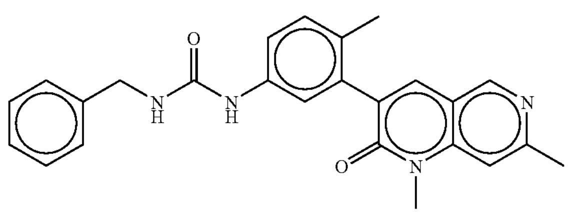 | $^1$H NMR 400 MHz (MeOD) δ 9.00 (s, 1H), 8.00 (s, 1H), 7.82 (s, 1H), 7.43 (d, J = 2 Hz, 1H), 7.32-7.31 (m, 4H), 7.25-7.20 (m, 3H), 4.38 (s, 2H), 3.82 (s, 3H), 2.82 (s, 3H), 2.15 (s, 3H); MS m/z 413.2 (M + 1) |
| 3 | 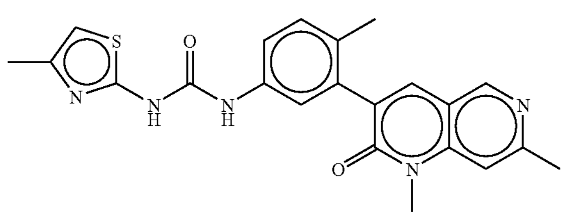 | $^1$H NMR 400 MHz (MeOD) δ 9.01 (s, 1H), 8.03 (s, 1H), 7.89 (s, 1H), 7.51 (bs, 1H), 7.40 (dd, J = 2,8 Hz, 1H), 7.25 (d, J = 8 Hz, 1H), 6.69 (s, 1H), 3.80 (s, 3H), 2.85 (s, 3H), 2.32 (s, 3H), 2.17 (s, 3H); MS m/z 420.2 (M + 1) |
| 4 | 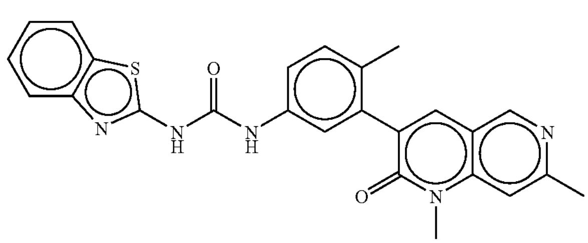 | $^1$H NMR 400 MHz (MeOD) δ 8.93 (s, 1H), 7.99 (s, 1H), 7.82 (s, 1H), 7.76 (d, J = 8 Hz, 1H), 7.62 (d, J = 8 Hz, 1H), 7.57 (d, J = 2 Hz, 1H), 7.41-7.35 (m, 2H), 7.27-7.21 (m, 2H), 3.77 (s, 3H), 2.81 (s, 3H), 2.16 (s, 3H); MS m/z 456.1 (M + 1) |

TABLE 6-continued

| F# | Structure | Physical Data<br>¹H NMR 400 MHz and/or MS (m/z) |
|---|---|---|
| 5 | 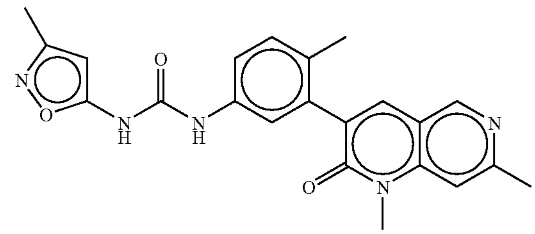 | MS m/z 404.2 (M + 1) |
| 6 | 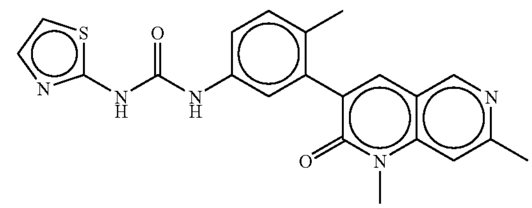 | ¹H NMR 400 MHz (DMSO-d₆) δ 10.51 (s, 1H), 8.91 (s, 1H), 8.81 (s, 1H), 7.96 (s, 1H), 7.43 (s, 1H), 7.41-7.31 (m, 2H), 7.21 (d, J = 8 Hz, 1H), 7.11 (bs, 1H), 3.65 (s, 3H), 2.62 (s, 3H), 2.10 (s, 3H); MS m/z 406.2 (M + 1) |
| 7 | 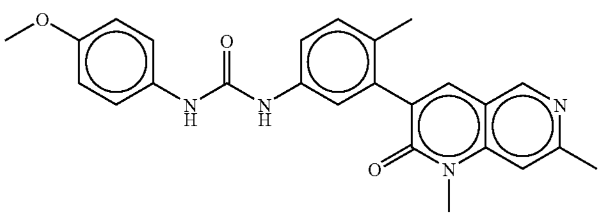 | ¹H NMR 400 MHz (MeOD) δ 8.99 (s, 1H), 8.00 (s, 1H), 7.85 (s, 1H), 7.46 (d, J = 2 Hz, 1H), 7.29 (d, J = 9 Hz, 2H), 7.27 (dd, J = 2, 8 Hz, 1H), 7.20 (d, J = 8 Hz, 1H), 6.85 (d, J = 9 Hz, 2H), 3.80 (s, 3H), 3.76 (s, 3H), 2.83 (s, 3H), 2.15 (s, 3H); MS m/z 429.2 (M + 1) |
| 8 | 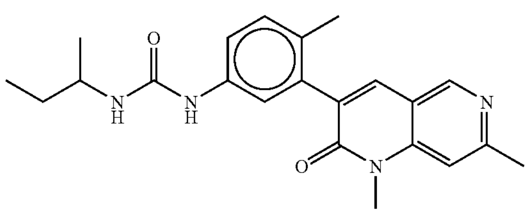 | MS m/z 379.3 (M + 1) |
| 9 | 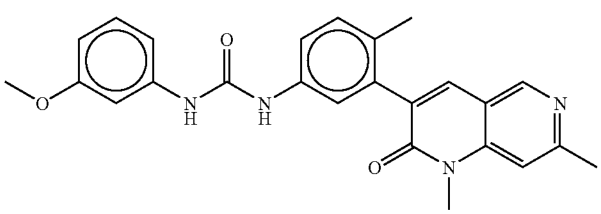 | ¹H NMR 400 MHz (MeOD) δ 8.94 (s, 1H), 7.99 (s, 1H), 7.82 (s, 1H), 7.47 (d, J = 2 Hz, 1H), 7.28 (dd, J = 2,8 Hz, 1H), 7.20 (d, J = 8 Hz, 1H), 7.16 (d, J = 9 Hz, 1H), 7.14-7.13 (m, 1H), 6.87 (dd, J = 2, 8 Hz, 1H), 6.58 (dd, J = 2, 8 Hz, 1H), 3.77 (s, 3H), 3.76 (s, 3H), 2.82 (s, 3H), 2.15 (s, 3H); MS m/z 429.2 (M + 1) |
| 10 | 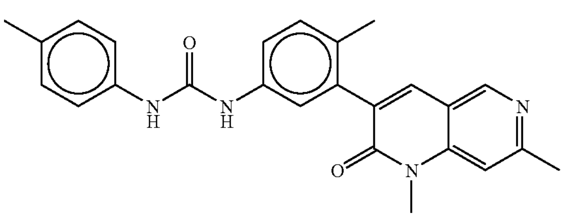 | ¹H NMR 400 MHz (MeOD) δ 8.99 (s, 1H), 8.00 (s, 1H), 7.85 (s, 1H), 7.47 (d, J = 2 Hz, 1H), 7.28 (dd, J = 2, 8 Hz, 1H), 7.27 (d, J = 9 Hz, 2H), 7.21 (d, J = 8 Hz, 1H), 7.09 (d, J = 9 Hz, 2H), 3.80 (s, 3H), 2.84 (s, 3H), 2.29 (s, 3H), 2.16 (s, 3H); MS m/z 413.2 (M + 1) |
| 11 | 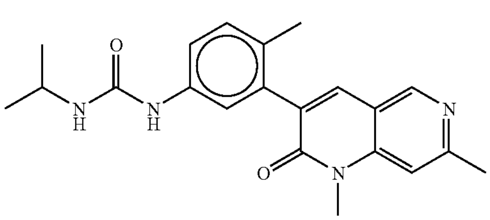 | MS m/z 365.2 (M + 1) |

TABLE 6-continued

| F# | Structure | Physical Data<br>¹H NMR 400 MHz and/or MS (m/z) |
|---|---|---|
| 12 | 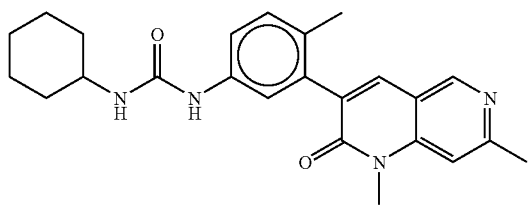 | MS m/z 405.3 (M + 1) |
| 13 | 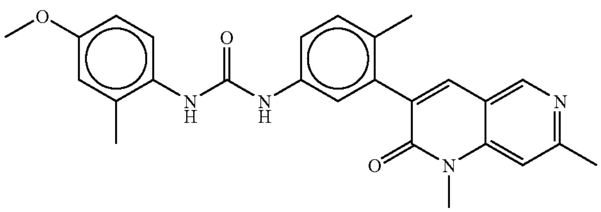 | ¹H NMR 400 MHz (MeOD) δ 8.76 (s, 1H), 7.93 (s, 1H), 7.47 (s, 1H), 7.36-7.32 (m, 2H), 7.21 (d, J = 8 Hz, 1H), 6.80 (d, J = 2 Hz, 1H), 6.75 (dd, J = 2, 8 Hz, 1H), 3.77 (s, 3H), 3.76 (s, 3H), 2.70 (s, 3H), 2.27 (s, 3H), 2.16 (s, 3H); MS m/z 443.3 (M + 1) |
| 14 | 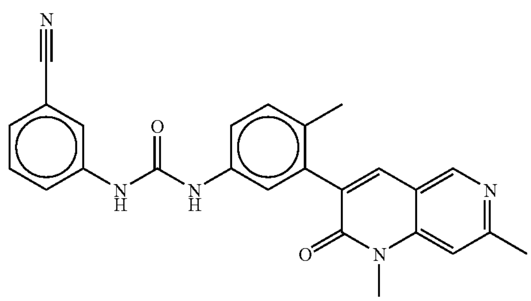 | MS m/z 424.3 (M + 1) |
| 15 | 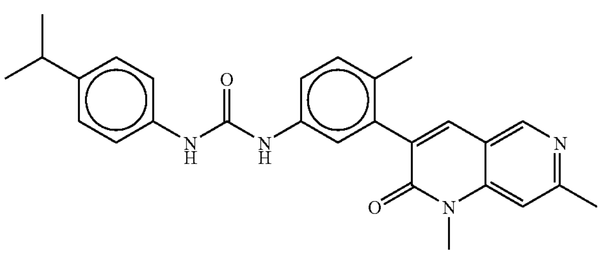 | ¹H NMR 400 MHz (MeOD) δ 9.03 (s, 1H), 8.03 (s, 1H), 7.85 (s, 1H), 7.49 (d, J = 2 Hz, 1H), 7.32 (d, J = 9 Hz, 2H), 7.28 (dd, J = 2,8 Hz, 1H), 7.23 (d, J = 8 Hz, 1H), 7.16 (d, J = 9 Hz, 2H), 3.82 (s, 3H), 2.86 (m, 1H), 2.83 (s, 3H), 2.17 (s, 3H), 1.23 (d, J = 4 Hz, 6H); MS m/z 441.3 (M + 1) |
| 16 | 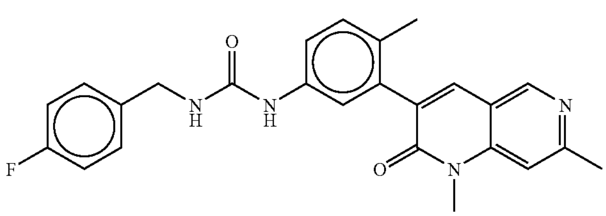 | ¹H NMR 400 MHz (MeOD) δ 9.04 (s, 1H), 8.00 (s, 1H), 7.88 (s, 1H), 7.42 (d, J = 2 Hz, 1H), 7.34-7.32 (m, 2H), 7.23 (dd, J = 2, 8 Hz, 1H), 7.19 (d, J = 8 Hz, 1H), 7.04 (m, 2H), 4.35 (s, 2H), 3.82 (s, 3H), 2.85 (s, 3H), 2.15 (s, 3H); MS m/z 431.3 (M + 1) |
| 17 | 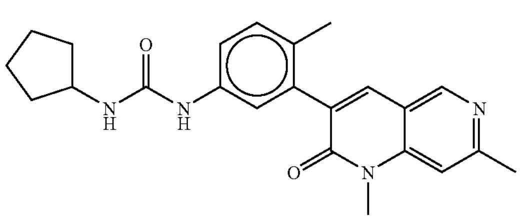 | ¹H NMR 400 MHz (MeOD) δ 9.04 (s, 1H), 8.00 (s, 1H), 7.88 (s, 1H), 7.38 (d, J = 2 Hz, 1H), 7.20 (dd, J = 2, 8 Hz, 1H), 7.17 (d, J = 8 Hz, 1H), 4.04 (q, J = 4 Hz, 1H), 3.82 (s, 3H), 2.85 (s, 3H), 2.14 (s, 3H), 1.95 (m, 2H), 1.73 (m, 2H), 1.62 (m, 2H), 1.45 (m, 2H); MS m/z 391.3 (M + 1) |

TABLE 6-continued

| F# | Structure | Physical Data<br>¹H NMR 400 MHz and/or MS (m/z) |
|---|---|---|
| 18 | 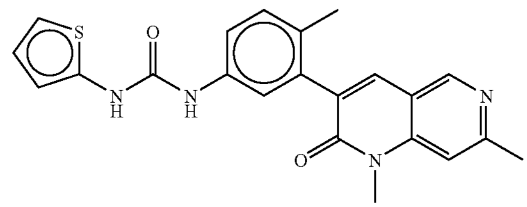 | MS m/z 405.2 (M + 1) |
| 19 | 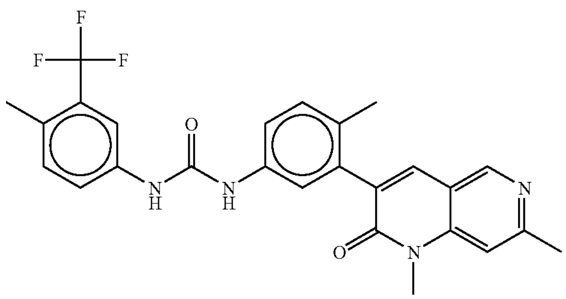 | ¹H NMR 400 MHz (MeOD) δ 9.01 (s, 1H), 8.03 (s, 1H), 7.85 (s, 1H), 7.84 (d, J = 2 Hz, 1H), 7.50 (d, J = 2 Hz, 1H), 7.47 (dd, J = 2, 8 Hz, 1H), 7.28 (dd, J = 2, 8 Hz, 1H), 7.27 (d, J = 8 Hz, 1H), 7.23 (d, J = 8 Hz, 1H), 3.81 (s, 3H), 2.84 (s, 3H), 2.41 (s, 3H), 2.17 (s, 3H); MS m/z 481.2 (M + 1) |
| 20 | 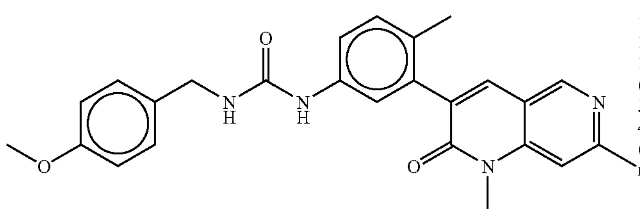 | ¹H NMR 400 MHz (DMSO-d₆) δ 9.05 (s, 1H), 8.53 (s, 1H), 8.01 (s, 1H), 7.79 (s, 1H), 7.44 (d, J = 2 Hz, 1H), 7.24-7.20 (m, 3H), 7.14 (d, J = 8 Hz, 1H), 6.89 (d, J = 9 Hz, 2H), 6.55 (t, J = 6 Hz, 1H), 4.20 (d, J = 6 Hz, 2H), 3.73 (s, 3H), 3.69 (s, 3H), 2.72 (s, 3H), 2.06 (s, 3H); MS m/z 443.2 (M + 1) |
| 21 | 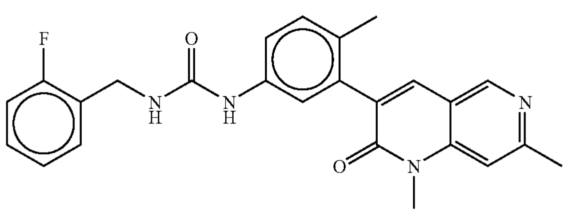 | ¹H NMR 400 MHz (DMSO-d₆) δ 9.09 (s, 1H), 8.65 (s, 1H), 8.03 (s, 1H), 7.85 (s, 1H), 7.46 (d, J = 2 Hz, 1H), 7.38-7.28 (m, 2H), 7.23-7.14 (m, 4H), 6.68 (bs, 1H), 4.32 (d, J = 6 Hz, 2H), 3.70 (s, 3H), 2.74 (s, 3H), 2.07 (s, 3H); MS m/z 431.2 (M + 1) |
| 22 | 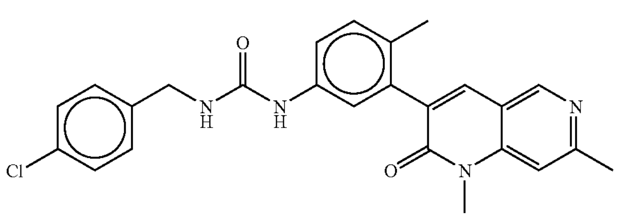 | ¹H NMR 400 MHz (DMSO-d₆) δ 9.04 (s, 1H), 8.63 (s, 1H), 8.00 (s, 1H), 7.78 (s, 1H), 7.44 (d, J = 2 Hz, 1H), 7.39 (d, J = 9 Hz, 2H), 7.30 (d, J = 9 Hz, 2H), 7.23 (dd, J = 2, 8 Hz, 1H), 7.14 (d, J = 8 Hz, 1H), 6.68 (t, J = 6 Hz, 1H), 4.26 (d, J = 6 Hz, 2H), 3.69 (s, 3H), 2.72 (s, 3H), 2.07 (s, 3H); MS m/z 447.1 (M + 1) |
| 23 | 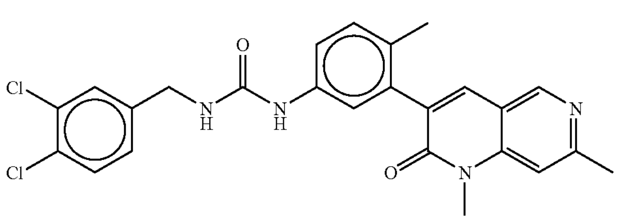 | ¹H NMR 400 MHz (DMSO-d₆) δ 9.04 (s, 1H), 8.07 (s, 1H), 8.00 (s, 1H), 7.77 (s, 1H), 7.59 (d, J = 8 Hz, 1H), 7.53 (d, J = 2 Hz, 1H), 7.43 (d, J = 2 Hz, 1H), 7.28 (dd, J = 2, 8 Hz, 1H), 7.23 (dd, J = 2, 8 Hz, 1H), 7.14 (d, J = 8 Hz, 1H), 6.75 (t, J = 6 Hz, 1H), 4.27 (d, J = 6 Hz, 2H), 3.69 (s, 3H), 2.71 (s, 3H), 2.07 (s, 3H); MS m/z 481.2 (M + 1) |

TABLE 6-continued

| F# | Structure | Physical Data<br>¹H NMR 400 MHz and/or MS (m/z) |
|---|---|---|
| 24 | 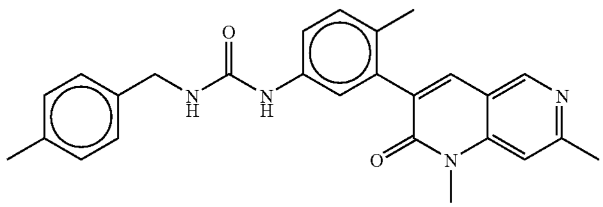 | ¹H NMR (400 MHz, DMSO-d₆) δ 9.04 (s, 1H), 8.57 (s, 1H), 8.0 (s, 1H), 7.77 (s, 1H), 7.42 (s, 1H), 7.23 (d, J = 8.8 Hz, 1H), 7.16 (m, 4H), 4.22 (d, J = 5.6 Hz, 2H), 2.71 (s, 3H), 2.49 (s, 3H), 2.27 (s, 3H), 2.06 (s, 3H); MS m/z 427.2 (M + 1) |
| 25 | 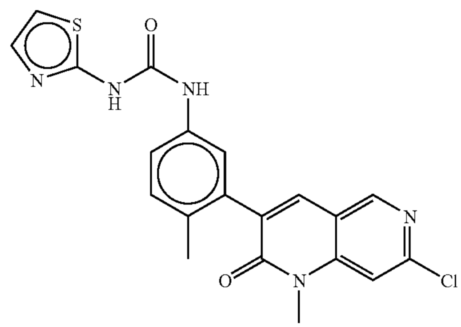 | ¹H NMR 400 MHz (DMSO-d₆) δ 10.52 (s, 1H), 8.94 (s, 1H), 8.78 (s, 1H), 8.02 (s, 1H), 7.69 (s, 1H), 7.44 (d, J = 2 Hz, 1H), 7.37-7.34 (m, 2H), 7.22 (d, J = 8 Hz, 1H), 7.11 (bs, 1H), 3.66 (s, 3H), 2.10 (s, 3H); MS m/z 426.2 (M + 1) |
| 26 | 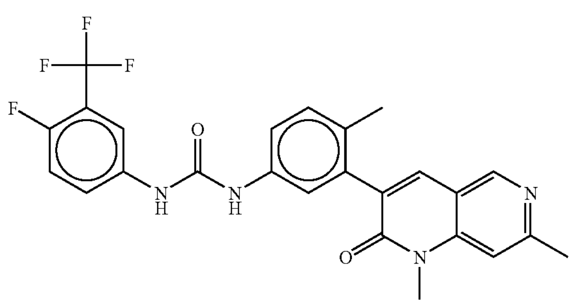 | ¹H NMR (400 MHz, CD₃OD) δ 8.77 (s, 1H), 7.94 (d, 1H), 7.88 (dd, 1H), 7.63 (dt, 1H), 7.47 (s, 1H), 7.36 (s, 1H), 7.34 (dd, 1H), 7.24 (d, 1H), 7.23 (dd, 1H), 3.77 (s, 3H), 2.69 (s, 3H), 2.17 (s, 3H); MS m/z 485.1 (M + 1) |
| 27 | 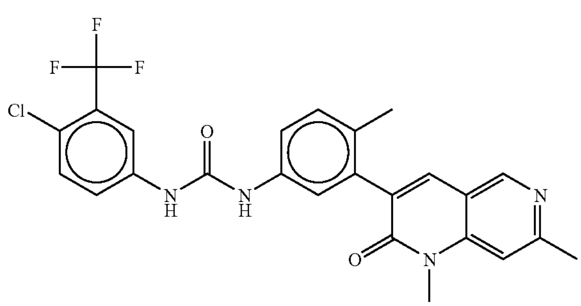 | ¹H NMR (400 MHz, CD₃OD) δ 8.77 (s, 1H), 7.99 (d, 1H), 7.94 (s, 1H), 7.63 (dd, 1H), 7.49 (d, 1H), 7.47 (s, 1H), 7.37 (s, 1H), 7.36 (dd, 1H), 7.23 (d, 1H), 3.77 (s, 3H), 2.69 (s, 3H), 2.17 (s, 3H); MS m/z 501.1 (M + 1) |
| 28 | 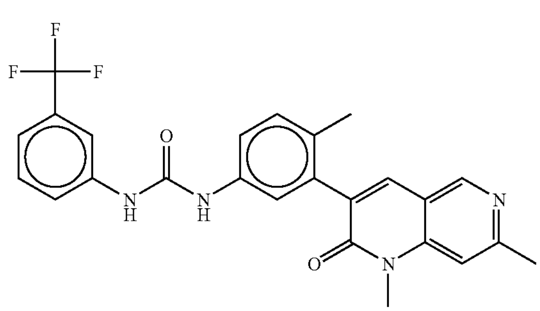 | ¹H NMR (400 MHz, CD₃OD) δ 8.77 (s, 1H), 7.95 (s, 1H), 7.89 (s, 1H), 7.60 (dd, 1H), 7.47 (s, 1H), 7.46 (t, 1H), 7.37 (s, 1H), 7.36 (dd, 1H), 7.28 (d, 1H), 7.24 (d, 1H), 3.77 (s, 3H), 2.69 (s, 3H), 2.17 (s, 3H); MS m/z 447.1 (M + 1) |

TABLE 6-continued

| F# | Structure | Physical Data<br>¹H NMR 400 MHz and/or MS (m/z) |
|---|---|---|
| 29 | 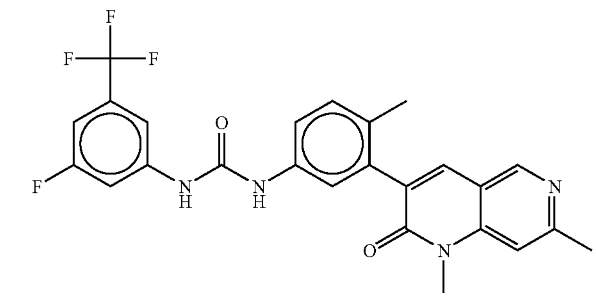 | ¹H NMR (400 MHz, CD₃OD) δ 8.77 (s, 1H), 7.95 (s, 1H), 7.61 (dt, 1H), 7.55 (s, 1H), 7.47 (s, 1H), 7.39 (s, 1H), 7.37 (dd, 1H), 7.24 (d, 1H), 7.01 (dt, 1H), 3.77 (s, 3H), 2.69 (s, 3H), 2.17 (s, 3H); MS m/z 485.1 (M + 1) |
| 30 | 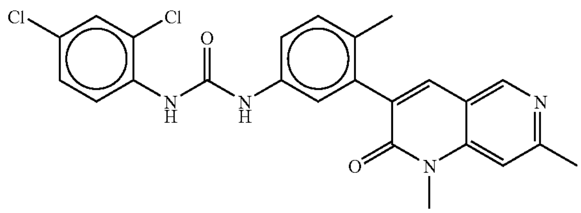 | ¹H NMR (400 MHz, CD₃OD) δ 8.77 (s, 1H), 8.13 (d, 1H), 7.94 (s, 1H), 7.48 (s, 1H), 7.47 (d, 1H), 7.39 (s, 1H), 7.38 (dd, 1H), 7.28 (dd, 1H), 7.23 (d, 1H), 3.77 (s, 3H), 2.69 (s, 3H), 2.16 (s, 3H); MS m/z 467.1 (M + 1) |

EXAMPLE 8

N-(3-(1,7-dimethyl-2-oxo-1,2-dihydro-1,6-naphthyridin-3-yl)-4-methylphenylcarbamoyl)-4-methoxybenzamide (G8)

General Procedure G

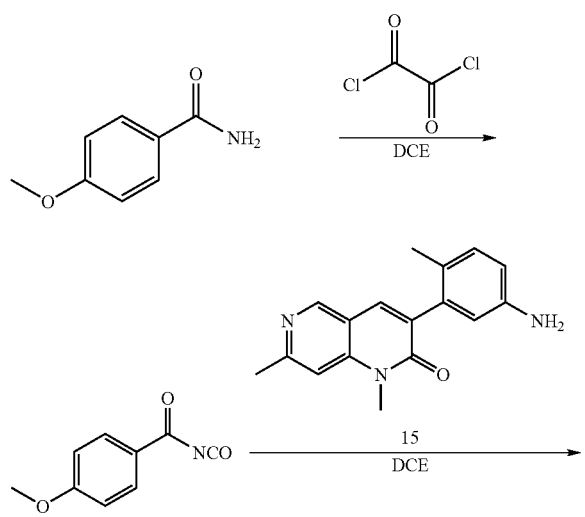

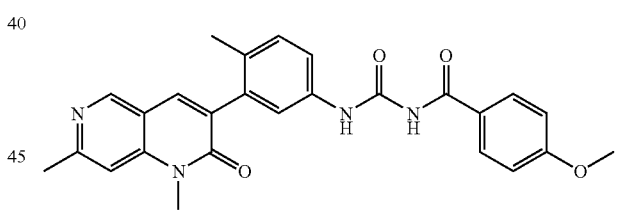

solution of 4-methoxybenzamide (50 mg, 0.33 mmol) in 1,2-dichloroethane (2 mL) is added oxalyl chloride (0.33 mmol). The reaction mixture is heated at 55° C. for 1 h. Upon cooling the reaction mixture, 3-(5-amino-2-methylphenyl)-1,7-dimethyl-1,6-naphthyridin-2(1H)-one 15 (0.16 mmol) is added and heating is continued for 8 h. The reaction is concentrated and purified by preparative LCMS to give the desired product G8. ¹H NMR (400 MHz, DMSO-d₆) δ 9.03 (s, 1H), 8.05 (m, 3H), 7.76 (s, 1H), 7.50 (m, 2H), 7.28 (d, J=8.0 Hz, 1H), 7.06 (d, J=8.8 Hz, 2H), 2.72 (s, 3H), 2.51 (s, 3H), 2.13 (s, 3H), 2.07 (s, 3H).

Table 7 describes compounds prepared following procedures described in Example 8, using appropriate reagents.

TABLE 7

| G# | Structure | Physical Data ¹H NMR 400 MHz and/or MS (m/z) |
|---|---|---|
| 1 | 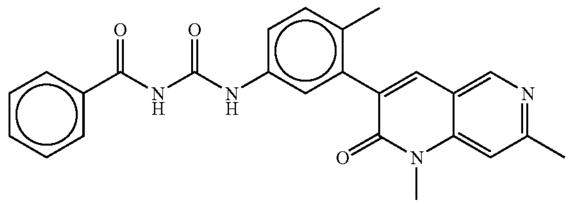 | ¹H NMR 400 MHz (DMSO-$d_6$) δ 11.04 (s, 1H), 10.86 (s, 1H), 8.82 (s, 1H), 8.03-7.99 (m, 3H), 7.68-7.64 (m, 1H), 7.57-7.52 (m, 3H), 7.48-7.46 (m, 2H), 7.26 (d, J = 8 Hz, 1H), 3.65 (s, 3H), 2.62 (s, 3H), 2.13 (s, 3H); MS m/z 427.1 (M + 1) |
| 2 | 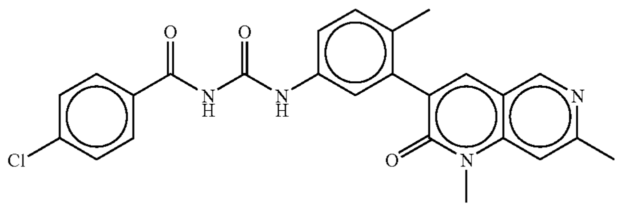 | MS m/z 461.1 (M + 1) |
| 3 | 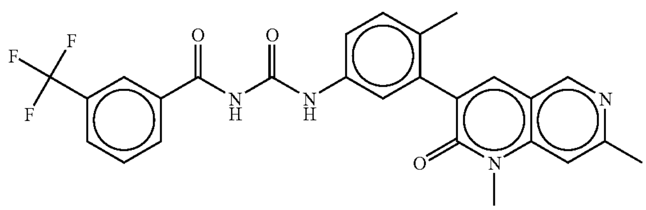 | ¹H NMR (400 MHz, DMSO-$d_6$) δ 11.3 (s, 1H), 10.7 (s, 1H), 9.0 (s, 1H), 8.36 (s, 1H), 8.29 (m, 1H), 8.05 (m, 2H), 7.79 (m, 1H), 7.71 (m, 2H), 7.51 (m, 1H), 7.28 (m, 1H), 7.07 (d, J = 49.6 Hz, 1H), 2.70 (s, 3H), 2.55 (s, 3H), 2.13 (s, 3H) MS m/z 495.1 (M + 1) |
| 4 | 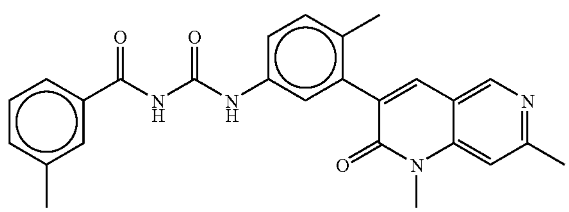 | ¹H NMR (400 MHz, DMSO-$d_6$) δ 10.9 (s, 1H), 10.8 (s, 1H), 9.03 (s, 1H), 8.06 (s, 1H), 7.80 (m, 2H), 7.46 (m, 2H), 7.28 (m, 2H), 7.13 (s, 1H), 7.0 (s, 1H), 2.71 (s, 3H), 2.55 (s, 3H), 2.38 (s, 3H), 2.13 (s, 3H); MS m/z 441.1 (M + 1) |
| 5 | 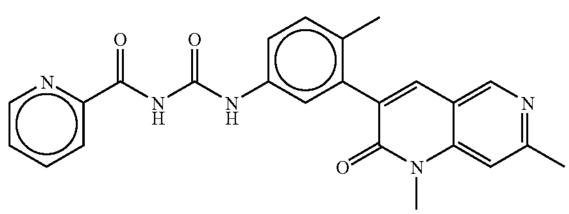 | ¹H NMR (400 MHz, DMSO-$d_6$) δ 10.43 (s, 1H), 10.39 (s, 1H), 9.10 (s, 1H), 8.70 (m, 1H), 8.05 (m, 2H), 7.83 (m, 2H), 7.65 (m, 1H), 7.31 (m, 1H), 7.18 (s, 1H), 7.0 (s, 1H), 2.74 (s, 3H), 2.13 (s, 3H), 2.07 (s, 3H). MS m/z 428.2 (M + 1) |
| 6 | 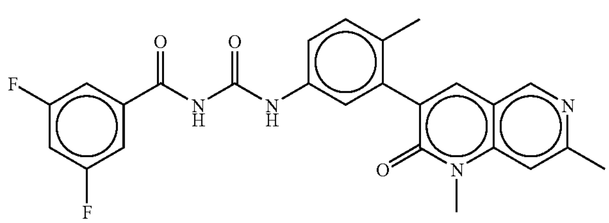 | MS m/z 463.1 (M + 1) |
| 7 | 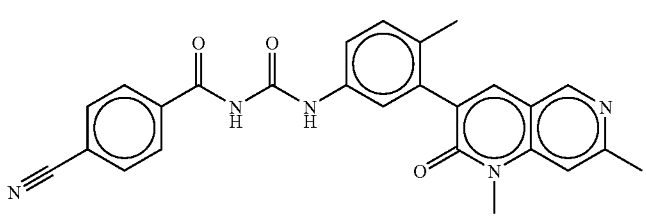 | ¹H NMR (400 MHz, DMSO-$d_6$) δ 11.3 (s, 1H), 10.7 (s, 1H), 9.02 (s, 1H), 8.12 (m, 1H), 8.04 (m, 1H), 7.74 (s, 1H), 7.50 (s, 2H), 7.28 (m, 2H), 7.13 (s, 1H), 7.0 (s, 1H), 2.71 (s, 3H), 2.55 (s, 3H), 2.13 (s, 3H). MS m/z 452.2 (M + 1) |

TABLE 7-continued

| G# | Structure | Physical Data
¹H NMR 400 MHz and/or MS (m/z) |
| --- | --- | --- |
| 8 | | ¹H NMR (400 MHz, DMSO-d₆) δ 9.03 (s, 1H), 8.05 (m, 3H), 7.76 (s, 1H), 7.50 (m, 2H), 7.28 (d, J = 8.0 Hz, 1H), 7.06 (d, J = 8.8 Hz, 2H), 2.72 (s, 3H), 2.51 (s, 3H), 2.13 (s, 3H), 2.07 (s, 3H). MS m/z 457.2 (M + 1) |
| 9 | | MS m/z 441.2 (M + 1) |
| 10 | | MS m/z 393.2 (M + 1) |
| 11 | | MS m/z 505.1 and 507.1 (M + 1) |
| 12 | | MS m/z 495.2 (M + 1) |
| 13 | | MS m/z 457.2 (M + 1) |
| 14 | | MS m/z 433.2 (M + 1) |

TABLE 7-continued

| G# | Structure | Physical Data<br>¹H NMR 400 MHz and/or MS (m/z) |
|---|---|---|
| 15 | 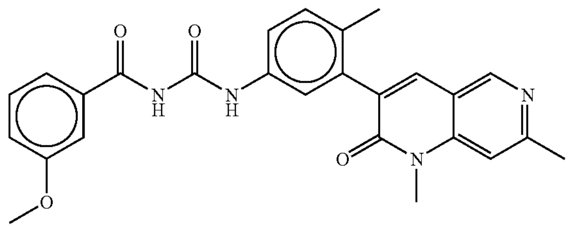 | MS m/z 457.2 (M + 1) |
| 16 | 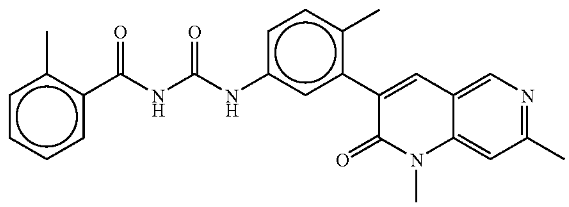 | MS m/z 441.2 (M + 1) |
| 17 | 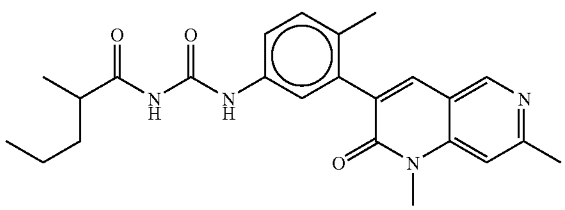 | MS m/z 421.2 (M + 1) |
| 18 | 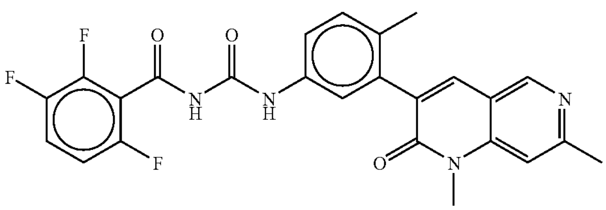 | MS m/z 481.2 (M + 1) |
| 19 | 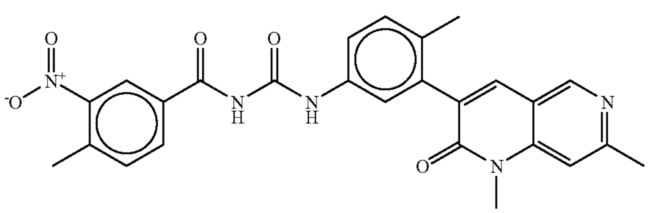 | MS m/z 486.2 (M + 1) |
| 20 | 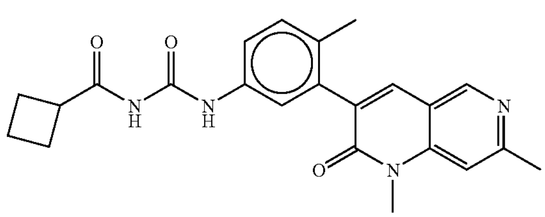 | MS m/z 405.2 (M + 1) |
| 21 | 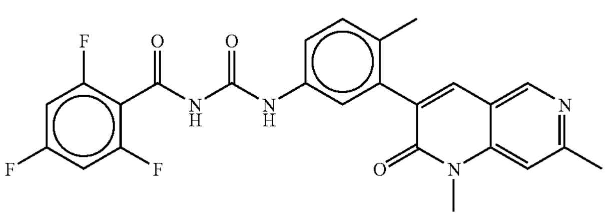 | MS m/z 481.2 (M + 1) |

TABLE 7-continued

| G# | Structure | Physical Data $^1$H NMR 400 MHz and/or MS (m/z) |
|---|---|---|
| 22 | 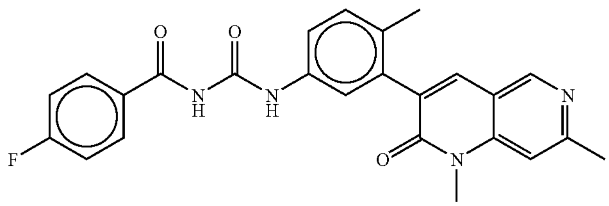 | MS m/z 445.2 (M + 1) |
| 23 | 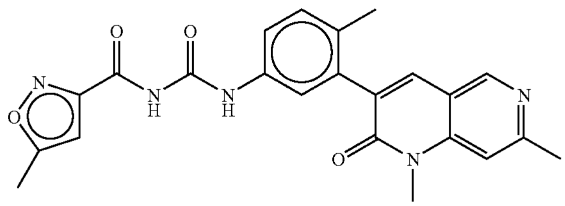 | MS m/z 432.2 (M + 1) |
| 24 | 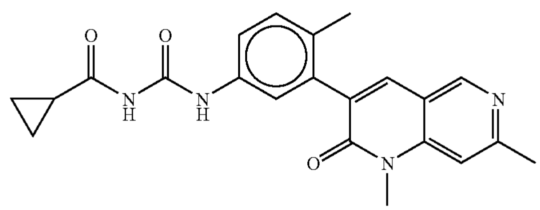 | MS m/z 391.2 (M + 1) |
| 25 | 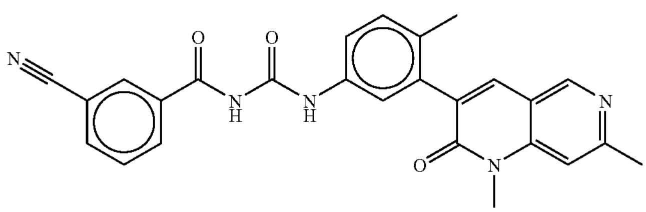 | MS m/z 455.2 (M + 1) |
| 26 | 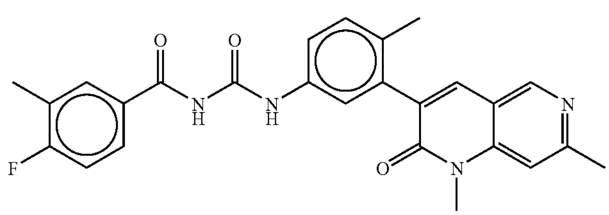 | MS m/z 459.2 (M + 1) |
| 27 | 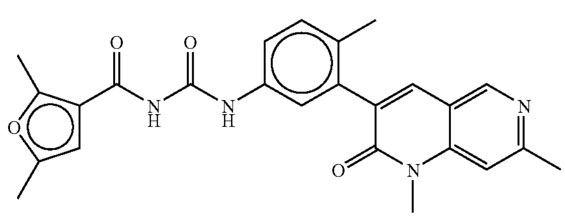 | MS m/z 445.2 (M + 1) |
| 28 | 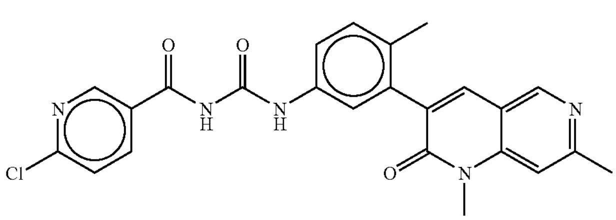 | MS m/z 462.1 (M + 1) |

TABLE 7-continued

| G# | Structure | Physical Data<br>¹H NMR 400 MHz and/or MS (m/z) |
|---|---|---|
| 29 | 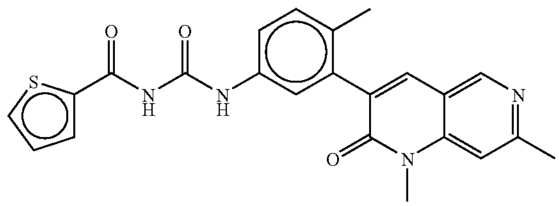 | MS m/z 433.2 (M + 1) |
| 30 | 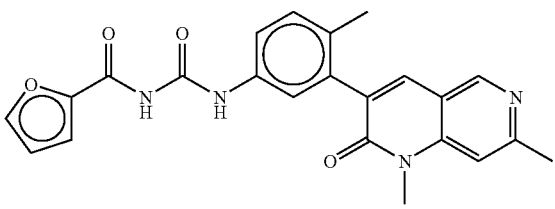 | MS m/z 417.2 (M + 1) |
| 31 | 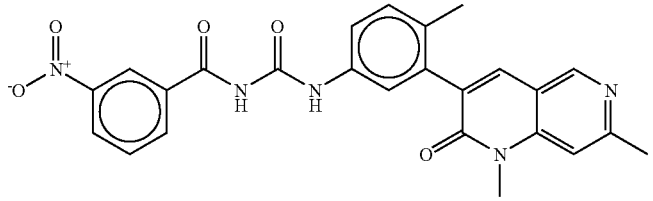 | MS m/z 472.2 (M + 1) |

EXAMPLE 9

1-acetophenonyl-3-(3-(1,2-dihydro-1,7-dimethyl-2-oxo-1,6-naphthyridin-3-yl)-4-methylphenyl)thiourea (H1)

General Procedure H

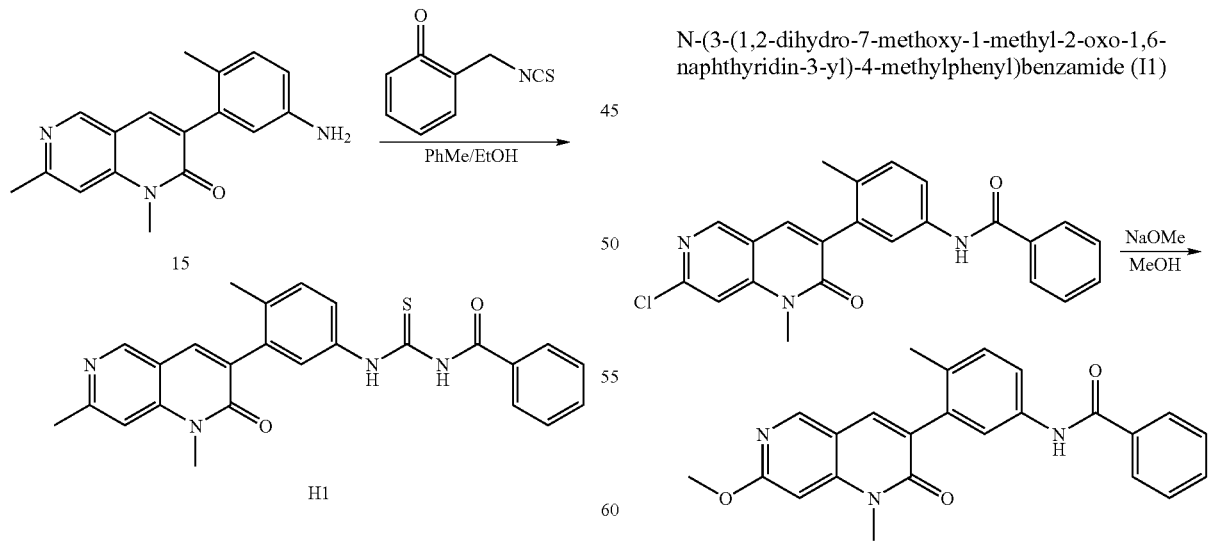

To a solution of benzoyl chloride (62 μL, 0.54 mmol) in acetonitrile (3 mL) is added KSCN (52 mg, 0.54 mmol) and heated at 55° C. for 1 h. Upon cooling to rt, the reaction is reduced to dryness and re-dissolved in ethanol (2 mL) followed by treatment with a solution of 15 in toluene/ethanol (5/1 mL). The heterogeneous reaction mixture is stirred at rt for 6 h then cooled with an ice bath and filtered with ethanol. The precipitate is washed with water and ethanol. The white solid is air dried under vacuum. ¹H NMR 400 MHz (DMSO-$d_6$) δ 12.65 (s, 1H), 11.60 (s, 1H), 8.83 (s, 1H), 8.00-7.97 (m, 3H), 7.72-7.65 (m, 2H), 7.57-7.52 (m, 3H), 7.47 (s, 1H), 7.34 (d, J=8 Hz, 1H), 3.66 (s, 3H), 2.62 (s, 3H), 2.17 (s, 3H); MS m/z 443.1 (M+1).

EXAMPLE 10

N-(3-(1,2-dihydro-7-methoxy-1-methyl-2-oxo-1,6-naphthyridin-3-yl)-4-methylphenyl)benzamide (I1)

N-(3-(7-chloro-1,2-dihydro-1-methyl-2-oxo-1,6-naphthyridin-3-yl)-4-methylphenyl)benzamide A6 (70 mg, 0.17 mmol) is treated with sodium methoxide (0.8 mL of a 0.5 M solution in methanol) and heated to 65° C. for 3 h. The reaction is cooled to rt and partitioned with EtOAc and aqueous ammonium chloride. The organic layer is washed with brine, dried over magnesium sulfate, filtered and solvent removed. Crude product is dissolved in DMF (1 mL) and purified by preparative LCMS to afford the desired product. $^1$H NMR 400 MHz (MeOD) δ 8.56 (s, 1H), 7.92 (d, J=8 Hz, 2H), 7.88 (s, 1H), 7.64-7.46 (m, 5H), 7.28 (d, J=8 Hz, 1H), 6.84 (1H), 4.05 (s, 3H), 3.71 (s, 3H), 2.20 (s, 3H); MS m/z 400.2 (M+1).

Table 8 describes other exemplary compounds of the invention, prepared following methods analogous to those described above.

N-(3-(7-chloro-1,2-dihydro-1-methyl-2-oxo-1,6-naphthyridin-3-yl)-4-methylphenyl)benzamide A6 (45 mg, 0.11 mmol) is dissolved in NMP (1 mL) and treated with dimethyl amine (0.56 mL of a 2.0 M solution in methanol). The reaction mixture is heated to 100° C. for 12 h. Upon cooling to rt, the reaction is purified by preparative LCMS. $^1$H NMR 400 MHz (DMSO-d$_6$) δ 10.23 (s, 1H), 8.51 (s, 1H), 7.97-7.94 (m, 2H), 7.78 (s, 1H), 7.68-7.66 (m, 2H), 7.61-7.51 (m, 3H), 7.23 (d, J=9 Hz, 1H), 6.37 (s, 1H), 3.61 (s, 3H), 3.20 (s, 6H), 2.12 (s, 3H); MS m/z 413.2 (M+1).

TABLE 8

| I# | Structure | Physical Data $^1$H NMR 400 MHz and/or MS (m/z) |
|---|---|---|
| 1 | 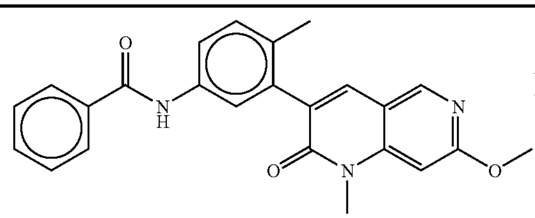 | $^1$H NMR 400 MHz (MeOD) δ 8.56 (s, 1H), 7.92 (d, J = 8 Hz, 2H), 7.88 (s, 1H), 7.64-7.46 (m, 5H), 7.28 (d, J = 8 Hz, 1H), 6.84 (1H), 4.05 (s, 3H), 3.71 (s, 3H), 2.20 (s, 3H); MS m/z 400.2 (M + 1) |
| 2 | 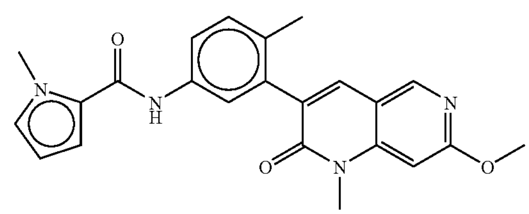 | $^1$H NMR 400 MHz (MeOD) δ 8.56 (s, 1H), 7.88 (s, 1H), 7.54 (dd, J = 2, 8 Hz, 1H), 7.53 (s, 1H), 7.24 (d, J = 9 Hz, 1H), 6.94 (dd, J = 2, 4 Hz, 1H), 6.87 (t, J = 2 Hz, 1H), 6.87 (s, 1H), 6.11 (dd, J = 2, 4 Hz, 1H), 4.06 (s, 3H), 3.92 (s, 3H), 3.71 (s, 3H), 2.18 (s, 3H); MS m/z 403.1 (M + 1) |

EXAMPLE 11

N-(3-(7-(dimethylamino)-1,2-dihydro-1-methyl-2-oxo-1,6-naphthyridin-3-yl)-4-methylphenyl)benzamide (J1)

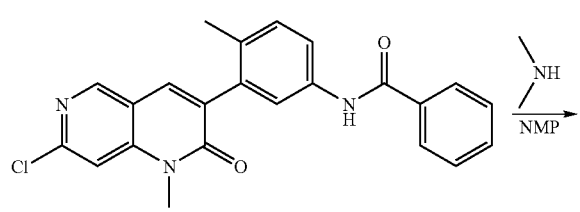

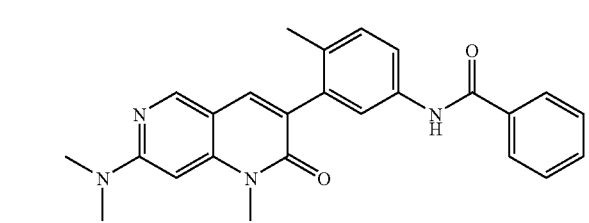

J1

EXAMPLE 12

1-(3-(7-(dimethylamino)-1,2-dihydro-1-methyl-2-oxo-1,6-naphthyridin-3-yl)-4-methylphenyl)-3-phenylurea (K1)

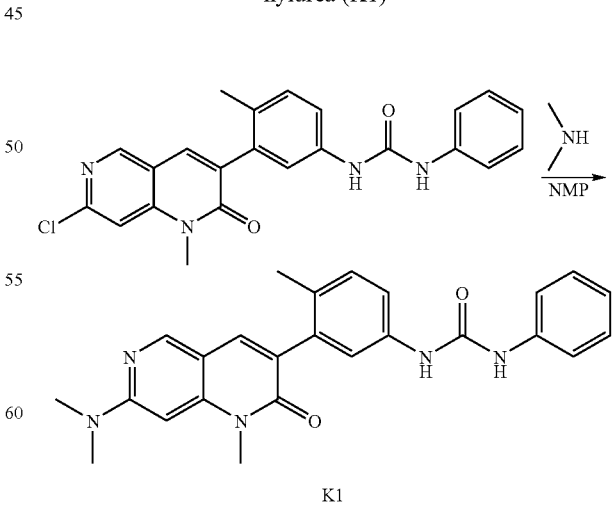

1-(3-(7-chloro-1,2-dihydro-1-methyl-2-oxo-1,6-naphthyridin-3-yl)-4-methylphenyl)-3-phenylurea A6 (50 mg, 0.12 mmol) is dissolved in NMP (1 mL) and treated with dimethyl amine (0.60 mL of a 2.0 M solution in methanol). The reaction mixture is heated to 100° C. for 12 h. Upon cooling to rt the reaction is purified by preparative LCMS. $^1$H NMR 400 MHz (DMSO-d$_6$) δ 8.65 (s, 1H), 8.62 (s, 1H), 8.50 (s, 1H), 7.75 (s, 1H), 7.45-7.42 (m, 2H), 7.38 (d, J=2 Hz, 1H), 7.29-7.25 (m, 3H), 7.15 (d, J=8 Hz, 1H), 6.96 (m, 1H), 6.37 (s, 1H), 3.60 (s, 3H), 3.19 (s, 6H), 2.08 (s, 3H); MS m/z 428.2 (M+1).

EXAMPLE 13

1-methyl-7-(methylthio)-2-oxo-1,6-naphthyridin-3-yl)-4-methylphenyl)benzamide (L1)

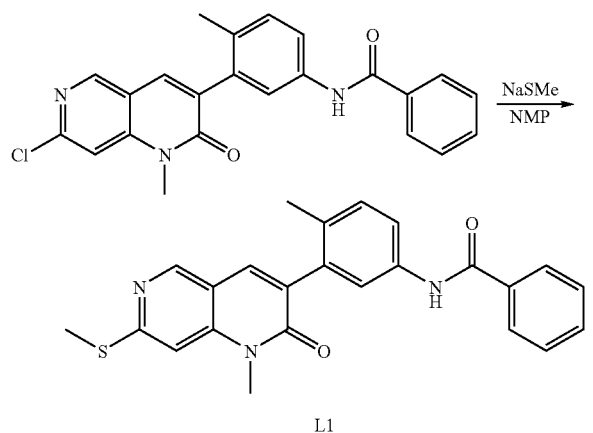

N-(3-(7-chloro-1,2-dihydro-1-methyl-2-oxo-1,6-naphthyridin-3-yl)-4-methylphenyl)benzamide A6 (70 mg 0.17 mmol) is dissolved in NMP (1 mL) and treated with sodium methanethiolate (15 mg, 0.21 mmol). The reaction mixture is heated to 100° C. for 12 h. The reaction is cooled to rt and partitioned with EtOAc and water. The organic layer is washed with brine, dried over magnesium sulfate, filtered and solvent removed. Crude product is dissolved in DMF (1 mL) and purified by preparative LCMS. $^1$H NMR 400 MHz (MeOD) δ 8.82 (s, 1H), 7.95-7.92 (m, 2H), 7.67-7.50 (m, 5H), 7.41 (s, 1H), 7.30 (d, J=8 Hz, 1H), 3.78 (s, 3H), 2.77 (s, 3H), 2.21 (s, 3H); MS m/z 416.1 (M+1).

EXAMPLE 14

3-(1,7-dimethyl-2-oxo-1,2-dihydro-1,6-naphthyridin-3-yl)-4-methyl-N-(5-methylpyridin-2-yl)benzamide (M6)

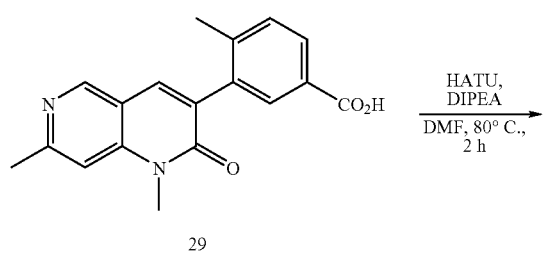

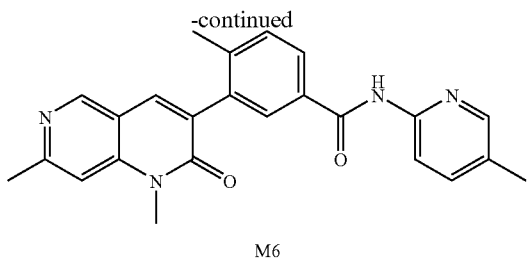

A solution of 3-(1,7-dimethyl-2-oxo-1,2-dihydro-1,6-naphthyridin-3-yl)-4-methylbenzoic acid 29 (50 mg, 0.17 mmol) in DMF (1 mL) is treated with HATU (97 mg, 0.255 mmol), 5-methylpyridin-2-amine (22 mg, 0.2 mmol) and DIPEA (0.089 mL, 0.51 mmol) at 80° C. for 2 h. The residue is purified by preparative LC/MS to give the desired product M6 as an off-white solid. $^1$H NMR (400 MHz, MeOH-d$_4$) δ 9.12 (s, 1H), 8.26 (m, 1H), 8.22 (d, J=8.7 Hz, 1H), 8.16 (s, 1H), 8.07 (dd, J=8, 1.6 Hz, 1H), 8.02 (s, 1H), 7.94 (s, 1H), 7.86 (m, 1H), 7.57 (d, J=8 Hz, 1H), 3.85 (s, 3H), 2.87 (s, 3H), 2.46 (s, 3H), 2.35 (s, 3H); LC/MS (M+1, m/z): 399.2.

EXAMPLE 15

3-(1,7-dimethyl-2-oxo-1,2-dihydro-1,6-naphthyridin-3-yl)-N-(5-fluoropyridin-2-yl)-4-methylbenzamide (M32)

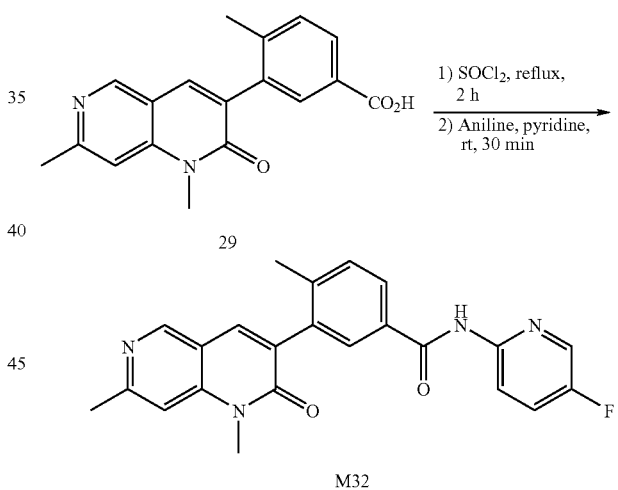

A solution of 3-(1,7-dimethyl-2-oxo-1,2-dihydro-1,6-naphthyridin-3-yl)-4-methylbenzoic acid 29 (154 mg, 0.5 mmol) in SOCl$_2$ (1 mL) is heated at reflux for 2 h. Excess SOCl$_2$ is removed in vacuo and the resultant solid is added to a solution of 5-fluoropyridin-2-amine (112 mg, 1 mmol) and pyridine (0.4 mL, 5 mmol) at rt. The resulting mixture is stirred for 30 min and evaporated. The residue is purified by preparative LC/MS to give the desired product M32 as an off-white solid. $^1$H NMR (400 MHz, DMSO-d$_6$) δ 8.84 (s, 1H), 8.28 (m, 1H), 8.04 (s, 1H), 7.95 (dd, J=8, 2 Hz, 1H), 7.86 (d, J=1.9 Hz, 1H), 7.65 (dt, J=9.1, 2.9 Hz, 1H), 7.57 (s, 1H), 7.48 (d, J=8 Hz, 1H), 3.8 (s, 3H), 2.73 (s, 3H), 2.32 (s, 3H); LC/MS (M+1, m/z): 403.1.

Table 9 describes other exemplary compounds of the invention, prepared following methods analogous to those described above.

TABLE 9

| M# | Structure | Physical Data ¹H NMR 400 MHz and/or MS (m/z) |
|---|---|---|
| 1 | 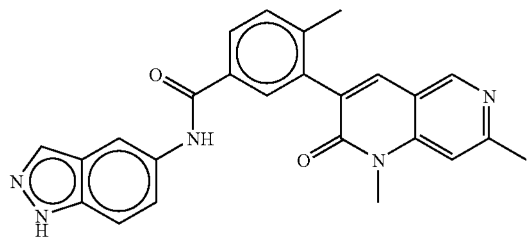 | ¹H NMR 400 MHz (DMSO-d$_6$) δ 10.25 (s, 1H), 8.98 (s, 1H), 8.22 (s, 1H), 8.10 (s, 1H), 8.06 (s, 1H), 7.97 (d, J = 8.0 Hz, 1H), 7.86 (s, 1H), 7.68 (s, 1H), 7.61 (d, J = 8.8 Hz, 1H), 7.51 (m, 2H), 7.12 (t, J = 51.2 Hz, 1H), 2.69 (s, 3H), 2.54 (s, 3H), 2.24 (s, 3H); MS m/z 424.1 (M + 1) |
| 2 | 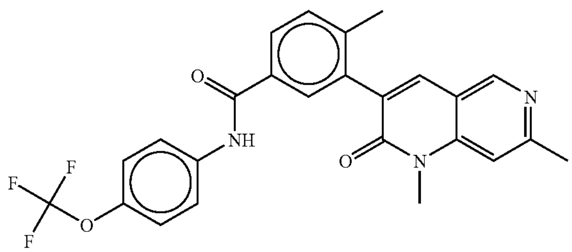 | ¹H NMR 400 MHz (DMSO-d$_6$) δ 10.4 (s, 1H), 8.96 (s, 1H), 8.09 (s, 1H), 7.95 (d, J = 8 Hz, 1H), 7.87 (m, 2H), 7.65 (s, 1H), 7.47 (d, J = 7.6 Hz, 1H), 7.36 (d, J = 8.4 Hz, 2H), 7.13 (t, J = 51.6 Hz, 1H), 2.68 (s, 3H), 2.55 (s, 3H), 2.24 (s, 3H); MS m/z 468.1 (M + 1) |
| 3 | 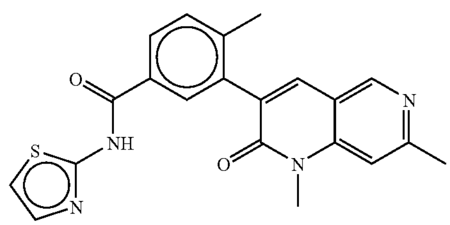 | MS m/z 391.1 (M + 1) |
| 4 | 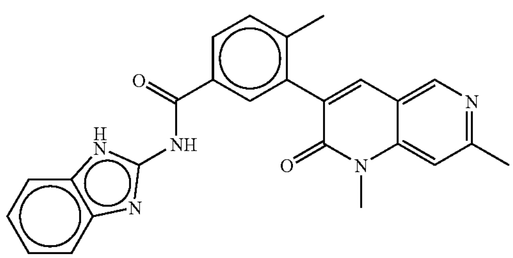 | MS m/z 424.2 (M + 1) |
| 5 | 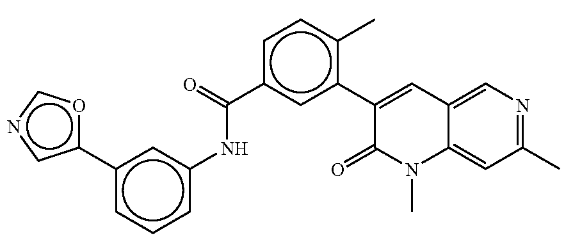 | ¹H NMR 400 MHz (DMSO-d$_6$) δ 10.4 (s, 1H), 8.96 (s, 1H), 8.18 (s, 1H), 8.10 (s, 1H), 7.98 (d, J = 7.6 Hz, 1H), 7.87 (m, 2H), 7.88 (s, 1H), 7.79 (d, J = 3.6 Hz, 1H), 7.68 (s, 2H), 7.46 (m, 3H), 7.11 (t, J = 51.2 Hz, 1H), 2.68 (s, 3H), 2.55 (s, 3H), 2.25 (s, 3H); MS m/z 451.2 (M + 1) |
| 6 | 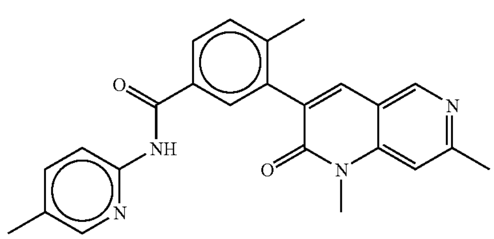 | ¹H NMR (400 MHz, MeOH-d$_4$) δ 9.12 (s, 1H), 8.26 (m, 1H), 8.22 (d, J = 8.7 Hz, 1H), 8.16 (s, 1H), 8.07 (dd, J = 8, 1.6 Hz, 1H), 8.02 (s, 1H), 7.94 (s, 1H), 7.86 (m, 1H), 7.57 (d, J = 8 Hz, 1H), 3.85 (s, 3H), 2.87 (s, 3H), 2.46 (s, 3H), 2.35 (s, 3H); MS m/z 399.2 (M + 1) |

TABLE 9-continued

| M# | Structure | Physical Data<br>¹H NMR 400 MHz and/or MS (m/z) |
|---|---|---|
| 7 | 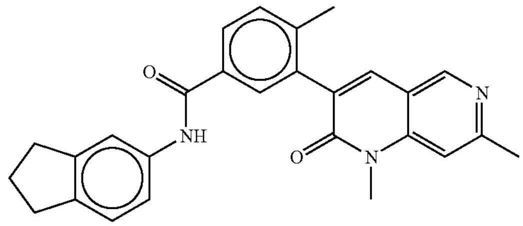 | ¹H NMR 400 MHz (DMSO-d₆) δ 10.1 (s, 1H), 8.98 (s, 1H), 8.10 (s, 1H), 7.93 (d, J = 7.6 Hz, 1H), 7.83 (s, 2H), 7.67 (d, J = 10 Hz, 2H), 7.45 (m, 2H), 7.17 (d, J = 8.4 Hz, 1H), 2.83 (m, 4H), 2.69 (s, 3H), 2.55 (s, 3H), 2.24 (s, 3H), 2.04 (m, 2H); MS m/z 424.2 (M + 1) |
| 8 | 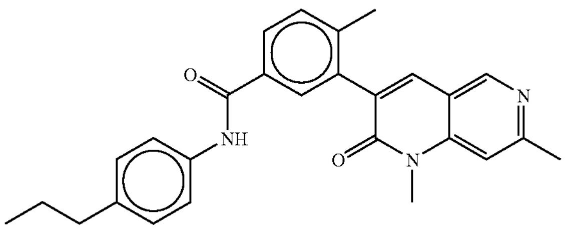 | ¹H NMR 400 MHz (DMSO-d₆) δ 10.15 (s, 1H), 8.99 (s, 1H), 8.09 (s, 1H), 7.94 (m, 1H), 7.83 (m, 1H), 7.69 (s, 1H), 7.64 (d, J = 8.4 Hz, 2H), 7.45 (d, J = 7.6 Hz, 1H), 7.15 (d, J = 8.4 Hz, 2H), 2.69 (s, 3H), 2.55 (s, 5H), 2.23 (s, 3H), 1.57 (q, J = 7.2 Hz, 2H), 0.9 (t, J = 7.2 Hz, 3H); MS m/z 426.2 (M + 1) |
| 9 | 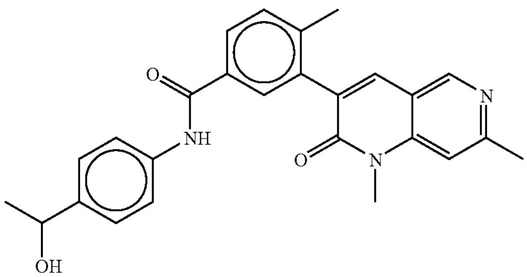 | ¹H NMR 400 MHz (DMSO-d₆) δ 10.2 (s, 1H), 8.98 (s, 1H), 8.10 (s, 1H), 7.95 (d, J = 7.2 Hz, 1H), 7.86 (m, 2H), 7.70 (m, 3H), 7.45 (d, J = 8 Hz, 1H), 7.27 (m, 1H), 7.06 (d, J = 7.2 Hz, 1H), 4.70 (m, 1H), 2.69 (s, 3H), 2.55 (s, 3H), 2.24 (s, 3H), 1.33 (s, 3H); MS m/z 428.2 (M + 1) |
| 10 | 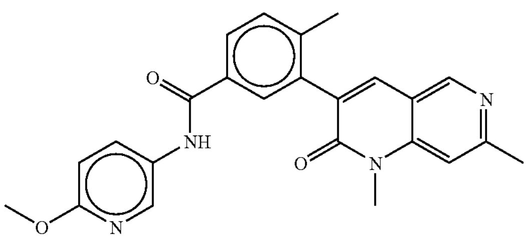 | ¹H NMR 400 MHz (DMSO-d₆) δ 10.3 (s, 1H), 9.0 (s, 1H), 8.50 (s, 1H), 8.11 (s, 1H), 8.03 (m, 1H), 7.96 (d, J = 8 Hz, 1H), 7.85 (m, 1H), 7.72 (m, 1H), 7.47 (m, 1H), 7.11 (t, J = 50.8 Hz, 1H), 6.84 (m, 1H), 3.84 (s, 3H), 2.7 (s, 3H), 2.55 (s, 3H), 2.25 (s, 3H); MS m/z 415.2 (M + 1) |
| 11 | 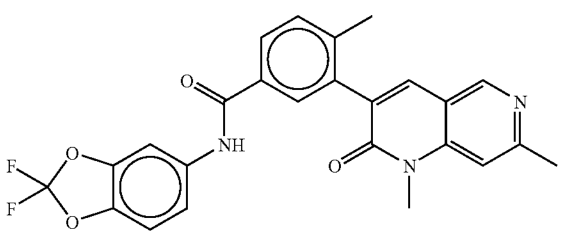 | ¹H NMR 400 MHz (DMSO-d₆) δ 10.4 (s, 1H), 8.92 (s, 1H), 8.08 (s, 1H), 7.92 (m, 2H), 7.83 (d, J = 1.2 Hz, 1H), 7.60 (d, J = 2.8 Hz, 1H), 7.48 (m, 2H), 7.39 (d, J = 8.4 Hz, 1H), 7.12 (t, J = 51.6 Hz, 1H), 2.67 (s, 3H), 2.51 (s, 3H), 2.24 (s, 3H); MS m/z 464.2 (M + 1) |
| 12 | 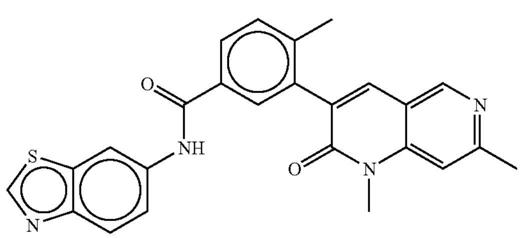 | ¹H NMR 400 MHz (DMSO-d₆) δ 10.5 (s, 1H), 8.97 (s, 1H), 8.67 (s, 1H), 8.11 (s, 1H), 8.05 (d, J = 9.2 Hz, 1H), 7.98 (d, J = 7.6 Hz, 1H), 7.87 (m, 1H), 7.82 (d, J = 8.4 Hz, 1.6 Hz, 1H), 7.67 (m, 1H), 7.48 (d, J = 8.4 Hz, 1H), 7.12 (t, J = 51.6 Hz, 1H), 2.69 (s, 3H), 2.55 (s, 3H), 2.24 (s, 3H); MS m/z 441.1 (M + 1) |

TABLE 9-continued

| M# | Structure | Physical Data<br>¹H NMR 400 MHz and/or MS (m/z) |
|---|---|---|
| 13 | 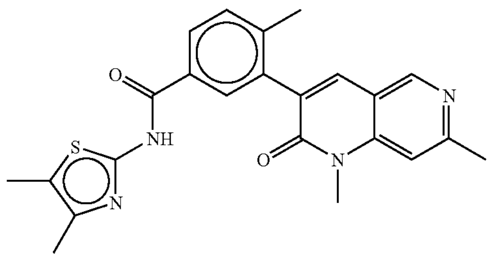 | ¹H NMR 400 MHz (DMSO-d₆) δ 9.0 (s, 1H), 8.10 (s, 1H), 8.04 (d, J = 7.6 Hz, 1H), 7.98 (m, 1H), 7.72 (s, 1H), 7.45 (d, J = 8 Hz, 1H), 7.12 (t, J = 51.2 Hz, 1H), 2.70 (s, 3H), 2.55 (s, 3H), 2.26 (s, 6H), 2.19 (s, 3H); MS m/z 419.2 (M + 1) |
| 14 | 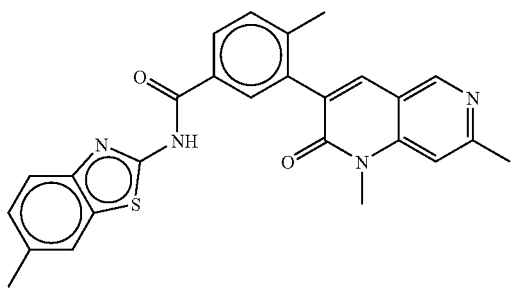 | ¹H NMR 400 MHz (DMSO-d₆) δ 8.97 (s, 1H), 8.11 (s, 1H), 8.03 (s, 1H), 7.79 (s, 1H), 7.67 (s, 1H), 7.5 (d, J = 8 Hz, 1H), 7.28 (d, J = 8.4 Hz, 1H), 2.69 (s, 3H), 2.54 (s, 3H), 2.42 (s, 3H), 2.26 (s, 3H); MS m/z 455.1 (M + 1) |
| 15 | 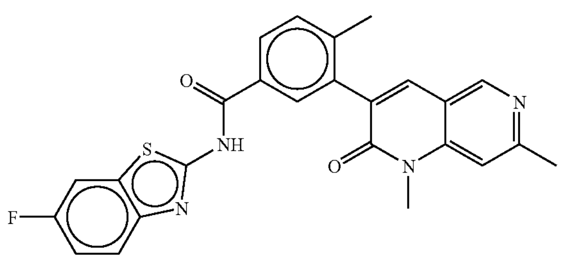 | ¹H NMR 400 MHz (DMSO-d₆) δ 8.83 (s, 1H), 8.06 (m, 3H), 7.92 (d, J = 8.8 Hz, 1H), 7.79 (m, 1H), 7.48 (m, 2H), 7.32 (m, 1H), 2.63 (s, 3H), 2.55 (s, 3H), 2.26 (s, 3H); MS m/z 459.1 (M + 1) |
| 16 | 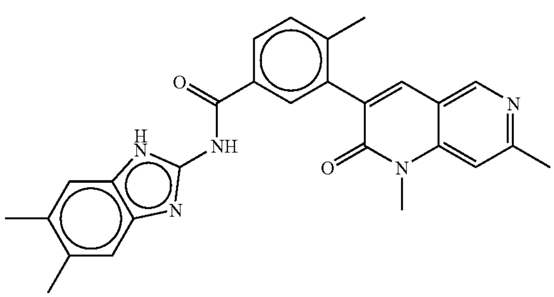 | ¹H NMR 400 MHz (DMSO-d₆) δ 8.98 (s, 1H), 8.11 (m, 2H), 7.98 (s, 1H), 7.69 (s, 1H), 7.51 (d, J = 8 Hz, 1H), 7.34 (s, 2H), 2.69 (s, 3H), 2.55 (s, 3H), 2.31 (s, 6H), 2.26 (s, 3H); MS m/z 452.2 (M + 1) |
| 17 | 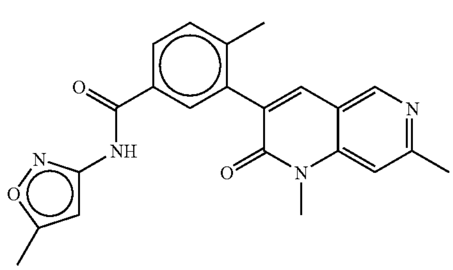 | ¹H NMR 400 MHz (DMSO-d₆) δ 11.3 (s, 1H), 8.99 (s, 1H), 8.09 (s, 1H), 7.98 (d, J = 8.4 Hz, 1H), 7.91 (s, 1H), 7.71 (s, 1H), 7.45 (d, J = 7.6 Hz, 1H), 2.70 (s, 3H), 2.55 (s, 3H), 2.41 (s, 3H), 2.24 (s, 3H); MS m/z 389.2 (M + 1) |

TABLE 9-continued

| M# | Structure | Physical Data<br>¹H NMR 400 MHz and/or MS (m/z) |
|---|---|---|
| 18 | 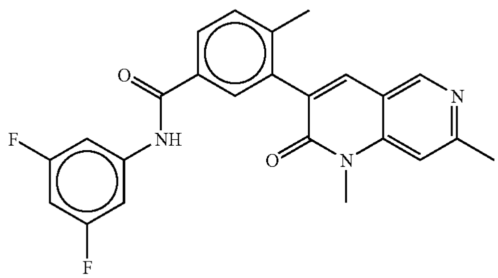 | MS m/z 420.1 (M + 1) |
| 19 | 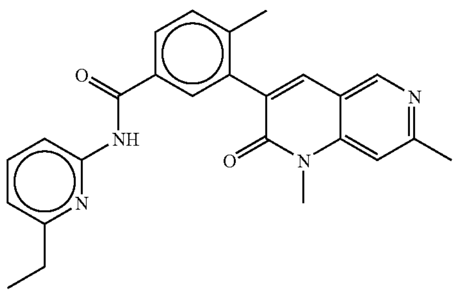 | ¹H NMR 400 MHz (DMSO-d₆) δ 9.08 (s, 1H), 8.14 (s, 1H), 8.04 (m, 2H), 7.94 (m, 1H), 7.82 (s, 1H), 7.76 (t, J = 7.6 Hz, 1H), 7.44 (m, 1H), 7.05 (d, J = 7.2 Hz, 1H), 2.74 (m, 5H), 2.55 (s, 3H), 1.24 (t, J = 7.6 Hz, 3H); MS m/z 413.2 (M + 1) |
| 20 | 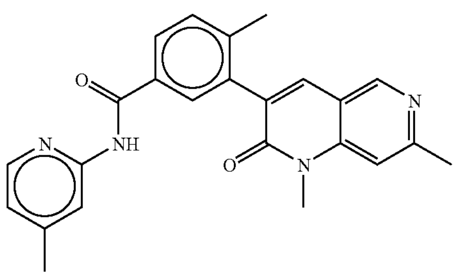 | ¹H NMR 400 MHz (DMSO-d₆) δ 9.07 (s, 1H), 8.25 (d, J = 4.8 Hz, 1H), 8.13 (s, 1H), 8.01 (d, J = 7.5 Hz, 1H), 7.96 (s, 1H), 7.91 (s, 1H), 7.81 (s, 1H), 7.47 (d, J = 8.3 Hz, 1H), 7.08 (d, J = 3.7 Hz, 1H), 2.73 (s, 3H), 2.51 (s, 3H), 2.37 (s, 3H), 2.24 (s, 3H); MS m/z 399.2 (M + 1) |
| 21 | 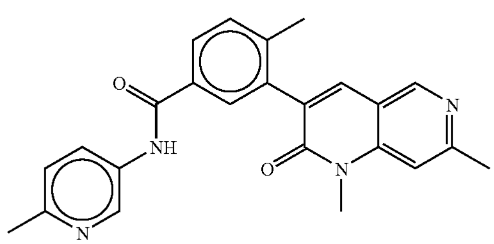 | MS m/z 399.2 (M + 1) |
| 22 | 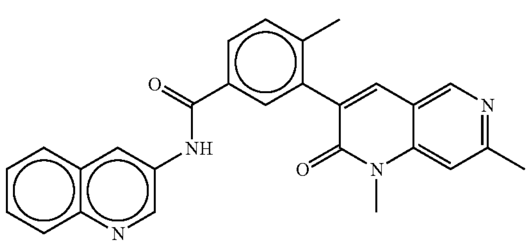 | MS m/z 435.2 (M + 1) |
| 23 | 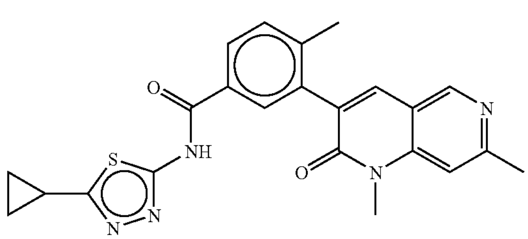 | ¹H NMR 400 MHz (DMSO-d₆) δ 9.02 (s, 1H), 8.11 (s, 1H), 8.06 (d, J = 6.7 Hz, 1H), 7.99 (s, 1H), 7.75 (s, 1H), 7.49 (d, J = 8 Hz, 1H), 2.71 (s, 3H), 2.51 (s, 3H), 2.4 (m, 1H), 2.24 (s, 3H), 1.15 (m, 2H), 1.0 (m, 2H); MS m/z 432.2 (M + 1) |

TABLE 9-continued

| M# | Structure | Physical Data ¹H NMR 400 MHz and/or MS (m/z) |
|---|---|---|
| 24 | 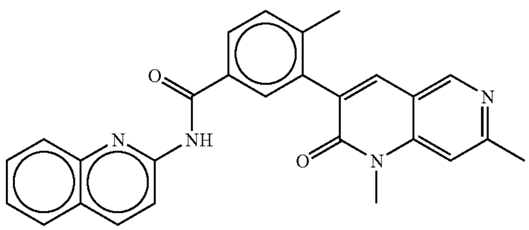 | MS m/z 435.2 (M + 1) |
| 25 | 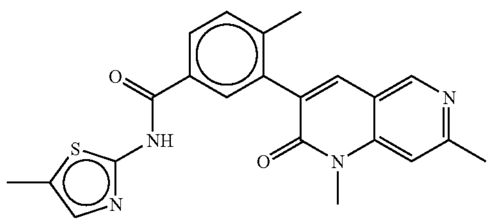 | ¹H NMR 400 MHz (DMSO-d₆) δ 9.07 (s, 1H), 8.12 (s, 1H), 8.05 (d, J = 8.1 Hz, 1H), 7.96 (s, 1H), 7.82 (s, 1H), 7.48 (d, J = 8 Hz, 1H), 7.21 (s, 1H), 2.73 (s, 3H), 2.51 (s, 3H), 2.36 (s, 3H), 2.24 (s, 3H); MS m/z 405.2 (M + 1) |
| 26 | 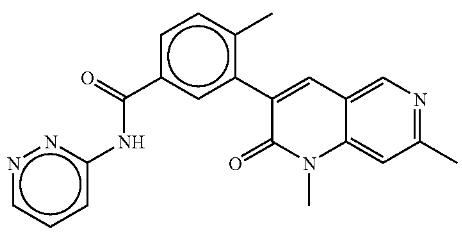 | MS m/z 386.2 (M + 1) |
| 27 | 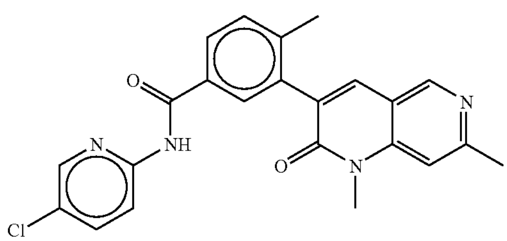 | ¹H NMR (400 MHz, DMSO-d₆) δ 10.99 (s, 1H), 9.17 (s, 1H), 8.44 (d, J = 2.2, 1H), 8.23 (d, J = 8.9 Hz, 1H), 8.18 (s, 1H), 8.03 (d, J = 7.7 Hz, 1H), 7.97 (dd, J = 8.9, 2.5 Hz, 1H), 7.93 (m, 2H), 7.47 (d, J = 8.2 Hz, 1H), 2.79 (s, 3H), 2.51 (s, 3H), 2.25 (s, 3H); MS m/z 419.1 (M + 1) |
| 28 | 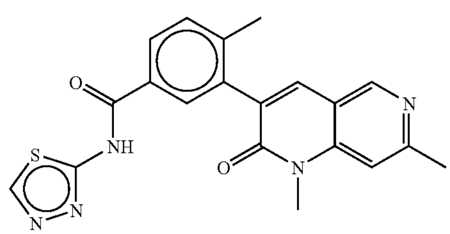 | ¹H NMR 400 MHz (DMSO-d₆) δ 9.21 (s, 1H), 8.97 (s, 1H), 8.09 (m, 2H), 8.02 (s, 1H), 7.67 (m, 1H), 7.5 (m, 1H), 2.69 (s, 3H), 2.55 (s, 3H), 2.25 (s, 3H); MS m/z 392.2 (M + 1) |
| 29 | 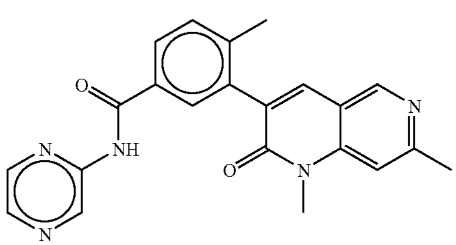 | MS m/z 386.1 (M + 1) |

TABLE 9-continued

| M# | Structure | Physical Data<br>¹H NMR 400 MHz and/or MS (m/z) |
|---|---|---|
| 30 | 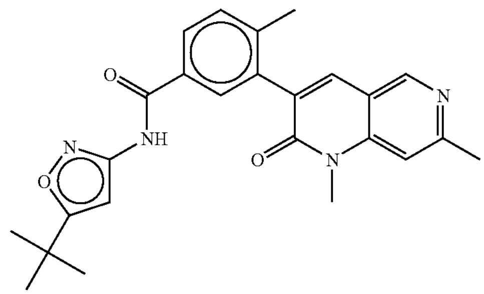 | MS m/z 431.2 (M + 1) |
| 31 | 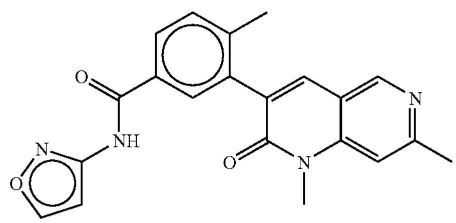 | MS m/z 375.1 (M + 1) |
| 32 | 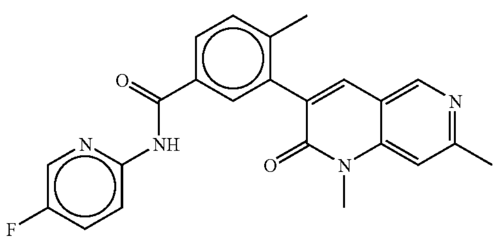 | ¹H NMR (400 MHz, MeOH-d₄) δ 8.84 (s, 1H), 8.28 (m, 1H), 8.04 (s, 1H), 7.95 (dd, J = 8,2 Hz, 1H), 7.86 (d, J = 1.9 Hz, 1H), 7.65 (dt, J = 9.1, 2.9 Hz, 1H), 7.57 (s, 1H), 7.48 (d, J = 8 Hz, 1H), 3.8 (s, 3H), 2.73 (s, 3H), 2.32 (s, 3H); MS m/z 403.2 (M + 1) |
| 33 | 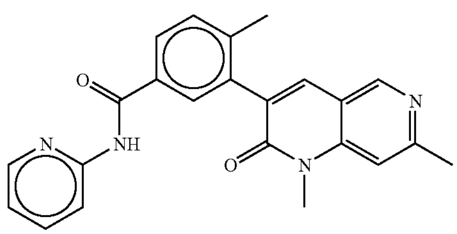 | ¹H NMR (400 MHz, DMSO-d₆) δ 9.09 (s, 1H), 8.39 (d, J = 3.5 Hz, 1H), 8.04 (s, 1H), 8.17 (d, J = 8.5 Hz, 1H), 8.15 (s, 1H), 8.04 (d, J = 8.1 Hz, 1H), 7.94 (s, 1H), 7.87 (dt, J = 8.9, 1.8 Hz, 1H), 7.84 (s, 1H), 7.46 (d, J = 8.1 Hz, 1H), 7.19 (dd, J = 7,5 Hz, 1H), 2.74 (s, 3H), 2.55 (s, 3H), 2.25 (s, 3H); MS m/z 385.1 (M + 1) |
| 34 | 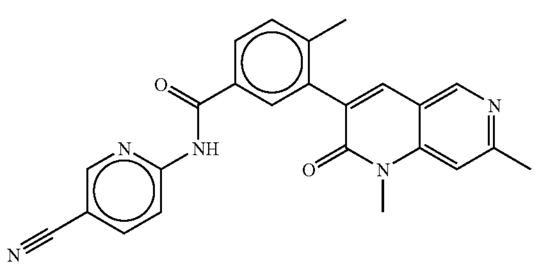 | MS m/z 410.2 (M + 1) |
| 35 | 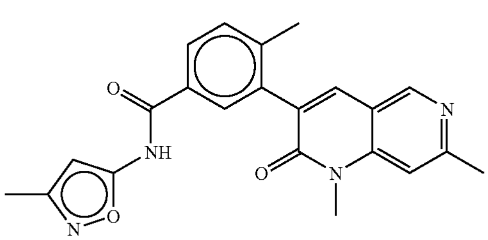 | ¹H NMR 400 MHz (DMSO-d₆) δ 11.92 (s, 1H), 9.03 (s, 1H), 8.11 (s, 1H), 8 (d, J = 7 Hz, 1H), 7.9 (s, 1H), 7.76 (s, 1H), 7.49 (d, J = 8.2 Hz, 1H), 6.32 (s, 1H), 2.72 (s, 3H), 2.51 (s, 3H), 2.24 (s, 3H), 2.22 (s, 3H); MS m/z 389.1 (M + 1) |

TABLE 9-continued

| M# | Structure | Physical Data<br>¹H NMR 400 MHz and/or MS (m/z) |
|---|---|---|
| 36 | 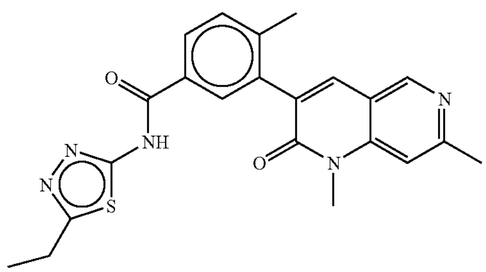 | ¹H NMR 400 MHz (DMSO-d₆) δ 9.0 (s, 1H), 8.11 (s, 1H), 8.08 (d, J = 7.9 Hz, 1H), 8.02 (s, 1H), 7.71 (s, 1H), 7.5 (d, J = 8 Hz, 1H), 3 (q, J = 7.6 Hz, 2H), 2.7 (s, 3H), 2.51 (s, 3H), 2.26 (s, 3H), 1.32 (t, J = 7.5 Hz, 3H); MS m/z 420.2 (M + 1) |
| 37 | 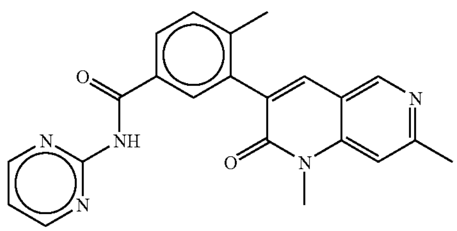 | MS m/z 386.2 (M + 1) |
| 38 | 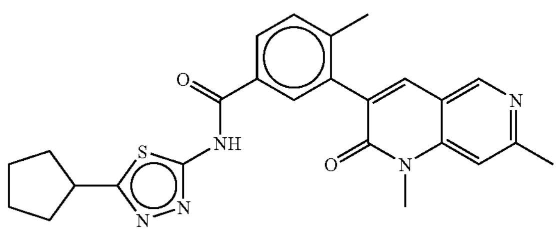 | MS m/z 460.2 (M + 1) |
| 39 | 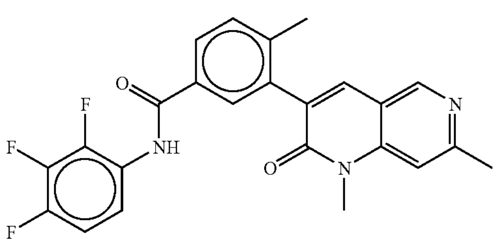 | ¹H NMR (400 MHz, DMSO-d₆) δ 10.35 (s, 1H), 9.02 (s, 1H), 8.12 (s, 1H), 7.97 (d, J = 7 Hz, 1H), 7.85 (s, 1H), 7.74 (s, 1H), 7.49 (d, J = 7.9 Hz, 1H), 7.36 (m, 2H), 2.71 (s, 3H), 2.51 (s, 3H), 2.25 (s, 3H); MS m/z 438.0 (M + 1) |
| 40 | 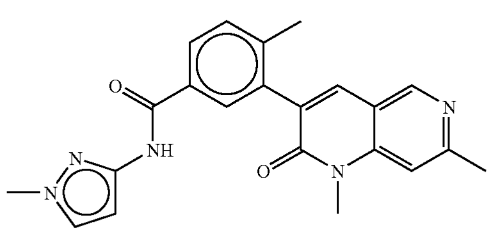 | MS m/z 388.2 (M + 1) |
| 41 | 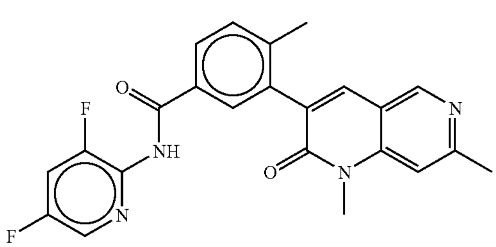 | MS m/z 421.2 (M + 1) |

TABLE 9-continued

| M# | Structure | Physical Data<br>¹H NMR 400 MHz and/or MS (m/z) |
|---|---|---|
| 42 | 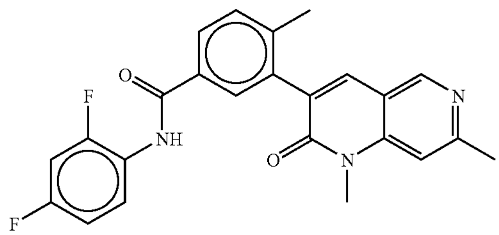 | MS m/z 420.1 (M + 1) |
| 43 | 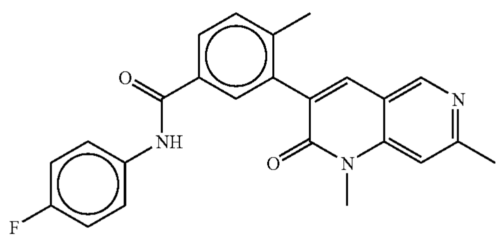 | MS m/z 402.2 (M + 1) |
| 44 | 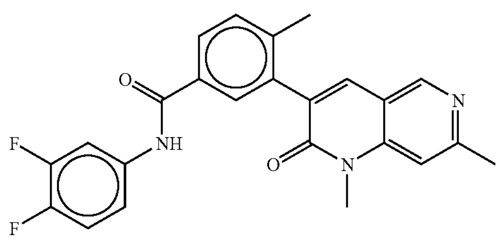 | MS m/z 420.2 (M + 1) |
| 45 | 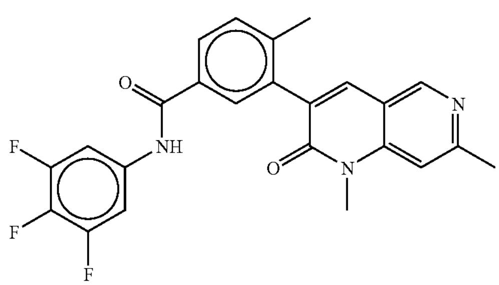 | MS m/z 438.2 (M + 1) |
| 46 | 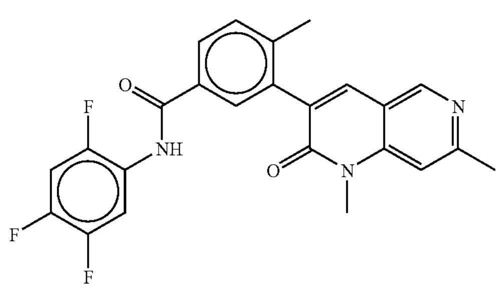 | MS m/z 438.2 (M + 1) |
| 47 | 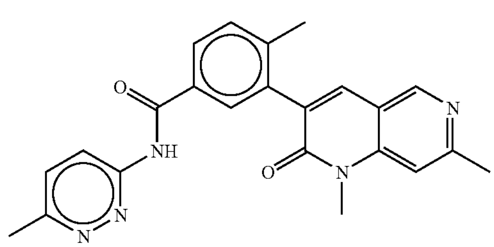 | MS m/z 400.2 (M + 1) |

EXAMPLE 16

3-(1,7-dimethyl-2-oxo-1,2-dihydro-1,6-naphthyridin-3-yl)-4-methyl-N-(phenylcarbamoyl)benzamide (N1)

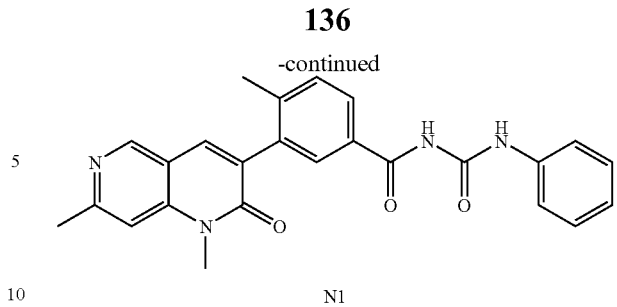

N1

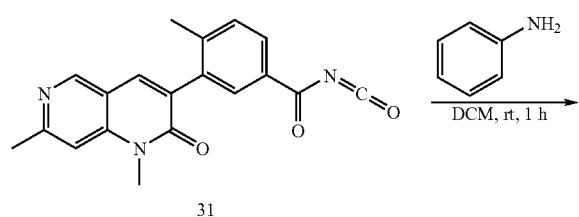

3-(1,7-Dimethyl-2-oxo-1,2-dihydro-1,6-naphthyridin-3-yl)-4-methylbenzoyl isocyanate 31 (10 mg, 0.03 mmol) is suspended in DCM at rt with aniline (3 mg, 0.3 mmol) for 1 h. Solvent is removed and the residue is purified by preparative LC/MS to give the desired product N1. $^1$H NMR (400 MHz, DMSO-$d_6$) δ 11 (s, 1H), 10.8 (s, 1H), 8.99 (s, 1H), 8.1 (s, 1H), 8.01 (d, J=8 Hz, 1H), 7.95 (s, 1H), 7.69 (s, 1H), 7.59 (s, 1H), 7.57 (s, 1H), 7.48 (d, J=7.9 Hz, 1H), 7.36 (m, 2H), 7.12 (t, J=7 Hz, 1H), 2.7 (s, 3H), 2.51 (s, 3H), 2.25 (s, 3H); LC/MS (M+1, m/z): 427.2.

Table 10 describes other exemplary compounds of the invention, prepared following methods analogous to those described above.

TABLE 10

| N# | Structure | Physical Data $^1$H NMR 400 MHz and/or MS (m/z) |
|---|---|---|
| 1 | 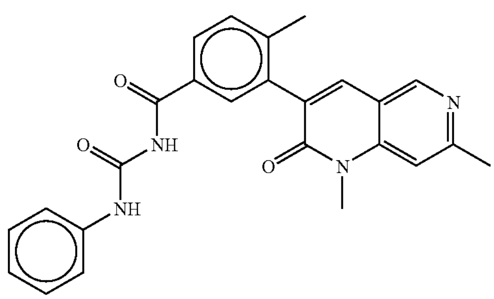 | $^1$H NMR (400 MHz, DMSO-$d_6$) δ 11 (s, 1H), 10.8 (s, 1H), 8.99 (s, 1H), 8.1 (s, 1H), 8.01 (d, J = 8 Hz, 1H), 7.95 (s, 1H), 7.69 (s, 1H), 7.59 (s, 1H), 7.57 (s, 1H), 7.48 (d, J = 7.9 Hz, 1H), 7.36 (m, 2H), 7.12 (t, J = 7 Hz, 1H), 2.7 (s, 3H), 2.51 (s, 3H), 2.25 (s, 3H); MS m/z 427.2 (M + 1) |
| 2 | 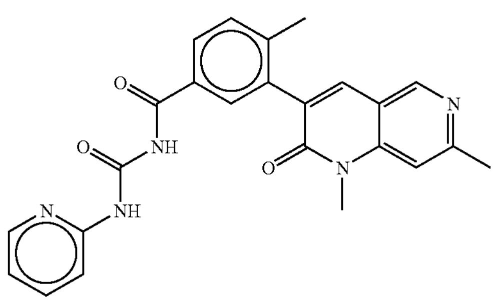 | $^1$H NMR (400 MHz, DMSO-$d_6$) δ 11.2 (s, 1H), 9.05 (s, 1H), 8.34 (d, J = 3.6 Hz, 1H), 8.13 (m, 2H), 8.03 (m, 2H), 7.93 (s, 1H), 7.85 (t, J = 7.4 Hz, 1H), 7.78 (s, 1H), 7.5 (d, J = 8.4 Hz, 1H), 7.16 (d, J = 6 Hz, 1H), 2.73 (s, 3H), 2.51 (s, 3H), 2.26 (s, 3H); MS m/z 428.2 (M + 1) |
| 3 | 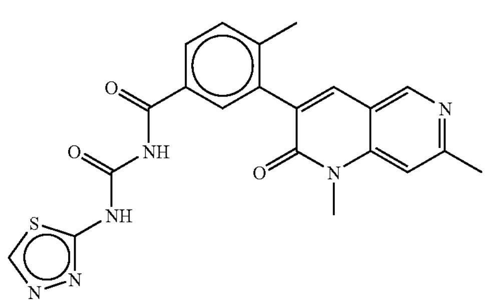 | MS m/z 435.1 (M + 1) |

TABLE 10-continued

| N# | Structure | Physical Data<br>¹H NMR 400 MHz and/or MS (m/z) |
|---|---|---|
| 4 | 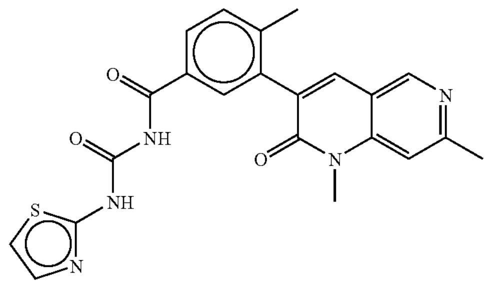 | ¹H NMR (400 MHz, DMSO-d₆) δ 11.5 (s, 1H), 8.99 (s, 1H), 8.1 (s, 1H), 8.02 (d, J = 7.4 Hz, 1H), 7.94 (s, 1H), 7.7 (s, 1H), 7.51 (m, 2H), 7.3 (d, J = 3 Hz, 1H), 3.7 (s, 1H), 2.7 (s, 3H), 2.51 (s, 3H), 2.26 (s, 3H); MS m/z 434.1 (M + 1) |
| 5 | 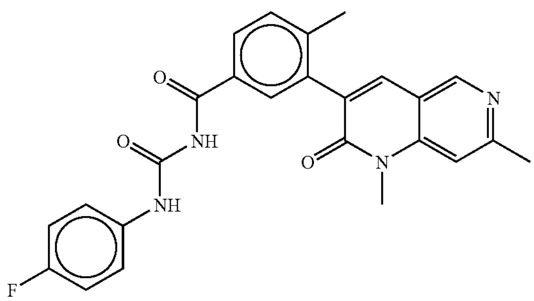 | MS m/z 445.2 (M + 1) |
| 6 | 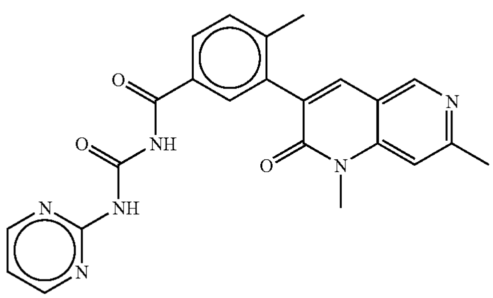 | MS m/z 429.1 (M + 1) |
| 7 | 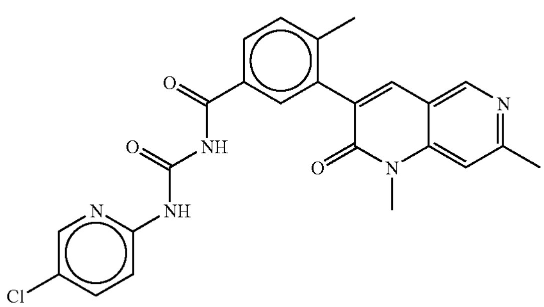 | MS m/z 462.1, 464.1 (M + 1) |
| 8 | 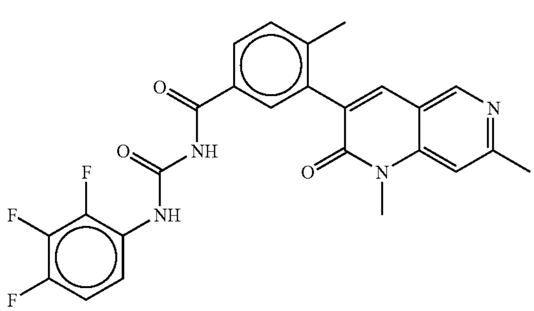 | MS m/z 481.2 (M + 1) |

TABLE 10-continued
| N# | Structure | Physical Data<br>¹H NMR 400 MHz and/or MS (m/z) |
|---|---|---|
| 9 | 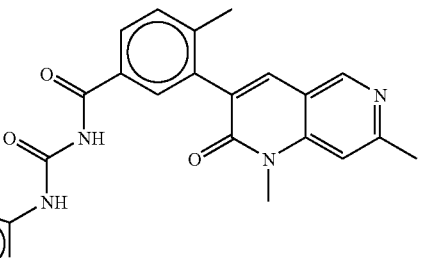 | MS m/z 448.2 (M + 1) |
| 10 | 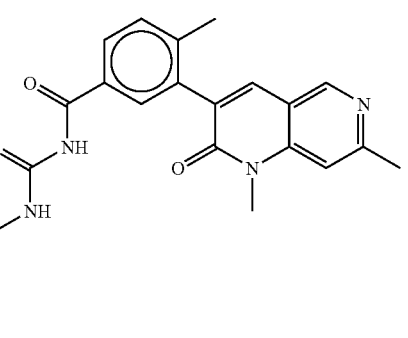 | MS m/z 442.2 (M + 1) |
| 11 | 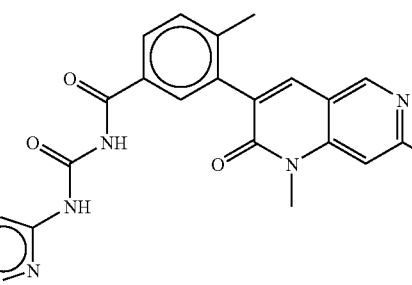 | MS m/z 475.2 (M + 1) |
| 12 | 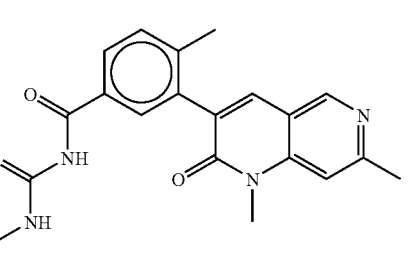 | MS m/z 418.2 (M + 1) |
| 13 | 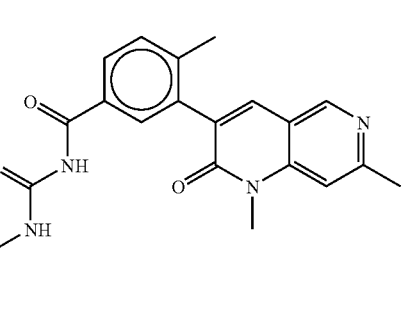 | MS m/z 432.1 (M + 1) |

TABLE 10-continued

| N# | Structure | Physical Data<br>¹H NMR 400 MHz and/or MS (m/z) |
|---|---|---|
| 14 | 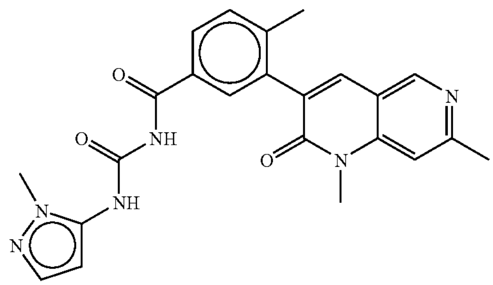 | MS m/z 431.2 (M + 1) |
| 15 | 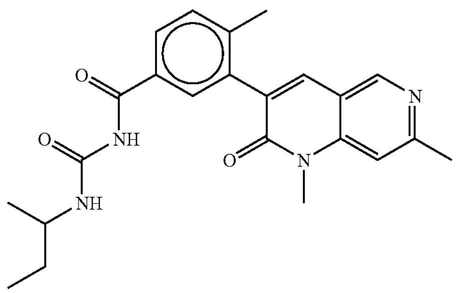 | ¹H NMR (400 MHz, DMSO-d₆) δ 10.6 (s, 1H), 8.96 (s, 1H), 8.54 (d, J = 7.9 Hz, 1H), 8.07 (s, 1H), 7.93 (d, J = 7.9 Hz, 1H), 7.87 (s, 1H), 7.67 (s, 1H), 7.44 (d, J = 8.1 Hz, 1H), 2.72 (s, 3H), 2.37 (s, 3H), 2.22 (s, 3H), 1.5 (t, J = 6.8 Hz, 1H), 1.14 (d, J = 6.3 Hz, 3H), 1.06 (t, J = 6.9 Hz, 2H), 0.88 (t, J = 7.1 Hz, 1H); MS m/z 407.2 (M + 1) |
| 16 | 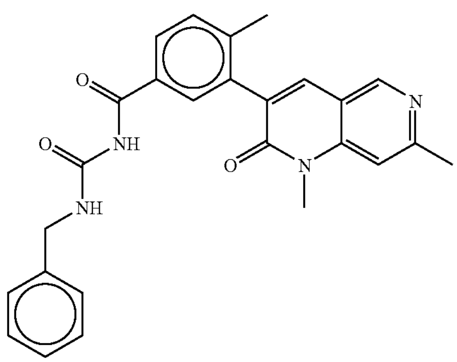 | MS m/z 441.2 (M + 1) |
| 17 | 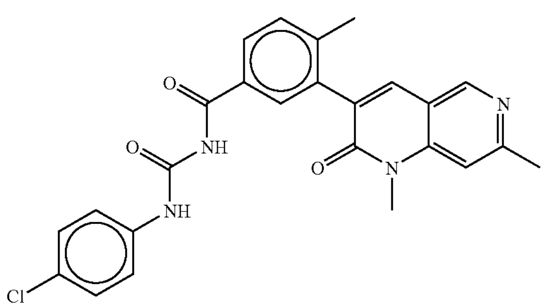 | MS m/z 461.1 (M + 1) |
| 18 | 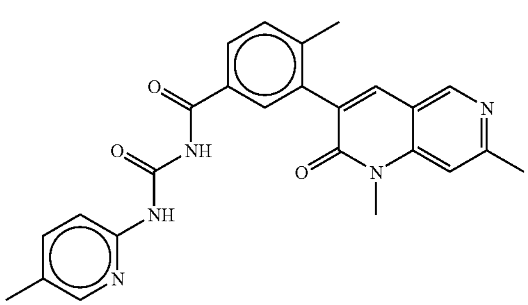 | MS m/z 442.2 (M + 1) |

TABLE 10-continued
| N# | Structure | Physical Data<br>¹H NMR 400 MHz and/or MS (m/z) |
|---|---|---|
| 19 | 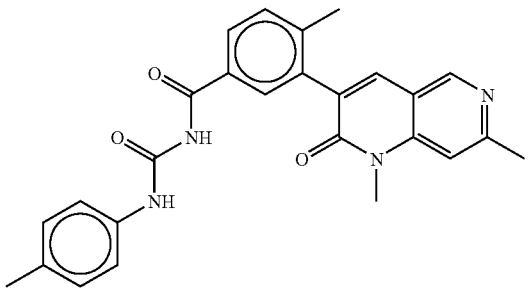 | MS m/z 441.2 (M + 1) |
| 20 | 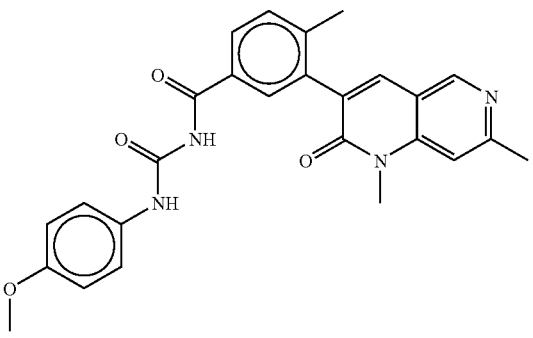 | MS m/z 457.2 (M + 1) |
| 21 | 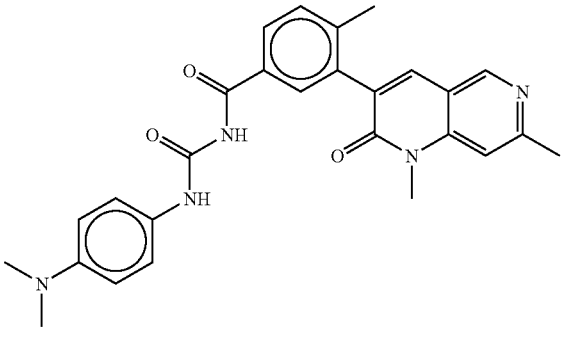 | MS m/z 470.2 (M + 1) |
| 22 | 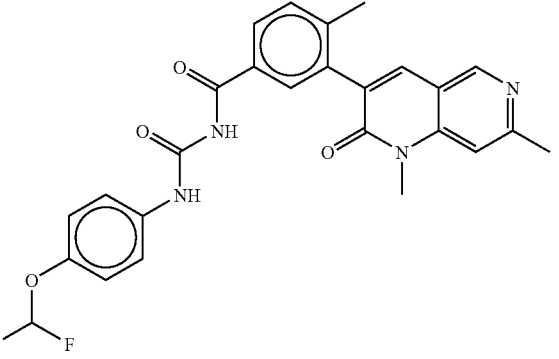 | ¹H NMR (400 MHz, DMSO-d₆) δ 11 (s, 1H), 10.8 (s, 1H), 8.89 (s, 1H), 8.07 (s, 1H), 7.99 (d, J = 7.3 Hz, 1H), 7.94 (s, 1H), 7.63 (d, J = 8 Hz, 2H), 7.56 (s, 1H), 7.48 (d, J = 7.7 Hz, 1H), 7.18 (d, J = 8.8 Hz, 2H), 7.17 (t, J = 74 Hz, 1H), 2.72 (s, 3H), 2.37 (s, 3H), 2.25 (s, 3H); MS m/z 493.2 (M + 1) |

Table 11 describes related compounds (1-5) and other compounds which may be prepared using any of the General Procedures A-N as described above.

TABLE 11

| | Structure | Physical Data $^1$H NMR 400 MHz and/or MS (m/z) |
|---|---|---|
| 1 | 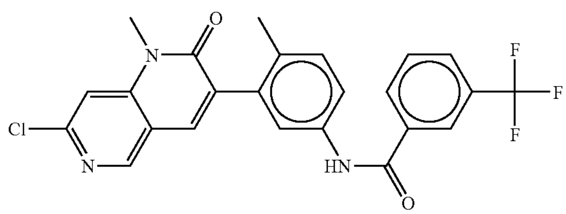 | $^1$H NMR (400 MHz, CDCl$_3$) δ 8.59 (s, 1H), 8.25 (s, 1H), 8.13 (s, 1H), 8.08 (d, J = 8.0 Hz, 1H), 7.78 (d, J = 7.9 Hz, 1H), 7.71 (s, 1H), 7.65-7.60 (m, 2H), 7.45 (dd, J = 8.2, 2.0 Hz, 1H), 7.32 (s, 1H), 7.20 (d, J = 8.4 Hz, 1H), 3.76 (s, 3H), 2.04 (s, 3H). |
| 2 | 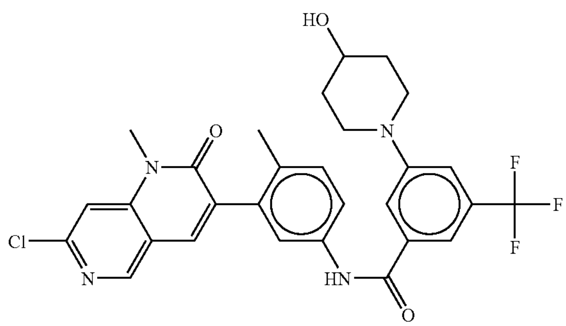 | $^1$H NMR 400 MHz (MeOD) δ 8.61 (s, 1H), 7.88 (s, 1H), 7.61 (s, 1H), 7.56-7.53 (m, 3H), 7.48 (s, 1H), 7.24 (s, 1H), 7.20 (d, 1H), 3.75-3.65 (m, 6H), 3.05-2.90 (m, 2H), 2.10 (s, 3H), 1.91-1.85 (m, 2H), 1.60-1.45 (m, 2H); MS m/z 571.2 (M + 1) |
| 3 | 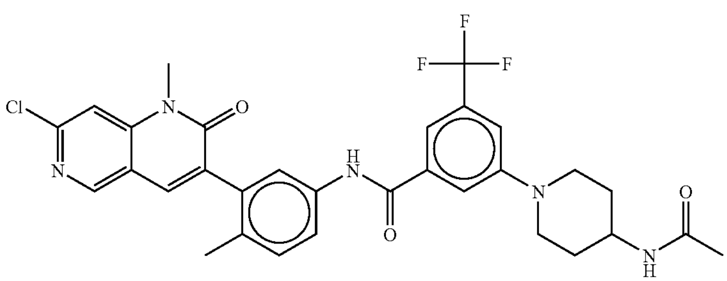 | $^1$H NMR (400 MHz, CD$_3$OD) δ 8.70 (s, H), 7.96 (s, 1H), 7.72 (s, 1H), 7.65 (s, 1H), 7.61-7.63 (m, 2H), 7.60 (s, 1H), 7.37 (s, 1H), 7.28 (d, 1H), 3.84-3.90 (m, 3H), 3.74 (s, 3H), 3.00 (dt, 2H), 2.19 (s, 3H), 1.97-2.02 (m, 2H), 1.94 (s, 3H), 1.61 (dq, 2H); MS m/z 612.2 (M + 1) |
| 4 | 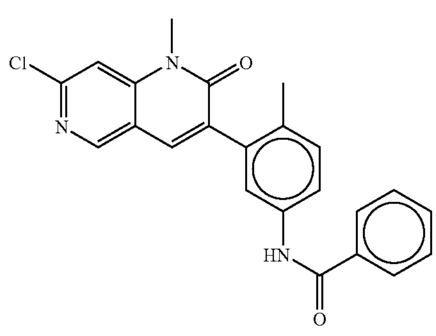 | MS m/z 426.1 (M + 1) |
| 5 | 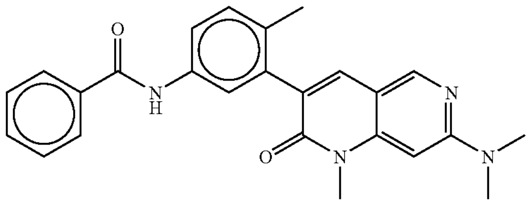 | $^1$H NMR 400 MHz (DMSO-d$_6$) δ 10.23 (s, 1H), 8.51 (s, 1H), 7.97-7.94 (m, 2H), 7.78 (s, 1H), 7.68-7.66 (m, 2H), 7.61-7.51 (m, 3H), 7.23 (d, J = 9 Hz, 1H), 6.37 (s, 1H), 3.61 (s, 3H), 3.20 (s, 6H), 2.12 (s, 3H); MS m/z 413.2 (M + 1) |

TABLE 11-continued

| | Structure | Physical Data $^1$H NMR 400 MHz and/or MS (m/z) |
|---|---|---|
| 6 | 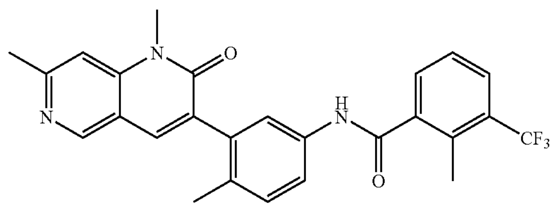 | |
| 7 | 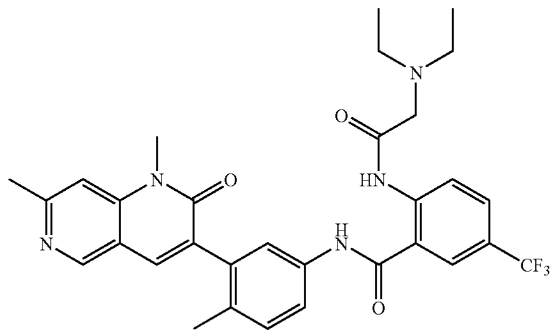 | |
| 8 | 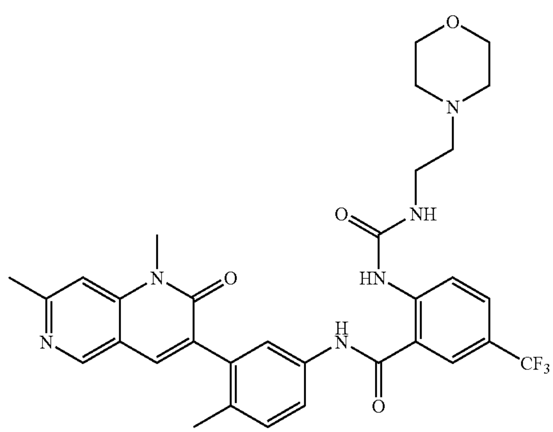 | |
| 9 | 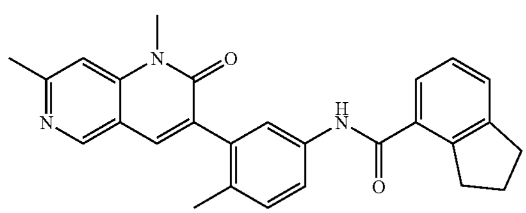 | |
| 10 | 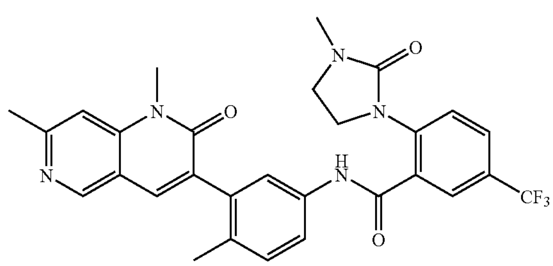 | |

TABLE 11-continued

| | Structure | Physical Data<br>¹H NMR 400 MHz and/or MS (m/z) |
|---|---|---|
| 11 | 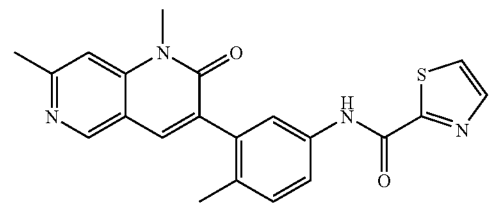 | |
| 12 | 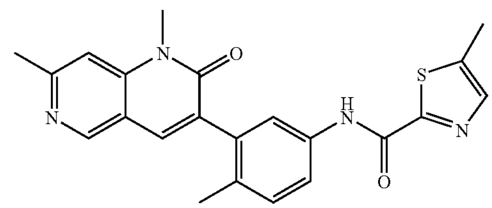 | |
| 13 | 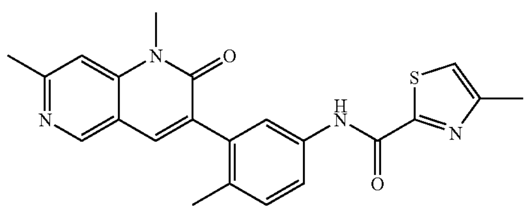 | |
| 14 | 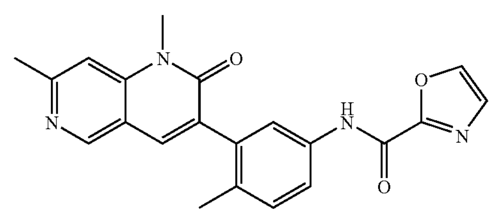 | |
| 15 | 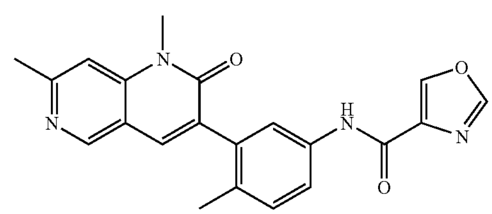 | |
| 16 | 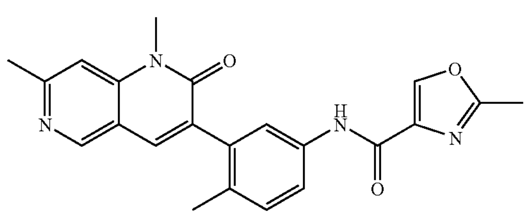 | |
| 17 | 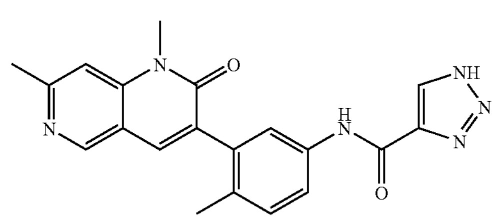 | |

TABLE 11-continued
| Structure | Physical Data<br>¹H NMR 400 MHz and/or MS (m/z) |
|---|---|
| 18 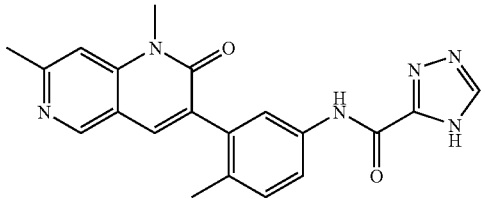 | |
| 19 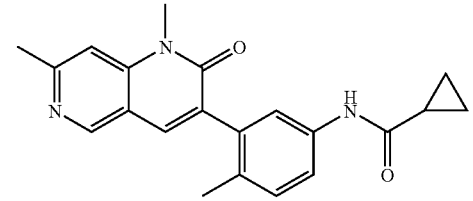 | |
| 20 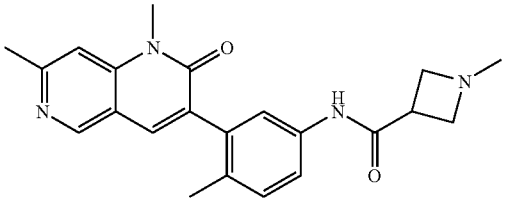 | |
| 21 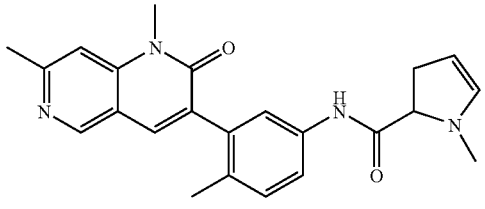 | |
| 22 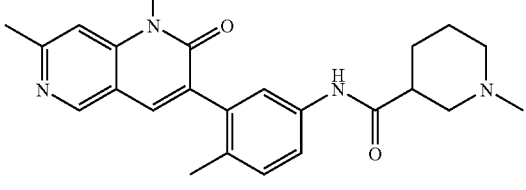 | |
| 23 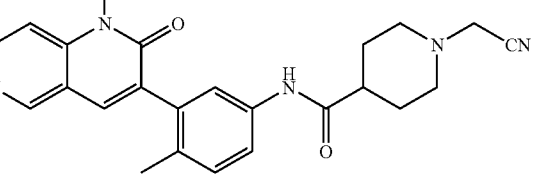 | |
| 24 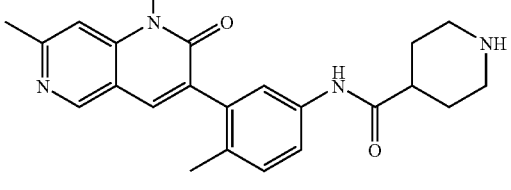 | |

TABLE 11-continued
| | Structure | Physical Data $^1$H NMR 400 MHz and/or MS (m/z) |
|---|---|---|
| 25 | 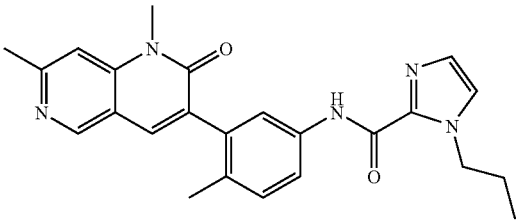 | |
| 26 | 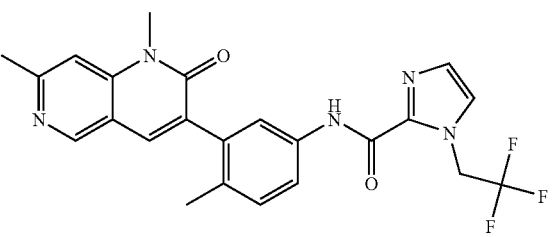 | |
| 27 | 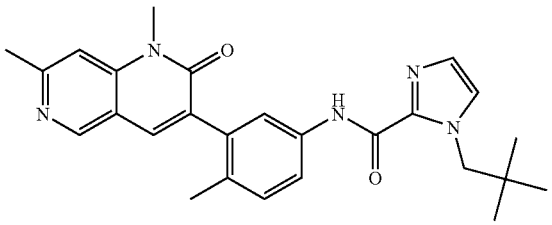 | |
| 28 | 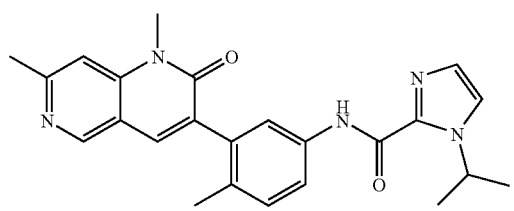 | |
| 29 | 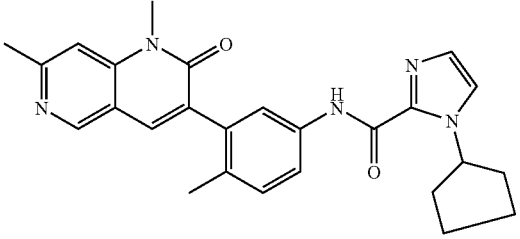 | |
| 30 | 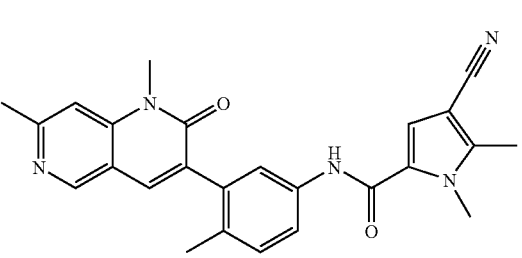 | |

TABLE 11-continued
| Structure | Physical Data $^1$H NMR 400 MHz and/or MS (m/z) |
|---|---|
| 31 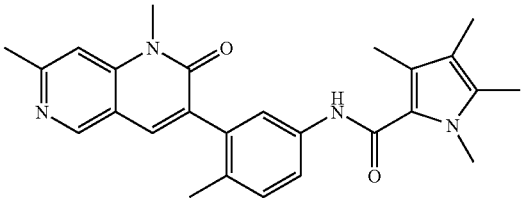 | |
| 32 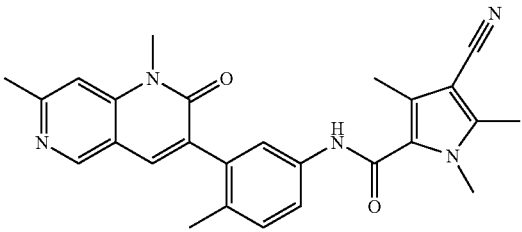 | |
| 33 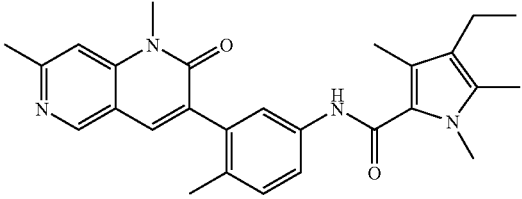 | |
| 34 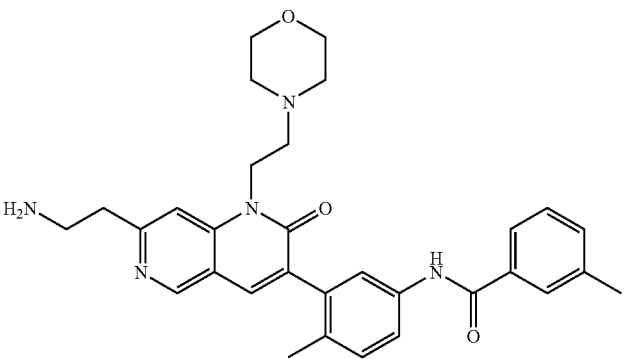 | |
| 35 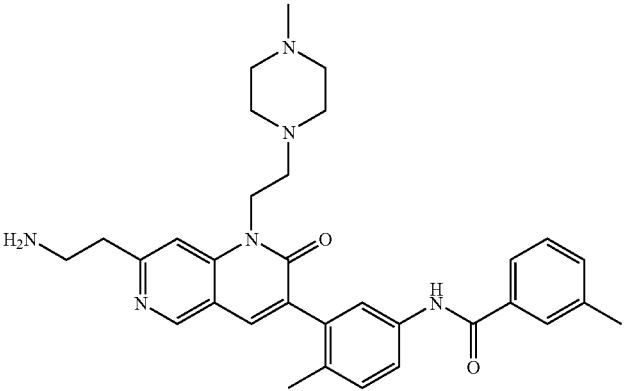 | |

TABLE 11-continued

| | Structure | Physical Data $^1$H NMR 400 MHz and/or MS (m/z) |
|---|---|---|
| 36 | 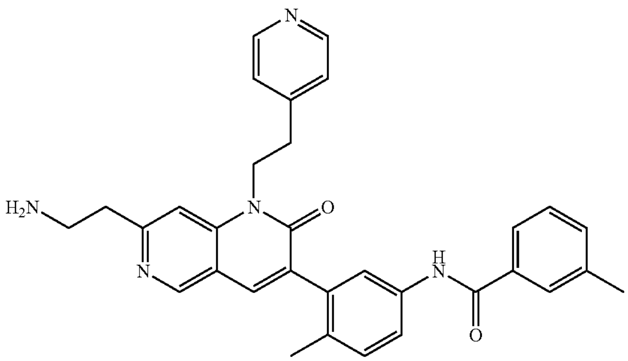 | |
| 37 | 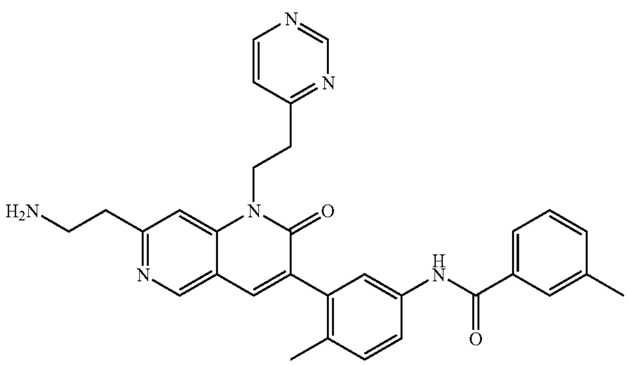 | |
| 38 | 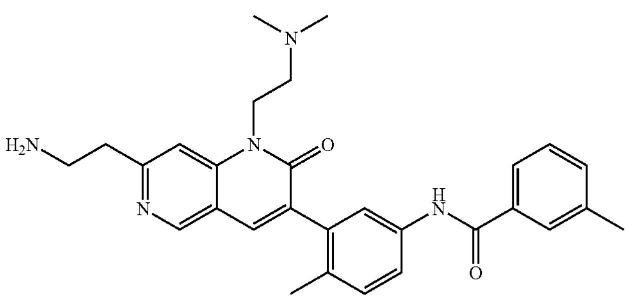 | |
| 39 | 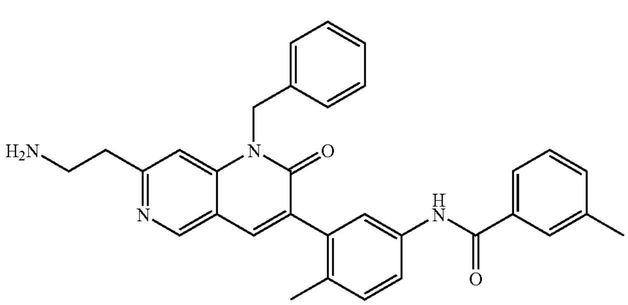 | |

TABLE 11-continued

| Structure | Physical Data $^1$H NMR 400 MHz and/or MS (m/z) |
|---|---|
| 40 | |
| 41 | |
| 42 | |
| 43 | |

TABLE 11-continued

| | Structure | Physical Data
$^1$H NMR 400 MHz and/or MS (m/z) |
|---|---|---|
| 44 | | |
| 45 | | |
| 46 | | |
| 47 | | |
| 48 | | |
| 49 | | |

TABLE 11-continued

| | Structure | Physical Data $^1$H NMR 400 MHz and/or MS (m/z) |
|---|---|---|
| 50 | 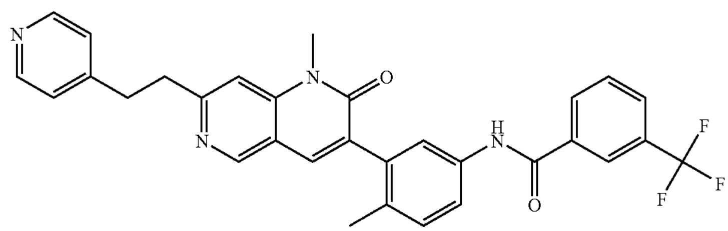 | |
| 51 | 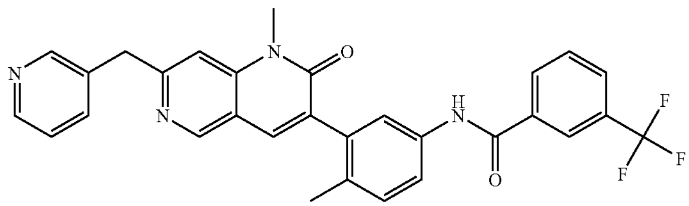 | |
| 52 | 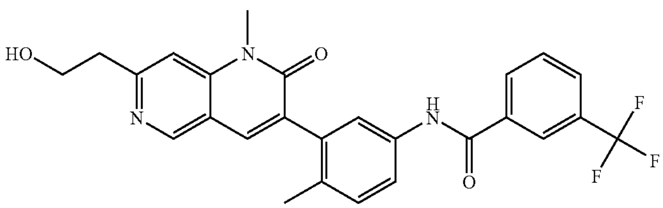 | |
| 53 | 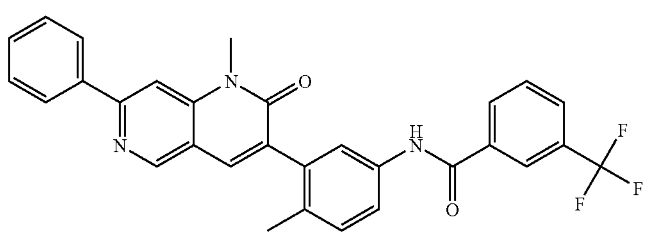 | |
| 54 | 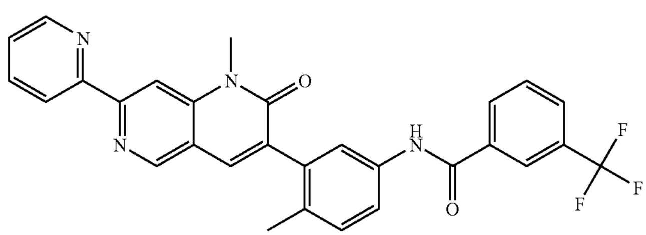 | |
| 55 | 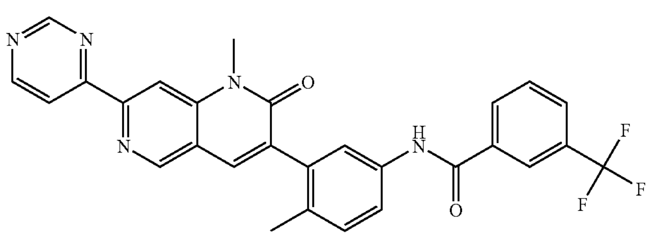 | |

TABLE 11-continued

| Structure | Physical Data<br>$^1$H NMR 400 MHz and/or MS (m/z) |
|---|---|
| 56 | |
| 57 | |
| 58 | |
| 59 | |
| 60 | |
| 61 | |

TABLE 11-continued

| | Structure | Physical Data $^1$H NMR 400 MHz and/or MS (m/z) |
|---|---|---|
| 62 | 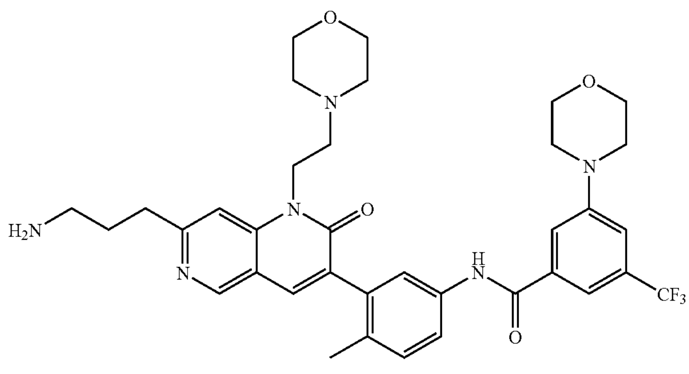 | |
| 63 | 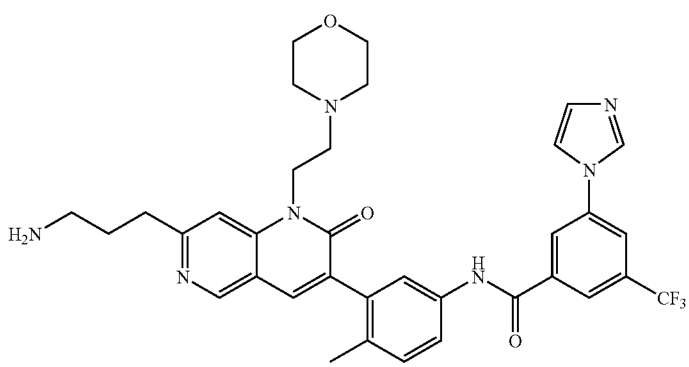 | |
| 64 | 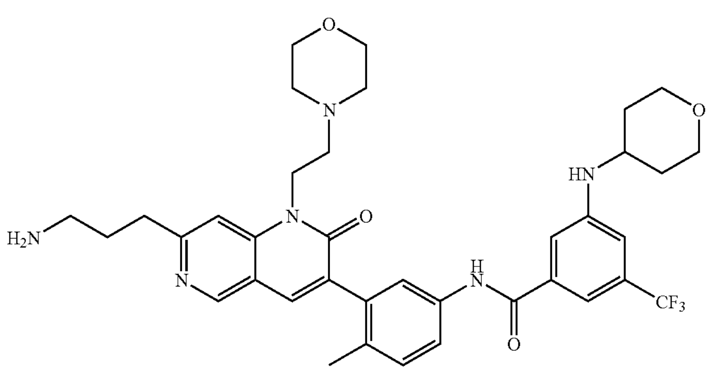 | |
| 65 | 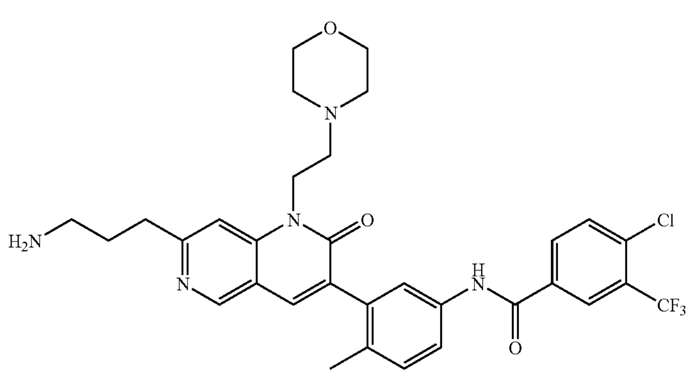 | |

TABLE 11-continued

| | Structure | Physical Data<br>¹H NMR 400 MHz and/or MS (m/z) |
|---|---|---|
| 66 | 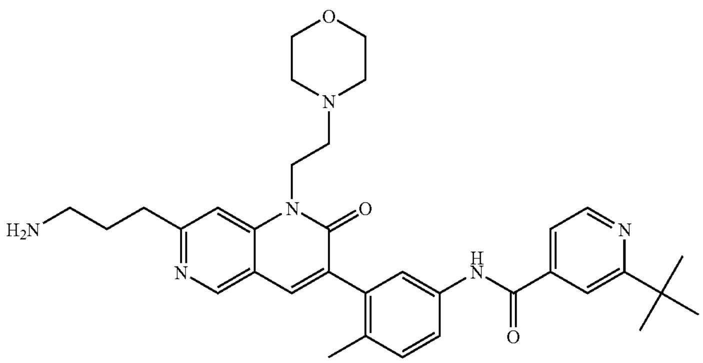 | |
| 67 | 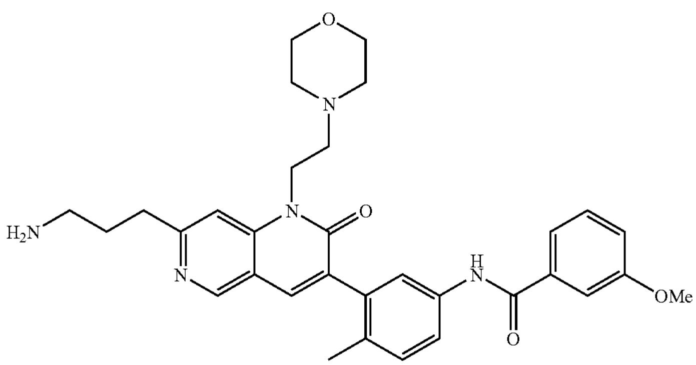 | |
| 68 | 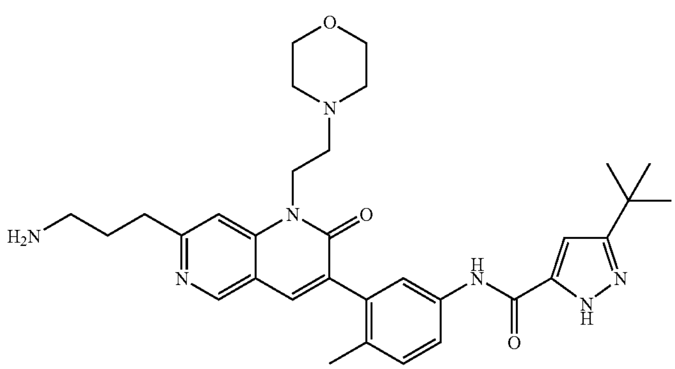 | |
| 69 | 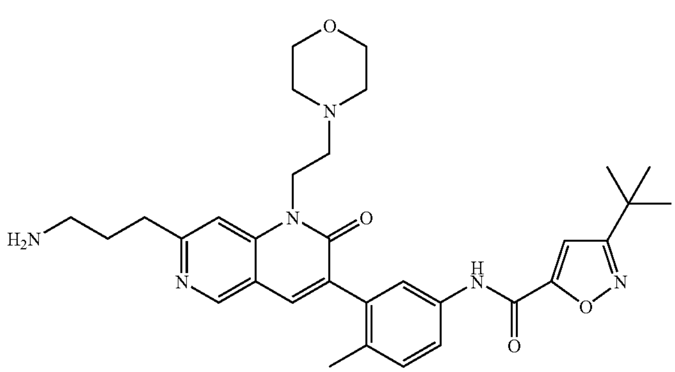 | |

TABLE 11-continued

| | Physical Data |
|---|---|
| Structure | ¹H NMR 400 MHz and/or MS (m/z) |

70

71

72

73

TABLE 11-continued

| Structure | Physical Data<br>¹H NMR 400 MHz and/or MS (m/z) |
|---|---|
| 74 | |
| 75 | |
| 76 | |
| 77 | |

Assays

Compounds of the invention are assayed to measure their capacity to inhibit protein kinases such as c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf or b-raf kinase, or mutant forms thereof, using assays generally described below, or using assays known in the art. For example, compounds of the present invention are assayed to measure their capacity to selectively inhibit the proliferation of wild type Ba/F3 cells and Ba/F3 cells transformed with Tel c-kit kinase and Tel PDGFR fused tyrosine kinases, and to selectively inhibit SCF dependent proliferation in Mo7e cells.

Proliferation Assay: BaF3 Library—Bright glo Readout Protocol

Compounds are tested for their ability to inhibit the proliferation of wt Ba/F3 cells and Ba/F3 cells transformed with Tel fused tyrosine kinases. Untransformed Ba/F3 cells are maintained in media containing recombinant IL3. Cells are plated into 384-well TC plates at 5,000 cells in 50 µl media per well, and test compound at 0.06 nM to 10 µM is added. The cells are then incubated for 48 hours at 37° C., 5% $CO_2$. After incubating the cells, 25 µL of BRIGHT GLO® (Promega) is added to each well following manufacturer's instructions, and the plates are read using Analyst GT-Luminescence mode-50000 integration time in RLU. $IC_{50}$ values, the concentration of compound required for 50% inhibition, are determined from a dose response curve.

Ba/F3 FL FLT3 Proliferation Assay

The murine cell line used is the Ba/F3 murine pro-B cell line that overexpresses full length FLT3 construct. These cells are maintained in RPMI 1640/10% fetal bovine serum (RPMI/FBS) supplemented with penicillin 50 µg/mL, streptomycin 50 µg/mL and L-glutamine 200 mM with the addition of murine recombinant IL3. Ba/F3 full length FLT3 cells undergo IL3 starvation for 16 hours and then plated into 384-well TC plates at 5,000 cells in 25 µL media per well; and test compound at 0.06 nM to 10 µM is added. After the compound addition, FLT3 ligand or IL3 for cytotoxicity control is added in 25 µl media per well at the appropriate concentrations. The cells are then incubated for 48 hours at 37° C., 5% $CO_2$. After incubating the cells, 25 µL of BRIGHT GLO® (Promega) is added to each well following manufacturer's instructions and the plates are read using Analyst GT-Luminescence mode-50000 integration time in RLU.

Mo7e Assay

Mo7e cells are a human promegakaryocytic leukemia cell line, which depends on SCF for proliferation. The compounds described herein are tested for inhibition of SCF dependent proliferation using Mo7e cells, which endogenously express c-kit in a 96-well format. Briefly, two-fold serially diluted test compounds (Cmax=10 µM) are evaluated for their antiproliferative activity of Mo7e cells stimulated with human recombinant SCF. After 48 hours of incubation at 37° C., cell viability is measured by using a MTT colorimetric assay from Promega.

Inhibition of Cellular BCR-Abl Dependent Proliferation (High Throughput Method)

The murine cell line 32D hemopoietic progenitor cell line may be transformed with BCR-Abl cDNA (32D-p210). These cells are maintained in RPMI/10% fetal calf serum (RPMI/FCS) supplemented with penicillin (50 µg/mL), streptomycin (50 µg/mL) and L-glutamine (200 mM). Untransformed 32D cells are similarly maintained with the addition of 15% of WEHI conditioned medium as a source of IL3.

50 µl of a 32D or 32D-p210 cells suspension are plated in Greiner 384 well microplates (black) at a density of 5000 cells per well. 50 nL of test compound (1 mM in DMSO stock solution) is added to each well (STI571 is included as a positive control). The cells are incubated for 72 hours at 37° C., 5% $CO_2$. 10 µl of a 60% ALAMAR BLUE™ solution (Tek diagnostics) is added to each well and the cells are incubated for an additional 24 hours. The fluorescence intensity (excitation at 530 nm; emission at 580 nm) is quantified using the ACQUEST™ system (Molecular Devices).

Inhibition of Cellular BCR-Abl Dependent Proliferation 32D-p210 cells are plated into 96-well TC plates at a density of 15,000 cells per well. 50 µL of two-fold serial dilutions of the test compound ($C_{max}$ is 40 µM) are added to each well (STI571 is included as a positive control). After incubating the cells for 48 hours at 37° C., 5% $CO_2$, 15 µL of MTT (Promega) is added to each well and the cells are incubated for an additional 5 hours. The optical density at 570 nm is quantified spectrophotometrically; and $IC_{50}$ values are determined from a dose response curve.

Effect on Cell Cycle Distribution 32D and 32D-p210 cells are plated into 6-well TC plates at 2.5×106 cells per well in 5 ml of medium, and test compound at 1 or 10 µM is added (STI571 is included as a control). The cells are then incubated for 24 or 48 hours at 37° C., 5% $CO_2$. Two mL of cell suspension is washed with PBS, fixed in 70% EtOH for 1 hour and treated with PBS/EDTA/RNase A for 30 minutes. Propidium iodide (Cf=10 µg/ml) is added and the fluorescence intensity is quantified by flow cytometry on the FACScalibur™ system (BD Biosciences). In some embodiments, test compounds of the present invention may demonstrate an apoptotic effect on the 32D-p210 cells but not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at 2×10⁵ cells per well in 50 µL of medium. 50 µL two-fold serial dilutions of test compounds ($C_{max}$ is 10 µM) are added to each well (STI571 is included as a positive control). The cells are incubated for 90 minutes at 37° C., 5% $CO_2$. The cells are then treated for 1 hour on ice with 150 µL of lysis buffer (50 mM Tris-HCl, pH 7.4, 150 mM NaCl, 5 mM EDTA, 1 mM EGTA and 1% NP-40) containing protease and phosphatase inhibitors. 50 µL of cell lysate is added to 96-well optiplates previously coated with anti-abl specific antibody and blocked. The plates are incubated for 4 hours at 4° C. After washing with TBS-Tween 20 buffer, 50 µL of alkaline-phosphatase conjugated anti-phosphotyrosine antibody is added and the plate is further incubated overnight at 4° C. After washing with TBS-Tween 20 buffer, 90 µL of a luminescent substrate are added, and the luminescence is quantified using the ACQUEST™ system (Molecular Devices).

Effect on Proliferation of Cells Expressing Mutant Forms of Bcr-abl

Compounds of the invention may be tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant BCR-Abl expressing cells and on the non-transformed cells may be tested at 10, 3.3, 1.1 and 0.37 µM as described above (in media lacking IL3). The $IC_{50}$ values of the compounds lacking toxicity on the untransformed cells are determined from the dose response curves obtained as described above.

FGFR3 (Enzymatic Assay)

Kinase activity assay with purified FGFR3 (Upstate) may be carried out in a final volume of 10 µL containing 0.25 µg/mL of enzyme in kinase buffer (30 mM Tris-HCl pH 7.5, 15 mM $MgCl_2$, 4.5 mM $MnCl_2$, 15 µM $Na_3VO_4$ and 50 µg/mL BSA), and substrates (5 µg/mL biotin-poly-EY(Glu, Tyr) (CIS-US, Inc.) and 3 µM ATP). Two solutions are made: the first solution of 5 µl containing the FGFR3 enzyme in kinase buffer is first dispensed into 384-format PROXIPLATE® (Perkin-Elmer) followed by addition of 50 nL of compounds dissolved in DMSO. A second solution (5 µl) containing the substrate (poly-EY) and ATP in kinase buffer is then added to each well. The reactions are incubated at room temperature for one hour, stopped by adding 10 µL of HTRF detection mixture, which contains 30 mM Tris-HCl pH 7.5, 0.5 M KF, 50 mM ETDA, 0.2 mg/mL BSA, 15 μg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 μM to 0.28 nM).

FGFR3 (Cellular Assay)

Compounds of the invention may be tested for their ability to inhibit transformed Ba/F3-TEL-FGFR3 cells proliferation, which is dependent on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 μL culture medium. Compounds of the invention are dissolved and diluted in dimethylsulfoxide (DMSO). Twelve points 1:3 serial dilutions are made into DMSO to create concentration gradients ranging typically from 10 mM to 0.05 μM. Cells are added with 50 nL of diluted compounds and incubated for 48 hours in a cell culture incubator. ALAMAR BLUE® (TREK Diagnostic Systems), which can be used to monitor the reducing environment created by proliferating cells, are added to cells at a final concentration of 10%. After an additional four hours of incubation in a 37° C. cell culture incubator, fluorescence signals from reduced ALAMAR BLUE® (excitation at 530 nm; emission at 580 nm) are quantified on Analyst GT (Molecular Devices Corp.). $IC_{50}$ values are calculated by linear regression analysis of the percentage inhibition of each compound at 12 concentrations.

FLT3 and PDGFRβ (Cellular Assay)

The effects of compounds of the invention on the cellular activity of FLT3 and PDGFRβ are conducted using identical methods as described above for FGFR3 cellular activity, except that instead of using Ba/F3-TEL-FGFR3, Ba/F3-FLT3-ITD and Ba/F3-Tel-PDGFRβ are used, respectively.

b-Raf (Enzymatic Assay)

Compounds of the invention may be tested for their ability to inhibit the activity of b-Raf. The assay is carried out in 384-well MaxiSorp plates (NUNC) with black walls and clear bottom. The substrate, IκBα is diluted in DPBS (1:750) and 15 μl is added to each well. The plates are incubated at 4° C. overnight and washed three times with TBST (25 mM Tris, pH 8.0, 150 mM NaCl and 0.05% Tween-20) using the EMBLA plate washer. Plates are blocked by Superblock (15 μl/well) for 3 hours at room temperature, washed 3 times with TBST and pat-dried. Assay buffer containing 20 μM ATP (101) is added to each well followed by 100 nL or 500 nL of compound. B-Raf is diluted in the assay buffer (1 μl into 25 μl) and 10 μl of diluted b-Raf is added to each well (0.4 μg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 μl is added to each well. The plates are incubated at 4° C. overnight and washed 6 times with TBST. AP-conjugated goat-anti-mouse IgG is diluted in Superblock (1:1,500) and 15 μl is added to each well. Plates are incubated at room temperature for 1 hour and washed 6 times with TBST. 15 μl of Attophos AP substrate is added to each well and plates are incubated at room temperature for 15 minutes. Plates are read on Acquest or Analyst GT using a Fluorescence Intensity Nanxin BBT anion (505 dichroic mirror).

b-Raf (Cellular Assay)

Compounds of the invention may be tested in A375 cells for their ability to inhibit phosphorylation of MEK. A375 cell line (ATCC) is derived from a human melanoma patient, and has a V599E mutation on the B-Raf gene. The levels of phosphorylated MEK are elevated due to the mutation of B-Raf. Sub-confluent to confluent A375 cells are incubated with compounds for two hours at 37° C. in serum free medium. Cells are then washed once with cold PBS and lysed with the lysis buffer containing 1% Triton X100. After centrifugation, the supernatants are subjected to SDS-PAGE, and then transferred to nitrocellulose membranes. The membranes are then subjected to Western blotting with anti-phospho-MEK antibody (ser217/221) (Cell Signaling). The amount of phosphorylated MEK is monitored by the density of phospho-MEK bands on the nitrocellulose membranes.

Human TG-HA-VSMC Proliferation Assay

Human TG-HA-VSMC cells (ATCC) are grown in DMEM supplemented with 10% FBS to 80-90% confluence prior to resuspending in DMEM supplemented with 1% FBS and 30 ng/mL recombinant human PDGF-BB at 6e4 cells/mL. Cells are then aliquoted into 384-well plates at 50 μL/well, incubated for 20 h at 37° C., then treated with 0.5 μL of 100× compounds for 48 h at 37° C. After the treatment, 25 μL of CellTiter-Glo is added to each well for 15 min, then the plates are read on the CLIPR (Molecular Devices)

Upstate Kinase Profiler™—Radio-Enzymatic Filter Binding Assay

Compounds of the invention may be assessed for their ability to inhibit individual members of a panel of kinases such as c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf and b-raf kinases. The compounds are tested in duplicates at a final concentration of 10 μM following this generic protocol. Note that the kinase buffer composition and the substrates vary for the different kinases included in the Upstate KinaseProfiler™ panel. Kinase buffer (2.5 μL, 10×-containing $MnCl_2$ when required), active kinase (0.001-0.01 Units; 2.5 μL), specific or Poly(Glu4-Tyr) peptide (5-500 μM or 0.01 mg/ml) in kinase buffer and kinase buffer (50 μM; 5 μL) are mixed in an eppendorf on ice. A Mg/ATP mix (10 μL; 67.5 or 33.75 mM $MgCl_2$, 450 or 225 μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid, and washed once with acetone for 5 minutes. The assay squares are transferred to a scintillation vial, scintillation cocktail (5 ml) are added and $^{32}$P incorporation (cpm) to the peptide substrate is quantified with a Beckman scintillation counter. Percentage inhibition is calculated for each reaction.

Compounds of Formula (1), (2) or (3) in free form or in pharmaceutically acceptable salt form, may exhibit valuable pharmacological properties, for example, as indicated by the in vitro tests described in this application. The $IC_{50}$ value in those experiments is given as that concentration of the test compound in question that results in a cell count that is 50% lower than that obtained using the control without inhibitor. In general, compounds of the invention have $IC_{50}$ values from 1 nM to 10 μM. In some examples, compounds of the invention have $IC_{50}$ values from 0.01 μM to 5 μM. In other examples, compounds of the invention have $IC_{50}$ values from 0.01 μM to 1 μM, or more particularly from 1 nM to 1 μM. In yet other examples, compounds of the invention have $IC_{50}$ values of less than 1 nM or more than 10 μM. Compounds of Formula (1) or (2) may exhibit a percentage inhibition of greater than 50%, or in other embodiments, may exhibit a percentage inhibition greater than about 70%, against one or more of the following kinases at 10 μM: c-kit, PDGFRα, PDGFRβ, CSF1R, Abl, BCR-Abl, CSK, JNK1, JNK2, p38, p70S6K, TGFβ, SRC, EGFR, trkB, FGFR3, FLT3, Fes, Lck, Syk, RAF, MKK4, MKK6, SAPK2β, BRK, KDR, c-raf or b-raf kinase, or mutant forms thereof.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:
1. A compound of Formula (1):

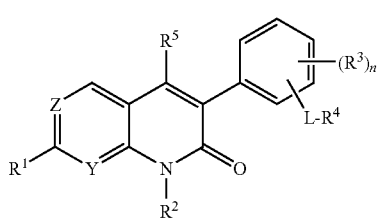

or a pharmaceutically acceptable salt thereof, wherein:
Y is CR and Z is N;
L is NR—C(O), C(O)NR, C(O)NRC(O)NR, NRC(O)NRC(O), NRC(O)NRCO, NRS(O)$_{0-2}$ or NRCONRS(O)$_{0-2}$;
$R^1$ is halo, $(CR_2)_k NR^7R^8$, $(CR_2)_k OR^9$, $(CR_2)_k SR^9$, aryl or heteroaryl; or $R^1$ is $C_{1-6}$ alkyl, $C_{2-6}$ alkenyl or $C_{2-6}$ alkynyl, wherein each of said $C_{1-6}$ alkyl and $C_{2-6}$ alkenyl is optionally substituted with ureayl, guanidyl, $O(C_{1-6}$ alkyl), or optionally substituted with $C_{3-7}$ cycloalkyl, phenyl, or heteroaryl, said phenyl is further optionally substituted with halo or an optionally halogenated $C_{1-6}$ alkyl;
$R^2$ is $(CR_2)_{1-4}OR^9$, $(CR_2)_{1-4}NR^7R^8$ or aryl; or $R^2$ is $C_{1-6}$ alkyl, $C_{2-6}$ alkenyl or $C_{2-6}$ alkynyl, wherein said $C_{1-6}$ alkyl is optionally substituted with phenyl, or heteroaryl;
$R^3$ is halo or $C_{1-6}$ alkyl;
$R^4$ is $(CR_2)_k R^6$, dihydroindenyl, $C_{1-6}$ alkyl or $(CR_2)_k OR^9$;
$R^5$ is H, halo or $C_{1-6}$ alkyl;
$R^6$ is $C_{3-7}$ cycloalkyl, aryl, heterocyclic ring or heteroaryl, each of which is optionally substituted with halo, cyano, nitro, $NR^7R^8$, $NRCOR^7$, $(CR_2)_p OR^{9'}$, $(CR_2)_p R^{10}$, or a $C_{1-6}$ alkyl optionally substituted with halo, hydroxyl, $C_{1-6}$ alkoxy or cyano;
$R^{9'}$ is H, an optionally halogenated $C_{1-6}$ alkyl or $(CR_2)_p R^{10}$;
$R^{10}$ is $C_{3-7}$ cycloalkyl, aryl, 5-7 membered heterocyclic ring, or heteroaryl, each of which is optionally substituted with halo, cyano, nitro, $NR^7R^8$, $NRCOR^7$, $NRC(O)(CR_2)_p NR^7R^8(7)$, $NRCONR(CR_2)_p NR^7R^8$, $OR^9$, or $C_{1-6}$ alkyl optionally substituted with hydroxyl;

$R^7$, $R^8$ and $R^9$ are independently H or $C_{1-6}$ alkyl; or $R^7$ and $R^8$ together with N in each $NR^7R^8$ may form a 5-7 membered heterocyclic ring;
each R is H or $C_{1-6}$ alkyl;
k is 0-6; and
n is 0-2;
provided L is C(O)NRC(O)NR, NRC(O)NRC(O), NRC(S)NRCO or NRCONRS(O)$_{0-2}$ when $R^1$ is halo or $(CR_2)_k NR^7R^8$ and $R^2$ is $C_{1-6}$ alkyl.

2. The compound of claim 1, wherein Y is CH.
3. The compound of claim 1, wherein $R^1$ is halo, $(CR_2)_{1-4}NR^7R^8$, $(CR_2)_k OR^9$, $(CR_2)_k SR^9$, phenyl, pyridyl or pyrimidinyl; or $R^1$ is $C_{1-6}$ alkyl, $C_{2-6}$ alkenyl or $C_{2-6}$ alkynyl, each of which is optionally substituted with ureayl, guanidyl, $O(C_{1-6}$ alkyl), or optionally substituted with $C_{3-7}$ cycloalkyl, phenyl, imidazolyl, thiazolyl, pyrimidinyl, furanyl or pyridyl, said phenyl is further optionally substituted with halo or an optionally halogenated $C_{1-6}$ alkyl;
$R^7$, $R^8$ and $R^9$ are independently H or $C_{1-6}$ alkyl; or $R^7$ and $R^8$ together with N may form morpholinyl or piperazinyl; and
each k is 0-4.

4. The compound of claim 1, wherein $R^2$ is $(CR_2)_{1-4}OR^9$, $(CR_2)_{1-4}NR^7R^8$ or phenyl; or $R^2$ is $C_{1-6}$ alkyl, $C_{2-6}$ alkenyl or $C_{2-6}$ alkynyl, each of which is optionally substituted with phenyl, pyridyl or pyrimidinyl; and
$R^7$, $R^8$ and $R^9$ are independently H or $C_{1-6}$ alkyl; or $R^7$ and $R^8$ together with N may form morpholinyl or piperazinyl.

5. The compound of claim 1, wherein n is 1; and $R^3$ is methyl or halo.
6. The compound of claim 1, wherein $R^4$ is $C_{1-6}$ alkyl.
7. The compound of claim 1, wherein $R^4$ is dihydroindenyl, $(CR_2)_k R^6$ or $(CR_2)_k O(C_{1-6}$ alkyl);
$R^6$ is phenyl, $C_{3-7}$ cycloalkyl, thiazolyl, thienyl, piperidinyl, piperazinyl, pyridinyl, pyridazinyl, pyrimidinyl, pyrazinyl, imidazolyl, pyrazolyl, furanyl, pyrrolyl, dihydropyrrolyl, oxazolyl, isoxazolyl, triazolyl, azetidinyl, thiadiazolyl, benzimidazolyl, quinolinyl, tetrahydroquinolinyl, benzothiazolyl, benzothiophenyl, benzodioxolyl, indazolyl, indolyl, or dihydrobenzofuranyl, each of which is optionally substituted with halo, cyano, nitro, $NR^7R^8$, $NRCOR^7$, $(CR_2)_p OR^{9'}$, $(CR_2)_p R^{10}$, or a $C_{1-6}$ alkyl optionally substituted with halo, hydroxyl, $C_{1-6}$ alkoxy or cyano; and
$R^7$, $R^8$, $R^{9'}$, $R^{10}$, R and p are as defined in claim 1; and
k is 0-4.

8. A pharmaceutical composition comprising a therapeutically effective amount of a compound of claim 1 and a pharmaceutically acceptable excipient.
9. The compound of claim 1, wherein $R^5$ is H.
10. The compound of claim 1, wherein said compound is of Formula (2):

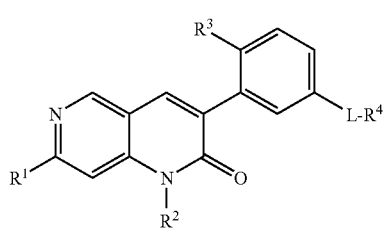

wherein $R^1$, $R^2$, $R^3$, $R^4$ and L are as defined in claim 1.

11. The compound of claim 10, wherein $R^1$, $R^2$ and $R^3$ are methyl.
12. The compound of claim 10, wherein $R^4$ is $C_{1-6}$ alkyl.
13. A compound selected from the group consisting of:
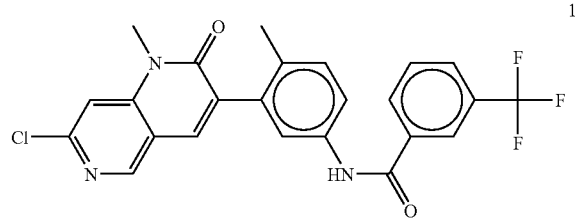
1
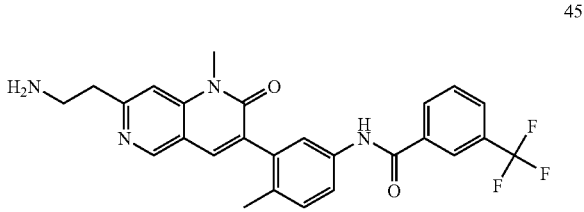
45
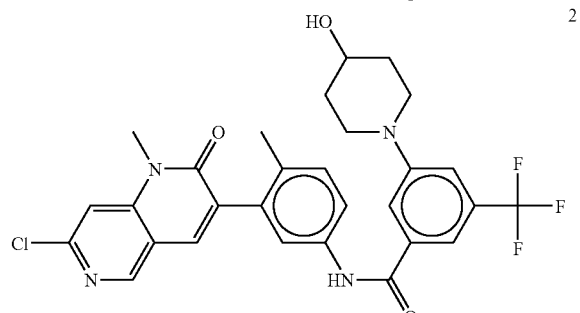
2
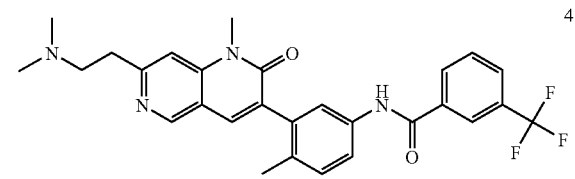
46
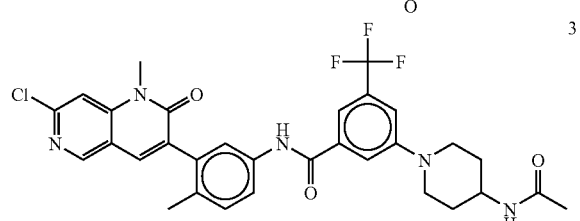
3
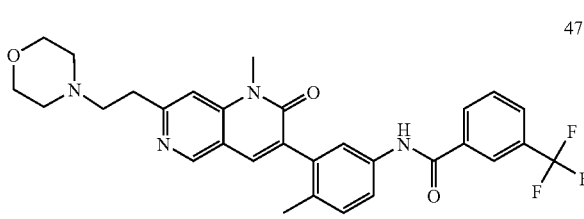
47
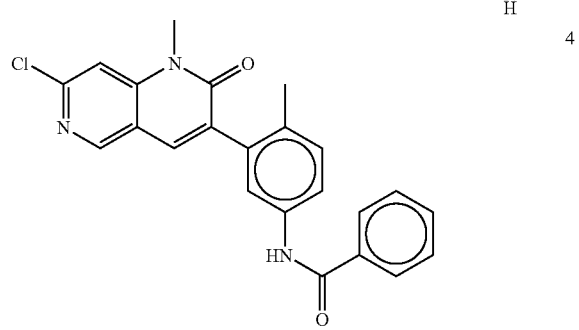
4
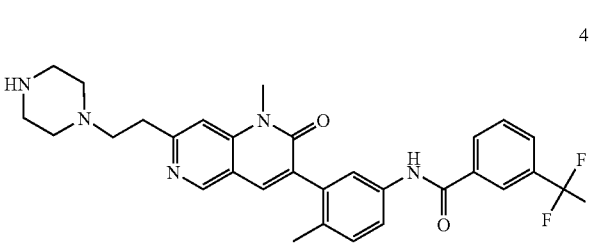
48
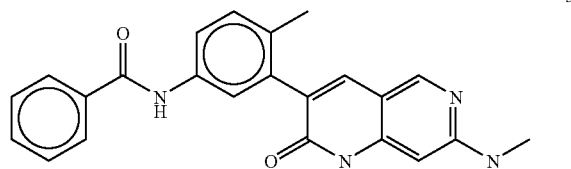
5
and
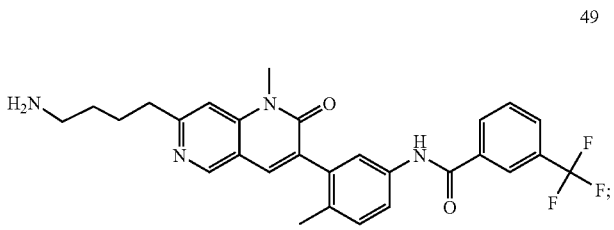
49
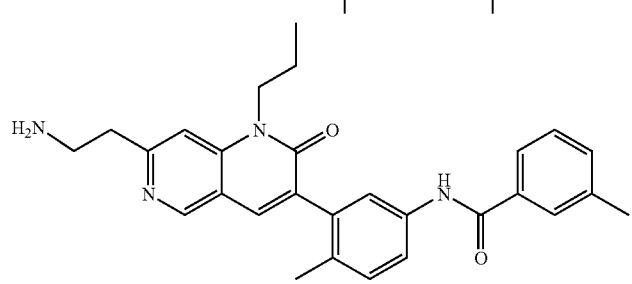
40
or a pharmaceutically acceptable salt thereof.

14. A pharmaceutical composition comprising a therapeutically effective amount of a compound of claim 10 and a pharmaceutically acceptable excipient.
15. The compound of claim 1, wherein said compound is selected from the group consisting of:
A1
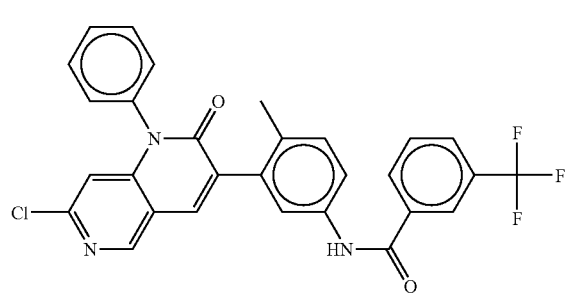
A2
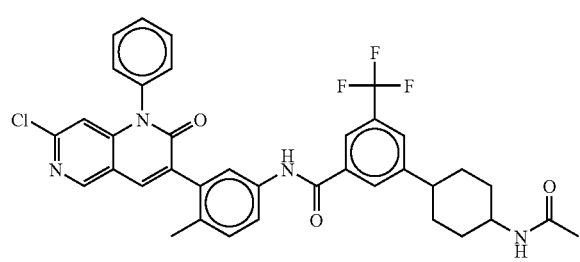
B1
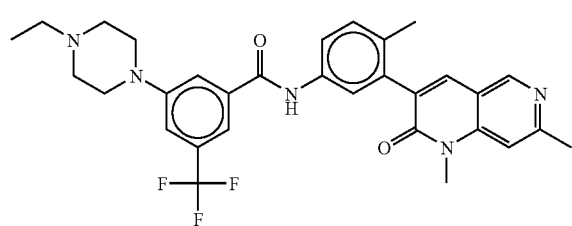
B2
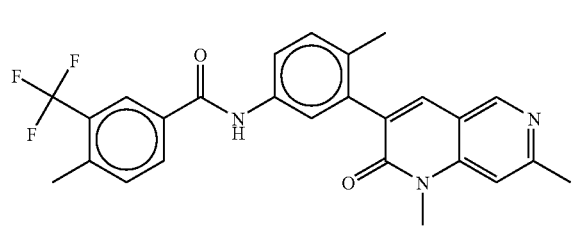
B3
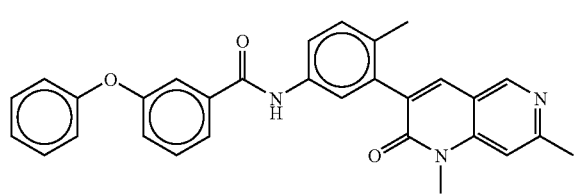
E18
E19
E20
E21
E22
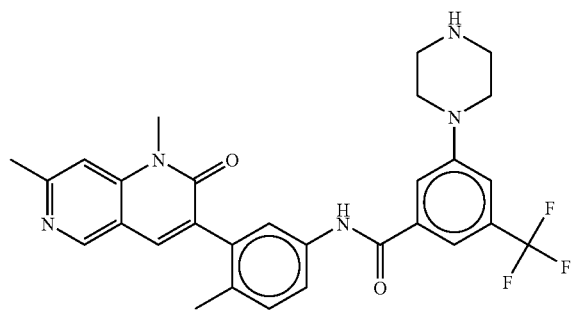

-continued
B4
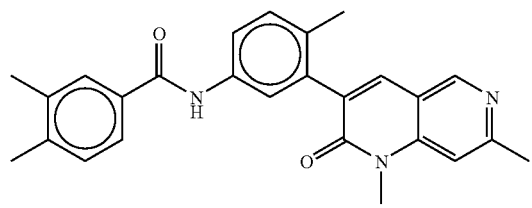
B5
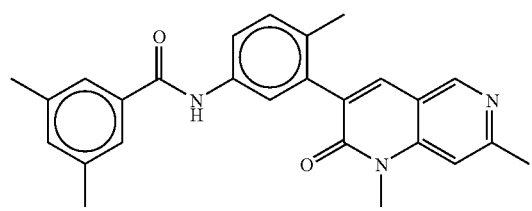
B6
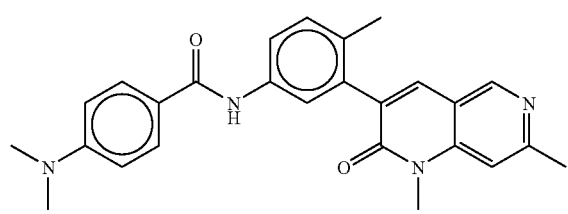
B7
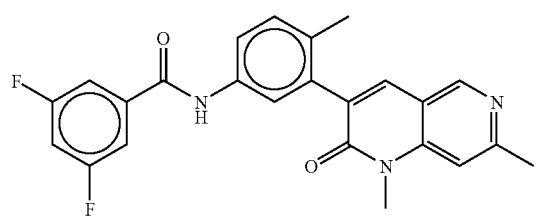
B8
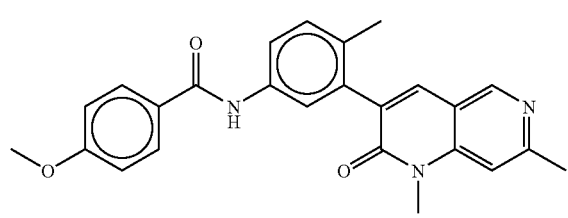
B9
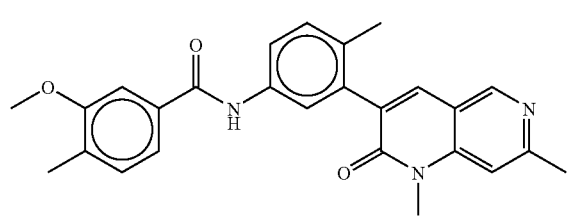
E23
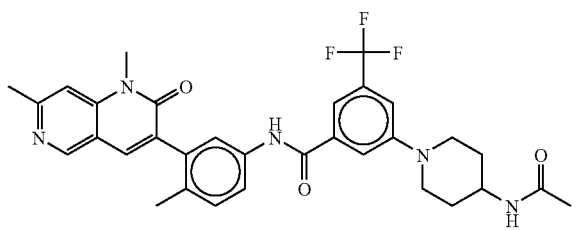
E24
E25
E26
E27
E28
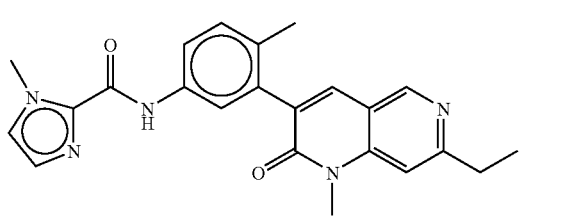

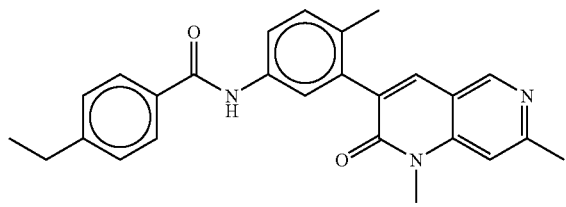
B10
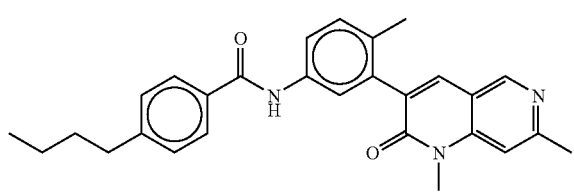
B11
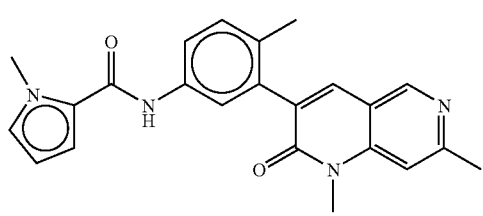
B12
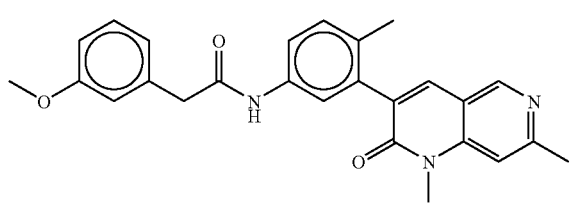
B13
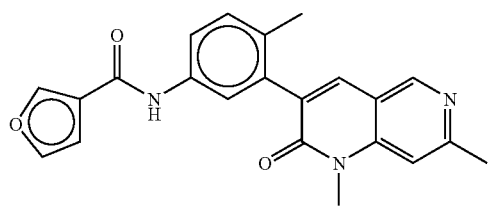
B14
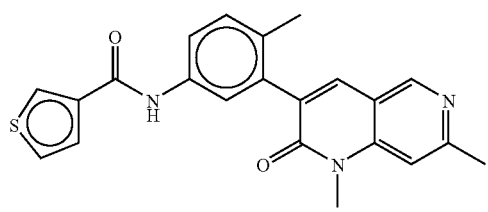
B15
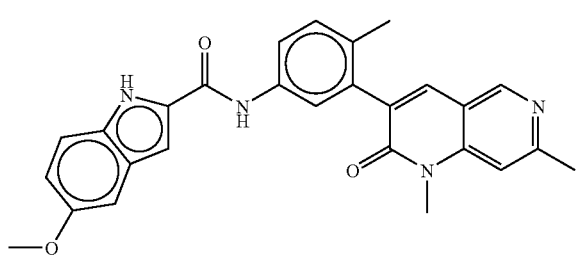
B16

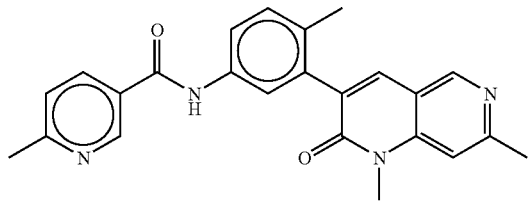
B17
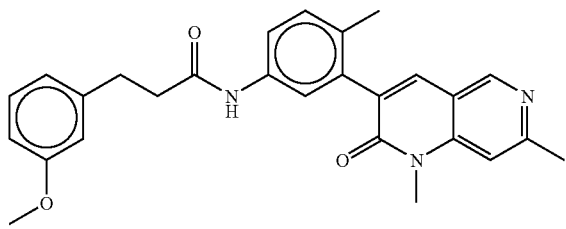
B18
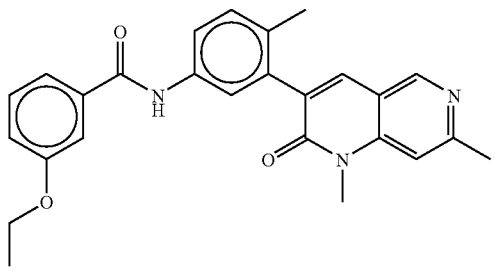
B19
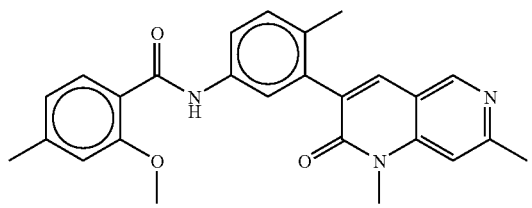
B20
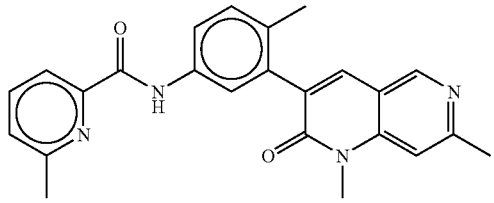
B21
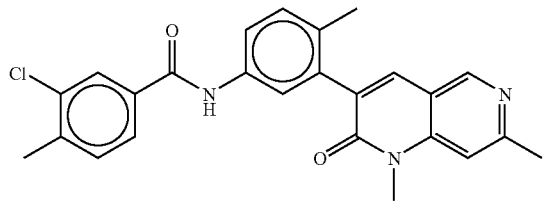
B22
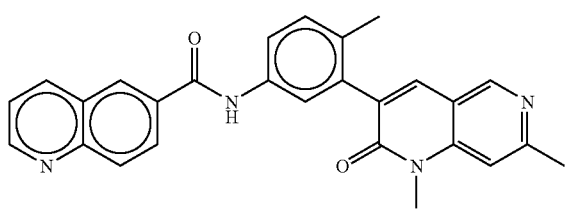
B23

-continued
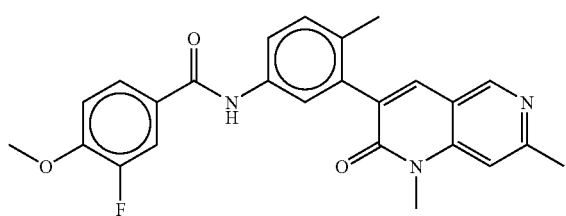
B24
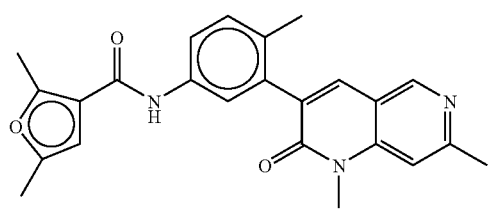
B25
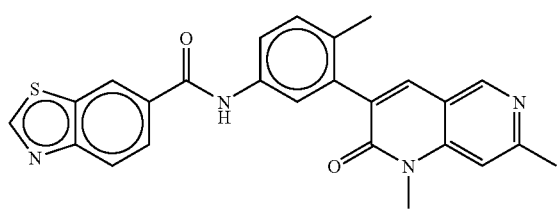
B26
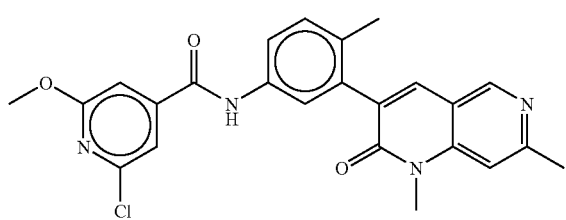
B27
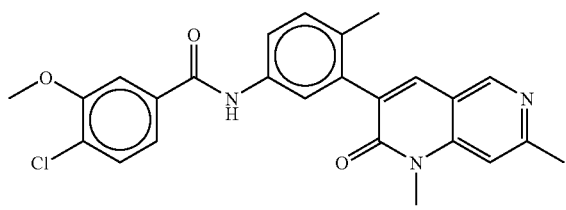
B28
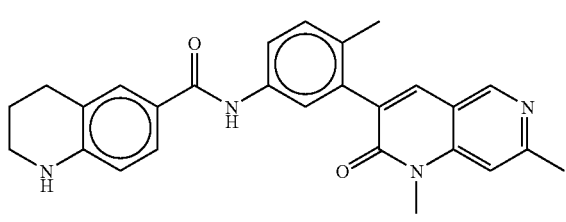
B29
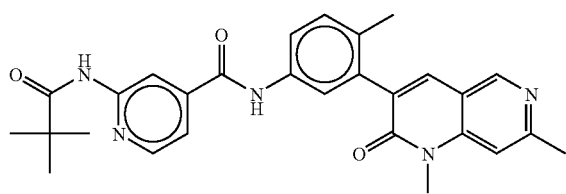
B30

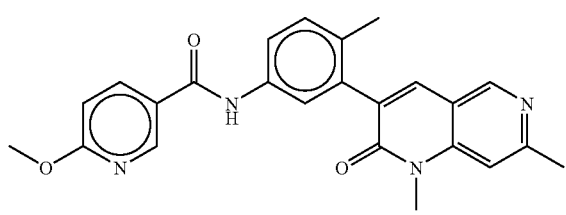 B31
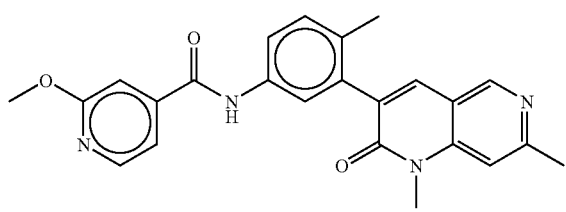 B32
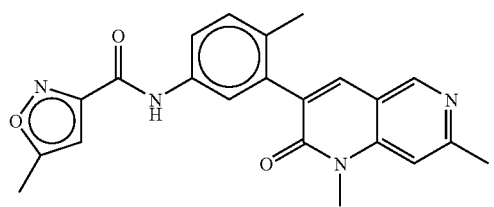 B33
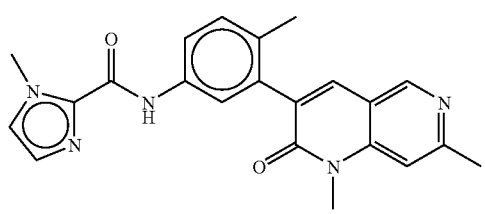 B34
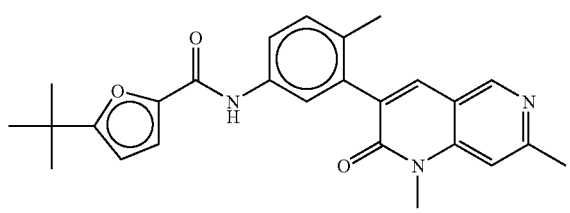 B35
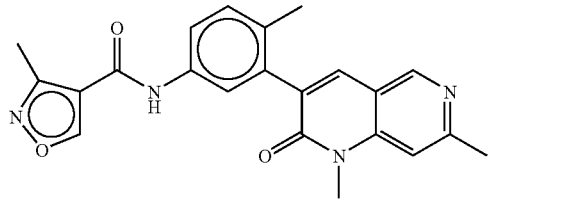 B36
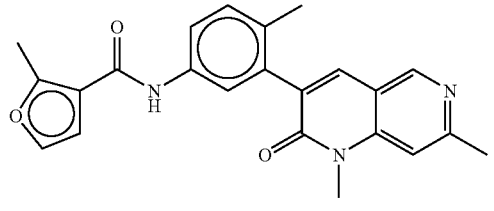 B37

-continued
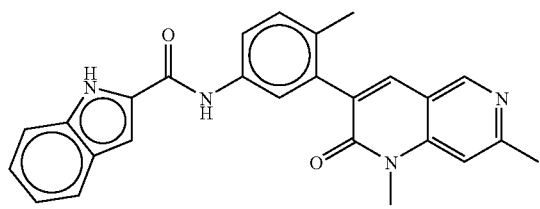
B38
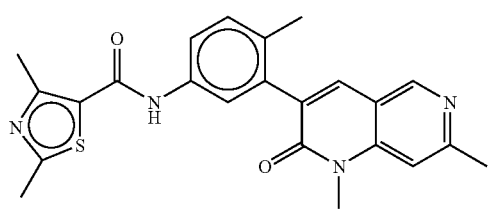
B39
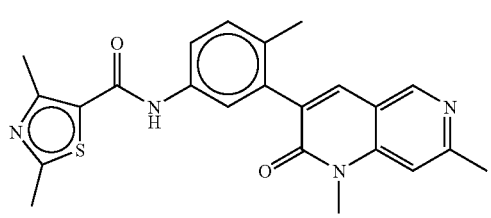
B40
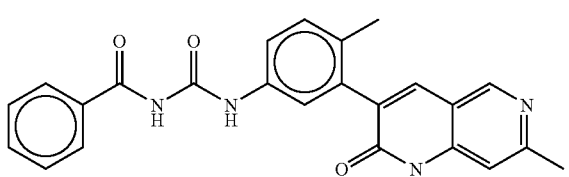
G1
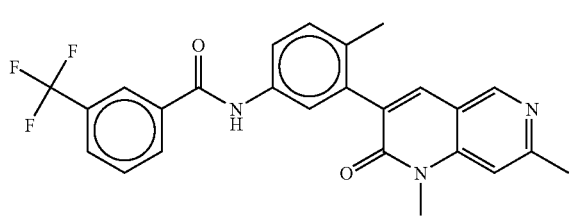
B41
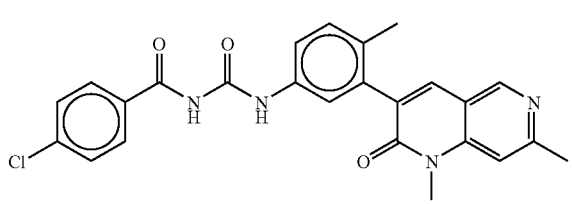
G2
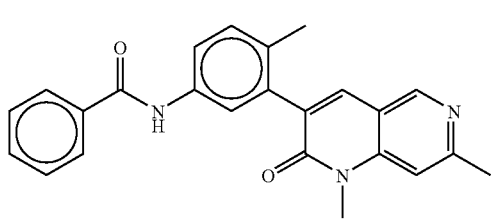
B42
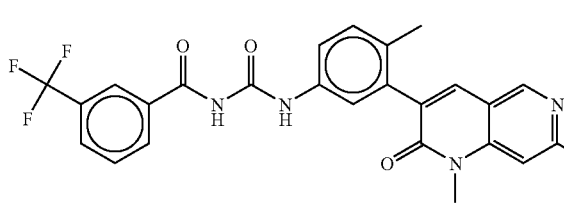
G3
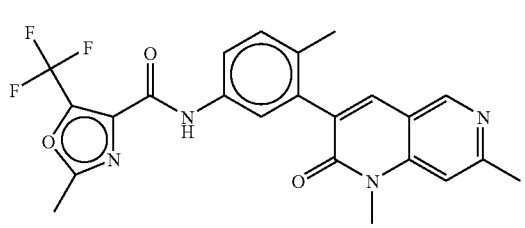
B43
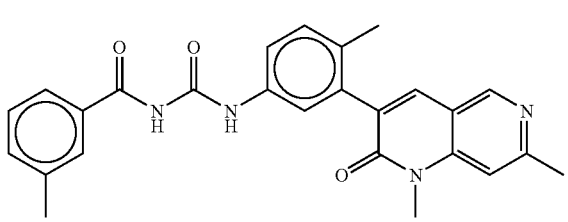
G4
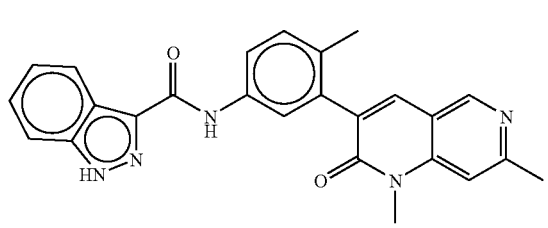
B44
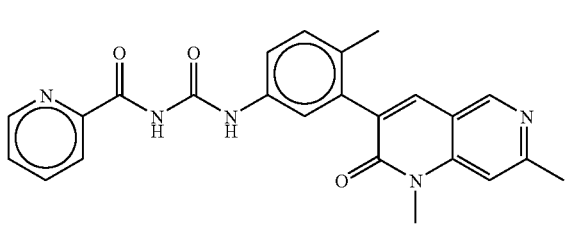
G5

-continued
B45
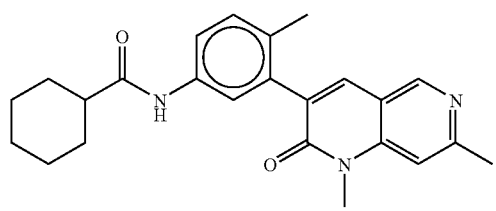
G6
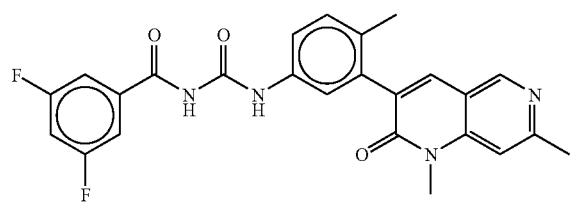
B46
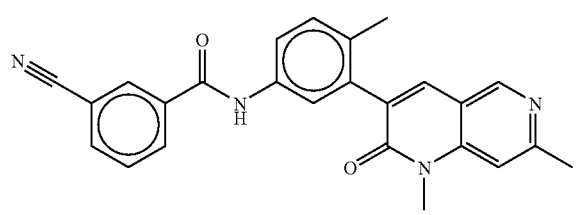
G7
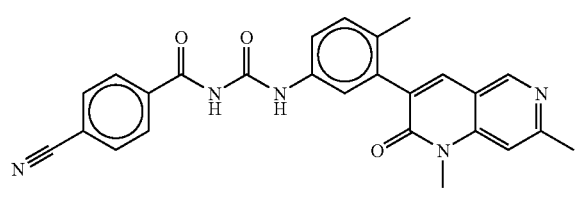
B47
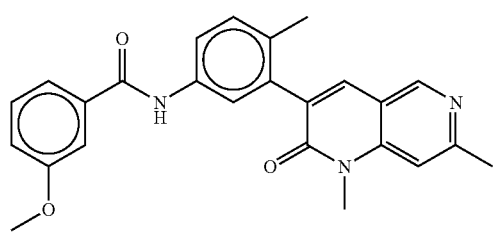
G8
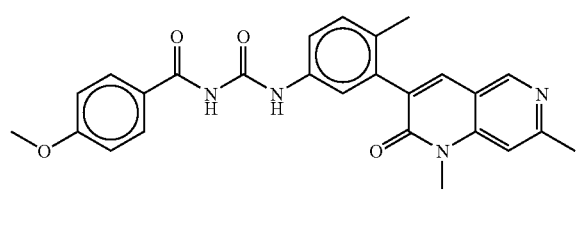
B48
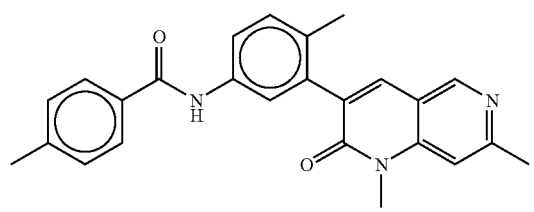
G9
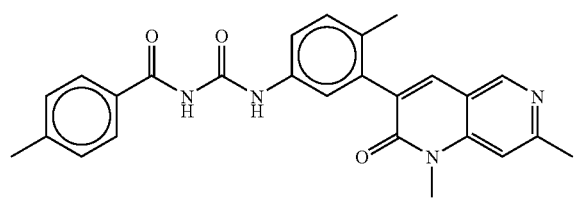
B49
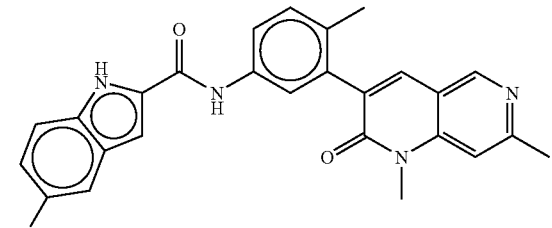
G10
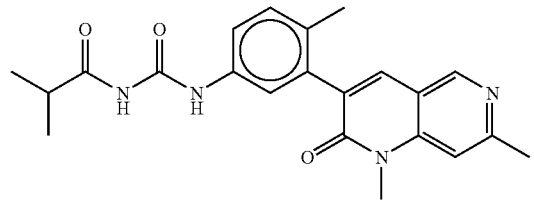
B50
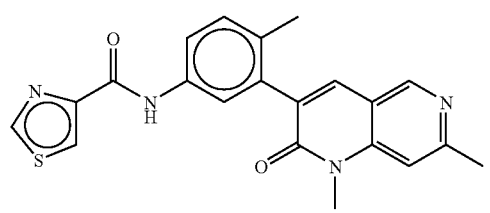
G11
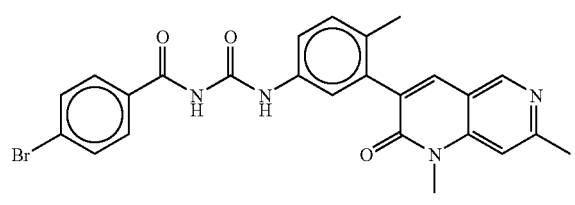

-continued
B51
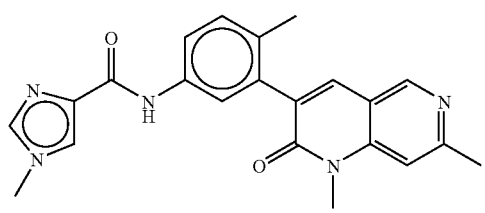
G12
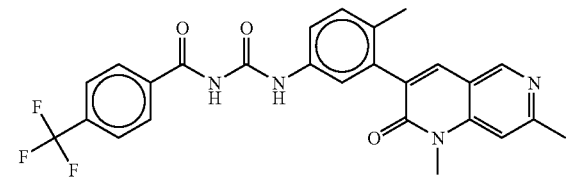
B52
G13
B53
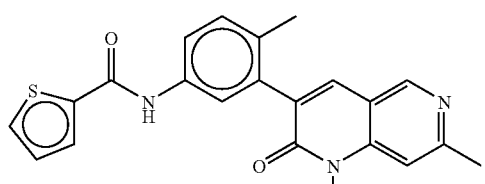
G14
B54
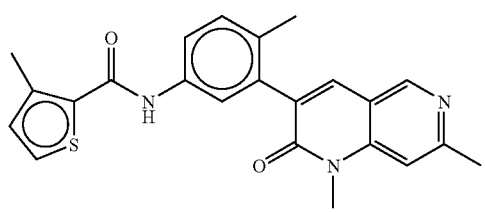
G15
B55
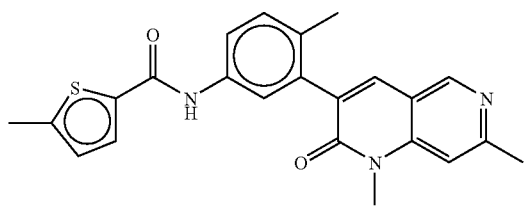
G16
B56
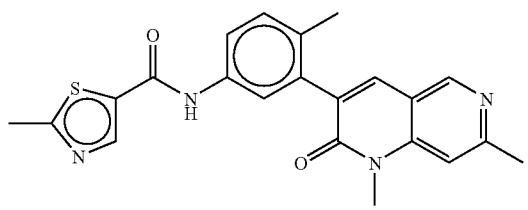
G17
B57
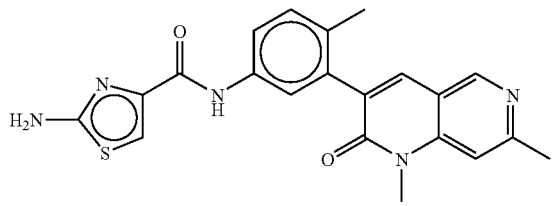
G18
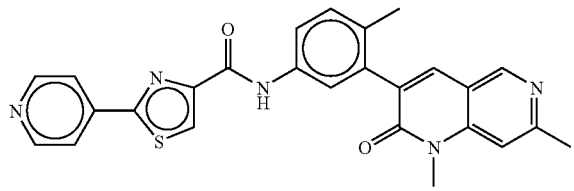
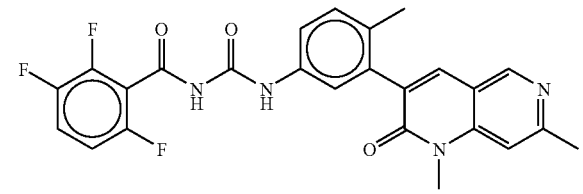

-continued
B58
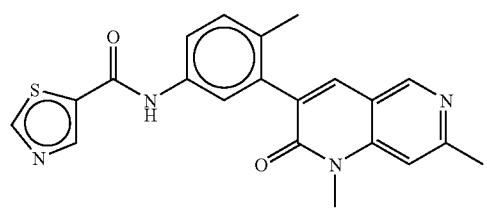
G19
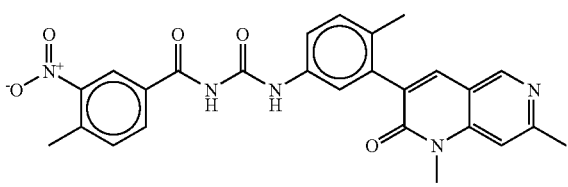
B59
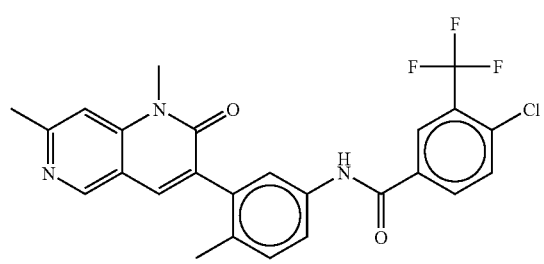
G20
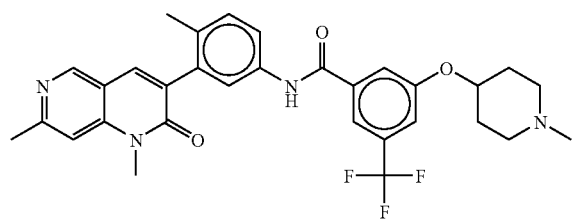
B60
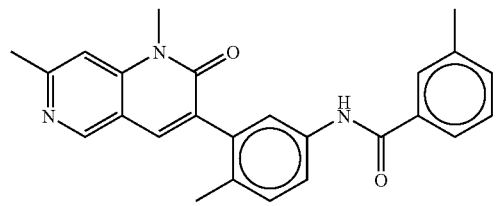
G21
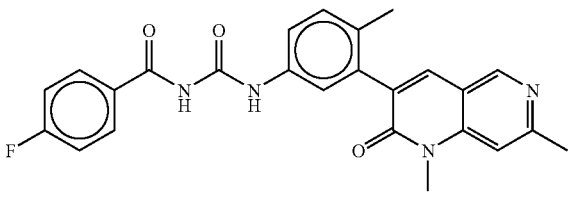
B61
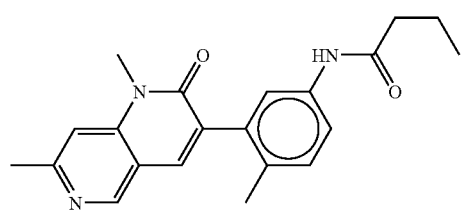
G22
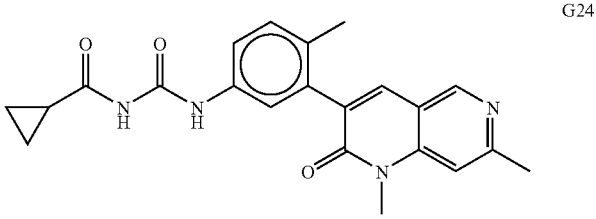
B62
B63

-continued
B64
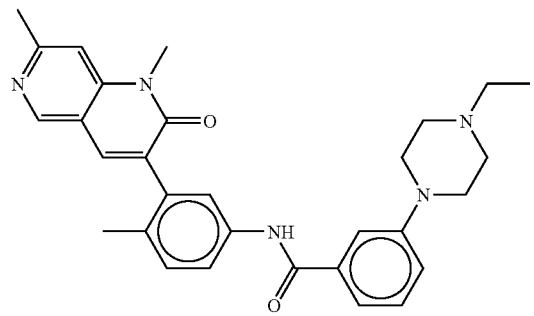
G25
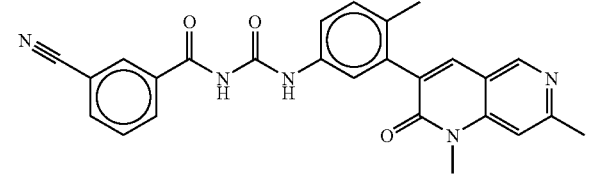
B65
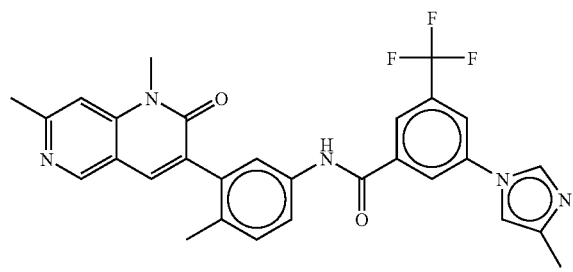
G26
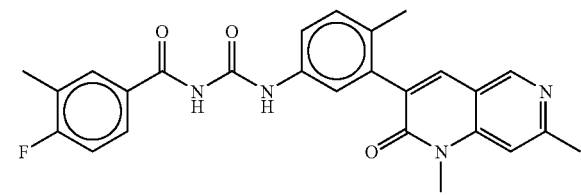
B66
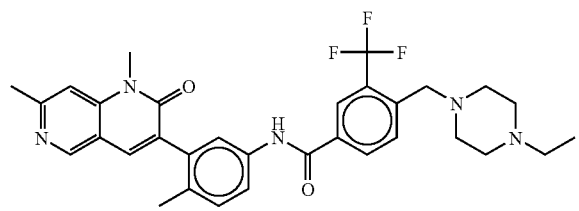
G27
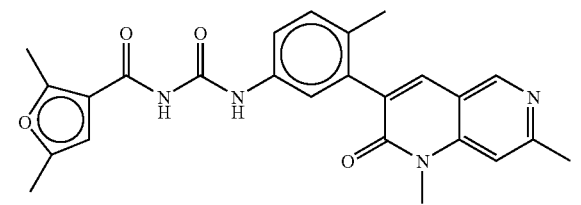
B67
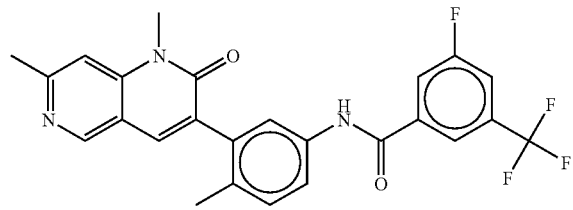
G28
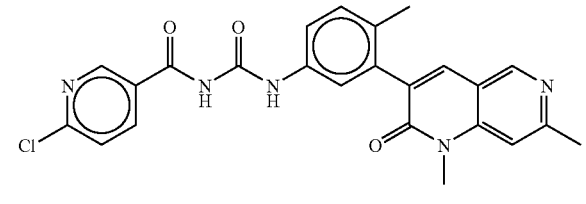
B68
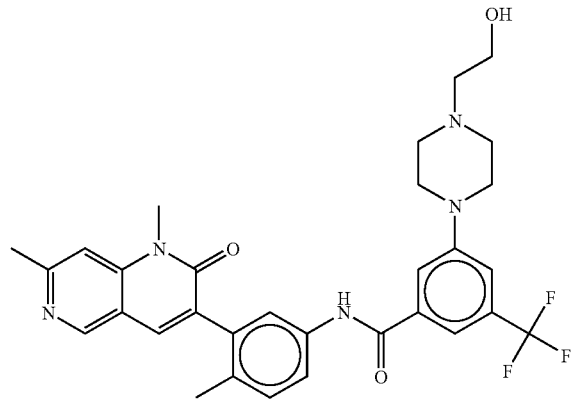
G29
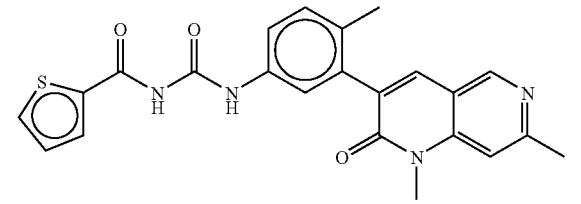

-continued
B69
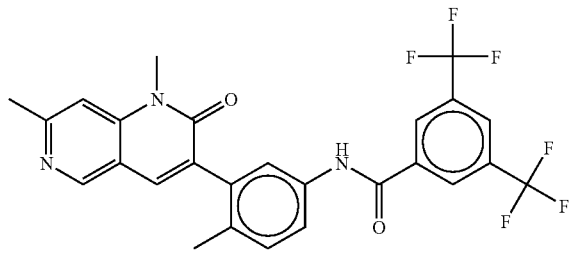
G30
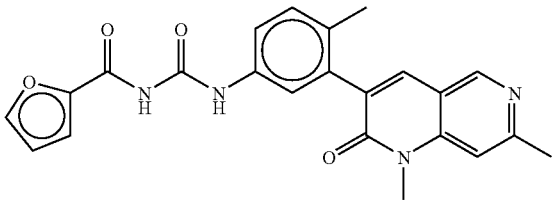
B70
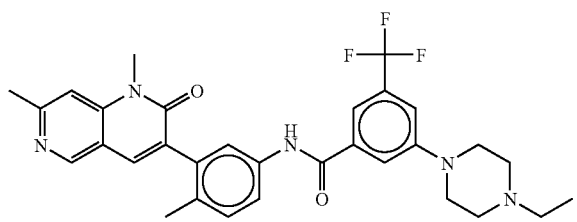
G31
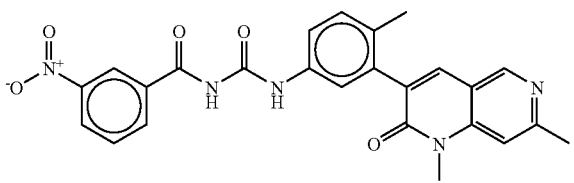
B71
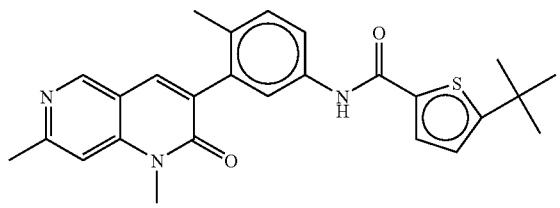
H1
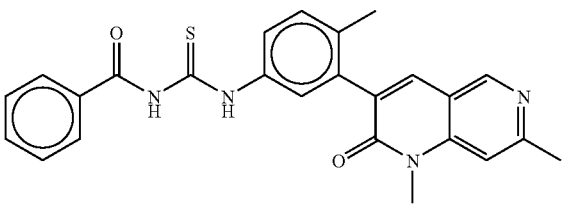
B72
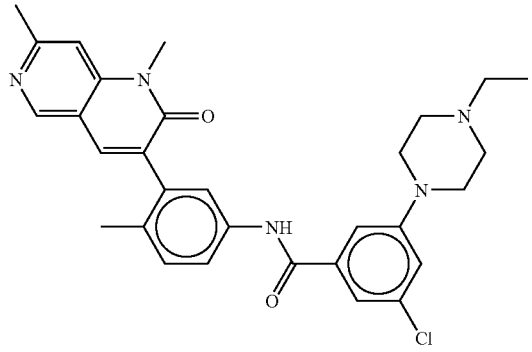
I1
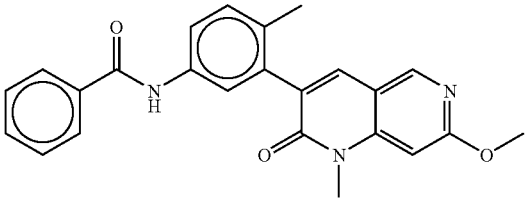
B73
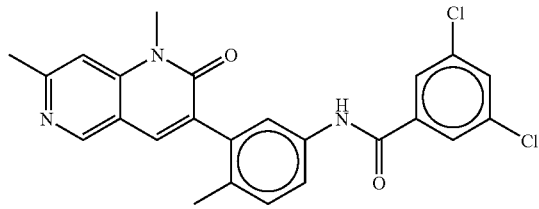
I2
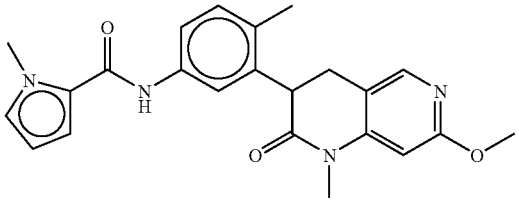

-continued
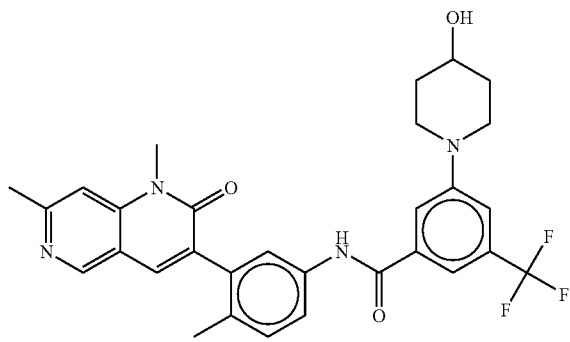
B74
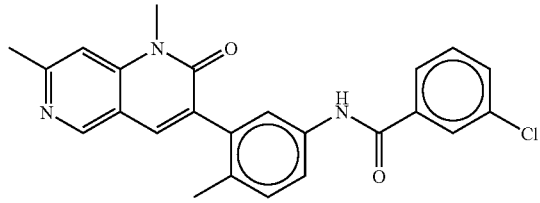
B75
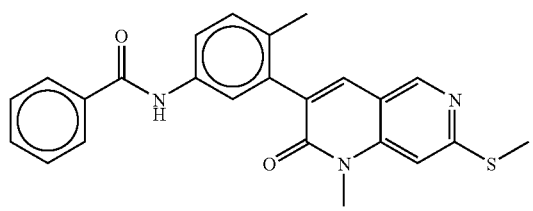
L1
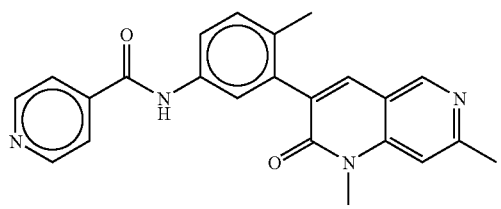
B76
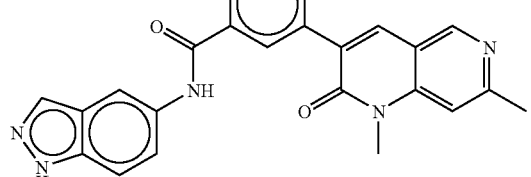
M1
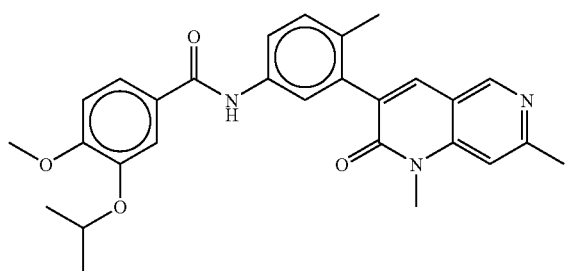
B77
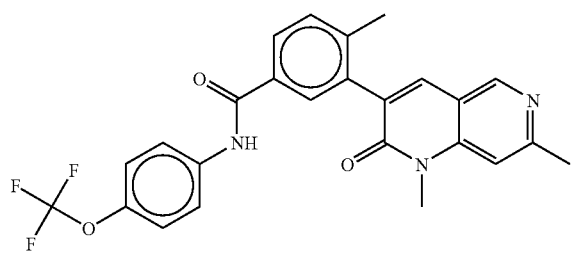
M2
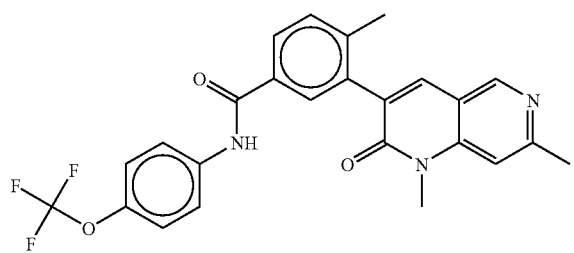
B78
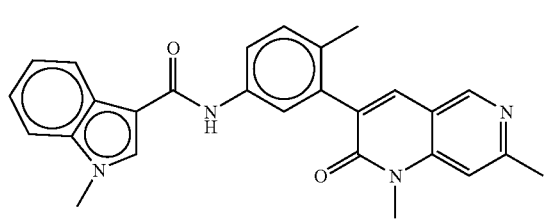
M3
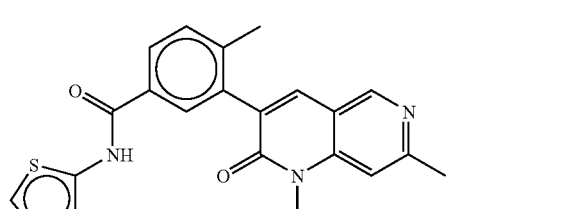
B79
M4
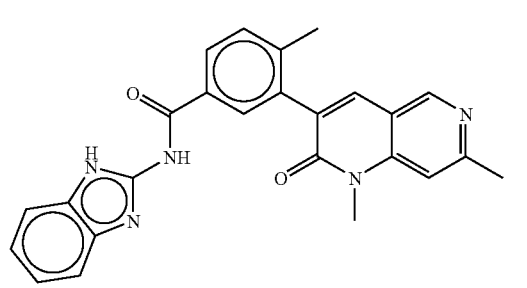

-continued
B80
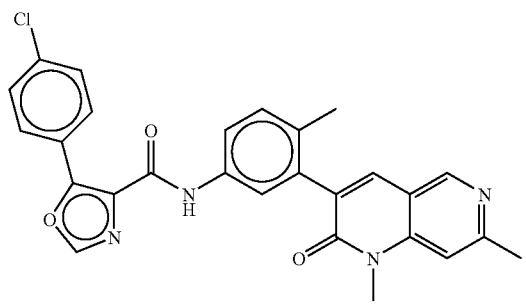
M5
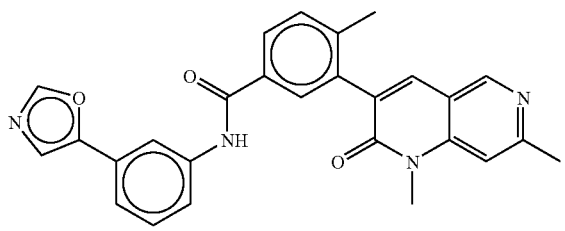
B81
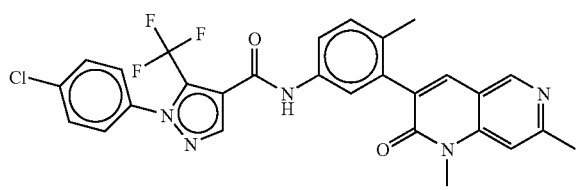
M6
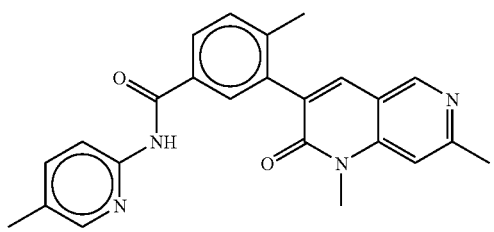
B82
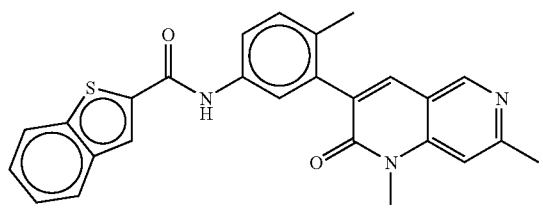
M7
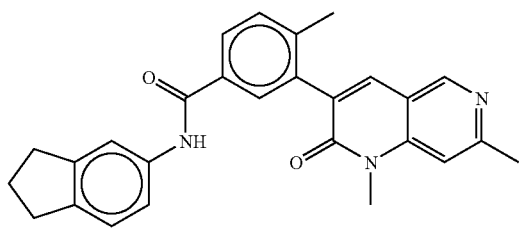
B83
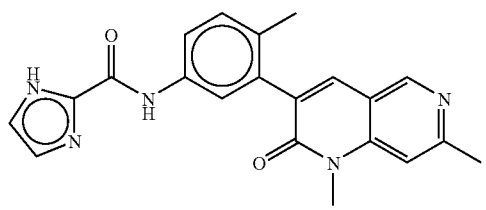
M8
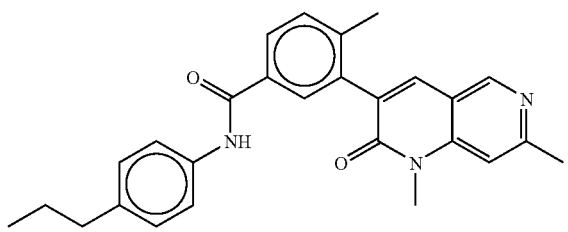
B84
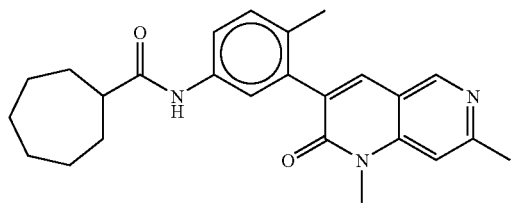
M9
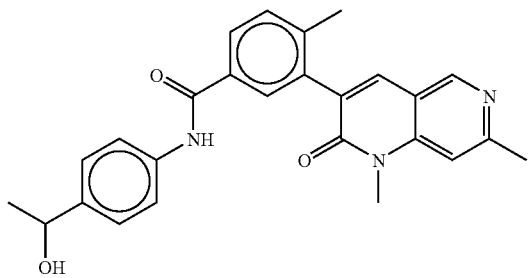
B85
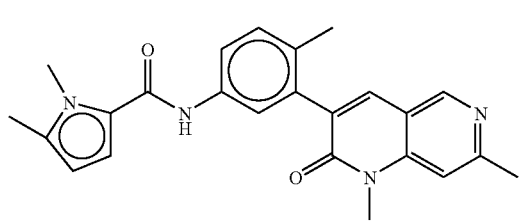
M10
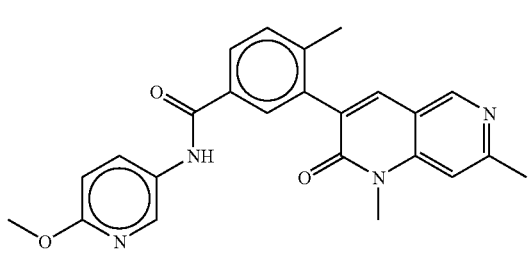

-continued
B86
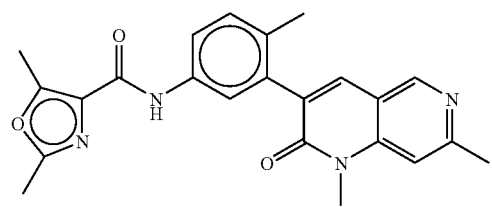
M11
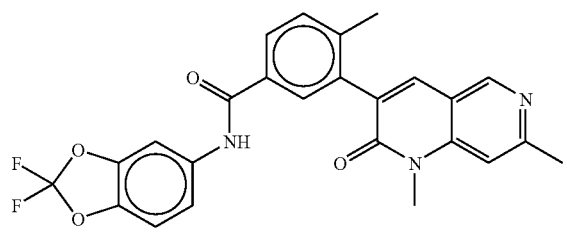
B87
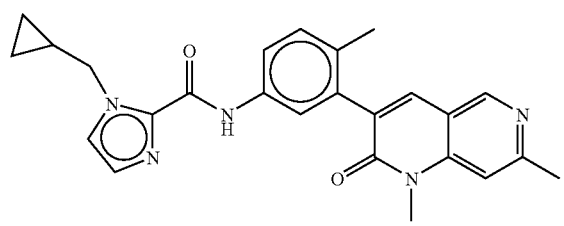
M12
B88
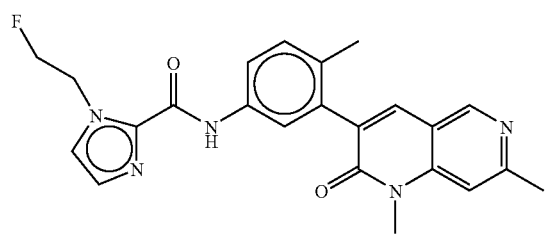
M13
B89
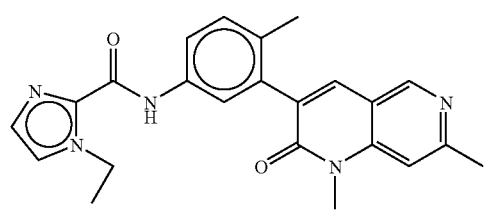
M14
B90
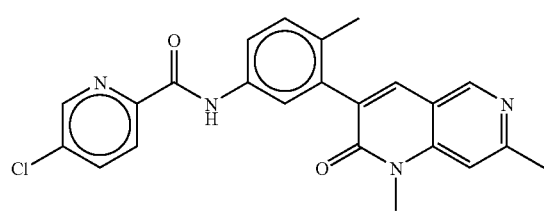
M15
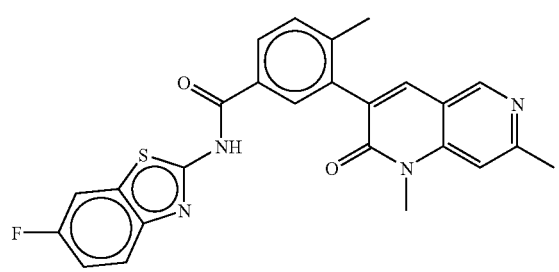

-continued
B91
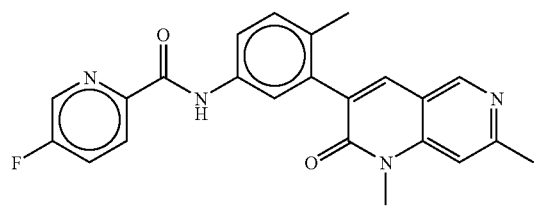
M16
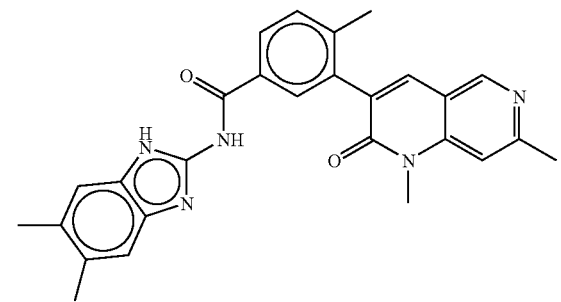
B92
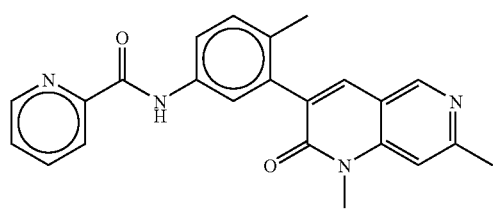
M17
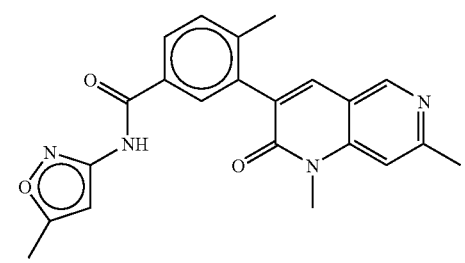
B93
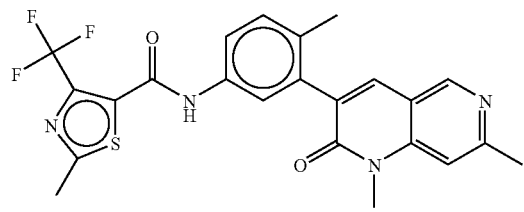
M18
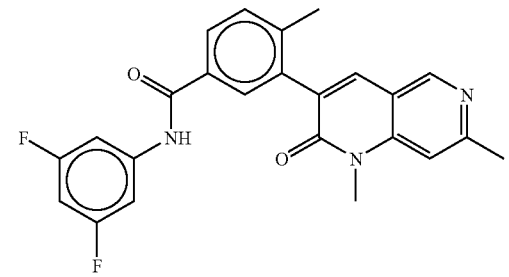
B94
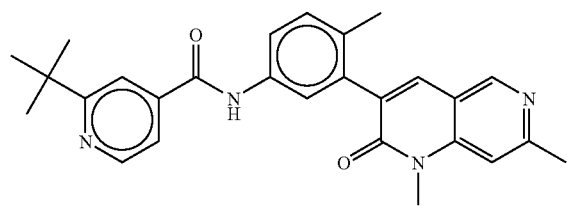
M19
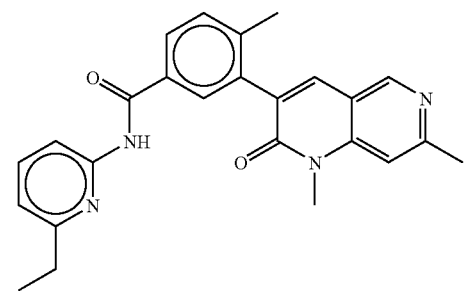
B95
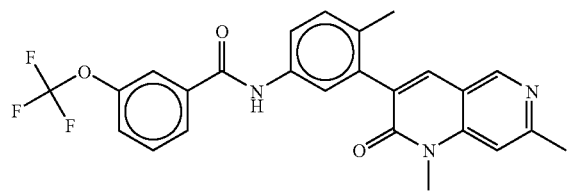
M20
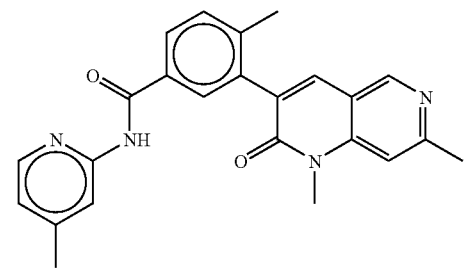

-continued
B96 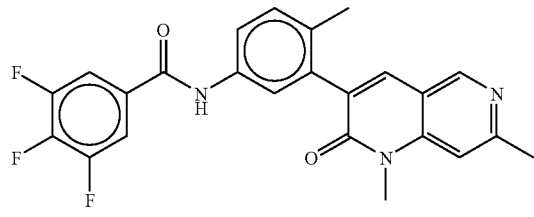
B97
B98
B99 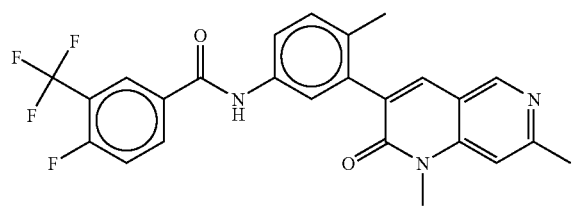
B100 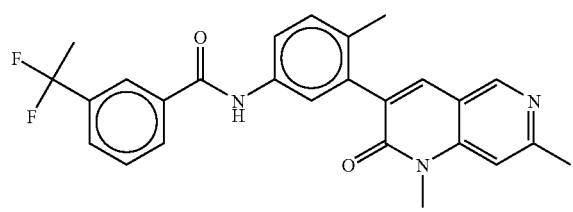
B101 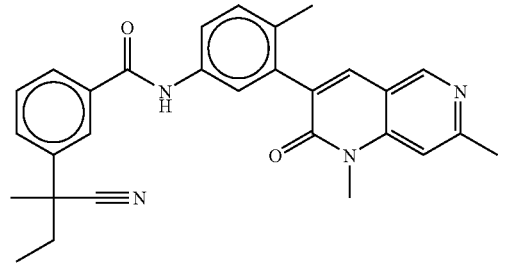
M21
M22 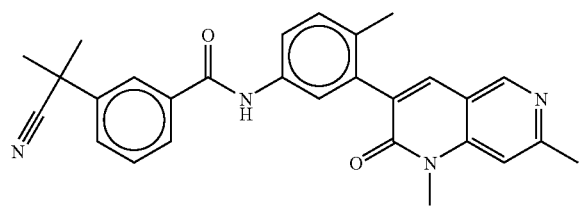
M23
M24 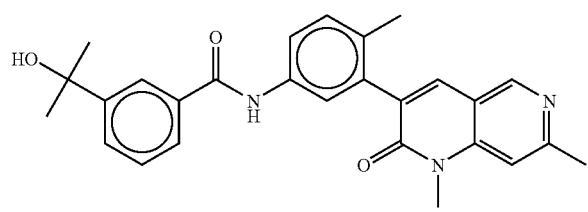
M25
M26 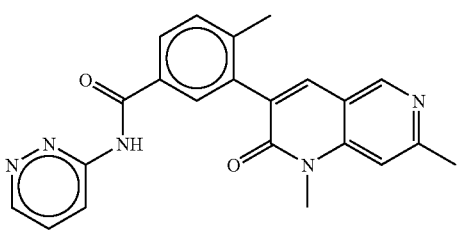

-continued
B102 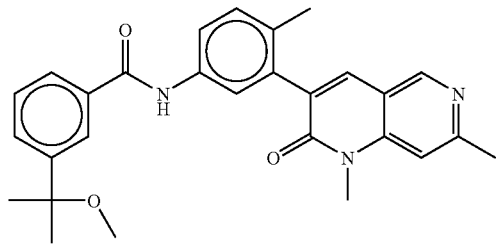 M27 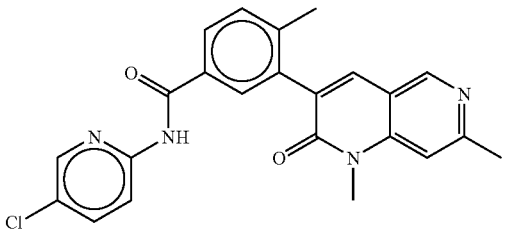
B103 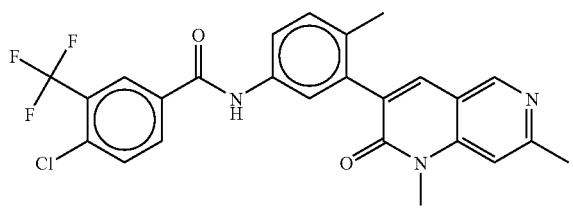 M28 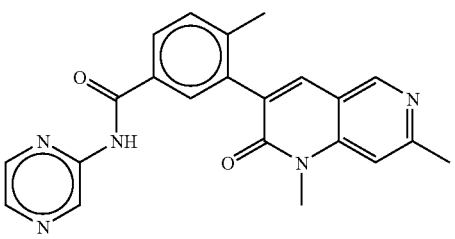
B104 M29
B105 M30
B106 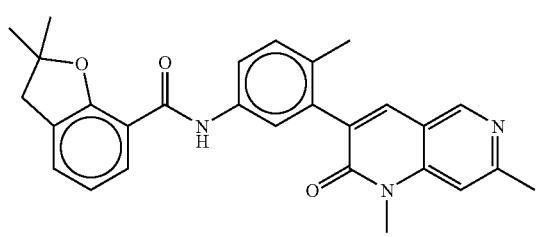 M31
B107 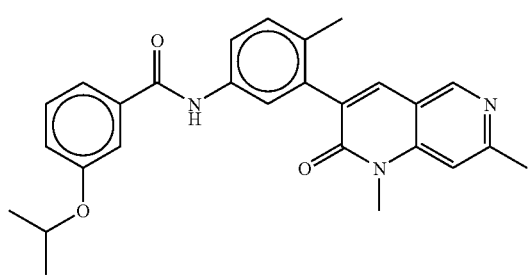 M32 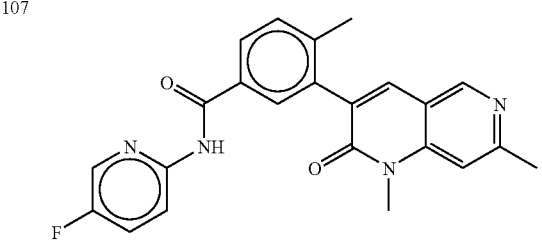

-continued
| B108 | M33 |
| --- | --- |
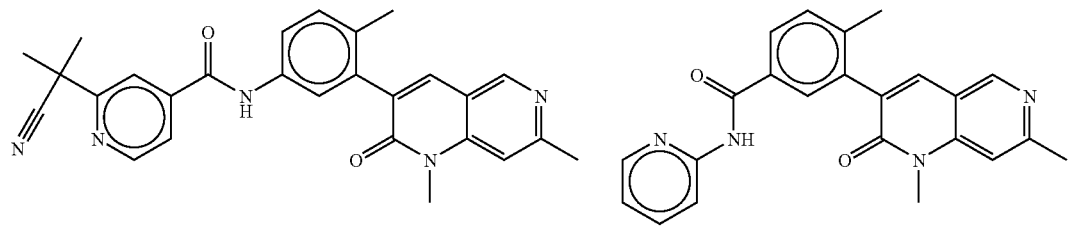
| B109 | M34 |
| --- | --- |
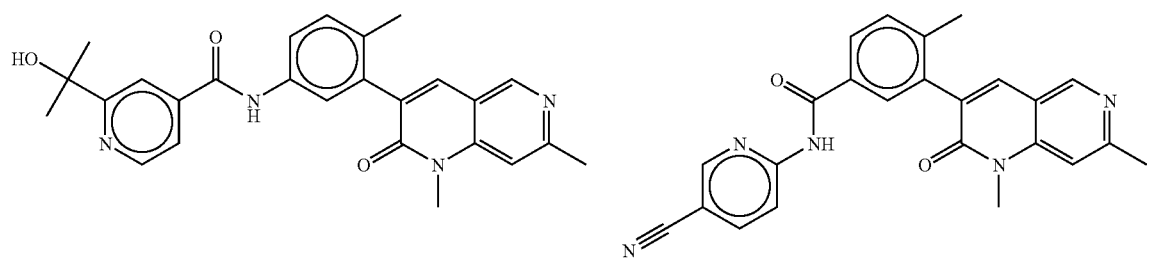
| B110 | M35 |
| --- | --- |
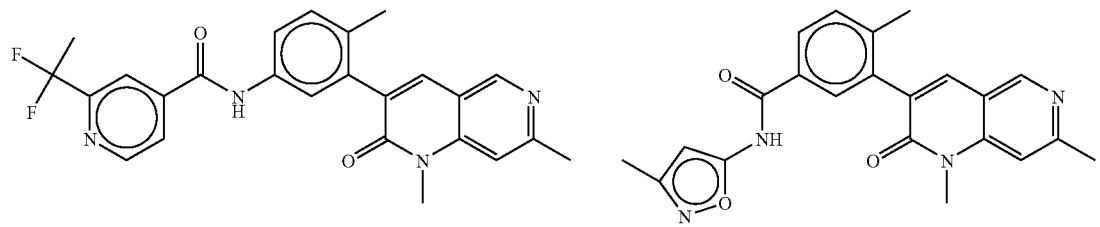
| C1 | M36 |
| --- | --- |
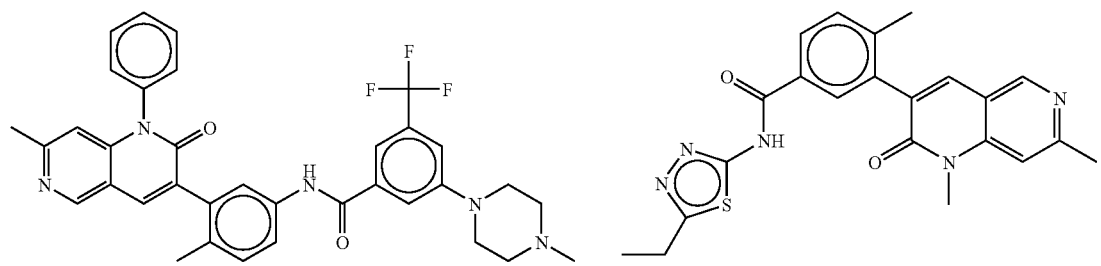
| C2 | M37 |
| --- | --- |
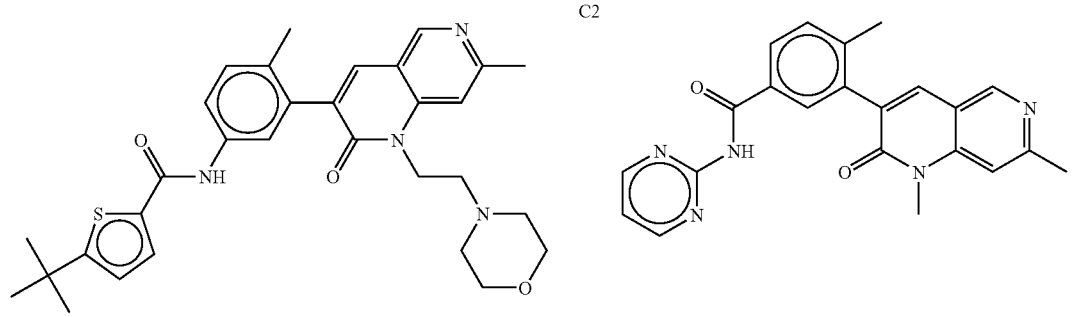

-continued
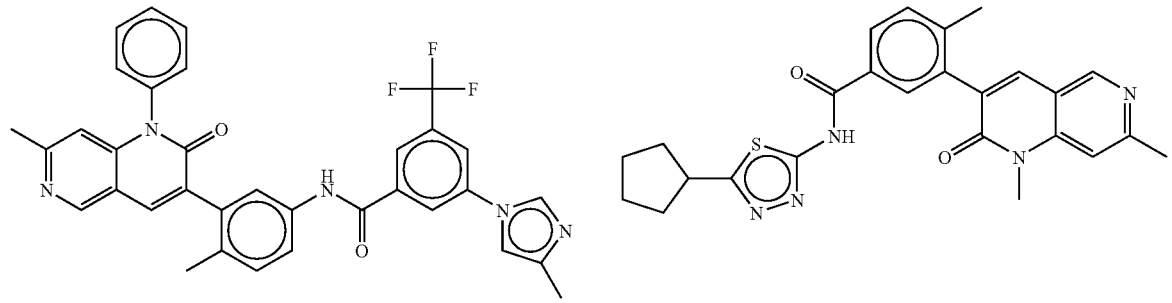
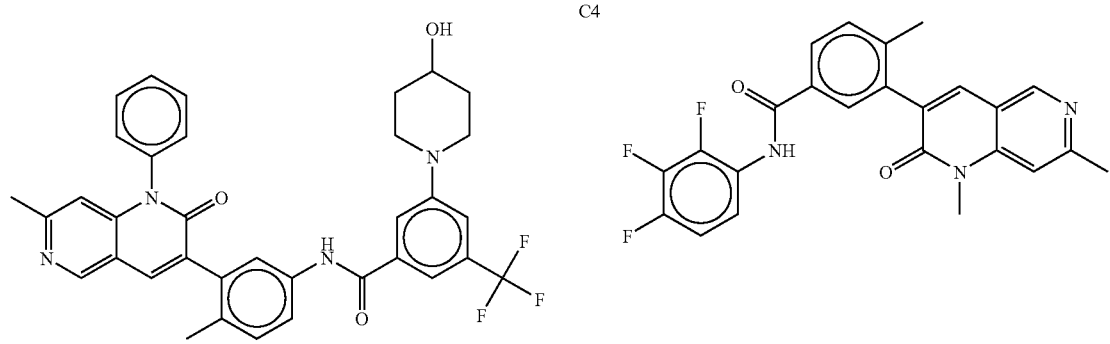
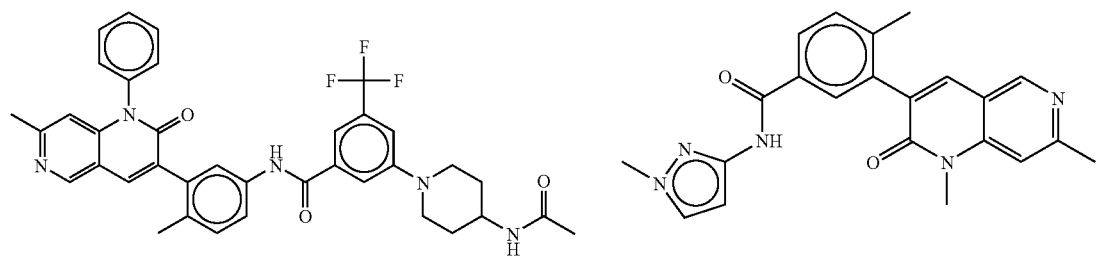
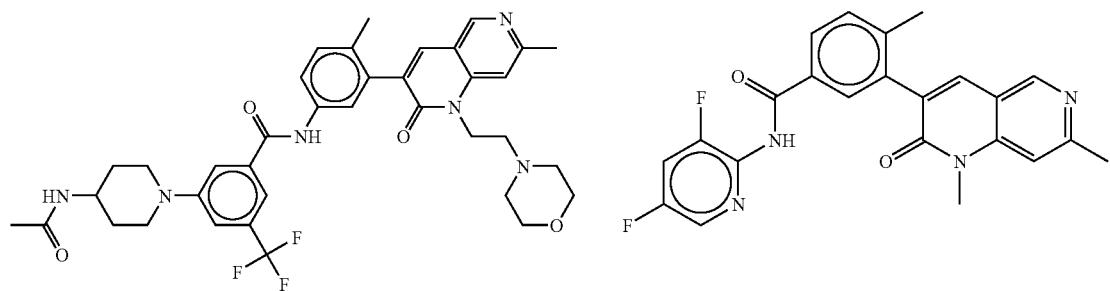
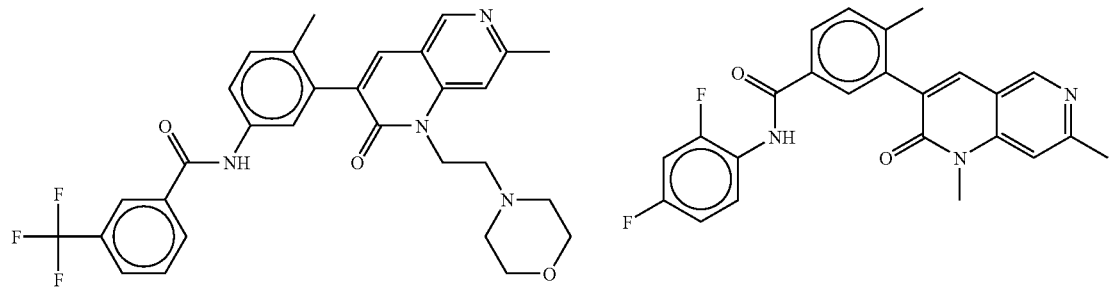

-continued
C8 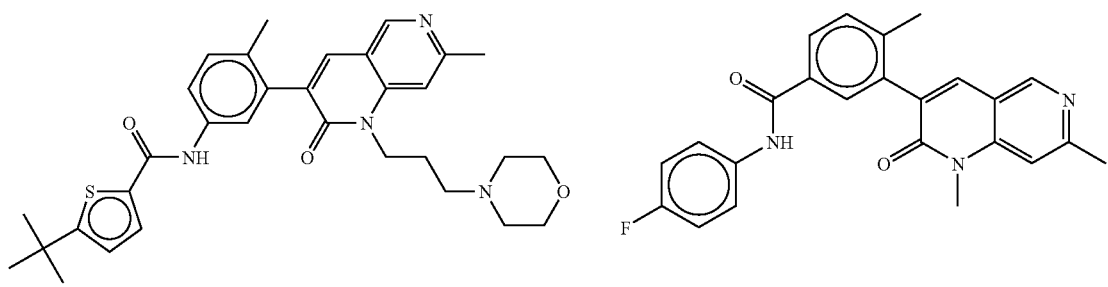 M43
C9 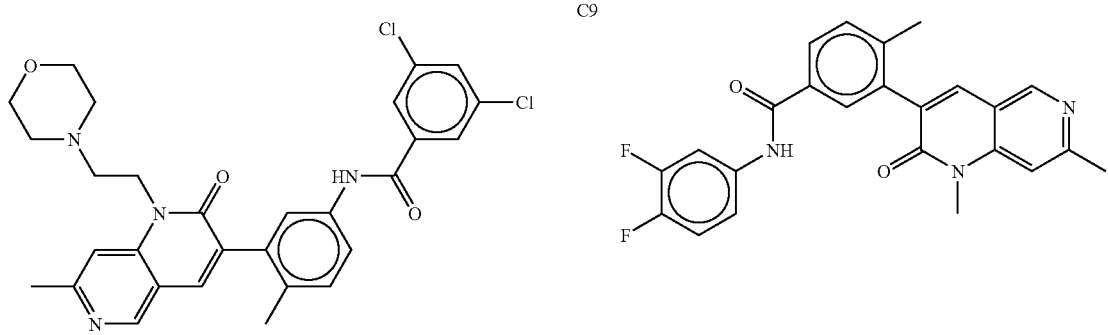 M44
C10 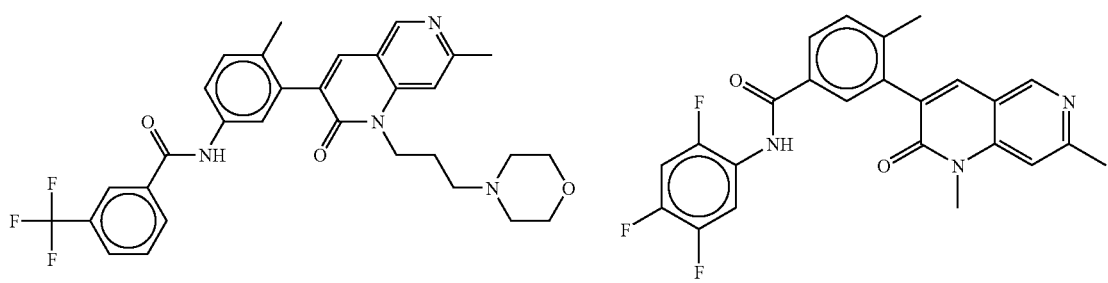 M45
C11 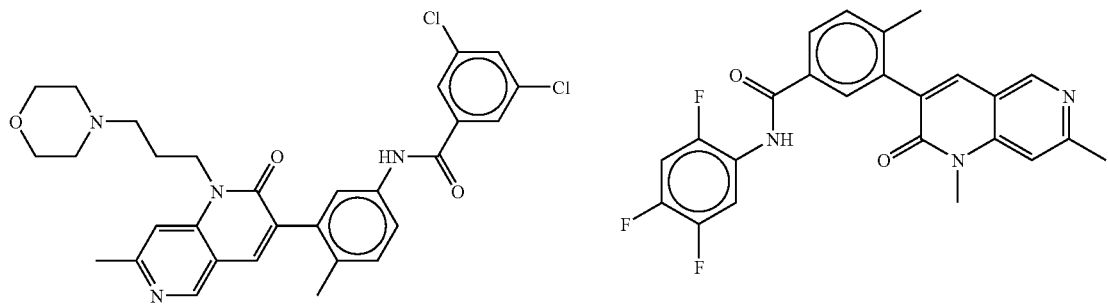 M46
C12 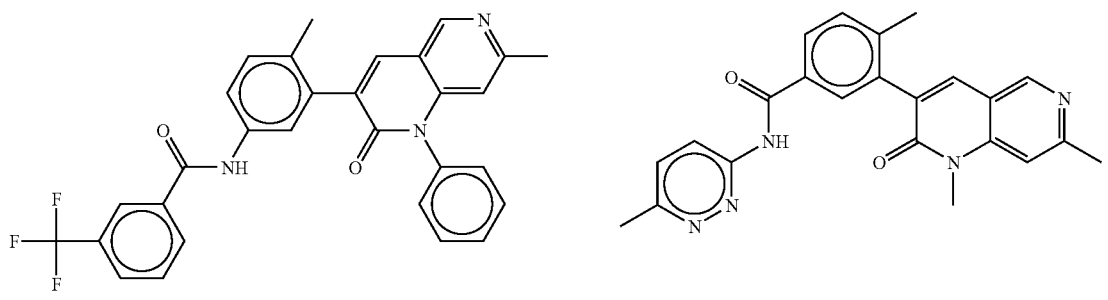 M47

-continued
C13
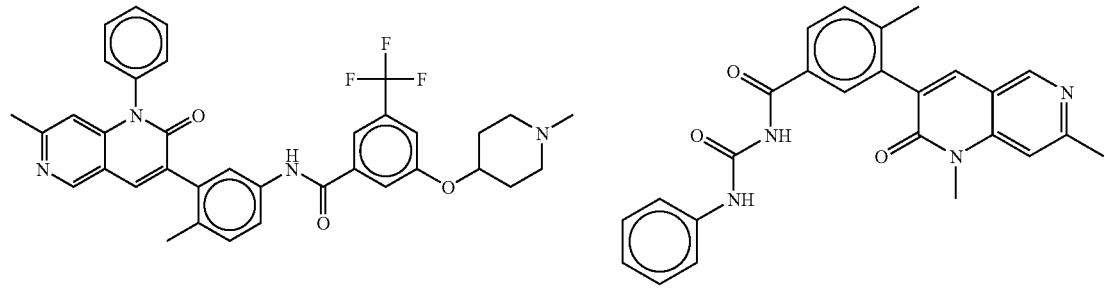
C14
D1
D2
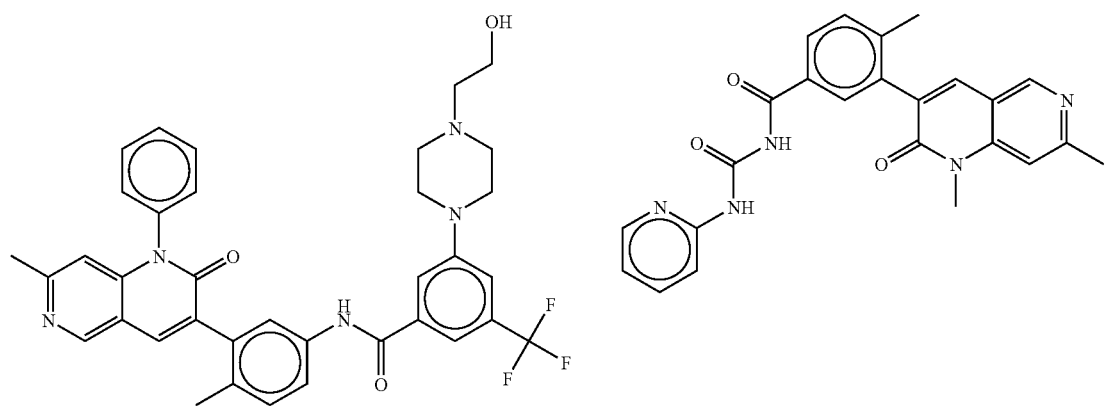
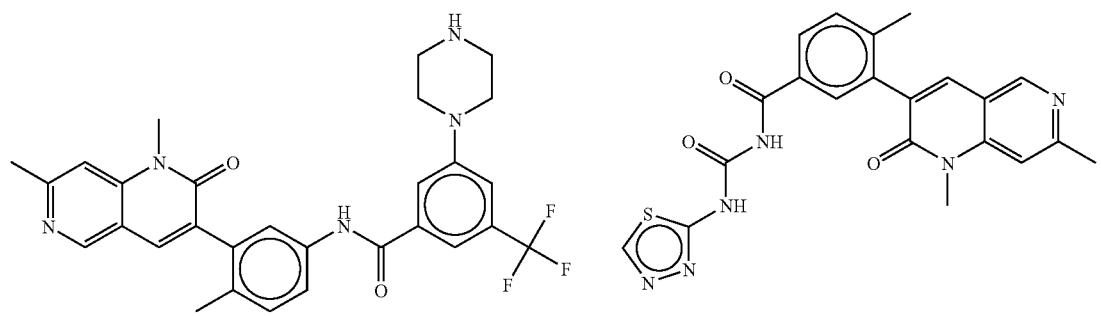
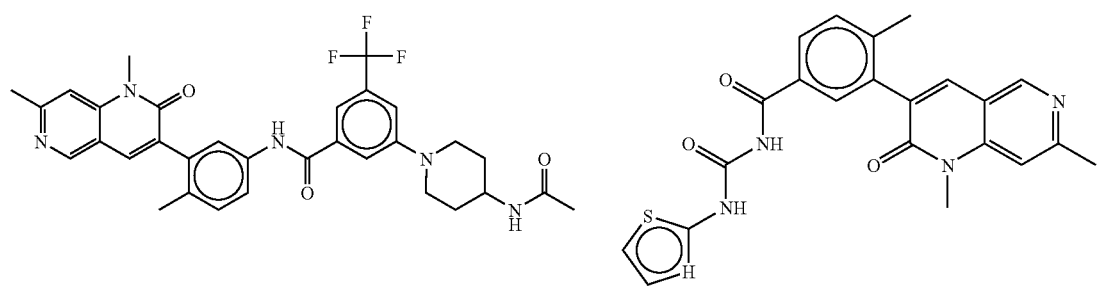
N1
N2
N3
N4

-continued
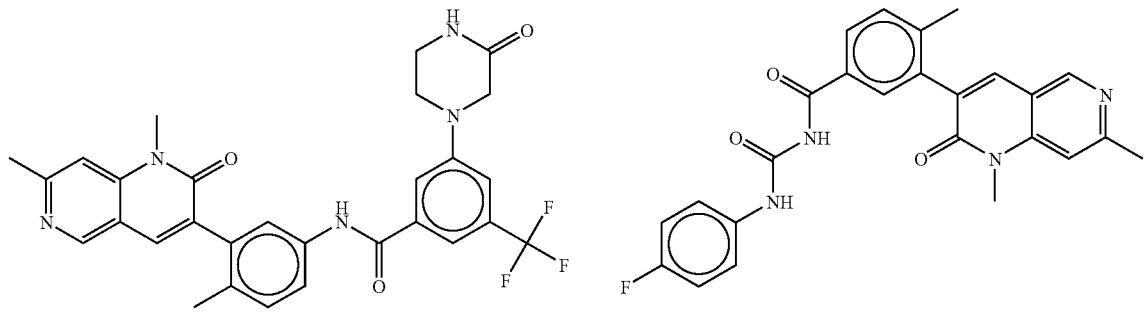
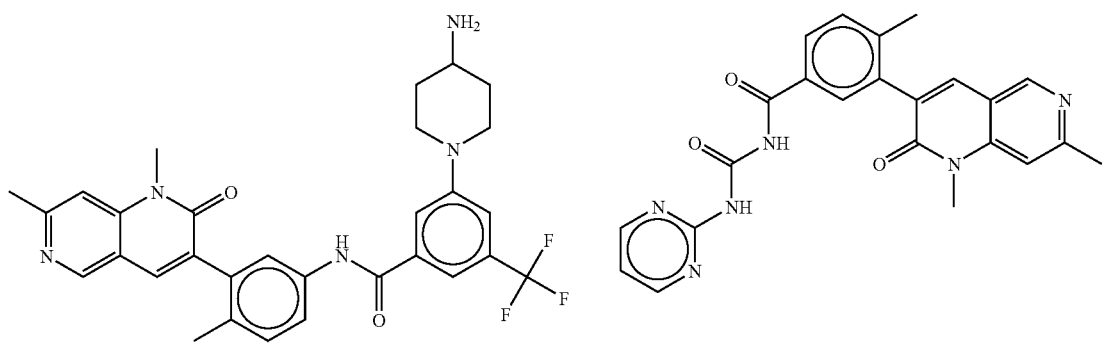
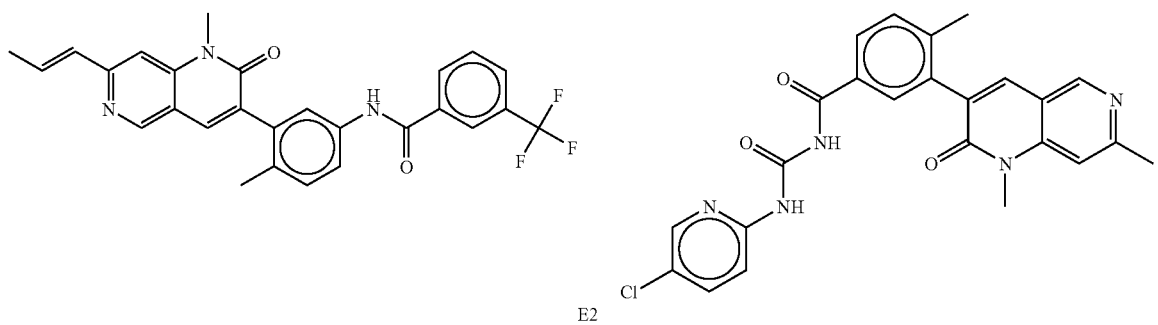
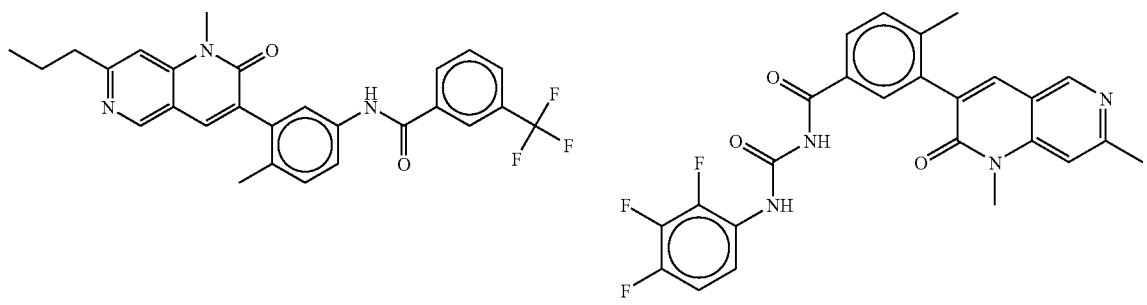
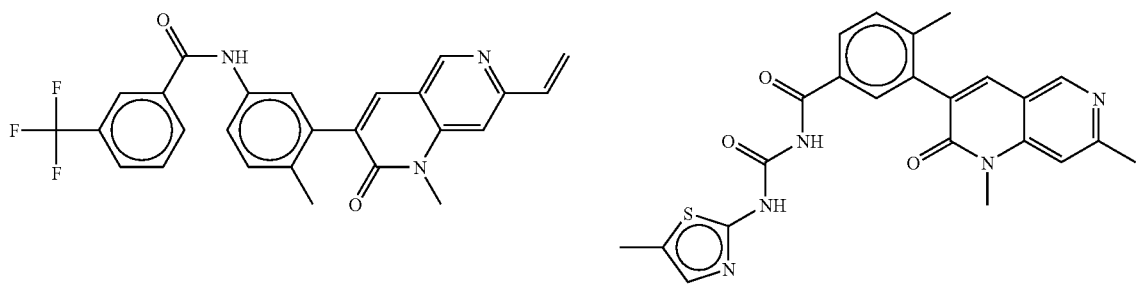

-continued
E4
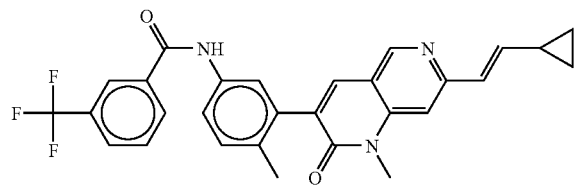
N10
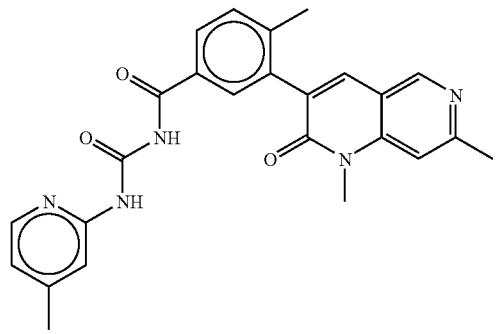
E5
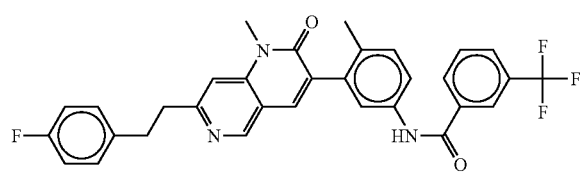
N11
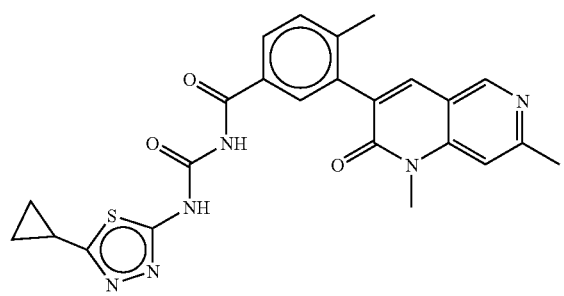
E6
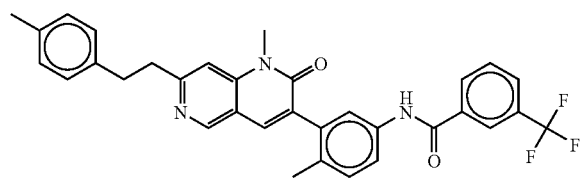
N12
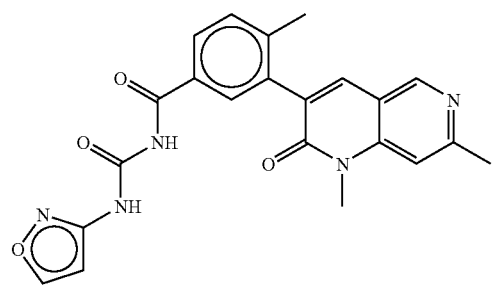
E7
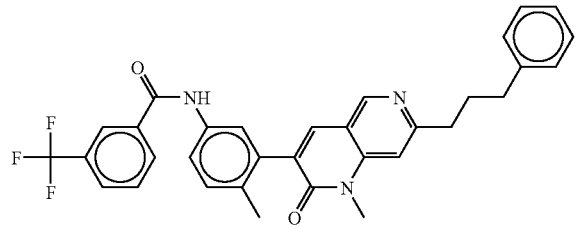
N13
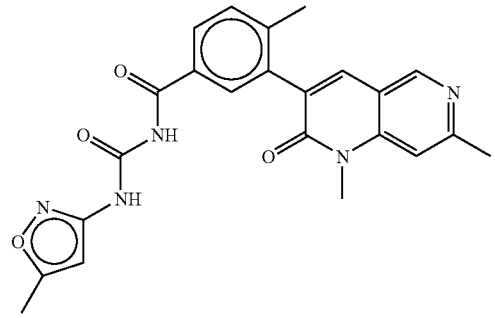
E8
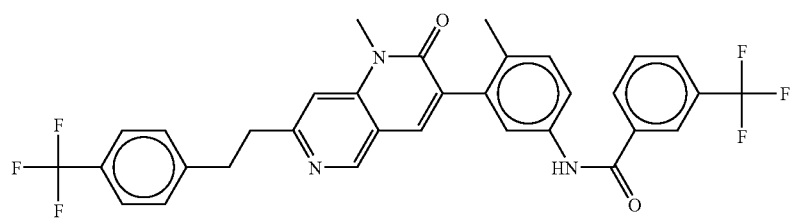

-continued
| 231 | 232 |
|---|---|
| N14 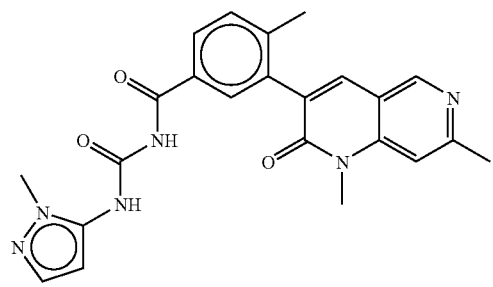 | E9 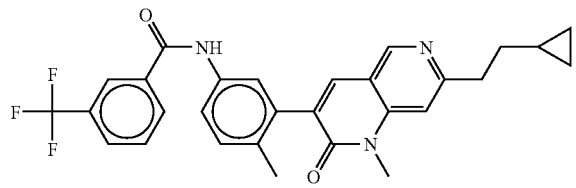 |
| N15 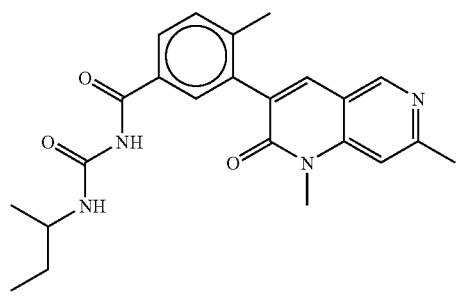 | E10 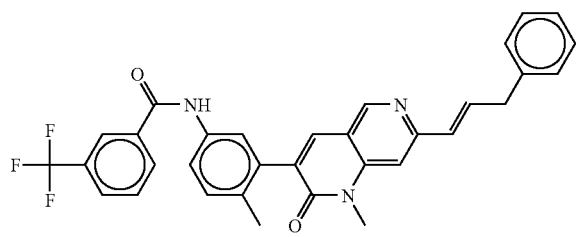 |
| N16 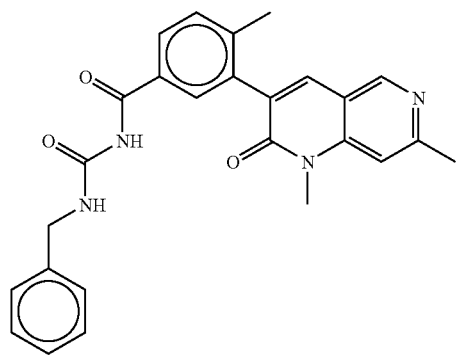 | |
| 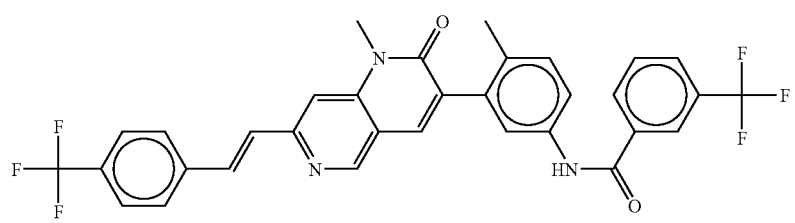 | E11 |
| N17 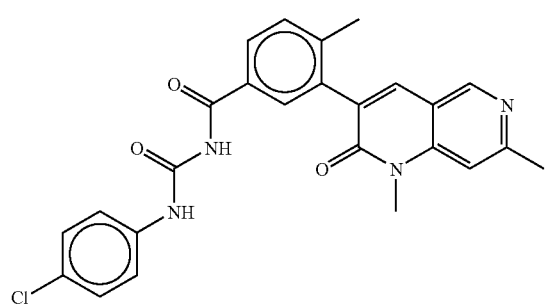 | E12 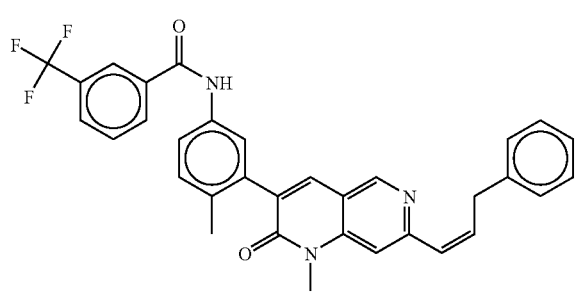 |

-continued
N18
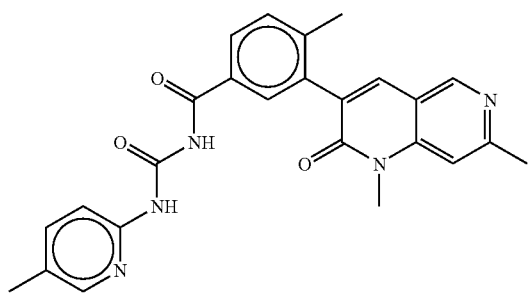
E13
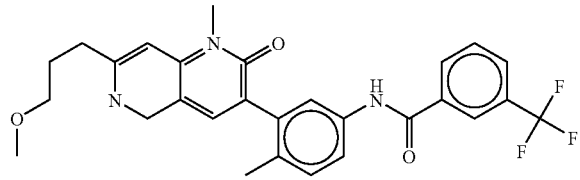
N19
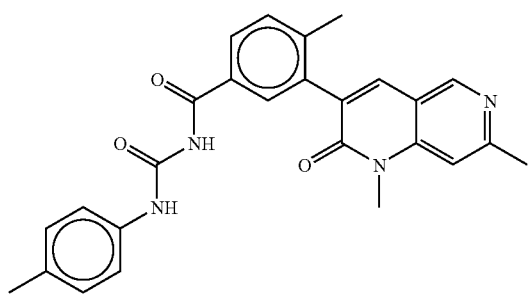
E14
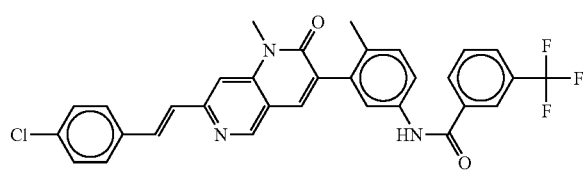
N20
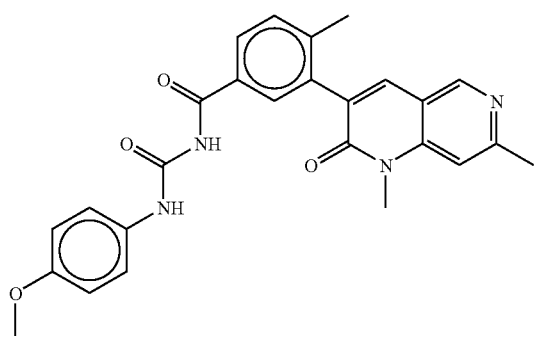
E15
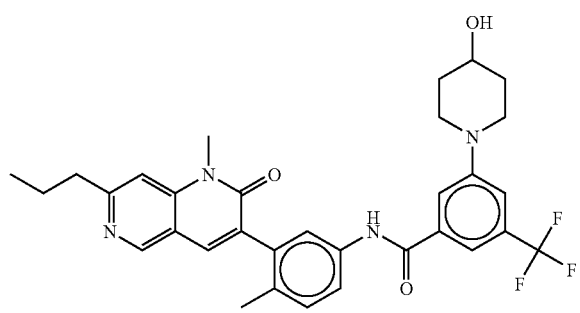
N21
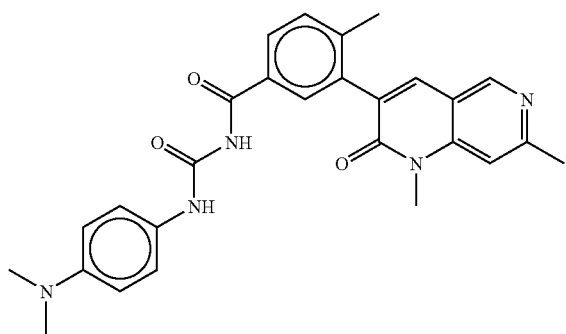
E16
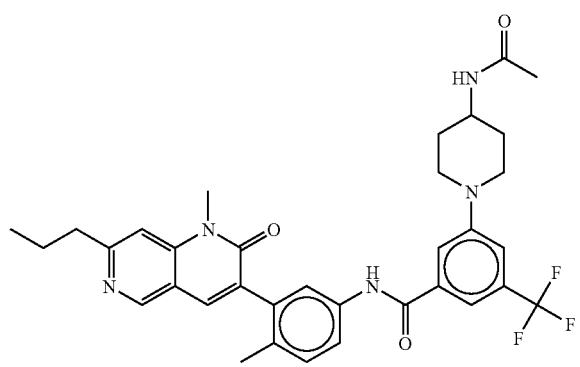

-continued
235 N22
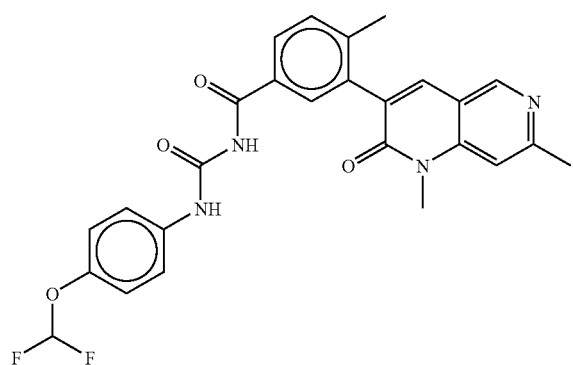
236 E17
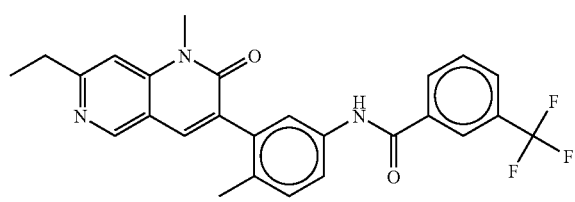
6
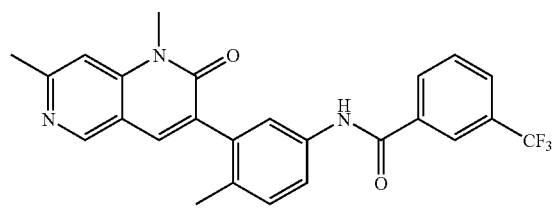
41
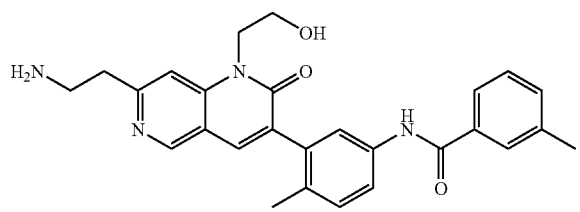
7
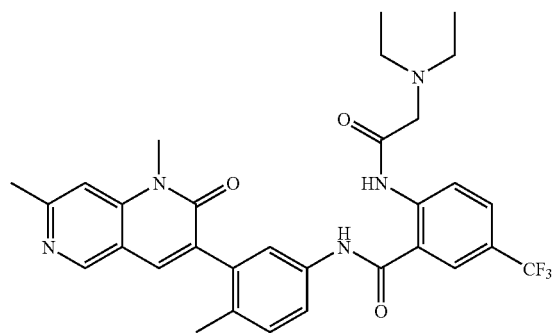
42
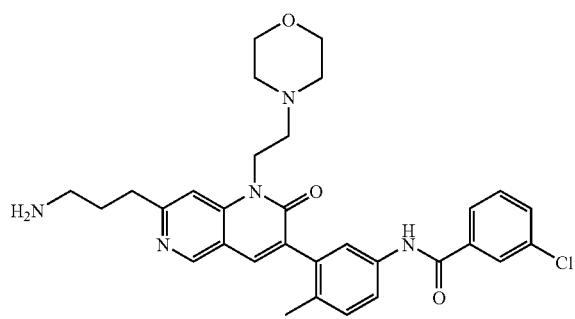
8
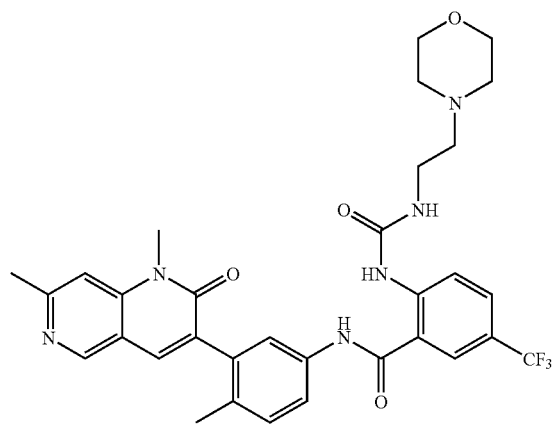
43
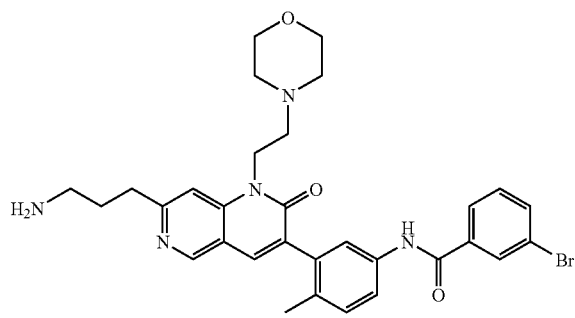

-continued
9
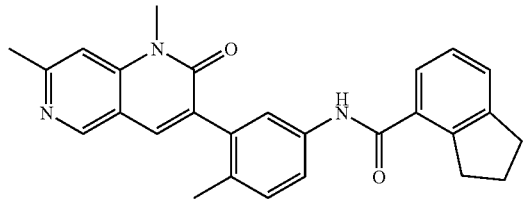
44
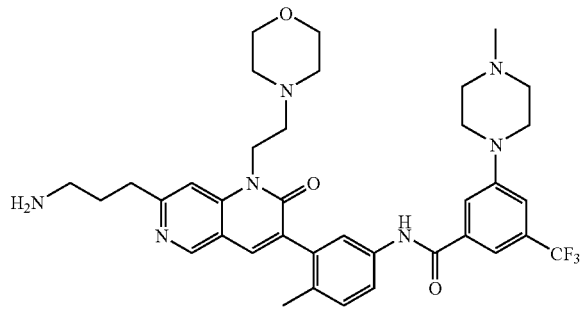
10
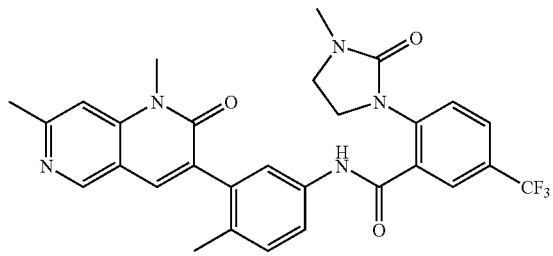
11
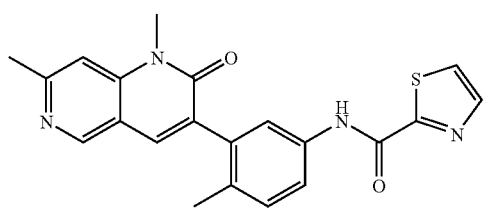
12
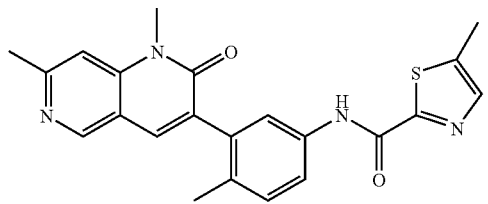
13
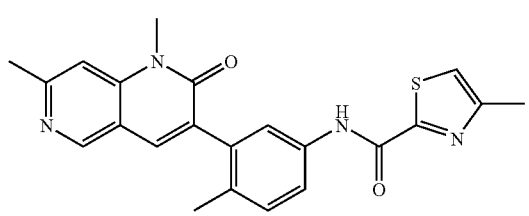
14
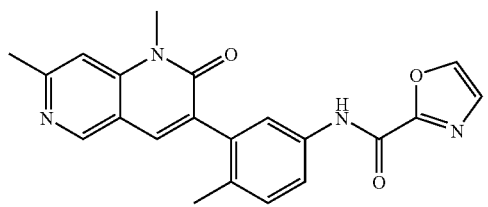

-continued
15
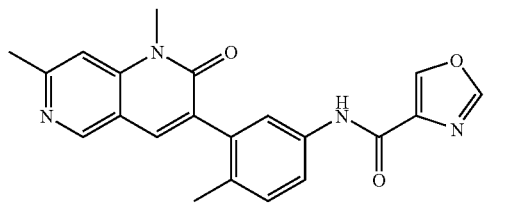
16
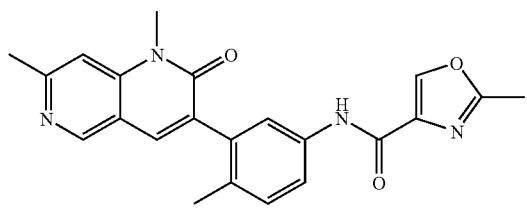
17
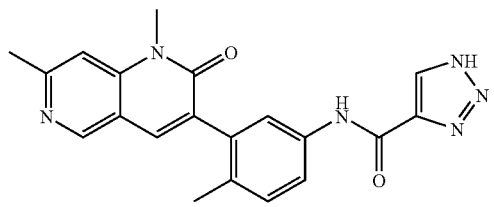
18
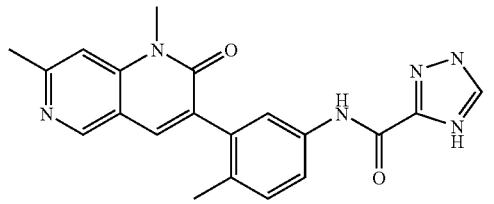
19
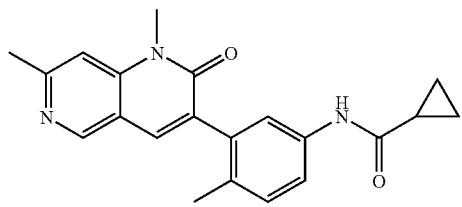
20
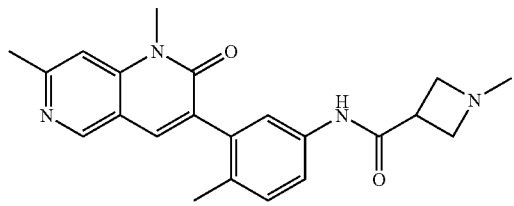
21
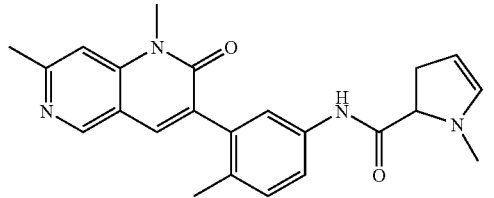
50
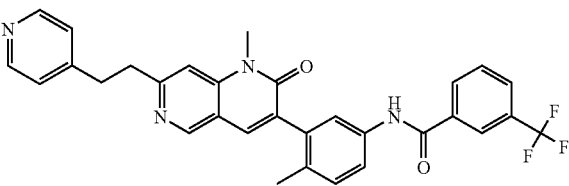
51
52
53
54
55
56
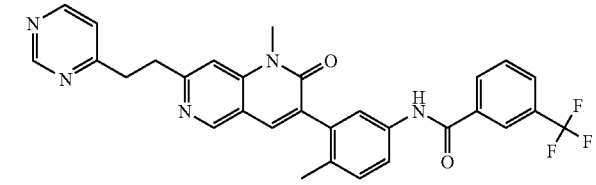

-continued
22
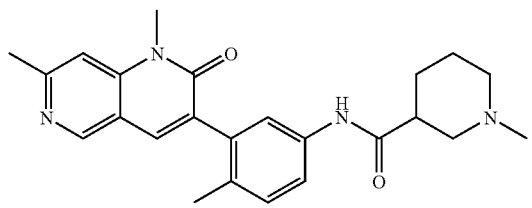
57
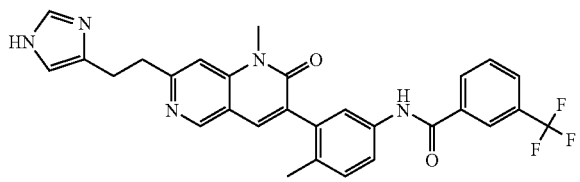
23
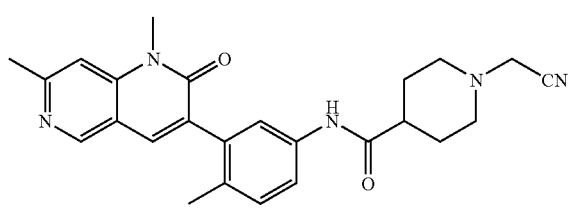
58
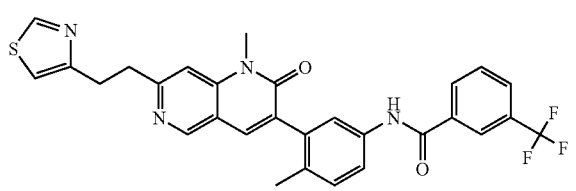
24
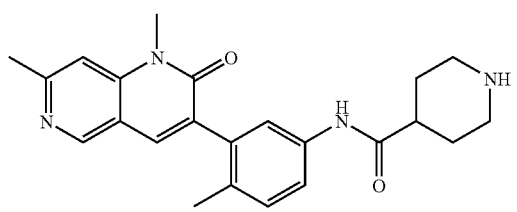
59
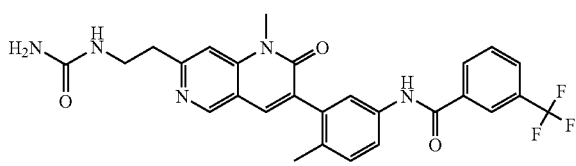
25
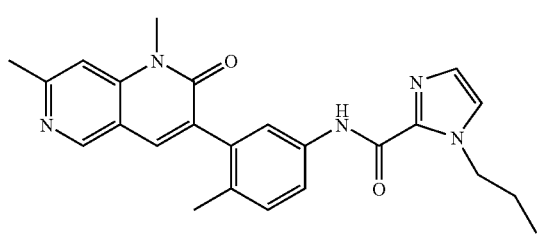
60
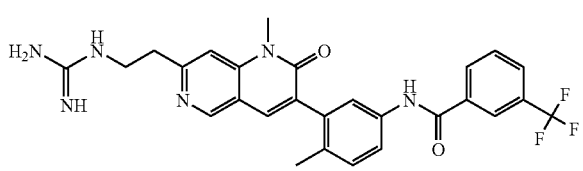
26
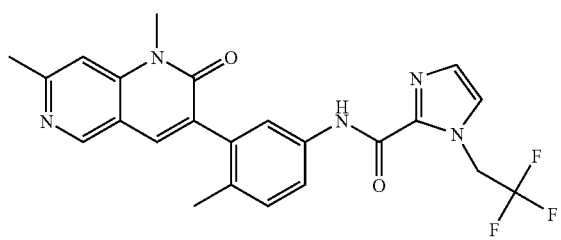
61
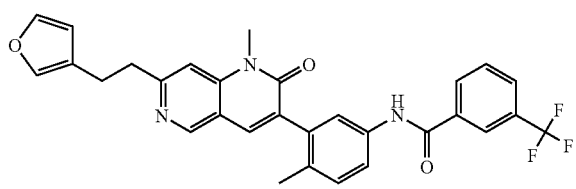
27
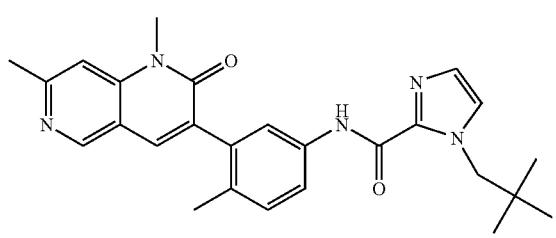
62
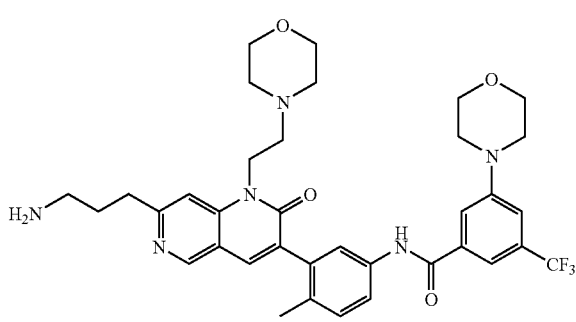

-continued
28
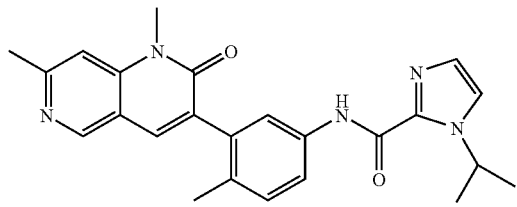
63
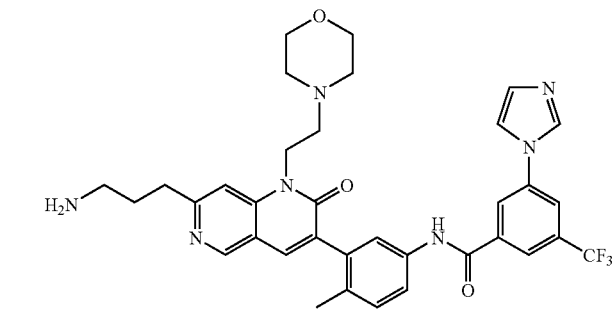
29
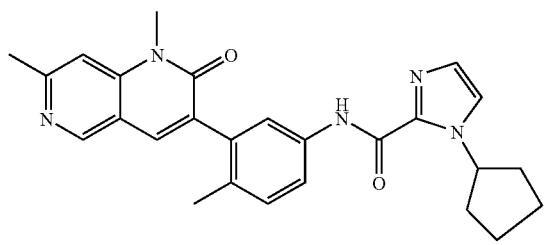
64
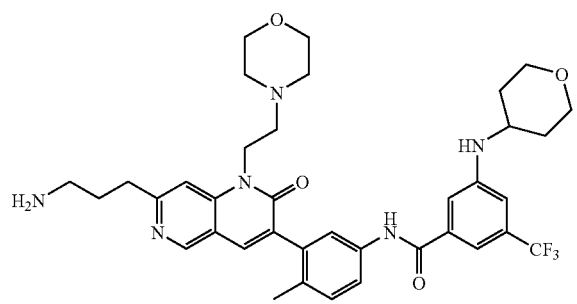
30
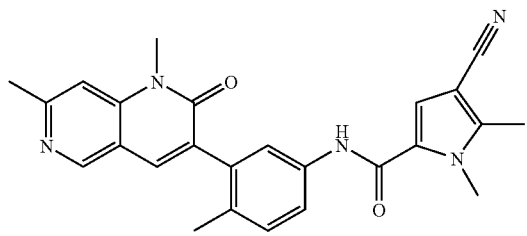
65
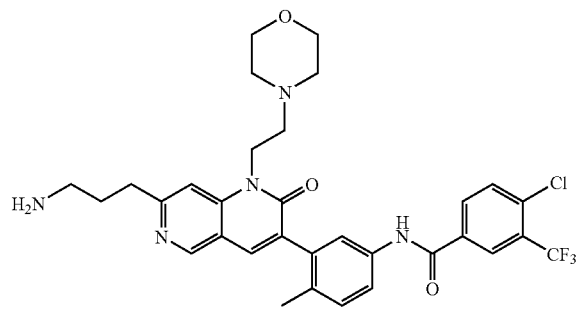
31
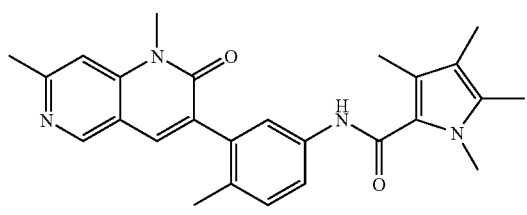
66
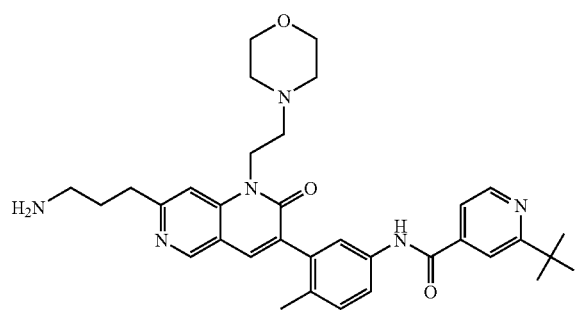
32
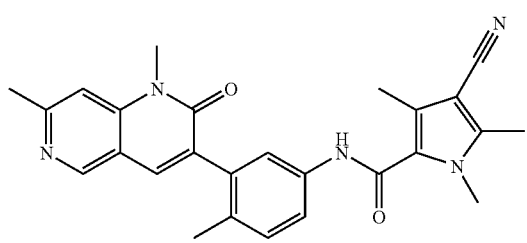
67
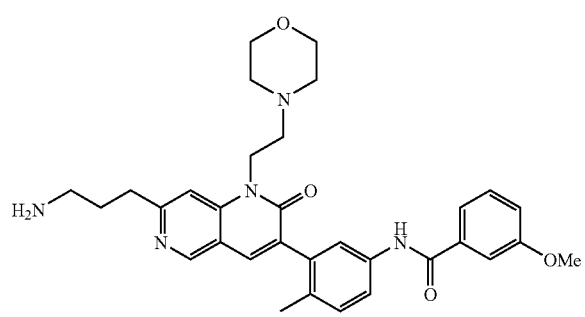

-continued
| 33 | 68 |
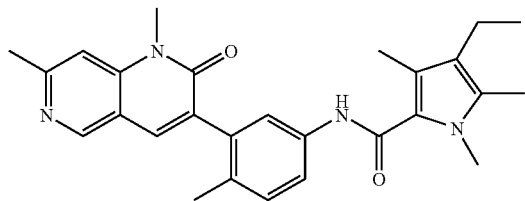
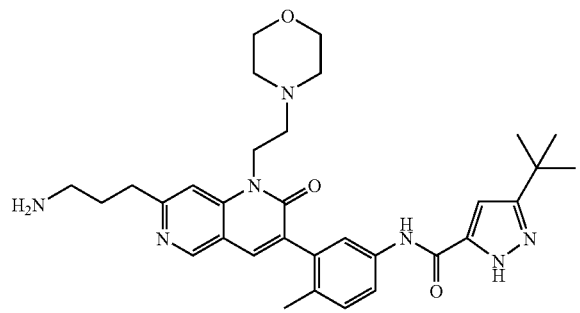
| 34 | 69 |
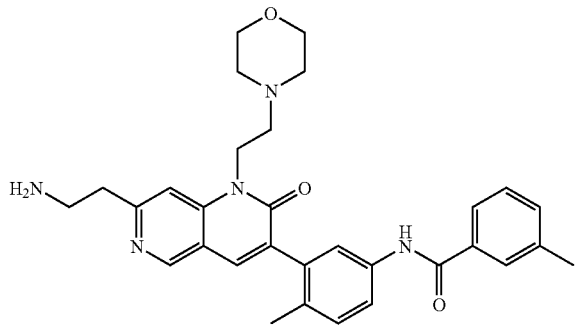
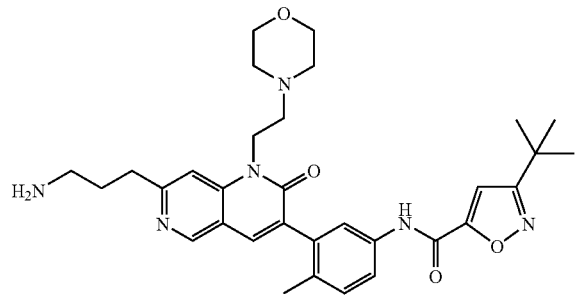
| 35 | 70 |
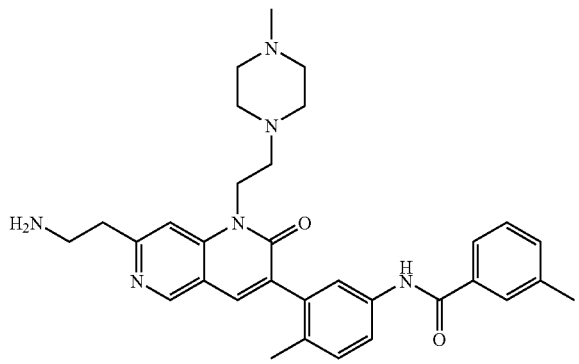
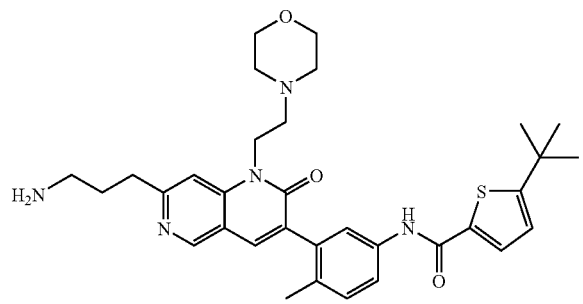
| 36 | 71 |
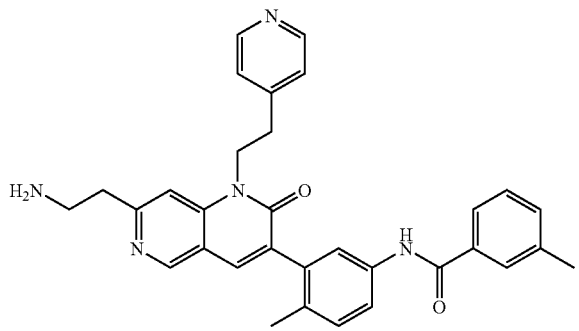
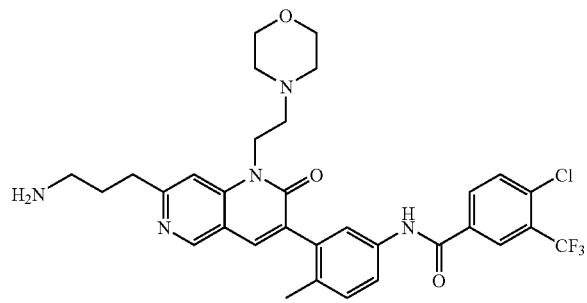

-continued
37
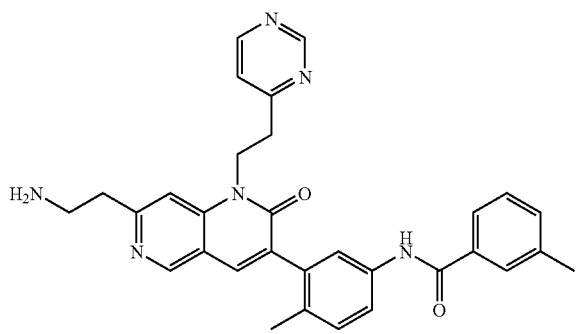
38
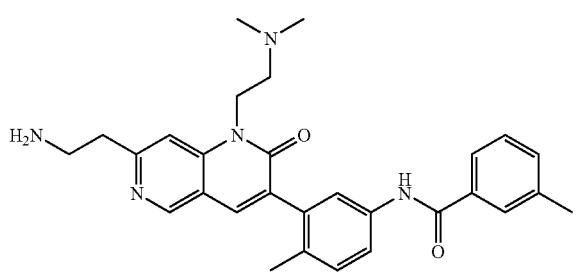
39
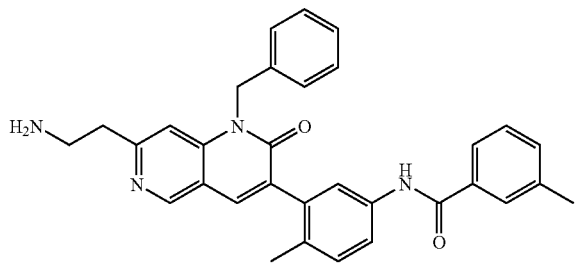
72
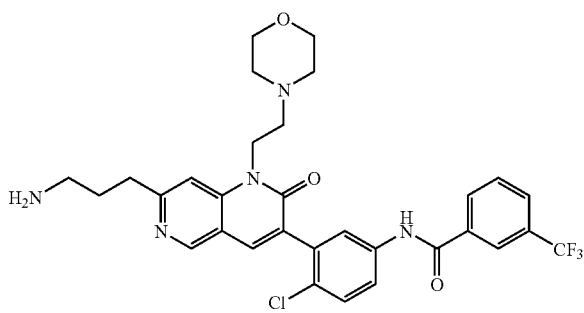
73
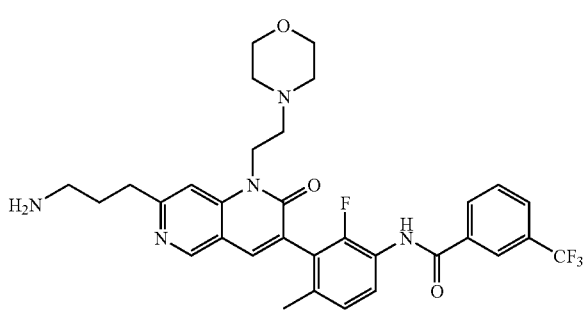
74
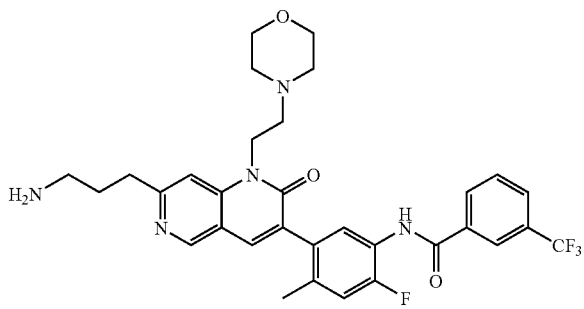
75
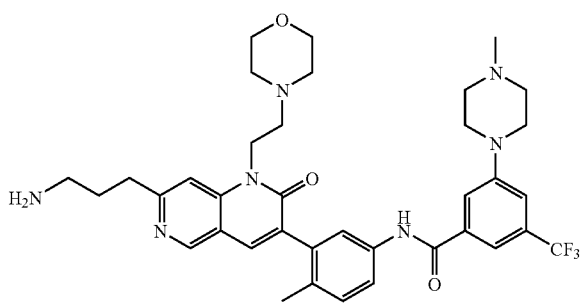
76
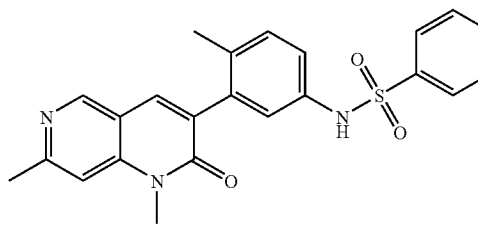
and
77
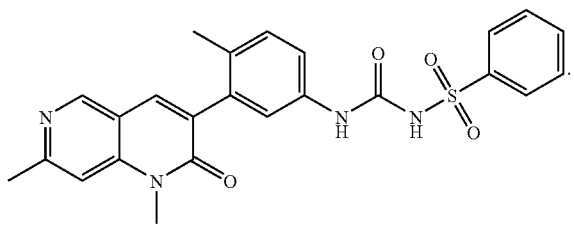

16. A pharmaceutical composition comprising a therapeutically effective amount of a compound of claim 15 and a pharmaceutically acceptable excipient.

17. A pharmaceutical composition comprising a therapeutically effective amount of a compound of claim 13 and a pharmaceutically acceptable excipient.

* * * * *